US012760110B2

(12) United States Patent
Orentas et al.

(10) Patent No.: US 12,760,110 B2
(45) Date of Patent: Oct. 13, 2026

(54) BINDERS AND CHIMERIC ANTIGEN RECEPTORS WHICH SPECIFICALLY BIND FIBROBLAST GROWTH FACTOR RECEPTOR 4

(71) Applicants: Seattle Children's Hospital, Seattle, WA (US); University of Pittsburgh—Of the Commonwealth System of Higher Education, Pittsburgh, PA (US)

(72) Inventors: Rimas J. Orentas, Seattle, WA (US); Dimiter Stanchev Dimitrov, Pittsburgh, PA (US); Wei Li, Pittsburgh, PA (US); Du-Sun Baek, Pittsburgh, PA (US)

(73) Assignee: Seattle Children's Hospital, Pittsburgh (PA)

(*) Notice: Subject to any disclaimer, the term of this patent is extended or adjusted under 35 U.S.C. 154(b) by 661 days.

(21) Appl. No.: 18/027,305

(22) PCT Filed: Oct. 8, 2021

(86) PCT No.: PCT/US2021/054287
§ 371 (c)(1),
(2) Date: Mar. 20, 2023

(87) PCT Pub. No.: WO2022/076898
PCT Pub. Date: Apr. 14, 2022

(65) Prior Publication Data

US 2024/0026012 A1 Jan. 25, 2024

Related U.S. Application Data

(60) Provisional application No. 63/089,985, filed on Oct. 9, 2020.

(51) Int. Cl.

| | |
|---|---|
| ***A61K 40/31*** | (2025.01) |
| ***A61K 35/17*** | (2025.01) |
| ***C07K 16/28*** | (2006.01) |
| ***C12N 5/078*** | (2010.01) |
| ***C12N 15/86*** | (2006.01) |

(52) U.S. Cl.
CPC .......... *C07K 16/2863* (2013.01); *A61K 35/17* (2013.01); *A61K 40/31* (2025.01); *C12N 5/0634* (2013.01); *C12N 15/86* (2013.01); *A61K 2239/21* (2023.05); *A61K 2239/22* (2023.05); *C12N 2510/00* (2013.01)

(58) Field of Classification Search
None
See application file for complete search history.

(56) References Cited

U.S. PATENT DOCUMENTS

| | | | |
|---|---|---|---|
| 6,750,325 | B1 | 6/2004 | Jolliffe et al. |
| 8,021,661 | B2 | 9/2011 | Glaser et al. |
| 8,394,927 | B2 | 3/2013 | Bange et al. |
| 9,266,955 | B2 | 2/2016 | Dennis et al. |
| 10,358,498 | B2 | 7/2019 | Abraham et al. |
| 11,078,286 | B2 | 8/2021 | Khan et al. |
| 2007/0248605 | A1 | 10/2007 | Hestir et al. |
| 2011/0052606 | A1 | 3/2011 | Spee et al. |
| 2011/0150870 | A1 | 6/2011 | Rader et al. |
| 2014/0121123 | A1 | 5/2014 | Wang et al. |
| 2017/0368169 | A1 | 12/2017 | Loew et al. |
| 2018/0318440 | A1 | 11/2018 | Khan et al. |
| 2018/0369373 | A1 | 12/2018 | Anceriz et al. |
| 2019/0233498 | A1 | 8/2019 | Loomis et al. |
| 2019/0233522 | A1 | 8/2019 | Forssmann et al. |
| 2019/0241667 | A1 | 8/2019 | Papadopoulos et al. |

FOREIGN PATENT DOCUMENTS

| | | |
|---|---|---|
| WO | WO 98/46778 | 5/1998 |
| WO | WO 98/22143 | 10/1998 |
| WO | WO 00/17376 | 3/2000 |
| WO | WO 18/039626 | 3/2018 |
| WO | WO 2019/034427 A1 | 2/2019 |

OTHER PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Research Communications. 307:198-205.*
Chen et al. (1999). J. Mol. biol. 293:865-881.*
Wu et al. (1999). J. Mol. Biol. 294:151-162.*

(Continued)

*Primary Examiner* — Christine J Saoud
*Assistant Examiner* — Jon M Lockard
(74) *Attorney, Agent, or Firm* — Knobbe, Martens, Olson & Bear, LLP

(57) ABSTRACT

Some embodiments of the methods and compositions provided herein include methods and materials involved in binding a binder (e.g., an antibody, antigen binding fragment, antibody domain, CAR, cell engager, and/or ADC) to an FGFR4 polypeptide. For example, binders (e.g., antibodies, antigen binding fragments, antibody domains, CARs, cell engagers, and/or ADCs) acidic box that bind to an FGFR4 polypeptide and methods and materials for using one or more such binding molecules to treat a mammal (e.g., a human) having cancer are provided. Some embodiments of the methods and compositions provided herein include chimeric antigen receptors (CARs) which specifically bind to fibroblast growth factor receptor 4 (FGFR4). Some embodiments include nucleic acids encoding such CARs, and cells containing such CARs. Some embodiments include the use of such CARs in safe and effective therapies for a cancer, such as an FGFR4-expressing cancer, such as a rhabdomyosarcoma.

20 Claims, 17 Drawing Sheets

Specification includes a Sequence Listing.

(56) References Cited

OTHER PUBLICATIONS

Rudikoff et al. (1982). PNAS. 79:1979-1983.*
Bluemel et al., Mar. 23, 2010, Epitope distance to the target cell membrane and antigen size determine the potency of T cell-mediated lysis by BiTE antibodies specific for a large melanoma surface antigen, Cancer Immunology, Immunotherapy, 59(8):1197-1209.
Dickopf et al., 2020, Format and geometries matter: structure-based design defines the functionality of bispecific antibodies, Computational and Structural Biotechnology Journal, 18:1221-1227.
Kulemzin et al., Jan. 2017, Engineering chimeric antigen receptors, Acta Naturae, 9(1):6-14.
Roda-Navarro et al., Jan. 10, 2020, Understanding the spatial topology of artificial immunological synapses assembled in T cell-redirecting strategies: a major issue in cancer immunotherapy, Frontiers in Cell and Developmental Biology, 7:Article 370, 5 pp.
Shivaprasad, Nityashree "T Cell Based Immunotherapy Targeting Fibroblast Growth Factor Receptor 4 As a Therpeutic Against Rhabdomyosarcoma" Doctorate Thesis, Georgetown University, Jun. 3, 2019.
International Search Report for PCT/US2021/054287 dated Feb. 15, 2022.
Alexandrov et al., Aug. 22, 2013, Signatures of mutational processes in human cancer, Nature 500(7462):415-421.
Ausubel et al., Current Protocols in Molecular Biology, Green Publishing Associates and John Wiley & Sons, New York, N.Y. (1994)).
Bosse et al., Sep. 11, 2017, Identification of GPC2 as an oncoprotein and candidate immunotherapeutic target in high-risk neuroblastoma, Cancer Cell, 32:295-305.
Brinkmann et al., 2017, The making of bispecific antibodies, MAbs., 9(2):182-212.
Chen et al., 2013, Fusion Protein Linkers: Property, Design and Functionality, Adv. Drug Deliv. Rev., 65(10):1357-1369.
Chen et al., 2017, CAR T-cell intrinsic PD-1 checkpoint blockade: a two-in-one approach for solid tumor immunotherapy,, 3 pp. Oncoimmunology, 6(2):e1273301.
Chen et al., Dec. 9, 2013, Targeting oxidative stress in embryonal rhabdomyosarcoma, Cancer Cell 24:710-724.
Chen et al., Jan. 2010, A large human domain antibody library combining heavy and light chain CDR3 diversity, Mol Immunol, 47:912-921.
Chen et al., Nov. 4, 2008, Human domain antibodies to conserved sterically restricted regions on gp120 as exceptionally potent cross-reactive HIV-1 neutralizers, PNAS 105(44):17121-17126.
Chen et al., Oct. 10, 2008, Construction of a large phage-displayed human antibody domain library with a scaffold based on a newly identified highly soluble, stable heavy chain variable domain, J Mol Biol 382:779-789.
Cherkassy et al., 2016, Human Car T cells with cell-intrinsic PD-1 checkpoint blockade resist tumor-mediated inhibition, J Clin Invest 126(8):3130-3144.
Chmielewski et al., 2004, T cell activation by antibody-like immunoreceptors: increase in affinity of the single-chain fragment domain above threshold does not increase T cell activation against antigen-positive target cells but decreases selectivity, J Immunol 173(12):7647-7653.
Davila-Gonzales et al., Mar. 1, 2018, Pharmacological inhibition of NOS activates ASK1/JNK Pathway Augmenting Docetaxel-Mediated Apoptosis in Triple-Negative Breast Cancer, Clin Cancer Res 24(5):1152-1162.
Elias et al., Feb. 1, 2008, Retinoic acid inhibits Th17 polarization and enhances PoxP3 expression through a Stat-3/Stat-5 independnet signaling pathway, Blood, 111(3):1013-1020.
Foster et al., Jun. 2008, Antitumor activity of EBV-specific T lymphocytes transduced with a dominant negative TGF-beta receptor, J Immuother 31(5):500-505.
Frenzel et al., Jul. 29, 2017, Expression of recombinant antibodies, Front Immunol., 4:217.
Gervasi et al., 2018, Parenteral protein formulations: An overview of approved products within the European UnionEur. J. Pharmaceutics and Biopharmaceutics, 131:8-24.
Giles et al., 2016, Activation of hematopoietic stem/progenitor cells promotes immunosuppression within the pre-metastatic niche, Cancer Res, 76:1335-1347.
Gordon-Alonso et al., 2017, Galectin-3 captures interferon-gamma in the tumor matric reducing chemokine gradient production and T-cell tumor infiltration, Nature Comm 8:793.
Haso et al., Feb. 14, 2013, Anti-CD22-chimeric antigen receptors targeting B-cell precursor acute lymphoblastic leukemia, Blood, 121(7):1165-1174.
Highfill et al., May 21, 2014, Disruption of CXCR2-mediated MDSC tumor trafficking enhances anti-PD1 efficacy, Sci Transl Med 6(237):237ra67.
James et al., May 15, 2008, Antigen sensitivity of CD22-specific chimeric TCR is modulated by target epitope distance from the cell membrane, J Immunol, 180(10):7028-7038.
Kohsaka et al., Jun. 2014, A recurrent neomorphic mutation in MYOD1 defines a clinically aggressive subsets of embryonal rhabdomyosarcoma associated with PI3K-AKT pathway mutations, Nat Genet 46:595-600.
Kunkele et al., Apr. 2015, Functional tuning of CARs reveals signaling threshold above which CD8+ CTL antitumor potency is attenuated due to cell Fas-FasL-dependent AICD, Cancer Immunol Res 3(4):368-379.
Lang et al., 2019, Fibroblast Growth Factor Receptor 4 Targeting in Cancer: New Insights into Mechanisms and Therapeutic Strategies, Cells 8:31, 13 pp.
Liu et al., Mar. 15, 2016, A chimeric switch-receptor targeting PD1 augments the efficacy of second-generation CAR T cells in advanced solid tumors, Cancer Res 76(6):1578-1590.
Long et al., Jun. 2015, 4-1BB costimulation ameliorates T cell exhaustion induced by tonic signaling of chimeric antigen receptors, Nat Med, 21(6):581-590.
Long et al., Oct. 2016, Reduction of MDSCs with all-trans retinoic acid improves CAR therapy efficacy for sarcomas, Cancer Immunol Res 4(10):869-880.
McKinnon et al., May 2018, Functional screening of FGFR4-driven tumorigenesis identified PI3K/mTOR inhibition as a therapeutic strategy in rhabdomyosarcoma, Oncogene 37(20):2630-2644.
Neumann et al., 1982, Gene transfer into mouse lyoma cells by electroporation in high electric fields, EMBO J., 1(7):841-845.
Orentas et al., Dec. 17, 2012, Identification of cell surface proteins as potential immunotherapy target in 12 pediatric cancers, Front Oncol 2:194, 16 pp.
Pappo et al., Feb. 1, 2007, Two consecutive phase II window trials or irinotecan alone or in combination with vincristine for the treatment of metastatic rhabdomyosarcoma: the Children's Oncology Group, J Clin Oncol 25(4):362-369.
Roidl et al., Mar. 15, 2009, Resistance to chemotherapy is associated with fibroblast growth factor receptor 4 up-regulation, Clin Cancer Res 15(9):2058-2066.
Rongvaux et al., Apr. 2014, Development and function of human innate immunce cells in a humanized mouse model, Nat Biotechnol 32(4):364-372.
Rudzinski et al., Dec. 2017, Histology, fusion status, and outcome in metastatic rhabdomyosarcoma: a report from the Children's Oncology Group, Pediatr Blood Cancer, 64(12):e26645.
Sambrook, et al., Molecular Cloning: A Laboratory Manual, 3d ed., Cold Spring Harbor Laboratory Press, Cold Spring Harbor, NY (TOC), (2001).
Santoiemma et al., 2015, Tumor infiltrating lymphocytes in ovarian cancer, Cancer Biol Ther, 16(6):807-820.
Schneider et al., 2018, Fully human immunoglobulin heavy chain only-derived CD33 CAR for the treatment of acute myeloid leukemia, AACR annual meeting, Cancer Res., 78(13_supplement):2561.
Shern et al., Feb. 2014. Comprehensive genomic analysis of rhabdomyosarcoma reveals a landscape of alterations affecting a common genetic axis in fusion-positive and fusion-negative tumors, Cancer Disc 4(2):216-231.
Shukla et al., Feb. 1, 2012, Oncogene mutation profiling of pediatric solid tumors reveals significant subsets of embryonal rhabdomyosarcoma

(56) References Cited

OTHER PUBLICATIONS and neuroblastoma with mutated genes in growth signaling pathways, Clin Canc Res 18(3):748-757.
Skapek et al., Sep. 2013, PAX-FOXO1 fusion status drives unfavorable outcome for children with rhabdomyosarcoma: a children's oncology group report, Pediatr Blood Cancer 60(9):1411-1417.
Stratton et al., Nov. 15, 1989, Detection of point mutations in N-ras and K-ras genes of human embryonal rhabdomyosarcoma using oligonucleotide probes and the polymerase chain reaction, Cancer Res 49:6324-6327.
Tan et al., Feb. 2015, Tumor stroma and chemokines control T-cell migration into melanoma following Temozolomide treatment, Oncolmmunology 4:2, e978709.
Taylor et al., 2009, Identification of FGFR4-activting mutations in human rhabdomyosarcomas that promote metastasis in xenotransplanted models, J Clin Invest 119(11):3395-3407.
Wang X, Chang WC, Wong CW, Colcher D, Sherman M, Ostberg JR, Forman SJ, Riddell SR, Jensen MC. 2011. A transgene-encided cell surface polypeptide for selection, in vivo tracking, and ablation of engineered cells, Blood, 118:1255-63.
Youn et al., Oct. 15, 2008, Subsets of myeloid-derived suppressor cells in tumor-bearing mice, J Immunol 181(8):5791-5802.

* cited by examiner

Exemplary Linker Sequences for scFv's, CARs, and/or cell engagers:

a) GGGGSGGSGSGGGGS (SEQ ID NO:244)

b) GGGGSGGSGSSGGGS (SEQ ID NO:245)

c) GGGGSGGGGSGGGGS (SEQ ID NO:246)

d) GGGGSGSGASSGGGS (SEQ ID NO:247)

e) GGGGSGSGASGGGGS (SEQ ID NO:248)

f) SGGGSGGGGSGGGGS (SEQ ID NO:249)

g) GSTSGSGKPGSGEGSTKG (SEQ ID NO:250)

h) PNGASQSSSASHTGSAPGS (SEQ ID NO:251)

i) PNGASNSGSAPDTSSAPGS (SEQ ID NO:252)

j) PNGASHSGSAPNTSSAPGS (SEQ ID NO:253)

k) PNGASESGSASKTSSASGS (SEQ ID NO:254)

l) PNGASNSGSAPKTGSASGS (SEQ ID NO:255)

m) PNGASKSGSASQTSSAPGS (SEQ ID NO:256)

n) PNGASHSSSASQTGSAPGS (SEQ ID NO:257)

o) PNGASKRSAPGS (SEQ ID NO:258)

p) PNGASHSGSAPHTSSASGS (SEQ ID NO:259)

q) RGRGRGRGRSRGGGS (SEQ ID NO:260)

r) SHGGSHGGGSGGGGS (SEQ ID NO:261)

s) GQAGR (SEQ ID NO:262)

t) GGGSGGGG (SEQ ID NO:263)

u) SGGGG (SEQ ID NO:264)

v) GGGGS (SEQ ID NO:265)

w) GGGGSGGGGSGGGGSGGGGSGGGGSGGGGS (SEQ ID NO:266)

FIG. 9

Exemplary hinges for CARs

Exemplary human IgG1-derived hinge
EPKSCDKTHTCPPCP (SEQ ID NO:267)

Exemplary human IgG2-derived hinge
DKTHTCPPCPAPPVA (SEQ ID NO:268)

Exemplary human IgG4-derived hinge
ESKYGPPCPPCP (SEQ ID NO:269)

Exemplary human CD8α-derived hinges
KPTTTPAPRPPTPAPTIASQPLSLRPEACRPAAGGAVHTRGLDFACDIY (SEQ ID NO:270)

TTTPAPRPPTPAPTIASQPLSLRPEACRPAAGGAVHTRGLDFACDIY (SEQ ID NO:271)

TTTPAPRPPTPAPTIASQPLSLRPEACRPAAGGAVHTRGLDFACD (SEQ ID NO:272)

Exemplary human CD28-derived hinge
IEVMYPPPYLDNERSNGTIIHVKGKHLCPSPLFPGPSKP (SEQ ID NO:273)

Exemplary short hinges
GGGGS (SEQ ID NO:274)

AAA (SEQ ID NO:275)

FIG. 10

Exemplary transmembrane domains for CARs

Exemplary human CD3ζ transmembrane domain
LCYLLDGILFIYGVILTALFL (SEQ ID NO:276)

Exemplary human CD4 transmembrane domain
MALIVLGGVAGLLLFIGLGIFF (SEQ ID NO:277)

Exemplary human CD8α transmembrane domains
IYIWAPLAGTCGVLLLSLVIT (SEQ ID NO:278)

IYIWAPLAGTCGVLLLSLVITLYC (SEQ ID NO:279)

IWAPLAGTCGVLLLSLVITLYC (SEQ ID NO:280)

IWAPLAGTCGVLLLSLVIT (SEQ ID NO:281)

Exemplary human CD28 transmembrane domain
FWVLVVVGGVLACYSLLVTVAFIIFWV (SEQ ID NO:282)

Exemplary human CD278 transmembrane domain
FWLPIGCAAFVVVCILGCILI (SEQ ID NO:283)

FIG. 11

Exemplary intracellular signaling domains for CARs

Exemplary human CD3ζ intracellular signaling domain
RVKFSRSADAPAYQQGQNQLYNELNLGRREEYDVLDKRRGRDPEMGGKPQRRKNPQE
GLYNELQKDKMAEAYSEIGMKGERRRGKGHDGLYQGLSTATKDTYDALHMQALPPR
(SEQ ID NO:284)

Exemplary human 4-1BB (CD137) intracellular signaling domain
KRGRKKLLYIFKQPFMRPVQTTQEEDGCSCRFPEEEEGGCEL (SEQ ID NO:285)

Exemplary human CD28 intracellular signaling domain
RSKRSRLLHSDYMNMTPRRPGPTRKHYQPYAPPRDFAAYRS (SEQ ID NO:286)

Exemplary human OX40 (CD134) intracellular signaling domain
ALYLLRRDQRLPPDAHKPPGGGSFRTPIQEEQADAHSTLAKI (SEQ ID NO:287)

Exemplary human CD278 intracellular signaling domain
CWLTKKKYSSSVHDPNGEYMFMRAVNTAKKSRLTDVTL (SEQ ID NO:288)

Exemplary human DAP10 intracellular signaling domain
LCARPRRSPAQEDGKVYINMPGRG (SEQ ID NO:289)

Exemplary human DAP12 intracellular signaling domain
YFLGRLVPRGRGAAEAATRKQRITETESPYQELQGQRSDVYSDLNTQRPYYK (SEQ ID NO:290)

Exemplary human CD27 intracellular signaling domain
QRRKYRSNKGESPVEPAEPCHYSCPREEEGSTIPIQEDYRKPEPACSP (SEQ ID NO:291)

FIG. 12

Exemplary antigen binding domains that bind to T cells

Exemplary anti-human CD3 scFv (clone OKT3)

Heavy chain:

QVQLVQSGGGVVQPGRSLRLSCKASGYTFTRYTMHWVRQAPGKGLEWIGYINPSRGYT
NYNQKVKDRFTISRDNSKNTAFLQMDSLRPEDTGVYFCARYYDDHYCLDYWGQGTPV
TVSS (SEQ ID NO:292)

Light chain:

DIQMTQSPSSLSASVGDRVTITCSASSSVSYMNWYQQTPGKAPKRWIYDTSKLASGVPS
RFSGSGSGTDYTFTISSLQPEDIATYYCQQWSSNPFTFGQGTKLQITR (SEQ ID NO: 293)

Exemplary anti-human CD3 scFv (clone UCHT1)

Heavy chain:

EVQLQQSGPELVKPGASMKISCKASGYSFTGYTMNWVKQSHGKNLEWMGLINPYKGV
STYNQKFKDKATLTVDKSSSTAYMELLSLTSEDSAVYYCARSGYYGDSDWYFDVWGQ
GTTLTVFS (SEQ ID NO: 294)

Light chain:

MDIQMTQTTSSLSASLGDRVTISCRASQDIRNYLNWYQQKPDGTVKLLIYYTSRLHSGV
PSKFSGSGSGTDYSLTISNLEQEDIATYFCQQGNTLPWTFAGGTKLEIK (SEQ ID NO: 295)

FIG. 13

Exemplary antigen binding domains that bind to NK cells

Exemplary anti-human CD16a scFv

Heavy chain:

EVQLVESGGGVVRPGGSLRLSCAASGFTFDDYGMSWVRQAPGKGLEWVSGINWNGGS TGYADSVKGFR3CDR3FR4RFTISRDNAKNSLYLQMNSLRAEDTAVYYCARGRSLLFDY WGQGTLVTVSR (SEQ ID NO: 296)

Light chain:

SSELTQDPAVSVALGQTVRITCQGDSLRSYYASWYQQKPGQAPVLVIYGKNNRPSGIPD RFSGSSSGNTASLTITGAQAEDEADYYCNSRDSSGNHVVFGGGTKLTVG (SEQ ID NO: 297)

Exemplary anti-human NKG2A scFv

Heavy chain:

EVQLVESGGGLVKPGGSLRLSCAASGFTFSSYAMSWVRQAPGKGLEWVSEISS GGSYTYYADSVKGRFTISRDNAKNSLYLQMNSLRAEDTAVYYCARHGDYPRFF DVWGQGTTVTVSS (SEQ ID NO: 298)

Light chain:

EIVLTQSPATLSLSPGERATLSCSASSSVSSYIYWYQQKPGQAPRLLIYLTSNLASGIPARF SGSGSGTDFTLTISSLEPEDFAVYYCQQWSGNPYTFGQGTKLEIK (SEQ ID NO: 299)

Exemplary anti-human NKG2D scFv

Heavy chain:

QVQLVESGGGLVKPGGSLRLSCAASGFTFSSYGMHWVRQAPGKGLEWVAFIRYDGSN KYYADSVKGRFTISRDNSKNTLYLQMNSLRAEDTAVYYCAKDRGLGDGTYFDYWGQG TTVTVSS (SEQ ID NO: 300)

Light chain:

QSALTQPASVSGSPGQSITISCSGSSSNIGNNAVNWYQQLPGKAPKLLIYYDDLLPS GVSDRFSGSKSGTSAFLAISGLQSEDEADYYCAAWDDSLNGPVFGGGTKLTVL (SEQ ID NO: 301)

FIG. 14

Exemplary anti-human NKp30 scFv

Alternative heavy chains with underline indicating the differences:

QVQLVQSGAEVKKPGASVKVSCKASGHTFTSYFMHWVRQAPGQGLEWMGIINPSDDYANYAQKFQGRVTMTRDTSTSTVYMELSSLRSEDTAVYYCATAIFDYWGQGTLVTVSS (SEQ ID NO: 302)

or

QVQLVQSGAEVKKPGASVKVSCKASGHTFTSYFMHWVRQAPGQGLEWMGIINPSDDYANYAQKFQGRVTMTRDTSTSTVYMELSSLRSEDTAVYYCATAIFDYWGQGTPVTVSS (SEQ ID NO: 303)

Light chain:

DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGGGTKVEIK (SEQ ID NO: 304)

Exemplary anti-human NKp46 scFv

Heavy chain:

EIQLQQSGAELVKPGASVKLSCTASGFNIKDTYFHWVKQRPEQGLEWIGRIDPANGNTKYDPKFHDKATIIADISSNTAYLOFSSLTSEDTAVYYCAANRYGYWGQGTTLTVSS (SEQ ID NO: 305)

Light chain:

DIVMTOAAPSIPVTPGESVSISCRSSKSLLYINGNTHLFWFLORPGOSPOLLIYRMSNLASGVPDRFSGSGSGTAFTLRISRVEAEDVGVYYCMOHLEYPFTFGSGTKLEIK (SEQ ID NO: 306)

Exemplary anti-human NKp46 scFv

Heavy chain:

QVQLQQSGPELVKPGASVKMSCKASGYTFTDYVINWGKQRSGQGLEWIGEIYPGSGTNYYNEKFKAKATLTADKSSNIAYMQLSSLTSEDSAVYFCARRGRYGLYAMDYWGQGTSVTVSS (SEQ ID NO: 307)

Light chain:

DIQMTQTTSSLSASLGDRVTISCRASQDISNYLNWYQQKPDGTVKLLIYYTSRLHSGVPSRFSGSGSGTDYSLTINNLEQEDIATYFCQQGNTRPWTFGGGTKLEIK (SEQ ID NO: 308)

Exemplary anti-human CD16a VH domain

EVQLVESGGGLVQPGGSLRLSCAASGFTFSNYGMSWVRQAPGKGLEWIGSIYYSGSTNYNPSLKSLVTISRDNSKNTLYLQMNSLRAEDTATYYCARESIDYWGQGTLVTVSS (SEQ ID NO: 309)

FIG. 14 (continued)

Linker + gOKT3-7 (anti-CD3 scFv)

GGGGSGGGGSGGGGSQVQLVQSGGGVVQPGRSLRLSCKASGYTFTRYTMHWVRQAPG
KGLEWIGYINPSRGYTNYNQKVKDRFTISRDNSKNTAFLQMDSLRPEDTGVYFCARYY
DDHYCLDYWGQGTPVTVSSGGGGSGGGGSGGGGSGGGGSGGGGSGGGGSDIQMTQSP
SSLSASVGDRVTITCSASSSVSYMNWYQQTPGKAPKRWIYDTSKLASGVPSRFSGSGSG
TDYTFTISSLQPEDIATYYCQQWSSNPFTFGQGTKLQITR (SEQ ID NO:310)

GGAGGTGGCGGGTCTGGTGGAGGCGGAAGCGGTGGTGGCGGATCCCAGGTCCAACT
GGTGCAAAGTGGAGGCGGCGTAGTACAGCCCGGTCGGTCCCTGCGGCTCAGCTGTA
AAGCAAGTGGGTACACTTTCACCAGATATACAATGCACTGGGTTAGACAGGCCCCC
GGCAAGGGTCTTGAATGGATAGGATATATCAACCCATCCCGCGGATATACAAACTA
CAATCAGAAGGTGAAGGACCGGTTCACGATTAGTAGAGACAACTCCAAAAACACTG
CGTTCCTTCAAATGGACTCATTGCGACCCGAGGACACTGGAGTGTATTTCTGTGCCA
GGTATTATGACGACCATTATTGCCTGGACTACTGGGGGCAAGGCACACCGGTTACGG
TATCTTCCGGAGGTGGCGGGTCTGGTGGAGGCGGAAGCGGTGGTGGCGGATCCGGG
GGAGGAGGCTCTGGCGGAGGCGGATCAGGGGGTGGAGGTTCCGACATTCAAATGAC
ACAATCCCCTAGTTCTTTGTCTGCGTCCGTGGGGGATCGGGTAACAATCACTTGCTCT
GCATCAAGCAGTGTTTCTTATATGAACTGGTATCAGCAGACACCCGGTAAGGCCCCA
AAACGATGGATTTATGACACGAGTAAACTCGCATCCGGGGTGCCTTCACGCTTCTCC
GGTTCTGGTTCCGGCACGGATTACACTTTCACCATCAGTAGCCTGCAACCTGAGGAC
ATTGCAACTTATTACTGTCAACAATGGAGCAGTAATCCATTCACGTTCGGCCAAGGG
ACAAAACTGCAGATTACTAGG (SEQ ID NO:311)

FIG. 15B

SEQUENCE LISTING

```
<160> NUMBER OF SEQ ID NOS: 311

<210> SEQ ID NO 1
<211> LENGTH: 122
<212> TYPE: PRT
<213> ORGANISM: Artificial Sequence
<220> FEATURE:
<223> OTHER INFORMATION: E9 binder

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Thr Val Ser Gly Phe Thr Phe Ser Ser Tyr
            20                  25                  30

Ala Leu Gly Trp Val Arg Gln Ala Pro Gly Lys Gly Leu Glu Trp Ile
        35                  40                  45

Gly Tyr Ile Tyr His Lys Gly Asp Thr Asn Tyr Asn Pro Ser Leu Lys
    50                  55                  60
```

```
Ser Leu Val Thr Ile Ser Arg Asp Asn Ser Lys Asn Thr Leu Tyr Leu
65                  70                  75                  80

Gln Met Asn Ser Leu Arg Ala Glu Asp Thr Ala Leu Tyr Tyr Cys Ala
                85                  90                  95

Lys Val Arg Trp Val Ser Ser Thr Ser Thr Leu Gly Phe Asp Tyr Trp
            100                 105                 110

Gly Gln Gly Thr Leu Val Thr Val Ser Ser
        115                 120


<210> SEQ ID NO 2
<211> LENGTH: 121
<212> TYPE: PRT
<213> ORGANISM: Artificial Sequence
<220> FEATURE:
<223> OTHER INFORMATION: A4 binder

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ile Ser Tyr
            20                  25                  30

Ala Met Ser Trp Val Arg Gln Ala Pro Gly Lys Gly Leu Glu Trp Met
        35                  40                  45

Ala Ile Ile Tyr Pro Asp Asp Ala Gly Thr Met Tyr Ser Pro Ser Phe
    50                  55                  60

Gln Gly Gln Val Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Arg Val Thr Met Val Arg Gly Val Ile Gly Phe Asp Pro Trp Gly
            100                 105                 110

Gln Gly Thr Leu Val Thr Val Ser Ser
        115                 120


<210> SEQ ID NO 3
<211> LENGTH: 121
<212> TYPE: PRT
<213> ORGANISM: Artificial Sequence
<220> FEATURE:
<223> OTHER INFORMATION: E61 binder

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Thr Phe Ser Gly Phe Thr Phe Ser Ser Tyr
            20                  25                  30

Ala Met Ser Trp Val Arg Gln Ala Pro Gly Lys Gly Leu Glu Trp Met
        35                  40                  45

Gly Ile Ile Tyr Pro Gly Asp Ser Asn Thr Ile Tyr Ser Pro Ser Phe
    50                  55                  60

Gln Gly Gln Val Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Ser Gly Ala Tyr Asp Gly Arg Ile Trp Phe Asp Pro Trp Gly
            100                 105                 110

Gln Gly Thr Leu Val Thr Val Ser Ser
```

115 120

<210> SEQ ID NO 4
<211> LENGTH: 128
<212> TYPE: PRT
<213> ORGANISM: Artificial Sequence
<220> FEATURE:
<223> OTHER INFORMATION: A7 binder

<400> SEQUENCE: 4

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Gly Met Ser Trp Val Arg Gln Ala Pro Gly Lys Gly Leu Glu Trp Ile
35 40 45

Gly Tyr Ile Tyr His Thr Gly Asn Thr Tyr Tyr Asn Pro Ser Leu Lys
50 55 60

Ser Arg Val Thr Ile Ser Arg Asp Asn Ser Lys Asn Thr Leu Tyr Leu
65 70 75 80

Gln Met Asn Ser Leu Arg Ala Glu Asp Thr Ala Ile Tyr Tyr Cys Ala
85 90 95

Arg Glu Gly Val Met Gly Gly Tyr His Thr Asp Pro Asn Tyr Tyr Tyr
100 105 110

Tyr Gly Met Asp Val Trp Gly Gln Gly Thr Thr Val Thr Val Ser Ser
115 120 125

<210> SEQ ID NO 5
<211> LENGTH: 124
<212> TYPE: PRT
<213> ORGANISM: Artificial Sequence
<220> FEATURE:
<223> OTHER INFORMATION: D92 binder

<400> SEQUENCE: 5

Glu Val Gln Leu Val Glu Ser Gly Gly Gly Leu Val Gln Pro Gly Gly
1 5 10 15

Ser Leu Arg Leu Ser Cys Val Ala Ser Gly Phe Thr Phe Ser Ser Tyr
20 25 30

Gly Met His Trp Val Arg Gln Ala Pro Gly Lys Gly Leu Glu Trp Ile
35 40 45

Gly Tyr Ser Tyr Tyr Ser Gly Ser Thr Tyr Tyr Asn Pro Ser Leu Lys
50 55 60

Ser Leu Val Thr Ile Ser Arg Asp Asn Ser Lys Asn Thr Leu Tyr Leu
65 70 75 80

Gln Met Asn Ser Leu Arg Ala Glu Asp Thr Ala Thr Tyr Tyr Cys Ala
85 90 95

Arg Asp Gly Ser Ser Trp Tyr Ser Phe Pro Tyr Tyr Tyr Gly Met Asp
100 105 110

Val Trp Gly Gln Gly Thr Thr Val Thr Val Ser Ser
115 120

<210> SEQ ID NO 6
<211> LENGTH: 113
<212> TYPE: PRT
<213> ORGANISM: Artificial Sequence
<220> FEATURE:
<223> OTHER INFORMATION: D8 binder

<400> SEQUENCE: 6

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Gly Met Ser Trp Val Arg Gln Ala Pro Gly Lys Ala Leu Glu Trp Ile
35 40 45

Gly Glu Ile Asn His Ser Gly Ser Thr Asn Tyr Asn Pro Ser Leu Lys
50 55 60

Ser Arg Val Thr Ile Ser Arg Asp Asn Ser Lys Asn Thr Leu Tyr Leu
65 70 75 80

Gln Met Asn Ser Leu Arg Ala Glu Asp Thr Ala Ile Tyr Tyr Cys Arg
85 90 95

Gly Gly Trp Val Gly Tyr Trp Gly Gln Gly Thr Leu Val Thr Val Ser
100 105 110

Ser

<210> SEQ ID NO 7
<211> LENGTH: 128
<212> TYPE: PRT
<213> ORGANISM: Artificial Sequence
<220> FEATURE:
<223> OTHER INFORMATION: F11 binder

<400> SEQUENCE: 7

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Gly Met Ser Trp Val Arg Gln Ala Pro Gly Gln Gly Leu Glu Trp Val
35 40 45

Ser Tyr Ile Ser Asn Gly Gly Gly Thr Met Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Thr Tyr Tyr Cys
85 90 95

Thr Arg Ala Pro Tyr Cys Ser Gly Gly Asp Cys Tyr Pro Met Ser Thr
100 105 110

His Glu Leu Asp Ser Trp Gly Gln Gly Thr Leu Val Thr Val Ser Ser
115 120 125

<210> SEQ ID NO 8
<211> LENGTH: 116
<212> TYPE: PRT
<213> ORGANISM: Artificial Sequence
<220> FEATURE:
<223> OTHER INFORMATION: C52 binder

<400> SEQUENCE: 8

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Leu Ser Ser Tyr
20 25 30

Trp Met Ser Trp Val Arg Gln Ala Pro Gly Lys Gly Leu Glu Trp Ile
35 40 45

Gly Val Ile Tyr Tyr Ser Gly Ala Thr Tyr Tyr Asn Pro Ser Leu Lys
50 55 60

Ser Leu Val Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Gly Ala Leu Asp Tyr Phe Asp Leu Trp Gly Gln Gly Ala Leu Val
100 105 110

Thr Val Ser Ser
115

<210> SEQ ID NO 9
<211> LENGTH: 254
<212> TYPE: PRT
<213> ORGANISM: Artificial Sequence
<220> FEATURE:
<223> OTHER INFORMATION: H4-VLVH binder

<400> SEQUENCE: 9

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Val Gly Val Tyr Tyr Cys Leu Gln Ile Thr His Trp Pro His
85 90 95

Thr Phe Gly Gln Gly Thr Lys Leu Glu Ile Lys Arg Gly Gly Gly Gly
100 105 110

Ser Gly Gly Gly Gly Ser Gly Gly Gly Gly Ser Gln Val Gln Leu Val
115 120 125

Glu Ser Gly Gly Gly Leu Val Lys Pro Gly Gly Ser Leu Arg Leu Ser
130 135 140

Cys Ala Ala Ser Gly Phe Thr Phe Ser Asp Tyr Tyr Met Ser Trp Ile
145 150 155 160

Arg Gln Ala Pro Gly Lys Gly Leu Glu Trp Val Ser Tyr Ile Ser Ser
165 170 175

Ser Gly Ser Thr Ile Tyr Tyr Ala Asp Ser Val Lys Gly Arg Phe Thr
180 185 190

Ile Ser Arg Asp Asn Ala Lys Asn Ser Leu Tyr Leu Gln Met Asn Ser
195 200 205

Leu Arg Ala Glu Asp Thr Ala Met Tyr Tyr Cys Ala Arg Asp Ala Pro
210 215 220

Asp Leu Leu Ala Val Pro Thr Val Ile Phe Ser Gly Tyr His Tyr Gly
225 230 235 240

Ala Asp Val Trp Gly Gln Gly Ala Thr Val Thr Val Ser Ser
245 250

<210> SEQ ID NO 10
<211> LENGTH: 254
<212> TYPE: PRT
<213> ORGANISM: Artificial Sequence
<220> FEATURE:
<223> OTHER INFORMATION: H4-VHVL binder

<400> SEQUENCE: 10

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Met Tyr Tyr Cys
                85                  90                  95

Ala Arg Asp Ala Pro Asp Leu Leu Ala Val Pro Thr Val Ile Phe Ser
            100                 105                 110

Gly Tyr His Tyr Gly Ala Asp Val Trp Gly Gln Gly Ala Thr Val Thr
        115                 120                 125

Val Ser Ser Gly Gly Gly Gly Ser Gly Gly Gly Gly Ser Gly Gly Gly
    130                 135                 140

Gly Ser Asp Ile Gln Met Thr Gln Ser Pro Ser Ser Leu Ser Ala Ser
145                 150                 155                 160

Val Gly Asp Arg Val Thr Ile Thr Cys Arg Ala Ser Gln Ser Ile Ser
                165                 170                 175

Ser Tyr Leu Asn Trp Tyr Gln Gln Lys Pro Gly Lys Ala Pro Lys Leu
            180                 185                 190

Leu Ile Tyr Ala Ala Ser Ser Leu Gln Ser Gly Val Pro Ser Arg Phe
        195                 200                 205

Ser Gly Ser Gly Ser Gly Thr Asp Phe Thr Leu Thr Ile Ser Ser Leu
    210                 215                 220

Gln Pro Glu Asp Val Gly Val Tyr Tyr Cys Leu Gln Ile Thr His Trp
225                 230                 235                 240

Pro His Thr Phe Gly Gln Gly Thr Lys Leu Glu Ile Lys Arg
                245                 250

<210> SEQ ID NO 11
<211> LENGTH: 246
<212> TYPE: PRT
<213> ORGANISM: Artificial Sequence
<220> FEATURE:
<223> OTHER INFORMATION: G6-VLVH binder

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ala Ala Thr Tyr Tyr Cys Gln His Tyr Gly Thr Phe Gly Gln
                85                  90                  95

Gly Thr Lys Leu Glu Ile Lys Arg Gly Gly Gly Gly Ser Gly Gly Gly

```
            100                 105                 110

Gly Ser Gly Gly Gly Gly Ser Gln Val Gln Leu Val Glu Ser Gly Gly
        115                 120                 125

Gly Leu Val Lys Pro Gly Gly Ser Leu Arg Leu Ser Cys Ala Ala Ser
    130                 135                 140

Gly Phe Thr Phe Ser Asp Tyr Tyr Met Ser Trp Ile Arg Gln Ala Pro
145                 150                 155                 160

Gly Lys Gly Leu Glu Trp Val Ser Tyr Ile Ser Ser Ser Gly Ser Thr
                165                 170                 175

Ile Tyr Tyr Ala Asp Ser Val Lys Gly Arg Phe Thr Ile Ser Arg Asp
            180                 185                 190

Asn Ala Lys Asn Ser Leu Tyr Leu Gln Met Asn Ser Leu Arg Ala Glu
        195                 200                 205

Asp Thr Ala Val Tyr Tyr Cys Ala Arg His Lys Thr Ser Leu Asn Asp
    210                 215                 220

Tyr Asp Phe Trp Ser Gly Tyr Leu Leu Asp Tyr Trp Gly Gln Gly Thr
225                 230                 235                 240

Leu Val Thr Val Ser Ser
                245


<210> SEQ ID NO 12
<211> LENGTH: 246
<212> TYPE: PRT
<213> ORGANISM: Artificial Sequence
<220> FEATURE:
<223> OTHER INFORMATION: G6-VHVL binder

<400> SEQUENCE: 12

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Lys Thr Ser Leu Asn Asp Tyr Asp Phe Trp Ser Gly Tyr
            100                 105                 110

Leu Leu Asp Tyr Trp Gly Gln Gly Thr Leu Val Thr Val Ser Ser Gly
        115                 120                 125

Gly Gly Gly Ser Gly Gly Gly Gly Ser Gly Gly Gly Gly Ser Asp Ile
    130                 135                 140

Gln Met Thr Gln Ser Pro Ser Ser Leu Ser Ala Ser Val Gly Asp Arg
145                 150                 155                 160

Val Thr Ile Thr Cys Arg Ala Ser Gln Ser Ile Ser Ser Tyr Leu Asn
                165                 170                 175

Trp Tyr Gln Gln Lys Pro Gly Lys Ala Pro Lys Leu Leu Ile Tyr Ala
            180                 185                 190

Ala Ser Ser Leu Gln Ser Gly Val Pro Ser Arg Phe Ser Gly Ser Gly
        195                 200                 205

Ser Gly Thr Asp Phe Thr Leu Thr Ile Ser Ser Leu Gln Pro Glu Asp
```

```
    210                 215                 220

Ala Ala Thr Tyr Tyr Cys Gln His Tyr Gly Thr Phe Gly Gln Gly Thr
225                 230                 235                 240

Lys Leu Glu Ile Lys Arg
                245


<210> SEQ ID NO 13
<211> LENGTH: 248
<212> TYPE: PRT
<213> ORGANISM: Artificial Sequence
<220> FEATURE:
<223> OTHER INFORMATION: C9-VLVH binder

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Leu Glu Ile Lys Arg Gly Gly Gly Gly
            100                 105                 110

Ser Gly Gly Gly Gly Ser Gly Gly Gly Gly Ser Gln Val Gln Leu Val
        115                 120                 125

Glu Ser Gly Gly Gly Leu Val Lys Pro Gly Gly Ser Leu Arg Leu Ser
    130                 135                 140

Cys Ala Ala Ser Gly Phe Thr Phe Ser Asp Tyr Tyr Met Ser Trp Ile
145                 150                 155                 160

Arg Gln Ala Pro Gly Lys Gly Leu Glu Trp Val Ser Tyr Ile Ser Ser
                165                 170                 175

Ser Gly Ser Thr Ile Tyr Tyr Ala Asp Ser Val Lys Gly Arg Phe Thr
            180                 185                 190

Ile Ser Arg Asp Asn Ala Lys Asn Ser Leu Tyr Leu Gln Met Asn Ser
        195                 200                 205

Leu Arg Ala Glu Asp Thr Ala Lys Tyr Tyr Cys Ala Thr Ala Val Phe
    210                 215                 220

Ser Leu Gly Pro Glu Gly Tyr Tyr Tyr Tyr Met Asp Val Trp Gly Lys
225                 230                 235                 240

Gly Thr Thr Val Thr Val Ser Ser
                245


<210> SEQ ID NO 14
<211> LENGTH: 248
<212> TYPE: PRT
<213> ORGANISM: Artificial Sequence
<220> FEATURE:
<223> OTHER INFORMATION: C9-VHVL H binder

<400> SEQUENCE: 14

Gln Val Gln Leu Val Glu Ser Gly Gly Gly Leu Val Lys Pro Gly Gly
1               5                   10                  15
```

Ser Leu Arg Leu Ser Cys Ala Ala Ser Gly Phe Thr Phe Ser Asp Tyr
20 25 30

Tyr Met Ser Trp Ile Arg Gln Ala Pro Gly Lys Gly Leu Glu Trp Val
35 40 45

Ser Tyr Ile Ser Ser Ser Gly Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Lys Tyr Tyr Cys
85 90 95

Ala Thr Ala Val Phe Ser Leu Gly Pro Glu Gly Tyr Tyr Tyr Tyr Met
100 105 110

Asp Val Trp Gly Lys Gly Thr Thr Val Thr Val Ser Ser Gly Gly Gly
115 120 125

Gly Ser Gly Gly Gly Gly Ser Gly Gly Gly Gly Ser Asp Ile Gln Met
130 135 140

Thr Gln Ser Pro Ser Ser Leu Ser Ala Ser Val Gly Asp Arg Val Thr
145 150 155 160

Ile Thr Cys Arg Ala Ser Gln Ser Ile Ser Ser Tyr Leu Asn Trp Tyr
165 170 175

Gln Gln Lys Pro Gly Lys Ala Pro Lys Leu Leu Ile Tyr Ala Ala Ser
180 185 190

Ser Leu Gln Ser Gly Val Pro Ser Arg Phe Ser Gly Ser Gly Ser Gly
195 200 205

Thr Asp Phe Thr Leu Thr Ile Ser Ser Leu Gln Pro Glu Asp Phe Ala
210 215 220

Val Tyr Tyr Cys Gln Gln Arg Ser Asn Trp Pro Pro Thr Phe Gly Gln
225 230 235 240

Gly Thr Lys Leu Glu Ile Lys Arg
245

<210> SEQ ID NO 15
<211> LENGTH: 247
<212> TYPE: PRT
<213> ORGANISM: Artificial Sequence
<220> FEATURE:
<223> OTHER INFORMATION: D7-VLVH binder

<400> SEQUENCE: 15

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Ile Ala Ala Tyr Tyr Cys Gln His Tyr Gly Thr Phe Gly Gln
85 90 95

Gly Thr Lys Leu Glu Ile Lys Arg Gly Gly Gly Gly Ser Gly Gly Gly
100 105 110

Gly Ser Gly Gly Gly Gly Ser Gln Val Gln Leu Val Glu Ser Gly Gly
115 120 125

```
Gly Leu Val Lys Pro Gly Gly Ser Leu Arg Leu Ser Cys Ala Ala Ser
    130                 135                 140

Gly Phe Thr Phe Ser Asp Tyr Tyr Met Ser Trp Ile Arg Gln Ala Pro
145                 150                 155                 160

Gly Lys Gly Leu Glu Trp Val Ser Tyr Ile Ser Ser Ser Gly Ser Thr
                165                 170                 175

Ile Tyr Tyr Ala Asp Ser Val Lys Gly Arg Phe Thr Ile Ser Arg Asp
            180                 185                 190

Asn Ala Lys Asn Ser Leu Tyr Leu Gln Met Asn Ser Leu Arg Ala Glu
        195                 200                 205

Asp Thr Ala Val Tyr Tyr Cys Ala Arg Asp Gly Tyr Pro Leu Gly Gly
    210                 215                 220

Gly Tyr Asp Phe Trp Ser Gly Tyr Tyr Pro Asp Tyr Trp Gly Gln Gly
225                 230                 235                 240

Thr Leu Val Thr Val Ser Ser
                245


<210> SEQ ID NO 16
<211> LENGTH: 247
<212> TYPE: PRT
<213> ORGANISM: Artificial Sequence
<220> FEATURE:
<223> OTHER INFORMATION: D7-VHVL binder

<400> SEQUENCE: 16

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Tyr Pro Leu Gly Gly Gly Tyr Asp Phe Trp Ser Gly
            100                 105                 110

Tyr Tyr Pro Asp Tyr Trp Gly Gln Gly Thr Leu Val Thr Val Ser Ser
        115                 120                 125

Gly Gly Gly Gly Ser Gly Gly Gly Gly Ser Gly Gly Gly Gly Ser Asp
    130                 135                 140

Ile Gln Met Thr Gln Ser Pro Ser Ser Leu Ser Ala Ser Val Gly Asp
145                 150                 155                 160

Arg Val Thr Ile Thr Cys Arg Ala Ser Gln Ser Ile Ser Ser Tyr Leu
                165                 170                 175

Asn Trp Tyr Gln Gln Lys Pro Gly Lys Ala Pro Lys Leu Leu Ile Tyr
            180                 185                 190

Ala Ala Ser Ser Leu Gln Ser Gly Val Pro Ser Arg Phe Ser Gly Ser
        195                 200                 205

Gly Ser Gly Thr Asp Phe Thr Leu Thr Ile Ser Ser Leu Gln Pro Glu
    210                 215                 220

Asp Ile Ala Ala Tyr Tyr Cys Gln His Tyr Gly Thr Phe Gly Gln Gly
225                 230                 235                 240
```

Thr Lys Leu Glu Ile Lys Arg
245

<210> SEQ ID NO 17
<211> LENGTH: 246
<212> TYPE: PRT
<213> ORGANISM: Artificial Sequence
<220> FEATURE:
<223> OTHER INFORMATION: B7-VLVH binder

<400> SEQUENCE: 17

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Val Tyr Tyr Cys Gln His Tyr Gly Thr Phe Gly Gln
85 90 95

Gly Thr Lys Val Glu Ile Lys Arg Gly Gly Gly Gly Ser Gly Gly Gly
100 105 110

Gly Ser Gly Gly Gly Gly Ser Gln Val Gln Leu Val Glu Ser Gly Gly
115 120 125

Gly Leu Val Lys Pro Gly Gly Ser Leu Arg Leu Ser Cys Ala Ala Ser
130 135 140

Gly Phe Thr Phe Ser Asp Tyr Tyr Met Ser Trp Ile Arg Gln Ala Pro
145 150 155 160

Gly Lys Gly Leu Glu Trp Val Ser Tyr Ile Ser Ser Ser Gly Ser Thr
165 170 175

Ile Tyr Tyr Ala Asp Ser Val Lys Gly Arg Phe Thr Ile Ser Arg Asp
180 185 190

Asn Ala Lys Asn Ser Leu Tyr Leu Gln Met Asn Ser Leu Arg Ala Glu
195 200 205

Asp Thr Ala Met Tyr Tyr Cys Ala Arg His Lys Thr Ser Leu Asn Asp
210 215 220

Tyr Asp Phe Trp Ser Gly Tyr Leu Leu Asp Tyr Trp Gly Gln Gly Thr
225 230 235 240

Leu Val Thr Val Ser Ser
245

<210> SEQ ID NO 18
<211> LENGTH: 246
<212> TYPE: PRT
<213> ORGANISM: Artificial Sequence
<220> FEATURE:
<223> OTHER INFORMATION: B7-VHVL binder

<400> SEQUENCE: 18

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp Tyr
20 25 30

Tyr Met Ser Trp Ile Arg Gln Ala Pro Gly Lys Gly Leu Glu Trp Val
35 40 45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Met Tyr Tyr Cys
                85                  90                  95

Ala Arg His Lys Thr Ser Leu Asn Asp Tyr Asp Phe Trp Ser Gly Tyr
            100                 105                 110

Leu Leu Asp Tyr Trp Gly Gln Gly Thr Leu Val Thr Val Ser Ser Gly
        115                 120                 125

Gly Gly Gly Ser Gly Gly Gly Gly Ser Gly Gly Gly Gly Ser Asp Ile
    130                 135                 140

Gln Met Thr Gln Ser Pro Ser Ser Leu Ser Ala Ser Val Gly Asp Arg
145                 150                 155                 160

Val Thr Ile Thr Cys Arg Ala Ser Gln Ser Ile Ser Ser Tyr Leu Asn
                165                 170                 175

Trp Tyr Gln Gln Lys Pro Gly Lys Ala Pro Lys Leu Leu Ile Tyr Ala
            180                 185                 190

Ala Ser Ser Leu Gln Ser Gly Val Pro Ser Arg Phe Ser Gly Ser Gly
        195                 200                 205

Ser Gly Thr Asp Phe Thr Leu Thr Ile Ser Ser Leu Gln Pro Glu Asp
    210                 215                 220

Phe Ala Val Tyr Tyr Cys Gln His Tyr Gly Thr Phe Gly Gln Gly Thr
225                 230                 235                 240

Lys Val Glu Ile Lys Arg
                245

<210> SEQ ID NO 19
<211> LENGTH: 246
<212> TYPE: PRT
<213> ORGANISM: Artificial Sequence
<220> FEATURE:
<223> OTHER INFORMATION: A6-VLVH binder

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ala Ala Thr Tyr Tyr Cys Gln Arg Tyr Gly Thr Phe Gly Gln
                85                  90                  95

Gly Thr Lys Val Asp Ile Lys Arg Gly Gly Gly Gly Ser Gly Gly Gly
            100                 105                 110

Gly Ser Gly Gly Gly Gly Ser Gln Val Gln Leu Val Glu Ser Gly Gly
        115                 120                 125

Gly Leu Val Lys Pro Gly Gly Ser Leu Arg Leu Ser Cys Ala Ala Ser
    130                 135                 140

Gly Phe Thr Phe Ser Asp Tyr Tyr Met Ser Trp Ile Arg Gln Ala Pro
145                 150                 155                 160

Gly Lys Gly Leu Glu Trp Val Ser Tyr Ile Ser Ser Ser Gly Ser Thr
165 170 175

Ile Tyr Tyr Ala Asp Ser Val Lys Gly Arg Phe Thr Ile Ser Arg Asp
180 185 190

Asn Ala Lys Asn Ser Leu Tyr Leu Gln Met Asn Ser Leu Arg Ala Glu
195 200 205

Asp Thr Ala Val Tyr Tyr Cys Ala Arg His Lys Thr Ser Leu Asn Asp
210 215 220

Tyr Asp Phe Trp Ser Gly Tyr Leu Leu Asp Tyr Trp Gly Gln Gly Thr
225 230 235 240

Leu Val Thr Val Ser Ser
245

<210> SEQ ID NO 20
<211> LENGTH: 246
<212> TYPE: PRT
<213> ORGANISM: Artificial Sequence
<220> FEATURE:
<223> OTHER INFORMATION: A6-VHVL binder

<400> SEQUENCE: 20

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp Tyr
20 25 30

Tyr Met Ser Trp Ile Arg Gln Ala Pro Gly Lys Gly Leu Glu Trp Val
35 40 45

Ser Tyr Ile Ser Ser Ser Gly Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg His Lys Thr Ser Leu Asn Asp Tyr Asp Phe Trp Ser Gly Tyr
100 105 110

Leu Leu Asp Tyr Trp Gly Gln Gly Thr Leu Val Thr Val Ser Ser Gly
115 120 125

Gly Gly Gly Ser Gly Gly Gly Gly Ser Gly Gly Gly Gly Ser Asp Ile
130 135 140

Gln Met Thr Gln Ser Pro Ser Ser Leu Ser Ala Ser Val Gly Asp Arg
145 150 155 160

Val Thr Ile Thr Cys Arg Ala Ser Gln Ser Ile Ser Ser Tyr Leu Asn
165 170 175

Trp Tyr Gln Gln Lys Pro Gly Lys Ala Pro Lys Leu Leu Ile Tyr Ala
180 185 190

Ala Ser Ser Leu Gln Ser Gly Val Pro Ser Arg Phe Ser Gly Ser Gly
195 200 205

Ser Gly Thr Asp Phe Thr Leu Thr Ile Ser Ser Leu Gln Pro Glu Asp
210 215 220

Ala Ala Thr Tyr Tyr Cys Gln Arg Tyr Gly Thr Phe Gly Gln Gly Thr
225 230 235 240

Lys Val Asp Ile Lys Arg
245

<210> SEQ ID NO 21

<211> LENGTH: 245
<212> TYPE: PRT
<213> ORGANISM: Artificial Sequence
<220> FEATURE:
<223> OTHER INFORMATION: C1-VLVH binder

<400> SEQUENCE: 21

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ala Ala Thr Tyr Tyr Cys Gln His Tyr Gly Thr Phe Gly Gln
                85                  90                  95

Gly Thr Lys Val Glu Ile Lys Arg Gly Gly Gly Gly Ser Gly Gly Gly
            100                 105                 110

Gly Ser Gly Gly Gly Gly Ser Gln Val Gln Leu Val Glu Ser Gly Gly
        115                 120                 125

Gly Leu Val Lys Pro Gly Gly Ser Leu Arg Leu Ser Cys Ala Ala Ser
    130                 135                 140

Gly Phe Thr Phe Ser Asp Tyr Tyr Met Ser Trp Ile Arg Gln Ala Pro
145                 150                 155                 160

Gly Lys Gly Leu Glu Trp Val Ser Tyr Ile Ser Ser Ser Gly Ser Thr
                165                 170                 175

Ile Tyr Tyr Ala Asp Ser Val Lys Gly Arg Phe Thr Ile Ser Arg Asp
            180                 185                 190

Asn Ala Lys Asn Ser Leu Tyr Leu Gln Met Asn Ser Leu Arg Ala Glu
        195                 200                 205

Asp Thr Ala Val Tyr Tyr Cys Ala Arg His Ala Pro His Lys His Tyr
    210                 215                 220

Asp Phe Trp Ser Gly Tyr Tyr Pro Asp Tyr Trp Gly Gln Gly Thr Leu
225                 230                 235                 240

Val Thr Val Ser Ser
                245
```

<210> SEQ ID NO 22
<211> LENGTH: 245
<212> TYPE: PRT
<213> ORGANISM: Artificial Sequence
<220> FEATURE:
<223> OTHER INFORMATION: C1-VHVL binder

<400> SEQUENCE: 22

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
```

```
65                  70                  75                  80

Leu Gln Met Asn Ser Leu Arg Ala Glu Asp Thr Ala Val Tyr Tyr Cys
                85                  90                  95

Ala Arg His Ala Pro His Lys His Tyr Asp Phe Trp Ser Gly Tyr Tyr
            100                 105                 110

Pro Asp Tyr Trp Gly Gln Gly Thr Leu Val Thr Val Ser Ser Gly Gly
        115                 120                 125

Gly Gly Ser Gly Gly Gly Gly Ser Gly Gly Gly Gly Ser Asp Ile Gln
    130                 135                 140

Met Thr Gln Ser Pro Ser Ser Leu Ser Ala Ser Val Gly Asp Arg Val
145                 150                 155                 160

Thr Ile Thr Cys Arg Ala Ser Gln Ser Ile Ser Ser Tyr Leu Asn Trp
                165                 170                 175

Tyr Gln Gln Lys Pro Gly Lys Ala Pro Lys Leu Leu Ile Tyr Ala Ala
            180                 185                 190

Ser Ser Leu Gln Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Ala
    210                 215                 220

Ala Thr Tyr Tyr Cys Gln His Tyr Gly Thr Phe Gly Gln Gly Thr Lys
225                 230                 235                 240

Val Glu Ile Lys Arg
                245


<210> SEQ ID NO 23
<211> LENGTH: 22
<212> TYPE: PRT
<213> ORGANISM: Artificial Sequence
<220> FEATURE:
<223> OTHER INFORMATION: Leader peptide

<400> SEQUENCE: 23

Met Leu Leu Leu Val Thr Ser Leu Leu Leu Cys Glu Leu Pro His Pro
1               5                   10                  15

Ala Phe Leu Leu Ile Pro
            20


<210> SEQ ID NO 24
<211> LENGTH: 69
<212> TYPE: PRT
<213> ORGANISM: Artificial Sequence
<220> FEATURE:
<223> OTHER INFORMATION: CD8 linker and transmembrane domains

<400> SEQUENCE: 24

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65


<210> SEQ ID NO 25
<211> LENGTH: 207
```

<212> TYPE: DNA
<213> ORGANISM: Artificial Sequence
<220> FEATURE:
<223> OTHER INFORMATION: CD8 linker and transmembrane domains

<400> SEQUENCE: 25
accactactc cggcacctag gccccccact ccggcaccga ccattgcatc acaaccactg 60
agtcttagac ctgaagcctg tcgacccgca gctgggggg cagtccacac acggggattg 120
gatttcgcct gcgatatata catttgggcg ccactggcag gcacctgcgg ggtcctgctc 180
ttgtcccttg tcatcaccct gtactgt 207

<210> SEQ ID NO 26
<211> LENGTH: 28
<212> TYPE: PRT
<213> ORGANISM: Artificial Sequence
<220> FEATURE:
<223> OTHER INFORMATION: CD28tm

<400> SEQUENCE: 26

Met Phe Trp Val Leu Val Val Val Gly Gly Val Leu Ala Cys Tyr Ser
1 5 10 15

Leu Leu Val Thr Val Ala Phe Ile Ile Phe Trp Val
20 25

<210> SEQ ID NO 27
<211> LENGTH: 84
<212> TYPE: DNA
<213> ORGANISM: Artificial Sequence
<220> FEATURE:
<223> OTHER INFORMATION: CD28tm

<400> SEQUENCE: 27
atgttctggg tgctggtggt ggtcggaggc gtgctggcct gctacagcct gctggtcacc 60
gtggccttca tcatcttttg ggtg 84

<210> SEQ ID NO 28
<211> LENGTH: 41
<212> TYPE: PRT
<213> ORGANISM: Artificial Sequence
<220> FEATURE:
<223> OTHER INFORMATION: CD28 cytoplasmic

<400> SEQUENCE: 28

Arg Ser Lys Arg Ser Arg Leu Leu His Ser Asp Tyr Met Asn Met Thr
1 5 10 15

Pro Arg Arg Pro Gly Pro Thr Arg Lys His Tyr Gln Pro Tyr Ala Pro
20 25 30

Pro Arg Asp Phe Ala Ala Tyr Arg Ser
35 40

<210> SEQ ID NO 29
<211> LENGTH: 42
<212> TYPE: PRT
<213> ORGANISM: Artificial Sequence
<220> FEATURE:
<223> OTHER INFORMATION: 4-1BB signaling domain

<400> SEQUENCE: 29

Lys Arg Gly Arg Lys Lys Leu Leu Tyr Ile Phe Lys Gln Pro Phe Met
1 5 10 15

Arg Pro Val Gln Thr Thr Gln Glu Glu Asp Gly Cys Ser Cys Arg Phe
20 25 30

```
Pro Glu Glu Glu Glu Gly Gly Cys Glu Leu
        35                  40


<210> SEQ ID NO 30
<211> LENGTH: 126
<212> TYPE: DNA
<213> ORGANISM: Artificial Sequence
<220> FEATURE:
<223> OTHER INFORMATION: 4-1BB signaling domain

<400> SEQUENCE: 30

aagagaggaa gaaagaagtt gttgtatatt ttcaaacagc cattcatgag gccggtccag     60

accactcagg aggaggatgg atgcagttgc cgctttccgg aagaggaaga gggtgggtgt    120

gaactc                                                               126


<210> SEQ ID NO 31
<211> LENGTH: 112
<212> TYPE: PRT
<213> ORGANISM: Artificial Sequence
<220> FEATURE:
<223> OTHER INFORMATION: CD3-zeta chain signaling domain

<400> SEQUENCE: 31

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 32
<211> LENGTH: 336
<212> TYPE: DNA
<213> ORGANISM: Artificial Sequence
<220> FEATURE:
<223> OTHER INFORMATION: CD3-zeta chain signaling domain

<400> SEQUENCE: 32

cgagttaaat tttctcgcag tgctgatgcc ccagcgtata aacagggtca gaaccaactg     60

tataatgaac tcaatttggg gaggcgagag gagtatgatg tattggacaa gcggcggggg    120

cgggatcctg aaatgggcgg taagccaagg cgcaagaatc cacaggaggg tttgtataat    180

gagttgcaga aggataaaat ggcggaagcg tattcagaaa tcggaatgaa gggagagcgc    240

cgcagaggga aagggcatga tggcctctac caaggtttgt caacagcgac caaggatacc    300

tatgacgcac ttcatatgca agcactgccc cccagg                              336


<210> SEQ ID NO 33
<211> LENGTH: 72
<212> TYPE: DNA
<213> ORGANISM: Artificial Sequence
<220> FEATURE:
```

<223> OTHER INFORMATION: T2A

<400> SEQUENCE: 33
ctcgagggcg gcggagaggg cagaggaagt cttctaacat gcggtgacgt ggaggagaat 60
cccggcccta gg 72

<210> SEQ ID NO 34
<211> LENGTH: 1005
<212> TYPE: DNA
<213> ORGANISM: Artificial Sequence
<220> FEATURE:
<223> OTHER INFORMATION: EGFRt

<400> SEQUENCE: 34
cgcaaagtgt gtaacggaat aggtattggt gaatttaaag actcactctc cataaatgct 60
acgaatatta aacacttcaa aaactgcacc tccatcagtg gcgatctcca catcctgccg 120
gtggcattta ggggtgactc cttcacacat actcctcctc tggatccaca ggaactggat 180
attctgaaaa ccgtaaagga aatcacaggg tttttgctga ttcaggcttg gcctgaaaac 240
aggacggacc tccatgcctt tgagaaccta gaaatcatac gcggcaggac caagcaacat 300
ggtcagtttt ctcttgcagt cgtcagcctg aacataacat ccttgggatt acgctccctc 360
aaggagataa gtgatggaga tgtgataatt tcaggaaaca aaaatttgtg ctatgcaaat 420
acaataaact ggaaaaaact gtttgggacc tccggtcaga aaaccaaaat tataagcaac 480
agaggtgaaa acagctgcaa ggccacaggc caggtctgcc atgccttgtg ctcccccgag 540
ggctgctggg gcccggagcc cagggactgc gtctcttgcc ggaatgtcag ccgaggcagg 600
gaatgcgtgg acaagtgcaa ccttctggag ggtgagccaa gggagtttgt ggagaactct 660
gagtgcatac agtgccaccc agagtgcctg cctcaggcca tgaacatcac ctgcacagga 720
cggggaccag acaactgtat ccagtgtgcc cactacattg acggccccca ctgcgtcaag 780
acctgcccgg caggagtcat gggagaaaac aacaccctgg tctggaagta cgcagacgcc 840
ggccatgtgt gccacctgtg ccatccaaac tgcacctacg gatgcactgg gccaggtctt 900
gaaggctgtc caacgaatgg gcctaagatc ccgtccatcg ccactgggat ggtgggggcc 960
ctcctcttgc tgctggtggt ggccctgggg atcggcctct tcatg 1005

<210> SEQ ID NO 35
<211> LENGTH: 12
<212> TYPE: PRT
<213> ORGANISM: Artificial Sequence
<220> FEATURE:
<223> OTHER INFORMATION: S (small) spacer

<400> SEQUENCE: 35

Glu Ser Lys Tyr Gly Pro Pro Cys Pro Pro Cys Pro
1 5 10

<210> SEQ ID NO 36
<211> LENGTH: 36
<212> TYPE: PRT
<213> ORGANISM: Artificial Sequence
<220> FEATURE:
<223> OTHER INFORMATION: S (small) spacer

<400> SEQUENCE: 36

Gly Ala Ala Thr Cys Thr Ala Ala Gly Thr Ala Cys Gly Gly Ala Cys
1 5 10 15

Cys Gly Cys Cys Cys Thr Gly Cys Cys Cys Cys Cys Cys Thr Thr Gly

```
            20                  25                  30

Cys Cys Cys Thr
        35


<210> SEQ ID NO 37
<211> LENGTH: 119
<212> TYPE: PRT
<213> ORGANISM: Artificial Sequence
<220> FEATURE:
<223> OTHER INFORMATION: M (medium) spacer

<400> SEQUENCE: 37

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115


<210> SEQ ID NO 38
<211> LENGTH: 357
<212> TYPE: DNA
<213> ORGANISM: Artificial Sequence
<220> FEATURE:
<223> OTHER INFORMATION: M (medium) spacer

<400> SEQUENCE: 38

gaatctaagt acggaccgcc ctgcccccct tgccctggcc agcctagaga accccaggtg      60

tacaccctgc ctcccagcca ggaagagatg accaagaacc aggtgtccct gacctgcctg     120

gtcaaaggct tctaccccag cgatatcgcc gtggaatggg agagcaacgg ccagcccgag     180

aacaactaca agaccacccc ccctgtgctg gacagcgacg gcagcttctt cctgtactcc     240

cggctgaccg tggacaagag ccggtggcag gaaggcaacg tcttcagctg cagcgtgatg     300

cacgaggccc tgcacaacca ctacacccag aagtccctga gcctgagcct gggcaag        357


<210> SEQ ID NO 39
<211> LENGTH: 229
<212> TYPE: PRT
<213> ORGANISM: Artificial Sequence
<220> FEATURE:
<223> OTHER INFORMATION: L (long) spacer

<400> SEQUENCE: 39

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45
```

```
Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

<210> SEQ ID NO 40
<211> LENGTH: 687
<212> TYPE: DNA
<213> ORGANISM: Artificial Sequence
<220> FEATURE:
<223> OTHER INFORMATION: L (long) spacer

<400> SEQUENCE: 40

```
gaatctaagt acggaccgcc ctgcccccct tgccctgccc ccgagttcga cggcggaccc      60

agcgtgttcc tgttcccccc caagcccaag gacaccctga tgatcagccg gacccccgag     120

gtgacctgcg tggtggtgga cgtgagccag gaagatcccg aggtccagtt caattggtac     180

gtggacggcg tggaagtgca caacgccaag accaagccca gagaggaaca gttccagagc     240

acctaccggg tggtgtctgt gctgaccgtg ctgcaccagg actggctgaa cggcaaagaa     300

tacaagtgca aggtgtccaa caagggcctg cccagcagca tcgaaaagac catcagcaag     360

gccaagggcc agcctcgcga gccccaggtg tacaccctgc ctccctccca ggaagagatg     420

accaagaacc aggtgtccct gacctgcctg gtgaagggct tctaccccag cgacatcgcc     480

gtggagtggg agagcaacgg ccagcctgag aacaactaca agaccacccc tcccgtgctg     540

gacagcgacg gcagcttctt cctgtacagc cggctgaccg tggacaagag ccggtggcag     600

gaaggcaacg tctttagctg cagcgtgatg cacgaggccc tgcacaacca ctacacccag     660

aagagcctga gcctgtccct gggcaag                                         687
```

<210> SEQ ID NO 41
<211> LENGTH: 361
<212> TYPE: PRT
<213> ORGANISM: Artificial Sequence
<220> FEATURE:
<223> OTHER INFORMATION: RJ146 CAR (D8/CD8 TM/4-1BB/CD3zeta)

<400> SEQUENCE: 41

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Asn Tyr Gly Met Ser Trp Val Arg Gln Ala Pro Gly
    50                  55                  60

Lys Ala Leu Glu Trp Ile Gly Glu Ile Asn His Ser Gly Ser Thr Asn
65                  70                  75                  80

Tyr Asn Pro Ser Leu Lys Ser Arg Val Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Ile Tyr Tyr Cys Arg Gly Gly Trp Val Gly Tyr Trp Gly Gln Gly
        115                 120                 125

Thr Leu Val Thr Val Ser Ser Ala Ala Ala Thr Thr Thr Pro Ala Pro
    130                 135                 140

Arg Pro Pro Thr Pro Ala Pro Thr Ile Ala Ser Gln Pro Leu Ser Leu
145                 150                 155                 160

Arg Pro Glu Ala Cys Arg Pro Ala Ala Gly Gly Ala Val His Thr Arg
                165                 170                 175

Gly Leu Asp Phe Ala Cys Asp Ile Tyr Ile Trp Ala Pro Leu Ala Gly
            180                 185                 190

Thr Cys Gly Val Leu Leu Leu Ser Leu Val Ile Thr Leu Tyr Cys Lys
        195                 200                 205

Arg Gly Arg Lys Lys Leu Leu Tyr Ile Phe Lys Gln Pro Phe Met Arg
    210                 215                 220

Pro Val Gln Thr Thr Gln Glu Glu Asp Gly Cys Ser Cys Arg Phe Pro
225                 230                 235                 240

Glu Glu Glu Glu Gly Gly Cys Glu Leu Arg Val Lys Phe Ser Arg Ser
                245                 250                 255

Ala Asp Ala Pro Ala Tyr Lys Gln Gly Gln Asn Gln Leu Tyr Asn Glu
            260                 265                 270

Leu Asn Leu Gly Arg Arg Glu Glu Tyr Asp Val Leu Asp Lys Arg Arg
        275                 280                 285

Gly Arg Asp Pro Glu Met Gly Gly Lys Pro Arg Arg Lys Asn Pro Gln
    290                 295                 300

Glu Gly Leu Tyr Asn Glu Leu Gln Lys Asp Lys Met Ala Glu Ala Tyr
305                 310                 315                 320

Ser Glu Ile Gly Met Lys Gly Glu Arg Arg Arg Gly Lys Gly His Asp
                325                 330                 335

Gly Leu Tyr Gln Gly Leu Ser Thr Ala Thr Lys Asp Thr Tyr Asp Ala
            340                 345                 350

Leu His Met Gln Ala Leu Pro Pro Arg
        355                 360
```

<210> SEQ ID NO 42
<211> LENGTH: 5
<212> TYPE: PRT
<213> ORGANISM: Artificial Sequence
<220> FEATURE:
<223> OTHER INFORMATION: E9 binder

<400> SEQUENCE: 42

Ser Tyr Ala Leu Gly
1 5

<210> SEQ ID NO 43
<211> LENGTH: 16
<212> TYPE: PRT
<213> ORGANISM: Artificial Sequence
<220> FEATURE:
<223> OTHER INFORMATION: E9 binder

<400> SEQUENCE: 43

Tyr Ile Tyr His Lys Gly Asp Thr Asn Tyr Asn Pro Ser Leu Lys Ser
1 5 10 15

<210> SEQ ID NO 44
<211> LENGTH: 14
<212> TYPE: PRT
<213> ORGANISM: Artificial Sequence
<220> FEATURE:
<223> OTHER INFORMATION: E9 binder

<400> SEQUENCE: 44

Val Arg Trp Val Ser Ser Thr Ser Thr Leu Gly Phe Asp Tyr
1 5 10

<210> SEQ ID NO 45
<211> LENGTH: 5
<212> TYPE: PRT
<213> ORGANISM: Artificial Sequence
<220> FEATURE:
<223> OTHER INFORMATION: A4 binder

<400> SEQUENCE: 45

Ser Tyr Ala Met Ser
1 5

<210> SEQ ID NO 46
<211> LENGTH: 17
<212> TYPE: PRT
<213> ORGANISM: Artificial Sequence
<220> FEATURE:
<223> OTHER INFORMATION: A4 binder

<400> SEQUENCE: 46

Ile Ile Tyr Pro Asp Asp Ala Gly Thr Met Tyr Ser Pro Ser Phe Gln
1 5 10 15

Gly

<210> SEQ ID NO 47
<211> LENGTH: 12
<212> TYPE: PRT
<213> ORGANISM: Artificial Sequence
<220> FEATURE:
<223> OTHER INFORMATION: A4 binder

<400> SEQUENCE: 47

Val Thr Met Val Arg Gly Val Ile Gly Phe Asp Pro
1 5 10

<210> SEQ ID NO 48
<211> LENGTH: 5
<212> TYPE: PRT
<213> ORGANISM: Artificial Sequence
<220> FEATURE:
<223> OTHER INFORMATION: E61 binder

<400> SEQUENCE: 48

Ser Tyr Ala Met Ser
1 5

<210> SEQ ID NO 49
<211> LENGTH: 19
<212> TYPE: PRT
<213> ORGANISM: Artificial Sequence
<220> FEATURE:
<223> OTHER INFORMATION: E61 binder

<400> SEQUENCE: 49

Met Gly Ile Ile Tyr Pro Gly Asp Ser Asn Thr Ile Tyr Ser Pro Ser
1 5 10 15

Phe Gln Gly

<210> SEQ ID NO 50
<211> LENGTH: 12
<212> TYPE: PRT
<213> ORGANISM: Artificial Sequence
<220> FEATURE:
<223> OTHER INFORMATION: E61 binder

<400> SEQUENCE: 50

Ser Gly Ala Tyr Asp Gly Arg Ile Trp Phe Asp Pro
1 5 10

<210> SEQ ID NO 51
<211> LENGTH: 5
<212> TYPE: PRT
<213> ORGANISM: Artificial Sequence
<220> FEATURE:
<223> OTHER INFORMATION: A7 binder

<400> SEQUENCE: 51

Asn Tyr Gly Met Ser
1 5

<210> SEQ ID NO 52
<211> LENGTH: 16
<212> TYPE: PRT
<213> ORGANISM: Artificial Sequence
<220> FEATURE:
<223> OTHER INFORMATION: A7 binder

<400> SEQUENCE: 52

Tyr Ile Tyr His Thr Gly Asn Thr Tyr Tyr Asn Pro Ser Leu Lys Ser
1 5 10 15

<210> SEQ ID NO 53
<211> LENGTH: 20
<212> TYPE: PRT
<213> ORGANISM: Artificial Sequence
<220> FEATURE:
<223> OTHER INFORMATION: A7 binder

<400> SEQUENCE: 53

Glu Gly Val Met Gly Gly Tyr His Thr Asp Pro Asn Tyr Tyr Tyr Tyr
1 5 10 15

Gly Met Asp Val
20

<210> SEQ ID NO 54
<211> LENGTH: 5

<212> TYPE: PRT
<213> ORGANISM: Artificial Sequence
<220> FEATURE:
<223> OTHER INFORMATION: D92 binder

<400> SEQUENCE: 54

Ser Tyr Gly Met His
1 5

<210> SEQ ID NO 55
<211> LENGTH: 16
<212> TYPE: PRT
<213> ORGANISM: Artificial Sequence
<220> FEATURE:
<223> OTHER INFORMATION: D92 binder

<400> SEQUENCE: 55

Tyr Ser Tyr Tyr Ser Gly Ser Thr Tyr Tyr Asn Pro Ser Leu Lys Ser
1 5 10 15

<210> SEQ ID NO 56
<211> LENGTH: 16
<212> TYPE: PRT
<213> ORGANISM: Artificial Sequence
<220> FEATURE:
<223> OTHER INFORMATION: D92 binder

<400> SEQUENCE: 56

Asp Gly Ser Ser Trp Tyr Ser Phe Pro Tyr Tyr Tyr Gly Met Asp Val
1 5 10 15

<210> SEQ ID NO 57
<211> LENGTH: 5
<212> TYPE: PRT
<213> ORGANISM: Artificial Sequence
<220> FEATURE:
<223> OTHER INFORMATION: D8 binder

<400> SEQUENCE: 57

Asn Tyr Gly Met Ser
1 5

<210> SEQ ID NO 58
<211> LENGTH: 16
<212> TYPE: PRT
<213> ORGANISM: Artificial Sequence
<220> FEATURE:
<223> OTHER INFORMATION: D8 binder

<400> SEQUENCE: 58

Glu Ile Asn His Ser Gly Ser Thr Asn Tyr Asn Pro Ser Leu Lys Ser
1 5 10 15

<210> SEQ ID NO 59
<211> LENGTH: 7
<212> TYPE: PRT
<213> ORGANISM: Artificial Sequence
<220> FEATURE:
<223> OTHER INFORMATION: D8 binder

<400> SEQUENCE: 59

Arg Gly Gly Trp Val Gly Tyr
1 5

<210> SEQ ID NO 60
<211> LENGTH: 5
<212> TYPE: PRT

<213> ORGANISM: Artificial Sequence
<220> FEATURE:
<223> OTHER INFORMATION: F11 binder

<400> SEQUENCE: 60

Asn Tyr Gly Met Ser
1 5

<210> SEQ ID NO 61
<211> LENGTH: 17
<212> TYPE: PRT
<213> ORGANISM: Artificial Sequence
<220> FEATURE:
<223> OTHER INFORMATION: F11 binder

<400> SEQUENCE: 61

Tyr Ile Ser Asn Gly Gly Gly Thr Met Tyr Tyr Ala Asp Ser Val Lys
1 5 10 15

Gly

<210> SEQ ID NO 62
<211> LENGTH: 21
<212> TYPE: PRT
<213> ORGANISM: Artificial Sequence
<220> FEATURE:
<223> OTHER INFORMATION: F11 binder

<400> SEQUENCE: 62

Thr Arg Ala Pro Tyr Cys Ser Gly Gly Asp Cys Tyr Pro Met Ser Thr
1 5 10 15

His Glu Leu Asp Ser
20

<210> SEQ ID NO 63
<211> LENGTH: 5
<212> TYPE: PRT
<213> ORGANISM: Artificial Sequence
<220> FEATURE:
<223> OTHER INFORMATION: C52 binder

<400> SEQUENCE: 63

Ser Tyr Trp Met Ser
1 5

<210> SEQ ID NO 64
<211> LENGTH: 16
<212> TYPE: PRT
<213> ORGANISM: Artificial Sequence
<220> FEATURE:
<223> OTHER INFORMATION: C52 binder

<400> SEQUENCE: 64

Val Ile Tyr Tyr Ser Gly Ala Thr Tyr Tyr Asn Pro Ser Leu Lys Ser
1 5 10 15

<210> SEQ ID NO 65
<211> LENGTH: 8
<212> TYPE: PRT
<213> ORGANISM: Artificial Sequence
<220> FEATURE:
<223> OTHER INFORMATION: C52 binder

<400> SEQUENCE: 65

Gly Ala Leu Asp Tyr Phe Asp Leu
1 5

<210> SEQ ID NO 66
<211> LENGTH: 11
<212> TYPE: PRT
<213> ORGANISM: Artificial Sequence
<220> FEATURE:
<223> OTHER INFORMATION: H4-VLVH binder

<400> SEQUENCE: 66

Arg Ala Ser Gln Ser Ile Ser Ser Tyr Leu Asn
1 5 10

<210> SEQ ID NO 67
<211> LENGTH: 7
<212> TYPE: PRT
<213> ORGANISM: Artificial Sequence
<220> FEATURE:
<223> OTHER INFORMATION: H4-VLVH binder

<400> SEQUENCE: 67

Ala Ala Ser Ser Leu Gln Ser
1 5

<210> SEQ ID NO 68
<211> LENGTH: 9
<212> TYPE: PRT
<213> ORGANISM: Artificial Sequence
<220> FEATURE:
<223> OTHER INFORMATION: H4-VLVH binder

<400> SEQUENCE: 68

Leu Gln Ile Thr His Trp Pro His Thr
1 5

<210> SEQ ID NO 69
<211> LENGTH: 5
<212> TYPE: PRT
<213> ORGANISM: Artificial Sequence
<220> FEATURE:
<223> OTHER INFORMATION: H4-VLVH binder

<400> SEQUENCE: 69

Asp Tyr Tyr Met Ser
1 5

<210> SEQ ID NO 70
<211> LENGTH: 17
<212> TYPE: PRT
<213> ORGANISM: Artificial Sequence
<220> FEATURE:
<223> OTHER INFORMATION: H4-VLVH binder

<400> SEQUENCE: 70

Tyr Ile Ser Ser Ser Gly Ser Thr Ile Tyr Tyr Ala Asp Ser Val Lys
1 5 10 15

Gly

<210> SEQ ID NO 71
<211> LENGTH: 22
<212> TYPE: PRT
<213> ORGANISM: Artificial Sequence
<220> FEATURE:
<223> OTHER INFORMATION: H4-VLVH binder

<400> SEQUENCE: 71

Asp Ala Pro Asp Leu Leu Ala Val Pro Thr Val Ile Phe Ser Gly Tyr
1 5 10 15

His Tyr Gly Ala Asp Val
20

<210> SEQ ID NO 72
<211> LENGTH: 5
<212> TYPE: PRT
<213> ORGANISM: Artificial Sequence
<220> FEATURE:
<223> OTHER INFORMATION: H4-VHVL binder

<400> SEQUENCE: 72

Asp Tyr Tyr Met Ser
1 5

<210> SEQ ID NO 73
<211> LENGTH: 17
<212> TYPE: PRT
<213> ORGANISM: Artificial Sequence
<220> FEATURE:
<223> OTHER INFORMATION: H4-VHVL binder

<400> SEQUENCE: 73

Tyr Ile Ser Ser Ser Gly Ser Thr Ile Tyr Tyr Ala Asp Ser Val Lys
1 5 10 15

Gly

<210> SEQ ID NO 74
<211> LENGTH: 22
<212> TYPE: PRT
<213> ORGANISM: Artificial Sequence
<220> FEATURE:
<223> OTHER INFORMATION: Binder H4-VHVL

<400> SEQUENCE: 74

Asp Ala Pro Asp Leu Leu Ala Val Pro Thr Val Ile Phe Ser Gly Tyr
1 5 10 15

His Tyr Gly Ala Asp Val
20

<210> SEQ ID NO 75
<211> LENGTH: 11
<212> TYPE: PRT
<213> ORGANISM: Artificial Sequence
<220> FEATURE:
<223> OTHER INFORMATION: H4-VHVL binder

<400> SEQUENCE: 75

Arg Ala Ser Gln Ser Ile Ser Ser Tyr Leu Asn
1 5 10

<210> SEQ ID NO 76
<211> LENGTH: 7
<212> TYPE: PRT
<213> ORGANISM: Artificial Sequence
<220> FEATURE:
<223> OTHER INFORMATION: H4-VHVL binder

<400> SEQUENCE: 76

Ala Ala Ser Ser Leu Gln Ser
1 5

<210> SEQ ID NO 77
<211> LENGTH: 9
<212> TYPE: PRT
<213> ORGANISM: Artificial Sequence
<220> FEATURE:
<223> OTHER INFORMATION: H4-VHVL binder

<400> SEQUENCE: 77

Leu Gln Ile Thr His Trp Pro His Thr
1 5

<210> SEQ ID NO 78
<211> LENGTH: 11
<212> TYPE: PRT
<213> ORGANISM: Artificial Sequence
<220> FEATURE:
<223> OTHER INFORMATION: G6-VLVH binder

<400> SEQUENCE: 78

Arg Ala Ser Gln Ser Ile Ser Ser Tyr Leu Asn
1 5 10

<210> SEQ ID NO 79
<211> LENGTH: 7
<212> TYPE: PRT
<213> ORGANISM: Artificial Sequence
<220> FEATURE:
<223> OTHER INFORMATION: G6-VLVH binder

<400> SEQUENCE: 79

Ala Ala Ser Ser Leu Gln Ser
1 5

<210> SEQ ID NO 80
<211> LENGTH: 5
<212> TYPE: PRT
<213> ORGANISM: Artificial Sequence
<220> FEATURE:
<223> OTHER INFORMATION: G6-VLVH binder

<400> SEQUENCE: 80

Gln His Tyr Gly Thr
1 5

<210> SEQ ID NO 81
<211> LENGTH: 5
<212> TYPE: PRT
<213> ORGANISM: Artificial Sequence
<220> FEATURE:
<223> OTHER INFORMATION: G6-VLVH binder

<400> SEQUENCE: 81

Asp Tyr Tyr Met Ser
1 5

<210> SEQ ID NO 82
<211> LENGTH: 17
<212> TYPE: PRT
<213> ORGANISM: Artificial Sequence
<220> FEATURE:
<223> OTHER INFORMATION: G6-VLVH binder

<400> SEQUENCE: 82

Tyr Ile Ser Ser Ser Gly Ser Thr Ile Tyr Tyr Ala Asp Ser Val Lys
1 5 10 15

Gly

<210> SEQ ID NO 83
<211> LENGTH: 18
<212> TYPE: PRT

<213> ORGANISM: Artificial Sequence
<220> FEATURE:
<223> OTHER INFORMATION: G6-VLVH binder

<400> SEQUENCE: 83

His Lys Thr Ser Leu Asn Asp Tyr Asp Phe Trp Ser Gly Tyr Leu Leu
1 5 10 15

Asp Tyr

<210> SEQ ID NO 84
<211> LENGTH: 5
<212> TYPE: PRT
<213> ORGANISM: Artificial Sequence
<220> FEATURE:
<223> OTHER INFORMATION: G6-VHVL binder

<400> SEQUENCE: 84

Asp Tyr Tyr Met Ser
1 5

<210> SEQ ID NO 85
<211> LENGTH: 17
<212> TYPE: PRT
<213> ORGANISM: Artificial Sequence
<220> FEATURE:
<223> OTHER INFORMATION: G6-VHVL binder

<400> SEQUENCE: 85

Tyr Ile Ser Ser Ser Gly Ser Thr Ile Tyr Tyr Ala Asp Ser Val Lys
1 5 10 15

Gly

<210> SEQ ID NO 86
<211> LENGTH: 18
<212> TYPE: PRT
<213> ORGANISM: Artificial Sequence
<220> FEATURE:
<223> OTHER INFORMATION: G6-VHVL binder

<400> SEQUENCE: 86

His Lys Thr Ser Leu Asn Asp Tyr Asp Phe Trp Ser Gly Tyr Leu Leu
1 5 10 15

Asp Tyr

<210> SEQ ID NO 87
<211> LENGTH: 11
<212> TYPE: PRT
<213> ORGANISM: Artificial Sequence
<220> FEATURE:
<223> OTHER INFORMATION: G6-VHVL binder

<400> SEQUENCE: 87

Arg Ala Ser Gln Ser Ile Ser Ser Tyr Leu Asn
1 5 10

<210> SEQ ID NO 88
<211> LENGTH: 7
<212> TYPE: PRT
<213> ORGANISM: Artificial Sequence
<220> FEATURE:
<223> OTHER INFORMATION: G6-VHVL binder

<400> SEQUENCE: 88

Ala Ala Ser Ser Leu Gln Ser
1 5

<210> SEQ ID NO 89
<211> LENGTH: 5
<212> TYPE: PRT
<213> ORGANISM: Artificial Sequence
<220> FEATURE:
<223> OTHER INFORMATION: G6-VHVL binder

<400> SEQUENCE: 89

Gln His Tyr Gly Thr
1 5

<210> SEQ ID NO 90
<211> LENGTH: 11
<212> TYPE: PRT
<213> ORGANISM: Artificial Sequence
<220> FEATURE:
<223> OTHER INFORMATION: C9-VLVH binder

<400> SEQUENCE: 90

Arg Ala Ser Gln Ser Ile Ser Ser Tyr Leu Asn
1 5 10

<210> SEQ ID NO 91
<211> LENGTH: 7
<212> TYPE: PRT
<213> ORGANISM: Artificial Sequence
<220> FEATURE:
<223> OTHER INFORMATION: C9-VLVH binder

<400> SEQUENCE: 91

Ala Ala Ser Ser Leu Gln Ser
1 5

<210> SEQ ID NO 92
<211> LENGTH: 9
<212> TYPE: PRT
<213> ORGANISM: Artificial Sequence
<220> FEATURE:
<223> OTHER INFORMATION: C9-VLVH binder

<400> SEQUENCE: 92

Gln Gln Arg Ser Asn Trp Pro Pro Thr
1 5

<210> SEQ ID NO 93
<211> LENGTH: 5
<212> TYPE: PRT
<213> ORGANISM: Artificial Sequence
<220> FEATURE:
<223> OTHER INFORMATION: C9-VLVH binder

<400> SEQUENCE: 93

Asp Tyr Tyr Met Ser
1 5

<210> SEQ ID NO 94
<211> LENGTH: 17
<212> TYPE: PRT
<213> ORGANISM: Artificial Sequence
<220> FEATURE:
<223> OTHER INFORMATION: C9-VLVH binder

<400> SEQUENCE: 94

Tyr Ile Ser Ser Ser Gly Ser Thr Ile Tyr Tyr Ala Asp Ser Val Lys
1 5 10 15

Gly

<210> SEQ ID NO 95
<211> LENGTH: 16
<212> TYPE: PRT
<213> ORGANISM: Artificial Sequence
<220> FEATURE:
<223> OTHER INFORMATION: C9-VLVH binder

<400> SEQUENCE: 95

Ala Val Phe Ser Leu Gly Pro Glu Gly Tyr Tyr Tyr Tyr Met Asp Val
1 5 10 15

<210> SEQ ID NO 96
<211> LENGTH: 5
<212> TYPE: PRT
<213> ORGANISM: Artificial Sequence
<220> FEATURE:
<223> OTHER INFORMATION: C9-VHVL H binder

<400> SEQUENCE: 96

Asp Tyr Tyr Met Ser
1 5

<210> SEQ ID NO 97
<211> LENGTH: 17
<212> TYPE: PRT
<213> ORGANISM: Artificial Sequence
<220> FEATURE:
<223> OTHER INFORMATION: C9-VHVL H binder

<400> SEQUENCE: 97

Tyr Ile Ser Ser Ser Gly Ser Thr Ile Tyr Tyr Ala Asp Ser Val Lys
1 5 10 15

Gly

<210> SEQ ID NO 98
<211> LENGTH: 16
<212> TYPE: PRT
<213> ORGANISM: Artificial Sequence
<220> FEATURE:
<223> OTHER INFORMATION: C9-VHVL H binder

<400> SEQUENCE: 98

Ala Val Phe Ser Leu Gly Pro Glu Gly Tyr Tyr Tyr Tyr Met Asp Val
1 5 10 15

<210> SEQ ID NO 99
<211> LENGTH: 11
<212> TYPE: PRT
<213> ORGANISM: Artificial Sequence
<220> FEATURE:
<223> OTHER INFORMATION: C9-VHVL H binder

<400> SEQUENCE: 99

Arg Ala Ser Gln Ser Ile Ser Ser Tyr Leu Asn
1 5 10

<210> SEQ ID NO 100
<211> LENGTH: 7
<212> TYPE: PRT
<213> ORGANISM: Artificial Sequence
<220> FEATURE:
<223> OTHER INFORMATION: C9-VHVL H binder

<400> SEQUENCE: 100

Ala Ala Ser Ser Leu Gln Ser
1               5

<210> SEQ ID NO 101
<211> LENGTH: 9
<212> TYPE: PRT
<213> ORGANISM: Artificial Sequence
<220> FEATURE:
<223> OTHER INFORMATION: C9-VHVL H binder

<400> SEQUENCE: 101

Gln Gln Arg Ser Asn Trp Pro Pro Thr
1               5

<210> SEQ ID NO 102
<211> LENGTH: 11
<212> TYPE: PRT
<213> ORGANISM: Artificial Sequence
<220> FEATURE:
<223> OTHER INFORMATION: D7-VLVH binder

<400> SEQUENCE: 102

Arg Ala Ser Gln Ser Ile Ser Ser Tyr Leu Asn
1               5                   10

<210> SEQ ID NO 103
<211> LENGTH: 7
<212> TYPE: PRT
<213> ORGANISM: Artificial Sequence
<220> FEATURE:
<223> OTHER INFORMATION: D7-VLVH binder

<400> SEQUENCE: 103

Ala Ala Ser Ser Leu Gln Ser
1               5

<210> SEQ ID NO 104
<211> LENGTH: 5
<212> TYPE: PRT
<213> ORGANISM: Artificial Sequence
<220> FEATURE:
<223> OTHER INFORMATION: D7-VLVH binder

<400> SEQUENCE: 104

Gln His Tyr Gly Thr
1               5

<210> SEQ ID NO 105
<211> LENGTH: 5
<212> TYPE: PRT
<213> ORGANISM: Artificial Sequence
<220> FEATURE:
<223> OTHER INFORMATION: D7-VLVH binder

<400> SEQUENCE: 105

Asp Tyr Tyr Met Ser
1               5

<210> SEQ ID NO 106
<211> LENGTH: 17
<212> TYPE: PRT
<213> ORGANISM: Artificial Sequence
<220> FEATURE:
<223> OTHER INFORMATION: D7-VLVH binder

<400> SEQUENCE: 106

Tyr Ile Ser Ser Ser Gly Ser Thr Ile Tyr Tyr Ala Asp Ser Val Lys

```
1               5                   10                  15

Gly


<210> SEQ ID NO 107
<211> LENGTH: 19
<212> TYPE: PRT
<213> ORGANISM: 'Artificial Sequence
<220> FEATURE:
<223> OTHER INFORMATION: D7-VLVH binder

<400> SEQUENCE: 107

Asp Gly Tyr Pro Leu Gly Gly Gly Tyr Asp Phe Trp Ser Gly Tyr Tyr
1               5                   10                  15

Pro Asp Tyr


<210> SEQ ID NO 108
<211> LENGTH: 5
<212> TYPE: PRT
<213> ORGANISM: Artificial Sequence
<220> FEATURE:
<223> OTHER INFORMATION: D7-VHVL binder

<400> SEQUENCE: 108

Asp Tyr Tyr Met Ser
1               5


<210> SEQ ID NO 109
<211> LENGTH: 17
<212> TYPE: PRT
<213> ORGANISM: Artificial Sequence
<220> FEATURE:
<223> OTHER INFORMATION: D7-VHVL binder

<400> SEQUENCE: 109

Tyr Ile Ser Ser Ser Gly Ser Thr Ile Tyr Tyr Ala Asp Ser Val Lys
1               5                   10                  15

Gly


<210> SEQ ID NO 110
<211> LENGTH: 19
<212> TYPE: PRT
<213> ORGANISM: Artificial Sequence
<220> FEATURE:
<223> OTHER INFORMATION: D7-VHVL binder

<400> SEQUENCE: 110

Asp Gly Tyr Pro Leu Gly Gly Gly Tyr Asp Phe Trp Ser Gly Tyr Tyr
1               5                   10                  15

Pro Asp Tyr


<210> SEQ ID NO 111
<211> LENGTH: 11
<212> TYPE: PRT
<213> ORGANISM: Artificial Sequence
<220> FEATURE:
<223> OTHER INFORMATION: D7-VHVL binder

<400> SEQUENCE: 111

Arg Ala Ser Gln Ser Ile Ser Ser Tyr Leu Asn
1               5                   10


<210> SEQ ID NO 112
<211> LENGTH: 7
<212> TYPE: PRT
```

<213> ORGANISM: Artificial Sequence
<220> FEATURE:
<223> OTHER INFORMATION: D7-VHVL binder

<400> SEQUENCE: 112

Ala Ala Ser Ser Leu Gln Ser
1 5

<210> SEQ ID NO 113
<211> LENGTH: 5
<212> TYPE: PRT
<213> ORGANISM: Artificial Sequence
<220> FEATURE:
<223> OTHER INFORMATION: D7-VHVL binder

<400> SEQUENCE: 113

Gln His Tyr Gly Thr
1 5

<210> SEQ ID NO 114
<211> LENGTH: 11
<212> TYPE: PRT
<213> ORGANISM: Artificial Sequence
<220> FEATURE:
<223> OTHER INFORMATION: B7-VLVH binder

<400> SEQUENCE: 114

Arg Ala Ser Gln Ser Ile Ser Ser Tyr Leu Asn
1 5 10

<210> SEQ ID NO 115
<211> LENGTH: 7
<212> TYPE: PRT
<213> ORGANISM: Artificial Sequence
<220> FEATURE:
<223> OTHER INFORMATION: B7-VLVH binder

<400> SEQUENCE: 115

Ala Ala Ser Ser Leu Gln Ser
1 5

<210> SEQ ID NO 116
<211> LENGTH: 5
<212> TYPE: PRT
<213> ORGANISM: Artificial Sequence
<220> FEATURE:
<223> OTHER INFORMATION: B7-VLVH binder

<400> SEQUENCE: 116

Gln His Tyr Gly Thr
1 5

<210> SEQ ID NO 117
<211> LENGTH: 5
<212> TYPE: PRT
<213> ORGANISM: Artificial Sequence
<220> FEATURE:
<223> OTHER INFORMATION: B7-VLVH binder

<400> SEQUENCE: 117

Asp Tyr Tyr Met Ser
1 5

<210> SEQ ID NO 118
<211> LENGTH: 17
<212> TYPE: PRT
<213> ORGANISM: Artificial Sequence
<220> FEATURE:
<223> OTHER INFORMATION: B7-VLVH binder

<400> SEQUENCE: 118

Tyr Ile Ser Ser Ser Gly Ser Thr Ile Tyr Tyr Ala Asp Ser Val Lys
1 5 10 15

Gly

<210> SEQ ID NO 119
<211> LENGTH: 18
<212> TYPE: PRT
<213> ORGANISM: Artificial Sequence
<220> FEATURE:
<223> OTHER INFORMATION: B7-VLVH binder

<400> SEQUENCE: 119

His Lys Thr Ser Leu Asn Asp Tyr Asp Phe Trp Ser Gly Tyr Leu Leu
1 5 10 15

Asp Tyr

<210> SEQ ID NO 120
<211> LENGTH: 5
<212> TYPE: PRT
<213> ORGANISM: Artificial Sequence
<220> FEATURE:
<223> OTHER INFORMATION: B7-VHVL binder

<400> SEQUENCE: 120

Asp Tyr Tyr Met Ser
1 5

<210> SEQ ID NO 121
<211> LENGTH: 17
<212> TYPE: PRT
<213> ORGANISM: Artificial Sequence
<220> FEATURE:
<223> OTHER INFORMATION: B7-VHVL binder

<400> SEQUENCE: 121

Tyr Ile Ser Ser Ser Gly Ser Thr Ile Tyr Tyr Ala Asp Ser Val Lys
1 5 10 15

Gly

<210> SEQ ID NO 122
<211> LENGTH: 18
<212> TYPE: PRT
<213> ORGANISM: Artificial Sequence
<220> FEATURE:
<223> OTHER INFORMATION: B7-VHVL binder

<400> SEQUENCE: 122

His Lys Thr Ser Leu Asn Asp Tyr Asp Phe Trp Ser Gly Tyr Leu Leu
1 5 10 15

Asp Tyr

<210> SEQ ID NO 123
<211> LENGTH: 11
<212> TYPE: PRT
<213> ORGANISM: Artificial Sequence
<220> FEATURE:
<223> OTHER INFORMATION: B7-VHVL binder

<400> SEQUENCE: 123

Arg Ala Ser Gln Ser Ile Ser Ser Tyr Leu Asn 1 5 10

<210> SEQ ID NO 124
<211> LENGTH: 7
<212> TYPE: PRT
<213> ORGANISM: Artificial Sequence
<220> FEATURE:
<223> OTHER INFORMATION: B7-VHVL binder

<400> SEQUENCE: 124

Ala Ala Ser Ser Leu Gln Ser
1 5

<210> SEQ ID NO 125
<211> LENGTH: 5
<212> TYPE: PRT
<213> ORGANISM: Artificial Sequence
<220> FEATURE:
<223> OTHER INFORMATION: B7-VHVL binder

<400> SEQUENCE: 125

Gln His Tyr Gly Thr
1 5

<210> SEQ ID NO 126
<211> LENGTH: 11
<212> TYPE: PRT
<213> ORGANISM: Artificial Sequence
<220> FEATURE:
<223> OTHER INFORMATION: A6-VLVH binder

<400> SEQUENCE: 126

Arg Ala Ser Gln Ser Ile Ser Ser Tyr Leu Asn
1 5 10

<210> SEQ ID NO 127
<211> LENGTH: 7
<212> TYPE: PRT
<213> ORGANISM: Artificial Sequence
<220> FEATURE:
<223> OTHER INFORMATION: A6-VLVH binder

<400> SEQUENCE: 127

Ala Ala Ser Ser Leu Gln Ser
1 5

<210> SEQ ID NO 128
<211> LENGTH: 5
<212> TYPE: PRT
<213> ORGANISM: Artificial Sequence
<220> FEATURE:
<223> OTHER INFORMATION: A6-VLVH binder

<400> SEQUENCE: 128

Gln Arg Tyr Gly Thr
1 5

<210> SEQ ID NO 129
<211> LENGTH: 5
<212> TYPE: PRT
<213> ORGANISM: Artificial Sequence
<220> FEATURE:
<223> OTHER INFORMATION: A6-VLVH binder

<400> SEQUENCE: 129

Asp Tyr Tyr Met Ser
1 5

<210> SEQ ID NO 130
<211> LENGTH: 17
<212> TYPE: PRT
<213> ORGANISM: Artificial Sequence
<220> FEATURE:
<223> OTHER INFORMATION: A6-VLVH binder

<400> SEQUENCE: 130

Tyr Ile Ser Ser Ser Gly Ser Thr Ile Tyr Tyr Ala Asp Ser Val Lys
1 5 10 15

Gly

<210> SEQ ID NO 131
<211> LENGTH: 18
<212> TYPE: PRT
<213> ORGANISM: Artificial Sequence
<220> FEATURE:
<223> OTHER INFORMATION: A6-VLVH binder

<400> SEQUENCE: 131

His Lys Thr Ser Leu Asn Asp Tyr Asp Phe Trp Ser Gly Tyr Leu Leu
1 5 10 15

Asp Tyr

<210> SEQ ID NO 132
<211> LENGTH: 5
<212> TYPE: PRT
<213> ORGANISM: Artificial Sequence
<220> FEATURE:
<223> OTHER INFORMATION: A6-VHVL binder

<400> SEQUENCE: 132

Asp Tyr Tyr Met Ser
1 5

<210> SEQ ID NO 133
<211> LENGTH: 17
<212> TYPE: PRT
<213> ORGANISM: Artificial Sequence
<220> FEATURE:
<223> OTHER INFORMATION: A6-VHVL binder

<400> SEQUENCE: 133

Tyr Ile Ser Ser Ser Gly Ser Thr Ile Tyr Tyr Ala Asp Ser Val Lys
1 5 10 15

Gly

<210> SEQ ID NO 134
<211> LENGTH: 18
<212> TYPE: PRT
<213> ORGANISM: Artificial Sequence
<220> FEATURE:
<223> OTHER INFORMATION: A6-VHVL binder

<400> SEQUENCE: 134

His Lys Thr Ser Leu Asn Asp Tyr Asp Phe Trp Ser Gly Tyr Leu Leu
1 5 10 15

Asp Tyr

<210> SEQ ID NO 135
<211> LENGTH: 11
<212> TYPE: PRT
<213> ORGANISM: Artificial Sequence
<220> FEATURE:
<223> OTHER INFORMATION: A6-VHVL binder

<400> SEQUENCE: 135

Arg Ala Ser Gln Ser Ile Ser Ser Tyr Leu Asn
1 5 10

<210> SEQ ID NO 136
<211> LENGTH: 7
<212> TYPE: PRT
<213> ORGANISM: Artificial Sequence
<220> FEATURE:
<223> OTHER INFORMATION: A6-VHVL binder

<400> SEQUENCE: 136

Ala Ala Ser Ser Leu Gln Ser
1 5

<210> SEQ ID NO 137
<211> LENGTH: 5
<212> TYPE: PRT
<213> ORGANISM: Artificial Sequence
<220> FEATURE:
<223> OTHER INFORMATION: A6-VHVL binder

<400> SEQUENCE: 137

Gln Arg Tyr Gly Thr
1 5

<210> SEQ ID NO 138
<211> LENGTH: 11
<212> TYPE: PRT
<213> ORGANISM: Artificial Sequence
<220> FEATURE:
<223> OTHER INFORMATION: C1-VLVH binder

<400> SEQUENCE: 138

Arg Ala Ser Gln Ser Ile Ser Ser Tyr Leu Asn
1 5 10

<210> SEQ ID NO 139
<211> LENGTH: 7
<212> TYPE: PRT
<213> ORGANISM: Artificial Sequence
<220> FEATURE:
<223> OTHER INFORMATION: C1-VLVH binder

<400> SEQUENCE: 139

Ala Ala Ser Ser Leu Gln Ser
1 5

<210> SEQ ID NO 140
<211> LENGTH: 5
<212> TYPE: PRT
<213> ORGANISM: Artificial Sequence
<220> FEATURE:
<223> OTHER INFORMATION: C1-VLVH binder

<400> SEQUENCE: 140

Gln His Tyr Gly Thr
1 5

<210> SEQ ID NO 141
<211> LENGTH: 5
<212> TYPE: PRT
<213> ORGANISM: Artificial Sequence
<220> FEATURE:

<223> OTHER INFORMATION: C1-VLVH binder

<400> SEQUENCE: 141

Asp Tyr Tyr Met Ser
1               5

<210> SEQ ID NO 142
<211> LENGTH: 17
<212> TYPE: PRT
<213> ORGANISM: Artificial Sequence
<220> FEATURE:
<223> OTHER INFORMATION: C1-VLVH binder

<400> SEQUENCE: 142

Tyr Ile Ser Ser Ser Gly Ser Thr Ile Tyr Tyr Ala Asp Ser Val Lys
1               5                   10                  15

Gly

<210> SEQ ID NO 143
<211> LENGTH: 17
<212> TYPE: PRT
<213> ORGANISM: Artificial Sequence
<220> FEATURE:
<223> OTHER INFORMATION: C1-VLVH binder

<400> SEQUENCE: 143

His Ala Pro His Lys His Tyr Asp Phe Trp Ser Gly Tyr Tyr Pro Asp
1               5                   10                  15

Tyr

<210> SEQ ID NO 144
<211> LENGTH: 5
<212> TYPE: PRT
<213> ORGANISM: Artificial Sequence
<220> FEATURE:
<223> OTHER INFORMATION: C1-VHVL binder

<400> SEQUENCE: 144

Asp Tyr Tyr Met Ser
1               5

<210> SEQ ID NO 145
<211> LENGTH: 17
<212> TYPE: PRT
<213> ORGANISM: Artificial Sequence
<220> FEATURE:
<223> OTHER INFORMATION: C1-VHVL binder

<400> SEQUENCE: 145

Tyr Ile Ser Ser Ser Gly Ser Thr Ile Tyr Tyr Ala Asp Ser Val Lys
1               5                   10                  15

Gly

<210> SEQ ID NO 146
<211> LENGTH: 17
<212> TYPE: PRT
<213> ORGANISM: Artificial Sequence
<220> FEATURE:
<223> OTHER INFORMATION: C1-VHVL binder

<400> SEQUENCE: 146

His Ala Pro His Lys His Tyr Asp Phe Trp Ser Gly Tyr Tyr Pro Asp
1               5                   10                  15

Tyr

<210> SEQ ID NO 147
<211> LENGTH: 11
<212> TYPE: PRT
<213> ORGANISM: Artificial Sequence
<220> FEATURE:
<223> OTHER INFORMATION: C1-VHVL binder

<400> SEQUENCE: 147

Arg Ala Ser Gln Ser Ile Ser Ser Tyr Leu Asn
1 5 10

<210> SEQ ID NO 148
<211> LENGTH: 7
<212> TYPE: PRT
<213> ORGANISM: Artificial Sequence
<220> FEATURE:
<223> OTHER INFORMATION: C1-VHVL binder

<400> SEQUENCE: 148

Ala Ala Ser Ser Leu Gln Ser
1 5

<210> SEQ ID NO 149
<211> LENGTH: 5
<212> TYPE: PRT
<213> ORGANISM: Artificial Sequence
<220> FEATURE:
<223> OTHER INFORMATION: C1-VHVL binder

<400> SEQUENCE: 149

Gln His Tyr Gly Thr
1 5

<210> SEQ ID NO 150
<211> LENGTH: 366
<212> TYPE: DNA
<213> ORGANISM: Artificial Sequence
<220> FEATURE:
<223> OTHER INFORMATION: E9 binder

<400> SEQUENCE: 150
gaggtgcagc tggttgaatc tggcggagga ctggttcagc ctggcggatc tctgagactg 60
agctgtaccg tgtccggctt caccttcagc tcttatgccc tcggctgggt ccgacaggct 120
cctggaaaag gactggaatg gatcggctac atctaccaca agggcgacac caactacaac 180
cccagcctga agtccctggt caccatcagc agagacaaca gcaagaacac cctgtacctg 240
cagatgaaca gcctgagagc cgaggacaca gccctgtact actgcgccaa agtccgctgg 300
gtgtccagca caagcaccct gggctttgat tattggggcc agggcacact ggtcaccgtg 360
tcatct 366

<210> SEQ ID NO 151
<211> LENGTH: 370
<212> TYPE: PRT
<213> ORGANISM: Artificial Sequence
<220> FEATURE:
<223> OTHER INFORMATION: RJ141 CAR: (E9/CD8 TM/4-1BB/CD3zeta)

<400> SEQUENCE: 151

Met Leu Leu Leu Val Thr Ser Leu Leu Leu Cys Glu Leu Pro His Pro
1 5 10 15

Ala Phe Leu Leu Ile Pro Glu Val Gln Leu Val Glu Ser Gly Gly Gly
20 25 30

```
Leu Val Gln Pro Gly Gly Ser Leu Arg Leu Ser Cys Thr Val Ser Gly
        35                  40                  45

Phe Thr Phe Ser Ser Tyr Ala Leu Gly Trp Val Arg Gln Ala Pro Gly
    50                  55                  60

Lys Gly Leu Glu Trp Ile Gly Tyr Ile Tyr His Lys Gly Asp Thr Asn
65                  70                  75                  80

Tyr Asn Pro Ser Leu Lys Ser Leu Val Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Leu Tyr Tyr Cys Ala Lys Val Arg Trp Val Ser Ser Thr Ser Thr
        115                 120                 125

Leu Gly Phe Asp Tyr Trp Gly Gln Gly Thr Leu Val Thr Val Ser Ser
    130                 135                 140

Ala Ala Ala Thr Thr Thr Pro Ala Pro Arg Pro Pro Thr Pro Ala Pro
145                 150                 155                 160

Thr Ile Ala Ser Gln Pro Leu Ser Leu Arg Pro Glu Ala Cys Arg Pro
                165                 170                 175

Ala Ala Gly Gly Ala Val His Thr Arg Gly Leu Asp Phe Ala Cys Asp
            180                 185                 190

Ile Tyr Ile Trp Ala Pro Leu Ala Gly Thr Cys Gly Val Leu Leu Leu
        195                 200                 205

Ser Leu Val Ile Thr Leu Tyr Cys Lys Arg Gly Arg Lys Lys Leu Leu
    210                 215                 220

Tyr Ile Phe Lys Gln Pro Phe Met Arg Pro Val Gln Thr Thr Gln Glu
225                 230                 235                 240

Glu Asp Gly Cys Ser Cys Arg Phe Pro Glu Glu Glu Glu Gly Gly Cys
                245                 250                 255

Glu Leu Arg Val Lys Phe Ser Arg Ser Ala Asp Ala Pro Ala Tyr Lys
            260                 265                 270

Gln Gly Gln Asn Gln Leu Tyr Asn Glu Leu Asn Leu Gly Arg Arg Glu
        275                 280                 285

Glu Tyr Asp Val Leu Asp Lys Arg Arg Gly Arg Asp Pro Glu Met Gly
    290                 295                 300

Gly Lys Pro Arg Arg Lys Asn Pro Gln Glu Gly Leu Tyr Asn Glu Leu
305                 310                 315                 320

Gln Lys Asp Lys Met Ala Glu Ala Tyr Ser Glu Ile Gly Met Lys Gly
                325                 330                 335

Glu Arg Arg Arg Gly Lys Gly His Asp Gly Leu Tyr Gln Gly Leu Ser
            340                 345                 350

Thr Ala Thr Lys Asp Thr Tyr Asp Ala Leu His Met Gln Ala Leu Pro
        355                 360                 365

Pro Arg
    370
```

<210> SEQ ID NO 152
<211> LENGTH: 1110
<212> TYPE: DNA
<213> ORGANISM: Artificial Sequence
<220> FEATURE:
<223> OTHER INFORMATION: RJ141 CAR: (E9/CD8 TM/4-1BB/CD3zeta)

<400> SEQUENCE: 152

```
atgcttctgc tcgtgacaag cctgctgctg tgcgagctgc cccaccctgc ctttctgctg      60
```

atccctgagg tgcagctggt tgaatctggc ggaggactgg ttcagcctgg cggatctctg 120
agactgagct gtaccgtgtc cggcttcacc ttcagctctt atgccctcgg ctgggtccga 180
caggctcctg gaaaaggact ggaatggatc ggctacatct accacaaggg cgacaccaac 240
tacaacccca gcctgaagtc cctggtcacc atcagcagag acaacagcaa gaacaccctg 300
tacctgcaga tgaacagcct gagagccgag gacacagccc tgtactactg cgccaaagtc 360
cgctgggtgt ccagcacaag caccctgggc tttgattatt ggggccaggg cacactggtc 420
accgtgtcat ctgcggccgc aaccactact ccggcaccta ggcccccac tccggcaccg 480 accattgcat cacaaccact gagtcttaga cctgaagcct gtcgacccgc agctgggggg 540
gcagtccaca cacggggatt ggatttcgcc tgcgatatat acatttgggc gccactggca 600
ggcacctgcg gggtcctgct cttgtccctt gtcatcaccc tgtactgtaa gagaggaaga 660
aagaagttgt tgtatatttt caaacagcca ttcatgaggc cggtccagac cactcaggag 720
gaggatggat gcagttgccg ctttccggaa gaggaagagg gtgggtgtga actccgagtt 780
aaattttctc gcagtgctga tgccccagcg tataaacagg gtcagaacca actgtataat 840
gaactcaatt tggggaggcg agaggagtat gatgtattgg acaagcggcg ggggcgggat 900
cctgaaatgg gcggtaagcc aaggcgcaag aatccacagg agggtttgta taatgagttg 960
cagaaggata aaatggcgga agcgtattca gaaatcggaa tgaagggaga gcgccgcaga 1020
gggaaagggc atgatggcct ctaccaaggt ttgtcaacag cgaccaagga tacctatgac 1080
gcacttcata tgcaagcact gccccccagg 1110

<210> SEQ ID NO 153
<211> LENGTH: 363
<212> TYPE: DNA
<213> ORGANISM: Artificial Sequence
<220> FEATURE:
<223> OTHER INFORMATION: A4 binder

<400> SEQUENCE: 153
gaggtgcagc tggttgaatc tggcggagga ctggttcagc ctggcggatc tctgagactg 60
agctgtgtgg ccagcggctt caccttcatc agctacgcca tgagctgggt ccgacaggcc 120
cctggaaaag gccttgagtg gatggccatt atctaccccg atgacgccgg caccatgtac 180
agccctagct tcagggccca agtgaccatc agccgggaca acagcaagaa caccctgtac 240
ctgcagatga acagcctgag agccgaggac acagccctgt actactgtgc cagagtgaca 300
atggtccgag gcgtgatcgg cttcgatcct tggggacagg gaaccctggt caccgtttct 360
tct 363

<210> SEQ ID NO 154
<211> LENGTH: 369
<212> TYPE: PRT
<213> ORGANISM: Artificial Sequence
<220> FEATURE:
<223> OTHER INFORMATION: RJ142 CAR (A4/CD8 TM/4-1BB/CD3zeta)

<400> SEQUENCE: 154

Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Val Ala Ser Gly
        35                  40                  45

Phe Thr Phe Ile Ser Tyr Ala Met Ser Trp Val Arg Gln Ala Pro Gly
50 55 60

Lys Gly Leu Glu Trp Met Ala Ile Ile Tyr Pro Asp Asp Ala Gly Thr
65 70 75 80

Met Tyr Ser Pro Ser Phe Gln Gly Gln Val Thr Ile Ser Arg Asp Asn
85 90 95

Ser Lys Asn Thr Leu Tyr Leu Gln Met Asn Ser Leu Arg Ala Glu Asp
100 105 110

Thr Ala Leu Tyr Tyr Cys Ala Arg Val Thr Met Val Arg Gly Val Ile
115 120 125

Gly Phe Asp Pro Trp Gly Gln Gly Thr Leu Val Thr Val Ser Ser Ala
130 135 140

Ala Ala Thr Thr Thr Pro Ala Pro Arg Pro Pro Thr Pro Ala Pro Thr
145 150 155 160

Ile Ala Ser Gln Pro Leu Ser Leu Arg Pro Glu Ala Cys Arg Pro Ala
165 170 175

Ala Gly Gly Ala Val His Thr Arg Gly Leu Asp Phe Ala Cys Asp Ile
180 185 190

Tyr Ile Trp Ala Pro Leu Ala Gly Thr Cys Gly Val Leu Leu Leu Ser
195 200 205

Leu Val Ile Thr Leu Tyr Cys Lys Arg Gly Arg Lys Lys Leu Leu Tyr
210 215 220

Ile Phe Lys Gln Pro Phe Met Arg Pro Val Gln Thr Thr Gln Glu Glu
225 230 235 240

Asp Gly Cys Ser Cys Arg Phe Pro Glu Glu Glu Glu Gly Gly Cys Glu
245 250 255

Leu Arg Val Lys Phe Ser Arg Ser Ala Asp Ala Pro Ala Tyr Lys Gln
260 265 270

Gly Gln Asn Gln Leu Tyr Asn Glu Leu Asn Leu Gly Arg Arg Glu Glu
275 280 285

Tyr Asp Val Leu Asp Lys Arg Arg Gly Arg Asp Pro Glu Met Gly Gly
290 295 300

Lys Pro Arg Arg Lys Asn Pro Gln Glu Gly Leu Tyr Asn Glu Leu Gln
305 310 315 320

Lys Asp Lys Met Ala Glu Ala Tyr Ser Glu Ile Gly Met Lys Gly Glu
325 330 335

Arg Arg Arg Gly Lys Gly His Asp Gly Leu Tyr Gln Gly Leu Ser Thr
340 345 350

Ala Thr Lys Asp Thr Tyr Asp Ala Leu His Met Gln Ala Leu Pro Pro
355 360 365

Arg

<210> SEQ ID NO 155
<211> LENGTH: 1107
<212> TYPE: DNA
<213> ORGANISM: Artificial Sequence
<220> FEATURE:
<223> OTHER INFORMATION: RJ142 CAR (A4/CD8 TM/4-1BB/CD3zeta)

<400> SEQUENCE: 155
atgcttctgc tcgtgacaag cctgctgctg tgcgagctgc cccaccctgc ctttctgctg 60
atccctgagg tgcagctggt tgaatctggc ggaggactgg ttcagcctgg cggatctctg 120
agactgagct gtgtggccag cggcttcacc ttcatcagct acgccatgag ctgggtccga 180
caggcccctg gaaaaggcct tgagtggatg gccattatct accccgatga cgccggcacc 240
atgtacagcc ctagctttca gggccaagtg accatcagcc gggacaacag caagaacacc 300
ctgtacctgc agatgaacag cctgagagcc gaggacacag ccctgtacta ctgtgccaga 360
gtgacaatgg tccgaggcgt gatcggcttc gatccttggg gacagggaac cctggtcacc 420
gtttcttctg cggccgcaac cactactccg gcacctaggc cccccactcc ggcaccgacc 480
attgcatcac aaccactgag tcttagacct gaagcctgtc gacccgcagc tgggggggca 540
gtccacacac ggggattgga tttcgcctgc gatatataca tttgggcgcc actggcaggc 600
acctgcgggg tcctgctctt gtcccttgtc atcaccctgt actgtaagag aggaagaaag 660
aagttgttgt atattttcaa acagccattc atgaggccgg tccagaccac tcaggaggag 720
gatggatgca gttgccgctt tccggaagag gaagagggtg ggtgtgaact ccgagttaaa 780
ttttctcgca gtgctgatgc cccagcgtat aaacagggtc agaaccaact gtataatgaa 840
ctcaatttgg ggaggcgaga ggagtatgat gtattggaca agcggcgggg gcgggatcct 900
gaaatgggcg gtaagccaag gcgcaagaat ccacaggagg gtttgtataa tgagttgcag 960
aaggataaaa tggcggaagc gtattcagaa atcggaatga agggagagcg ccgcagaggg 1020
aaagggcatg atggcctcta ccaaggtttg tcaacagcga ccaaggatac ctatgacgca 1080
cttcatatgc aagcactgcc ccccagg 1107

<210> SEQ ID NO 156
<211> LENGTH: 363
<212> TYPE: DNA
<213> ORGANISM: Artificial Sequence
<220> FEATURE:
<223> OTHER INFORMATION: E61 binder

<400> SEQUENCE: 156
gaggtgcagc tggttgaatc tggcggagga ctggttcagc ctggcggatc tctgagactg 60
tcctgcacct tcagcggctt caccttctcc agctacgcca tgagctgggt ccgacaggct 120
cctggcaaag gccttgagtg gatgggcatc atctaccccg gcgacagcaa caccatctac 180
agccctagct tccagggcca agtgaccatc agccgggaca acagcaagaa caccctgtac 240
ctgcagatga acagcctgag agccgaggac accgccacct actactgtgc tagaagcggc 300
gcctacgacg gccggatttg gtttgatcct tggggccagg gcaccctggt cacagtttct 360
tct 363

<210> SEQ ID NO 157
<211> LENGTH: 369
<212> TYPE: PRT
<213> ORGANISM: Artificial Sequence
<220> FEATURE:
<223> OTHER INFORMATION: RJ143 CAR (E61/CD8 TM/4-1BB/CD3zeta)

<400> SEQUENCE: 157

Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Thr Phe Ser Gly
        35                  40                  45

Phe Thr Phe Ser Ser Tyr Ala Met Ser Trp Val Arg Gln Ala Pro Gly
    50                  55                  60

Lys Gly Leu Glu Trp Met Gly Ile Ile Tyr Pro Gly Asp Ser Asn Thr
65                  70                  75                  80

```
Ile Tyr Ser Pro Ser Phe Gln Gly Gln Val Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Thr Tyr Tyr Cys Ala Arg Ser Gly Ala Tyr Asp Gly Arg Ile
        115                 120                 125

Trp Phe Asp Pro Trp Gly Gln Gly Thr Leu Val Thr Val Ser Ser Ala
    130                 135                 140

Ala Ala Thr Thr Thr Pro Ala Pro Arg Pro Pro Thr Pro Ala Pro Thr
145                 150                 155                 160

Ile Ala Ser Gln Pro Leu Ser Leu Arg Pro Glu Ala Cys Arg Pro Ala
                165                 170                 175

Ala Gly Gly Ala Val His Thr Arg Gly Leu Asp Phe Ala Cys Asp Ile
            180                 185                 190

Tyr Ile Trp Ala Pro Leu Ala Gly Thr Cys Gly Val Leu Leu Leu Ser
        195                 200                 205

Leu Val Ile Thr Leu Tyr Cys Lys Arg Gly Arg Lys Lys Leu Leu Tyr
    210                 215                 220

Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Glu Gly Gly Cys Glu
                245                 250                 255

Leu Arg Val Lys Phe Ser Arg Ser Ala Asp Ala Pro Ala Tyr Lys Gln
            260                 265                 270

Gly Gln Asn Gln Leu Tyr Asn Glu Leu Asn Leu Gly Arg Arg Glu Glu
        275                 280                 285

Tyr Asp Val Leu Asp Lys Arg Arg Gly Arg Asp Pro Glu Met Gly Gly
    290                 295                 300

Lys Pro Arg Arg Lys Asn Pro Gln Glu Gly Leu Tyr Asn Glu Leu Gln
305                 310                 315                 320

Lys Asp Lys Met Ala Glu Ala Tyr Ser Glu Ile Gly Met Lys Gly Glu
                325                 330                 335

Arg Arg Arg Gly Lys Gly His Asp Gly Leu Tyr Gln Gly Leu Ser Thr
            340                 345                 350

Ala Thr Lys Asp Thr Tyr Asp Ala Leu His Met Gln Ala Leu Pro Pro
        355                 360                 365

Arg
```

```
<210> SEQ ID NO 158
<211> LENGTH: 1107
<212> TYPE: DNA
<213> ORGANISM: Artificial Sequence
<220> FEATURE:
<223> OTHER INFORMATION: RJ143 CAR (E61/CD8 TM/4-1BB/CD3zeta)

<400> SEQUENCE: 158

atgcttctgc tcgtgacaag cctgctgctg tgcgagctgc cccaccctgc ctttctgctg     60

atccctgagg tgcagctggt tgaatctggc ggaggactgg ttcagcctgg cggatctctg    120

agactgtcct gcaccttcag cggcttcacc ttctccagct acgccatgag ctgggtccga    180

caggctcctg gcaaaggcct tgagtggatg ggcatcatct accccggcga cagcaacacc    240

atctacagcc ctagcttcca gggccaagtg accatcagcc gggacaacag caagaacacc    300

ctgtacctgc agatgaacag cctgagagcc gaggacaccg ccacctacta ctgtgctaga    360
```

agcggcgcct acgacggccg gatttggttt gatccttggg gccagggcac cctggtcaca 420
gtttcttctg cggccgcaac cactactccg gcacctaggc cccccactcc ggcaccgacc 480
attgcatcac aaccactgag tcttagacct gaagcctgtc gacccgcagc tggggggggca 540 gtccacacac ggggattgga tttcgcctgc gatatataca tttgggcgcc actggcaggc 600
acctgcgggg tcctgctctt gtcccttgtc atcaccctgt actgtaagag aggaagaaag 660
aagttgttgt atattttcaa acagccattc atgaggccgg tccagaccac tcaggaggag 720
gatggatgca gttgccgctt tccggaagag gaagagggtg ggtgtgaact ccgagttaaa 780
ttttctcgca gtgctgatgc cccagcgtat aaacagggtc agaaccaact gtataatgaa 840
ctcaatttgg ggaggcgaga ggagtatgat gtattggaca agcggcgggg gcgggatcct 900
gaaatgggcg gtaagccaag gcgcaagaat ccacaggagg gtttgtataa tgagttgcag 960
aaggataaaa tggcggaagc gtattcagaa atcggaatga agggagagcg ccgcagaggg 1020
aaagggcatg atggcctcta ccaaggtttg tcaacagcga ccaaggatac ctatgacgca 1080
cttcatatgc aagcactgcc ccccagg 1107

<210> SEQ ID NO 159
<211> LENGTH: 384
<212> TYPE: DNA
<213> ORGANISM: Artificial Sequence
<220> FEATURE:
<223> OTHER INFORMATION: A7 binder

<400> SEQUENCE: 159
gaggtgcagc tggttgaatc tggcggagga ctggttcagc ctggcggatc tctgagactg 60
tcttgtgccg ccagcggctt caccttcagc aactacggca tgagctgggt ccgacaggcc 120
cctggaaaag gccttgagtg gatcggctac atctaccaca ccggcaacac ctactacaac 180
cccagcctga agtccagagt gaccatcagc cgggacaaca gcaagaacac cctgtacctg 240
cagatgaaca gcctgagagc cgaggacacc gccatctact actgtgccag agaaggcgtg 300
atgggcggct accacacaga ccccaattac tactactatg gcatggacgt gtggggccag 360
ggcaccacag tgacagtttc ttct 384

<210> SEQ ID NO 160
<211> LENGTH: 376
<212> TYPE: PRT
<213> ORGANISM: Artificial Sequence
<220> FEATURE:
<223> OTHER INFORMATION: RJ144 CAR (A7/CD8 TM/4-1BB/CD3zeta)

<400> SEQUENCE: 160

Met Leu Leu Leu Val Thr Ser Leu Leu Leu Cys Glu Leu Pro His Pro
1 5 10 15

Ala Phe Leu Leu Ile Pro Glu Val Gln Leu Val Glu Ser Gly Gly Gly
20 25 30

Leu Val Gln Pro Gly Gly Ser Leu Arg Leu Ser Cys Ala Ala Ser Gly
35 40 45

Phe Thr Phe Ser Asn Tyr Gly Met Ser Trp Val Arg Gln Ala Pro Gly
50 55 60

Lys Gly Leu Glu Trp Ile Gly Tyr Ile Tyr His Thr Gly Asn Thr Tyr
65 70 75 80

Tyr Asn Pro Ser Leu Lys Ser Arg Val Thr Ile Ser Arg Asp Asn Ser
85 90 95

Lys Asn Thr Leu Tyr Leu Gln Met Asn Ser Leu Arg Ala Glu Asp Thr

```
            100                 105                 110

Ala Ile Tyr Tyr Cys Ala Arg Glu Gly Val Met Gly Gly Tyr His Thr
        115                 120                 125

Asp Pro Asn Tyr Tyr Tyr Tyr Gly Met Asp Val Trp Gly Gln Gly Thr
    130                 135                 140

Thr Val Thr Val Ser Ser Ala Ala Ala Thr Thr Thr Pro Ala Pro Arg
145                 150                 155                 160

Pro Pro Thr Pro Ala Pro Thr Ile Ala Ser Gln Pro Leu Ser Leu Arg
                165                 170                 175

Pro Glu Ala Cys Arg Pro Ala Ala Gly Gly Ala Val His Thr Arg Gly
            180                 185                 190

Leu Asp Phe Ala Cys Asp Ile Tyr Ile Trp Ala Pro Leu Ala Gly Thr
        195                 200                 205

Cys Gly Val Leu Leu Leu Ser Leu Val Ile Thr Leu Tyr Cys Lys Arg
    210                 215                 220

Gly Arg Lys Lys Leu Leu Tyr Ile Phe Lys Gln Pro Phe Met Arg Pro
225                 230                 235                 240

Val Gln Thr Thr Gln Glu Glu Asp Gly Cys Ser Cys Arg Phe Pro Glu
                245                 250                 255

Glu Glu Glu Gly Gly Cys Glu Leu Arg Val Lys Phe Ser Arg Ser Ala
            260                 265                 270

Asp Ala Pro Ala Tyr Lys Gln Gly Gln Asn Gln Leu Tyr Asn Glu Leu
        275                 280                 285

Asn Leu Gly Arg Arg Glu Glu Tyr Asp Val Leu Asp Lys Arg Arg Gly
    290                 295                 300

Arg Asp Pro Glu Met Gly Gly Lys Pro Arg Arg Lys Asn Pro Gln Glu
305                 310                 315                 320

Gly Leu Tyr Asn Glu Leu Gln Lys Asp Lys Met Ala Glu Ala Tyr Ser
                325                 330                 335

Glu Ile Gly Met Lys Gly Glu Arg Arg Arg Gly Lys Gly His Asp Gly
            340                 345                 350

Leu Tyr Gln Gly Leu Ser Thr Ala Thr Lys Asp Thr Tyr Asp Ala Leu
        355                 360                 365

His Met Gln Ala Leu Pro Pro Arg
    370                 375
```

```
<210> SEQ ID NO 161
<211> LENGTH: 1128
<212> TYPE: DNA
<213> ORGANISM: Artificial Sequence
<220> FEATURE:
<223> OTHER INFORMATION: RJ144 CAR (A7/CD8 TM/4-1BB/CD3zeta)

<400> SEQUENCE: 161

atgcttctgc tcgtgacaag cctgctgctg tgcgagctgc cccaccctgc ctttctgctg     60

atccctgagg tgcagctggt tgaatctggc ggaggactgg ttcagcctgg cggatctctg    120

agactgtctt gtgccgccag cggcttcacc ttcagcaact acggcatgag ctgggtccga    180

caggcccctg gaaaaggcct tgagtggatc ggctacatct accacaccgg caacacctac    240

tacaacccca gcctgaagtc cagagtgacc atcagccggg acaacagcaa gaacaccctg    300

tacctgcaga tgaacagcct gagagccgag gacaccgcca tctactactg tgccagagaa    360

ggcgtgatgg gcggctacca cacagacccc aattactact actatggcat ggacgtgtgg    420

ggccagggca ccacagtgac agtttcttct gcggccgcaa ccactactcc ggcacctagg    480
```

```
cccccactc cggcaccgac cattgcatca caaccactga gtcttagacc tgaagcctgt    540

cgacccgcag ctggggggc agtccacaca cggggattgg atttcgcctg cgatatatac    600

atttgggcgc cactggcagg cacctgcggg gtcctgctct tgtcccttgt catcaccctg    660

tactgtaaga gaggaagaaa gaagttgttg tatattttca aacagccatt catgaggccg    720

gtccagacca ctcaggagga ggatggatgc agttgccgct ttccggaaga ggaagagggt    780

gggtgtgaac tccgagttaa attttctcgc agtgctgatg ccccagcgta taaacagggt    840

cagaaccaac tgtataatga actcaatttg ggaggcgag aggagtatga tgtattggac    900

aagcggcggg ggcgggatcc tgaaatgggc ggtaagccaa ggcgcaagaa tccacaggag    960

ggtttgtata atgagttgca gaaggataaa atggcggaag cgtattcaga aatcggaatg   1020

aagggagagc gccgcagagg gaaagggcat gatggcctct accaaggttt gtcaacagcg   1080

accaaggata cctatgacgc acttcatatg caagcactgc cccccagg               1128
```

<210> SEQ ID NO 162
<211> LENGTH: 372
<212> TYPE: DNA
<213> ORGANISM: Artificial Sequence
<220> FEATURE:
<223> OTHER INFORMATION: D92 binder

<400> SEQUENCE: 162

```
gaggtgcagc tggttgaatc tggcggagga ctggttcagc ctggcggatc tctgagactg     60

agctgtgtgg ccagcggctt cacctttagc agctacggca tgcactgggt ccgacaggca    120

cctggcaaag gcctggaatg gatcggctac agctactaca gcggcagcac ctactacaac    180

cccagcctga agtccctggt caccatcagc agagacaaca gcaagaacac cctgtacctg    240

cagatgaaca gcctgagagc cgaggacacc gccacctact attgtgccag agatggcagc    300

agctggtaca gcttccccta ctactatggc atggacgtgt ggggccaggg caccacagtg    360

acagtttctt ct                                                        372
```

<210> SEQ ID NO 163
<211> LENGTH: 372
<212> TYPE: PRT
<213> ORGANISM: Artificial Sequence
<220> FEATURE:
<223> OTHER INFORMATION: RJ145 CAR (D92/CD8 TM/4-1BB/CD3zeta)

<400> SEQUENCE: 163

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Val Ala Ser Gly
        35                  40                  45

Phe Thr Phe Ser Ser Tyr Gly Met His Trp Val Arg Gln Ala Pro Gly
    50                  55                  60

Lys Gly Leu Glu Trp Ile Gly Tyr Ser Tyr Tyr Ser Gly Ser Thr Tyr
65                  70                  75                  80

Tyr Asn Pro Ser Leu Lys Ser Leu Val Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Thr Tyr Tyr Cys Ala Arg Asp Gly Ser Ser Trp Tyr Ser Phe Pro
        115                 120                 125
```

Tyr Tyr Tyr Gly Met Asp Val Trp Gly Gln Gly Thr Thr Val Thr Val
130 135 140

Ser Ser Ala Ala Ala Thr Thr Thr Pro Ala Pro Arg Pro Pro Thr Pro
145 150 155 160

Ala Pro Thr Ile Ala Ser Gln Pro Leu Ser Leu Arg Pro Glu Ala Cys
165 170 175

Arg Pro Ala Ala Gly Gly Ala Val His Thr Arg Gly Leu Asp Phe Ala
180 185 190

Cys Asp Ile Tyr Ile Trp Ala Pro Leu Ala Gly Thr Cys Gly Val Leu
195 200 205

Leu Leu Ser Leu Val Ile Thr Leu Tyr Cys Lys Arg Gly Arg Lys Lys
210 215 220

Leu Leu Tyr Ile Phe Lys Gln Pro Phe Met Arg Pro Val Gln Thr Thr
225 230 235 240

Gln Glu Glu Asp Gly Cys Ser Cys Arg Phe Pro Glu Glu Glu Glu Gly
245 250 255

Gly Cys Glu Leu Arg Val Lys Phe Ser Arg Ser Ala Asp Ala Pro Ala
260 265 270

Tyr Lys Gln Gly Gln Asn Gln Leu Tyr Asn Glu Leu Asn Leu Gly Arg
275 280 285

Arg Glu Glu Tyr Asp Val Leu Asp Lys Arg Arg Gly Arg Asp Pro Glu
290 295 300

Met Gly Gly Lys Pro Arg Arg Lys Asn Pro Gln Glu Gly Leu Tyr Asn
305 310 315 320

Glu Leu Gln Lys Asp Lys Met Ala Glu Ala Tyr Ser Glu Ile Gly Met
325 330 335

Lys Gly Glu Arg Arg Arg Gly Lys Gly His Asp Gly Leu Tyr Gln Gly
340 345 350

Leu Ser Thr Ala Thr Lys Asp Thr Tyr Asp Ala Leu His Met Gln Ala
355 360 365

Leu Pro Pro Arg
370

<210> SEQ ID NO 164
<211> LENGTH: 1116
<212> TYPE: DNA
<213> ORGANISM: Artificial Sequence
<220> FEATURE:
<223> OTHER INFORMATION: RJ145 CAR (D92/CD8 TM/4-1BB/CD3zeta)

<400> SEQUENCE: 164
atgcttctgc tcgtgacaag cctgctgctg tgcgagctgc cccaccctgc ctttctgctg 60
atccctgagg tgcagctggt tgaatctggc ggaggactgg ttcagcctgg cggatctctg 120
agactgagct gtgtggccag cggcttcacc tttagcagct acggcatgca ctgggtccga 180
caggcacctg gcaaaggcct ggaatggatc ggctacagct actacagcgg cagcacctac 240
tacaacccca gcctgaagtc cctggtcacc atcagcagag acaacagcaa gaacaccctg 300
tacctgcaga tgaacagcct gagagccgag gacaccgcca cctactattg tgccagagat 360
ggcagcagct ggtacagctt cccctactac tatggcatgg acgtgtgggg ccagggcacc 420
acagtgacag tttcttctgc ggccgcaacc actactccgg cacctaggcc ccccactccg 480
gcaccgacca ttgcatcaca accactgagt cttagacctg aagcctgtcg acccgcagct 540 ggggggcag tccacacacg ggattggat ttcgcctgcg atatatacat ttgggcgcca 600
ctggcaggca cctgcggggt cctgctcttg tcccttgtca tcaccctgta ctgtaagaga 660
ggaagaaaga agttgttgta tattttcaaa cagccattca tgaggccggt ccagaccact 720
caggaggagg atggatgcag ttgccgcttt ccggaagagg aagagggtgg gtgtgaactc 780
cgagttaaat tttctcgcag tgctgatgcc ccagcgtata aacagggtca gaaccaactg 840
tataatgaac tcaatttggg gaggcgagag gagtatgatg tattggacaa gcggcggggg 900
cgggatcctg aaatgggcgg taagccaagg cgcaagaatc cacaggaggg tttgtataat 960
gagttgcaga aggataaaat ggcggaagcg tattcagaaa tcggaatgaa gggagagcgc 1020
cgcagaggga aagggcatga tggcctctac caaggtttgt caacagcgac caaggatacc 1080
tatgacgcac ttcatatgca agcactgccc cccagg 1116

<210> SEQ ID NO 165
<211> LENGTH: 339
<212> TYPE: DNA
<213> ORGANISM: Artificial Sequence
<220> FEATURE:
<223> OTHER INFORMATION: D8 binder

<400> SEQUENCE: 165
gaggtgcagc tggttgaatc tggcggagga ctggttcagc ctggcggatc tctgagactg 60
tcttgtgccg ccagcggctt caccttcagc aactacggca tgagctgggt ccgacaggcc 120
cctggaaaag ccctggaatg gatcggcgag atcaaccaca gcggcagcac caactacaac 180
cccagcctga agtccagagt gaccatcagc cgggacaaca gcaagaacac cctgtacctg 240
cagatgaaca gcctgagagc cgaggacacc gccatctact actgtagagg cggctgggtc 300
ggatattggg gccagggaac actggtcacc gtgtctagt 339

<210> SEQ ID NO 166
<211> LENGTH: 361
<212> TYPE: PRT
<213> ORGANISM: Artificial Sequence
<220> FEATURE:
<223> OTHER INFORMATION: RJ146 CAR (D8/CD8 TM/4-1BB/CD3zeta)

<400> SEQUENCE: 166

Met Leu Leu Leu Val Thr Ser Leu Leu Leu Cys Glu Leu Pro His Pro
1 5 10 15

Ala Phe Leu Leu Ile Pro Glu Val Gln Leu Val Glu Ser Gly Gly Gly
20 25 30

Leu Val Gln Pro Gly Gly Ser Leu Arg Leu Ser Cys Ala Ala Ser Gly
35 40 45

Phe Thr Phe Ser Asn Tyr Gly Met Ser Trp Val Arg Gln Ala Pro Gly
50 55 60

Lys Ala Leu Glu Trp Ile Gly Glu Ile Asn His Ser Gly Ser Thr Asn
65 70 75 80

Tyr Asn Pro Ser Leu Lys Ser Arg Val Thr Ile Ser Arg Asp Asn Ser
85 90 95

Lys Asn Thr Leu Tyr Leu Gln Met Asn Ser Leu Arg Ala Glu Asp Thr
100 105 110

Ala Ile Tyr Tyr Cys Arg Gly Gly Trp Val Gly Tyr Trp Gly Gln Gly
115 120 125

Thr Leu Val Thr Val Ser Ser Ala Ala Ala Thr Thr Thr Pro Ala Pro
130 135 140

Arg Pro Pro Thr Pro Ala Pro Thr Ile Ala Ser Gln Pro Leu Ser Leu
145 150 155 160

Arg Pro Glu Ala Cys Arg Pro Ala Ala Gly Gly Ala Val His Thr Arg
                165                 170                 175

Gly Leu Asp Phe Ala Cys Asp Ile Tyr Ile Trp Ala Pro Leu Ala Gly
            180                 185                 190

Thr Cys Gly Val Leu Leu Leu Ser Leu Val Ile Thr Leu Tyr Cys Lys
        195                 200                 205

Arg Gly Arg Lys Lys Leu Leu Tyr Ile Phe Lys Gln Pro Phe Met Arg
    210                 215                 220

Pro Val Gln Thr Thr Gln Glu Glu Asp Gly Cys Ser Cys Arg Phe Pro
225                 230                 235                 240

Glu Glu Glu Glu Gly Gly Cys Glu Leu Arg Val Lys Phe Ser Arg Ser
                245                 250                 255

Ala Asp Ala Pro Ala Tyr Lys Gln Gly Gln Asn Gln Leu Tyr Asn Glu
            260                 265                 270

Leu Asn Leu Gly Arg Arg Glu Glu Tyr Asp Val Leu Asp Lys Arg Arg
        275                 280                 285

Gly Arg Asp Pro Glu Met Gly Gly Lys Pro Arg Arg Lys Asn Pro Gln
    290                 295                 300

Glu Gly Leu Tyr Asn Glu Leu Gln Lys Asp Lys Met Ala Glu Ala Tyr
305                 310                 315                 320

Ser Glu Ile Gly Met Lys Gly Glu Arg Arg Arg Gly Lys Gly His Asp
                325                 330                 335

Gly Leu Tyr Gln Gly Leu Ser Thr Ala Thr Lys Asp Thr Tyr Asp Ala
            340                 345                 350

Leu His Met Gln Ala Leu Pro Pro Arg
        355                 360

<210> SEQ ID NO 167
<211> LENGTH: 1083
<212> TYPE: DNA
<213> ORGANISM: Artificial Sequence
<220> FEATURE:
<223> OTHER INFORMATION: RJ146 CAR (D8/CD8 TM/4-1BB/CD3zeta)

<400> SEQUENCE: 167
atgcttctgc tcgtgacaag cctgctgctg tgcgagctgc cccaccctgc ctttctgctg 60
atccctgagg tgcagctggt tgaatctggc ggaggactgg ttcagcctgg cggatctctg 120
agactgtctt gtgccgccag cggcttcacc ttcagcaact acggcatgag ctgggtccga 180
caggcccctg gaaaagccct ggaatggatc ggcgagatca accacagcgg cagcaccaac 240
tacaacccca gcctgaagtc cagagtgacc atcagccggg acaacagcaa gaacaccctg 300
tacctgcaga tgaacagcct gagagccgag gacaccgcca tctactactg tagaggcggc 360
tgggtcggat attggggcca gggaacactg gtcaccgtgt ctagtgcggc cgcaaccact 420
actccggcac ctaggccccc cactccggca ccgaccattg catcacaacc actgagtctt 480
agacctgaag cctgtcgacc cgcagctggg ggggcagtcc acacacgggg attggatttc 540
gcctgcgata tatacatttg ggcgccactg gcaggcacct gcggggtcct gctcttgtcc 600
cttgtcatca ccctgtactg taagagagga agaaagaagt tgttgtatat tttcaaacag 660
ccattcatga ggccggtcca gaccactcag gaggaggatg gatgcagttg ccgctttccg 720
gaagaggaag agggtgggtg tgaactccga gttaaatttt ctcgcagtgc tgatgcccca 780
gcgtataaac agggtcagaa ccaactgtat aatgaactca atttggggag gcgagaggag 840
tatgatgtat tggacaagcg gcgggggcgg gatcctgaaa tgggcggtaa gccaaggcgc 900

```
aagaatccac aggagggttt gtataatgag ttgcagaagg ataaaatggc ggaagcgtat    960

tcagaaatcg gaatgaaggg agagcgccgc agagggaaag ggcatgatgg cctctaccaa   1020

ggtttgtcaa cagcgaccaa ggatacctat gacgcacttc atatgcaagc actgcccccc   1080

agg                                                                 1083


<210> SEQ ID NO 168
<211> LENGTH: 384
<212> TYPE: DNA
<213> ORGANISM: artifiical sequence
<220> FEATURE:
<223> OTHER INFORMATION: F11 binder

<400> SEQUENCE: 168

gaggtgcagc tggttgaatc tggcggagga ctggttcagc ctggcggatc tctgagactg     60

tcttgtgccg ccagcggctt caccttcagc aactacggca tgagctgggt ccgacaggct    120

cctggacaag gcttggagtg ggtgtcctac atcagcaatg gcggcggaac catgtactac    180

gccgacagcg tgaagggcag attcaccatc agccgggaca acagcaagaa caccctgtac    240

ctgcagatga acagcctgag agccgaggac accgccacct actactgtac aagagcccct    300

tactgctctg gcggcgactg ctaccctatg agcacacacg agctggattc ttggggccag    360

ggcacactgg tcacagtgtc atct                                           384


<210> SEQ ID NO 169
<211> LENGTH: 376
<212> TYPE: PRT
<213> ORGANISM: Artificial Sequence
<220> FEATURE:
<223> OTHER INFORMATION: RJ147 CAR (F11/CD8 TM/4-1BB/CD3zeta)

<400> SEQUENCE: 169

Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Asn Tyr Gly Met Ser Trp Val Arg Gln Ala Pro Gly
    50                  55                  60

Gln Gly Leu Glu Trp Val Ser Tyr Ile Ser Asn Gly Gly Gly Thr Met
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Thr Tyr Tyr Cys Thr Arg Ala Pro Tyr Cys Ser Gly Gly Asp
        115                 120                 125

Cys Tyr Pro Met Ser Thr His Glu Leu Asp Ser Trp Gly Gln Gly Thr
    130                 135                 140

Leu Val Thr Val Ser Ser Ala Ala Ala Thr Thr Thr Pro Ala Pro Arg
145                 150                 155                 160

Pro Pro Thr Pro Ala Pro Thr Ile Ala Ser Gln Pro Leu Ser Leu Arg
                165                 170                 175

Pro Glu Ala Cys Arg Pro Ala Ala Gly Gly Ala Val His Thr Arg Gly
            180                 185                 190
```

```
Leu Asp Phe Ala Cys Asp Ile Tyr Ile Trp Ala Pro Leu Ala Gly Thr
        195                 200                 205

Cys Gly Val Leu Leu Leu Ser Leu Val Ile Thr Leu Tyr Cys Lys Arg
    210                 215                 220

Gly Arg Lys Lys Leu Leu Tyr Ile Phe Lys Gln Pro Phe Met Arg Pro
225                 230                 235                 240

Val Gln Thr Thr Gln Glu Glu Asp Gly Cys Ser Cys Arg Phe Pro Glu
                245                 250                 255

Glu Glu Glu Gly Gly Cys Glu Leu Arg Val Lys Phe Ser Arg Ser Ala
            260                 265                 270

Asp Ala Pro Ala Tyr Lys Gln Gly Gln Asn Gln Leu Tyr Asn Glu Leu
        275                 280                 285

Asn Leu Gly Arg Arg Glu Glu Tyr Asp Val Leu Asp Lys Arg Arg Gly
    290                 295                 300

Arg Asp Pro Glu Met Gly Gly Lys Pro Arg Arg Lys Asn Pro Gln Glu
305                 310                 315                 320

Gly Leu Tyr Asn Glu Leu Gln Lys Asp Lys Met Ala Glu Ala Tyr Ser
                325                 330                 335

Glu Ile Gly Met Lys Gly Glu Arg Arg Arg Gly Lys Gly His Asp Gly
            340                 345                 350

Leu Tyr Gln Gly Leu Ser Thr Ala Thr Lys Asp Thr Tyr Asp Ala Leu
        355                 360                 365

His Met Gln Ala Leu Pro Pro Arg
    370                 375
```

<210> SEQ ID NO 170
<211> LENGTH: 1128
<212> TYPE: DNA
<213> ORGANISM: Artificial Sequence
<220> FEATURE:
<223> OTHER INFORMATION: RJ147 CAR (F11/CD8 TM/4-1BB/CD3zeta)

<400> SEQUENCE: 170

```
atgcttctgc tcgtgacaag cctgctgctg tgcgagctgc cccaccctgc ctttctgctg     60

atccctgagg tgcagctggt tgaatctggc ggaggactgg ttcagcctgg cggatctctg    120

agactgtctt gtgccgccag cggcttcacc ttcagcaact acggcatgag ctgggtccga    180

caggctcctg gacaaggctt ggagtgggtg tcctacatca gcaatggcgg cggaaccatg    240

tactacgccg acagcgtgaa gggcagattc accatcagcc gggacaacag caagaacacc    300

ctgtacctgc agatgaacag cctgagagcc gaggacaccg ccacctacta ctgtacaaga    360

gccccttact gctctggcgg cgactgctac cctatgagca cacacgagct ggattcttgg    420

ggccagggca cactggtcac agtgtcatct gcggccgcaa ccactactcc ggcacctagg    480

ccccccactc cggcaccgac cattgcatca caaccactga gtcttagacc tgaagcctgt    540

cgacccgcag ctgggggggc agtccacaca cggggattgg atttcgcctg cgatatatac    600

atttgggcgc cactggcagg cacctgcggg gtcctgctct tgtcccttgt catcaccctg    660

tactgtaaga gaggaagaaa gaagttgttg tatattttca aacagccatt catgaggccg    720

gtccagacca ctcaggagga ggatggatgc agttgccgct ttccggaaga ggaagagggt    780

gggtgtgaac tccgagttaa attttctcgc agtgctgatg ccccagcgta taaacagggt    840

cagaaccaac tgtataatga actcaatttg gggaggcgag aggagtatga tgtattggac    900

aagcggcggg ggcgggatcc tgaaatgggc ggtaagccaa ggcgcaagaa tccacaggag    960

ggtttgtata atgagttgca gaaggataaa atggcggaag cgtattcaga aatcggaatg   1020
```

aagggagagc gccgcagagg gaaagggcat gatggcctct accaaggttt gtcaacagcg 1080
accaaggata cctatgacgc acttcatatg caagcactgc cccccagg 1128

<210> SEQ ID NO 171
<211> LENGTH: 348
<212> TYPE: DNA
<213> ORGANISM: Artificial Sequence
<220> FEATURE:
<223> OTHER INFORMATION: C52 binder

<400> SEQUENCE: 171
gaggtgcagc tggttgaatc tggcggagga ctggttcagc ctggcggatc tctgagactg 60
tcttgtgccg ccagcggctt taccctgagc agctactgga tgagctgggt ccgacaggcc 120
cctggcaaag gactggaatg gatcggcgtg atctactaca gcggcgccac ctactacaac 180
cccagcctga agtctctggt caccatcagc cgggacaaca gcaagaacac cctgtacctg 240
cagatgaaca gcctgagagc cgaggacacc gccgtgtact attgtgctag aggcgccctg 300
gactacttcg acctttgggg acaaggcgcc ctcgtgacag tctcttct 348

<210> SEQ ID NO 172
<211> LENGTH: 364
<212> TYPE: PRT
<213> ORGANISM: Artificial Sequence
<220> FEATURE:
<223> OTHER INFORMATION: RJ148 CAR (C52/CD8 TM/4-1BB/CD3zeta)

<400> SEQUENCE: 172

Met Leu Leu Leu Val Thr Ser Leu Leu Leu Cys Glu Leu Pro His Pro
1 5 10 15

Ala Phe Leu Leu Ile Pro Glu Val Gln Leu Val Glu Ser Gly Gly Gly
20 25 30

Leu Val Gln Pro Gly Gly Ser Leu Arg Leu Ser Cys Ala Ala Ser Gly
35 40 45

Phe Thr Leu Ser Ser Tyr Trp Met Ser Trp Val Arg Gln Ala Pro Gly
50 55 60

Lys Gly Leu Glu Trp Ile Gly Val Ile Tyr Tyr Ser Gly Ala Thr Tyr
65 70 75 80

Tyr Asn Pro Ser Leu Lys Ser Leu Val Thr Ile Ser Arg Asp Asn Ser
85 90 95

Lys Asn Thr Leu Tyr Leu Gln Met Asn Ser Leu Arg Ala Glu Asp Thr
100 105 110

Ala Val Tyr Tyr Cys Ala Arg Gly Ala Leu Asp Tyr Phe Asp Leu Trp
115 120 125

Gly Gln Gly Ala Leu Val Thr Val Ser Ser Ala Ala Ala Thr Thr Thr
130 135 140

Pro Ala Pro Arg Pro Pro Thr Pro Ala Pro Thr Ile Ala Ser Gln Pro
145 150 155 160

Leu Ser Leu Arg Pro Glu Ala Cys Arg Pro Ala Ala Gly Gly Ala Val
165 170 175

His Thr Arg Gly Leu Asp Phe Ala Cys Asp Ile Tyr Ile Trp Ala Pro
180 185 190

Leu Ala Gly Thr Cys Gly Val Leu Leu Leu Ser Leu Val Ile Thr Leu
195 200 205

Tyr Cys Lys Arg Gly Arg Lys Lys Leu Leu Tyr Ile Phe Lys Gln Pro
210 215 220

```
Phe Met Arg Pro Val Gln Thr Thr Gln Glu Glu Asp Gly Cys Ser Cys
225                 230                 235                 240

Arg Phe Pro Glu Glu Glu Glu Gly Gly Cys Glu Leu Arg Val Lys Phe
                245                 250                 255

Ser Arg Ser Ala Asp Ala Pro Ala Tyr Lys Gln Gly Gln Asn Gln Leu
            260                 265                 270

Tyr Asn Glu Leu Asn Leu Gly Arg Arg Glu Glu Tyr Asp Val Leu Asp
        275                 280                 285

Lys Arg Arg Gly Arg Asp Pro Glu Met Gly Gly Lys Pro Arg Arg Lys
    290                 295                 300

Asn Pro Gln Glu Gly Leu Tyr Asn Glu Leu Gln Lys Asp Lys Met Ala
305                 310                 315                 320

Glu Ala Tyr Ser Glu Ile Gly Met Lys Gly Glu Arg Arg Arg Gly Lys
                325                 330                 335

Gly His Asp Gly Leu Tyr Gln Gly Leu Ser Thr Ala Thr Lys Asp Thr
            340                 345                 350

Tyr Asp Ala Leu His Met Gln Ala Leu Pro Pro Arg
        355                 360
```

<210> SEQ ID NO 173
<211> LENGTH: 1092
<212> TYPE: DNA
<213> ORGANISM: Artificial Sequence
<220> FEATURE:
<223> OTHER INFORMATION: RJ148 CAR (C52/CD8 TM/4-1BB/CD3zeta)

<400> SEQUENCE: 173

```
atgcttctgc tcgtgacaag cctgctgctg tgcgagctgc cccaccctgc ctttctgctg     60

atccctgagg tgcagctggt tgaatctggc ggaggactgg ttcagcctgg cggatctctg    120

agactgtctt gtgccgccag cggctttacc ctgagcagct actggatgag ctgggtccga    180

caggcccctg gcaaaggact ggaatggatc ggcgtgatct actacagcgg cgccacctac    240

tacaacccca gcctgaagtc tctggtcacc atcagccggg acaacagcaa gaacaccctg    300

tacctgcaga tgaacagcct gagagccgag gacaccgccg tgtactattg tgctagaggc    360

gccctggact acttcgacct ttggggacaa ggcgccctcg tgacagtctc ttctgcggcc    420

gcaaccacta ctccggcacc taggcccccc actccggcac cgaccattgc atcacaacca    480

ctgagtctta gacctgaagc ctgtcgaccc gcagctgggg gggcagtcca cacacgggga    540

ttggatttcg cctgcgatat atacatttgg gcgccactgg caggcacctg cggggtcctg    600

ctcttgtccc ttgtcatcac cctgtactgt aagagaggaa gaaagaagtt gttgtatatt    660

ttcaaacagc cattcatgag gccggtccag accactcagg aggaggatgg atgcagttgc    720

cgctttccgg aagaggaaga gggtgggtgt gaactccgag ttaaattttc tcgcagtgct    780

gatgccccag cgtataaaca gggtcagaac caactgtata atgaactcaa tttggggagg    840

cgagaggagt atgatgtatt ggacaagcgg cgggggcggg atcctgaaat gggcggtaag    900

ccaaggcgca agaatccaca ggagggtttg tataatgagt tgcagaagga taaaatggcg    960

gaagcgtatt cagaaatcgg aatgaaggga gagcgccgca gagggaaagg gcatgatggc   1020

ctctaccaag gtttgtcaac agcgaccaag gatacctatg acgcacttca tatgcaagca   1080

ctgcccccca gg                                                       1092
```

<210> SEQ ID NO 174
<211> LENGTH: 108
<212> TYPE: PRT

<213> ORGANISM: Artificial Sequence
<220> FEATURE:
<223> OTHER INFORMATION: H4 L chain

<400> SEQUENCE: 174

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Gly Val Tyr Tyr Cys Leu Gln Ile Thr His Trp Pro His
                85                  90                  95

Thr Phe Gly Gln Gly Thr Lys Leu Glu Ile Lys Arg
            100                 105

<210> SEQ ID NO 175
<211> LENGTH: 324
<212> TYPE: DNA
<213> ORGANISM: Artificial Sequence
<220> FEATURE:
<223> OTHER INFORMATION: H4 L chain

<400> SEQUENCE: 175
gacatccaga tgacacagag ccctagcagc ctgtctgcca gcgtgggaga cagagtgacc     60
atcacctgta gagccagcca gagcatcagc agctacctga actggtatca gcagaagccc    120
ggcaaggccc ctaaactgct gatctatgcc gccagctctc tgcagtctgg cgtgccatct    180
agattttccg gcagcggctc tggcaccgac ttcaccctga ccatatctag cctgcagcct    240
gaggacgtgg gcgtgtacta ctgcctgcag atcacacact ggccccacac atttggccag    300
ggcaccaagc tggaaatcaa gaga                                           324

<210> SEQ ID NO 176
<211> LENGTH: 131
<212> TYPE: PRT
<213> ORGANISM: Artificial Sequence
<220> FEATURE:
<223> OTHER INFORMATION: H4 H chain

<400> SEQUENCE: 176

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Met Tyr Tyr Cys
                85                  90                  95

Ala Arg Asp Ala Pro Asp Leu Leu Ala Val Pro Thr Val Ile Phe Ser
            100                 105                 110

```
Gly Tyr His Tyr Gly Ala Asp Val Trp Gly Gln Gly Ala Thr Val Thr
        115                 120                 125

Val Ser Ser
    130
```

<210> SEQ ID NO 177
<211> LENGTH: 393
<212> TYPE: DNA
<213> ORGANISM: Artificial Sequence
<220> FEATURE:
<223> OTHER INFORMATION: H4 H chain

<400> SEQUENCE: 177

```
caagttcagc tggttgaatc tggcggcgga ctggttaagc ctggcggttc tctgagactg     60

agctgtgccg cctccggctt caccttcagc gactactaca tgagctggat cagacaggcc    120

cctggcaaag gcctggaatg ggtgtcctac atcagctcca gcggcagcac catctactac    180

gccgatagcg tgaagggcag attcaccatc agccgggaca acgccaagaa cagcctgtac    240

ctgcagatga actccctgag agccgaggac accgccatgt actattgcgc cagagatgcc    300

cctgacctgc tggctgtgcc taccgtgatc tttagcggct accactacgg cgctgacgtt    360

tggggacaag gcgccacagt gacagtgtct agt                                 393
```

<210> SEQ ID NO 178
<211> LENGTH: 762
<212> TYPE: DNA
<213> ORGANISM: Artificial Sequence
<220> FEATURE:
<223> OTHER INFORMATION: H4LH binder

<400> SEQUENCE: 178

```
gacatccaga tgacacagag ccctagcagc ctgtctgcca gcgtgggaga cagagtgacc     60

atcacctgta gagccagcca gagcatcagc agctacctga actggtatca gcagaagccc    120

ggcaaggccc ctaaactgct gatctatgcc gccagctctc tgcagtctgg cgtgccatct    180

agattttccg gcagcggctc tggcaccgac ttcaccctga ccatatctag cctgcagcct    240

gaggacgtgg gcgtgtacta ctgcctgcag atcacacact ggccccacac atttggccag    300

ggcaccaagc tggaaatcaa gagaggtggc ggaggatctg gcggaggtgg aagcggcgga    360

ggcggatctc aagttcagct ggttgaatct ggcggcggac tggttaagcc tggcggttct    420

ctgagactga gctgtgccgc ctccggcttc accttcagcg actactacat gagctggatc    480

agacaggccc ctggcaaagg cctggaatgg gtgtcctaca tcagctccag cggcagcacc    540

atctactacg ccgatagcgt gaagggcaga ttcaccatca gccgggacaa cgccaagaac    600

agcctgtacc tgcagatgaa ctccctgaga gccgaggaca ccgccatgta ctattgcgcc    660

agagatgccc ctgacctgct ggctgtgcct accgtgatct ttagcggcta ccactacggc    720

gctgacgttt ggggacaagg cgccacagtg acagtgtcta gt                       762
```

<210> SEQ ID NO 179
<211> LENGTH: 762
<212> TYPE: DNA
<213> ORGANISM: Artificial Sequence
<220> FEATURE:
<223> OTHER INFORMATION: H4HL binder

<400> SEQUENCE: 179

```
caagttcagc tggttgaatc tggcggcgga ctggttaagc ctggcggttc tctgagactg     60
```

```
agctgtgccg cctccggctt caccttcagc gactactaca tgagctggat cagacaggcc    120

cctggcaaag gcctggaatg ggtgtcctac atcagctcca gcggcagcac catctactac    180

gccgatagcg tgaagggcag attcaccatc agccgggaca acgccaagaa cagcctgtac    240

ctgcagatga actccctgag agccgaggac accgccatgt actattgcgc cagagatgcc    300

cctgacctgc tggctgtgcc taccgtgatc tttagcggct accactacgg cgctgacgtt    360

tggggacaag gcgccacagt gacagtgtct agtggtggcg gaggatctgg cggaggtgga    420

agcggcggag gcggatctga catccagatg acacagagcc ctagcagcct gtctgccagc    480

gtgggagaca gagtgaccat cacctgtaga gccagccaga gcatcagcag ctacctgaac    540

tggtatcagc agaagcccgg caaggcccct aaactgctga tctatgccgc cagctctctg    600

cagtctggcg tgccatctag attttccggc agcggctctg gcaccgactt caccctgacc    660

atatctagcc tgcagcctga ggacgtgggc gtgtactact gcctgcagat cacacactgg    720

ccccacacat ttggccaggg caccaagctg gaaatcaaga ga                        762
```

```
<210> SEQ ID NO 180
<211> LENGTH: 502
<212> TYPE: PRT
<213> ORGANISM: Artificial Sequence
<220> FEATURE:
<223> OTHER INFORMATION: RJ149LH CAR (H4LH/CD8 TM/4-1BB/CD3zeta)

<400> SEQUENCE: 180

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Ser Ile Ser Ser Tyr Leu Asn Trp Tyr Gln Gln Lys Pro Gly Lys
    50                  55                  60

Ala Pro Lys Leu Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Val Gly Val Tyr Tyr Cys Leu Gln
            100                 105                 110

Ile Thr His Trp Pro His Thr Phe Gly Gln Gly Thr Lys Leu Glu Ile
        115                 120                 125

Lys Arg Gly Gly Gly Gly Ser Gly Gly Gly Gly Ser Gly Gly Gly Gly
    130                 135                 140

Ser Gln Val Gln Leu Val Glu Ser Gly Gly Gly Leu Val Lys Pro Gly
145                 150                 155                 160

Gly Ser Leu Arg Leu Ser Cys Ala Ala Ser Gly Phe Thr Phe Ser Asp
                165                 170                 175

Tyr Tyr Met Ser Trp Ile Arg Gln Ala Pro Gly Lys Gly Leu Glu Trp
            180                 185                 190

Val Ser Tyr Ile Ser Ser Ser Gly Ser Thr Ile Tyr Tyr Ala Asp Ser
        195                 200                 205

Val Lys Gly Arg Phe Thr Ile Ser Arg Asp Asn Ala Lys Asn Ser Leu
    210                 215                 220

Tyr Leu Gln Met Asn Ser Leu Arg Ala Glu Asp Thr Ala Met Tyr Tyr
225                 230                 235                 240
```

```
Cys Ala Arg Asp Ala Pro Asp Leu Leu Ala Val Pro Thr Val Ile Phe
                245                 250                 255

Ser Gly Tyr His Tyr Gly Ala Asp Val Trp Gly Gln Gly Ala Thr Val
            260                 265                 270

Thr Val Ser Ser Ala Ala Ala Thr Thr Thr Pro Ala Pro Arg Pro Pro
        275                 280                 285

Thr Pro Ala Pro Thr Ile Ala Ser Gln Pro Leu Ser Leu Arg Pro Glu
    290                 295                 300

Ala Cys Arg Pro Ala Ala Gly Gly Ala Val His Thr Arg Gly Leu Asp
305                 310                 315                 320

Phe Ala Cys Asp Ile Tyr Ile Trp Ala Pro Leu Ala Gly Thr Cys Gly
                325                 330                 335

Val Leu Leu Leu Ser Leu Val Ile Thr Leu Tyr Cys Lys Arg Gly Arg
            340                 345                 350

Lys Lys Leu Leu Tyr Ile Phe Lys Gln Pro Phe Met Arg Pro Val Gln
        355                 360                 365

Thr Thr Gln Glu Glu Asp Gly Cys Ser Cys Arg Phe Pro Glu Glu Glu
    370                 375                 380

Glu Gly Gly Cys Glu Leu Arg Val Lys Phe Ser Arg Ser Ala Asp Ala
385                 390                 395                 400

Pro Ala Tyr Lys Gln Gly Gln Asn Gln Leu Tyr Asn Glu Leu Asn Leu
                405                 410                 415

Gly Arg Arg Glu Glu Tyr Asp Val Leu Asp Lys Arg Arg Gly Arg Asp
            420                 425                 430

Pro Glu Met Gly Gly Lys Pro Arg Arg Lys Asn Pro Gln Glu Gly Leu
        435                 440                 445

Tyr Asn Glu Leu Gln Lys Asp Lys Met Ala Glu Ala Tyr Ser Glu Ile
    450                 455                 460

Gly Met Lys Gly Glu Arg Arg Arg Gly Lys Gly His Asp Gly Leu Tyr
465                 470                 475                 480

Gln Gly Leu Ser Thr Ala Thr Lys Asp Thr Tyr Asp Ala Leu His Met
                485                 490                 495

Gln Ala Leu Pro Pro Arg
            500
```

<210> SEQ ID NO 181
<211> LENGTH: 1506
<212> TYPE: DNA
<213> ORGANISM: Artificial Sequence
<220> FEATURE:
<223> OTHER INFORMATION: RJ149LH CAR (H4LH/CD8 TM/4-1BB/CD3zeta)

<400> SEQUENCE: 181

```
atgcttctgc tcgtgacaag cctgctgctg tgcgagctgc cccaccctgc ctttctgctg      60

atccctgaca tccagatgac acagagccct agcagcctgt ctgccagcgt gggagacaga     120

gtgaccatca cctgtagagc cagccagagc atcagcagct acctgaactg gtatcagcag     180

aagcccggca aggcccctaa actgctgatc tatgccgcca gctctctgca gtctggcgtg     240

ccatctagat tttccggcag cggctctggc accgacttca ccctgaccat atctagcctg     300

cagcctgagg acgtgggcgt gtactactgc ctgcagatca cacactggcc ccacacattt     360

ggccagggca ccaagctgga aatcaagaga ggtggcggag gatctggcgg aggtggaagc     420

ggcggaggcg gatctcaagt tcagctggtt gaatctggcg gcggactggt taagcctggc     480

ggttctctga gactgagctg tgccgcctcc ggcttcacct tcagcgacta ctacatgagc     540
```

```
tggatcagac aggcccctgg caaaggcctg gaatgggtgt cctacatcag ctccagcggc    600

agcaccatct actacgccga tagcgtgaag ggcagattca ccatcagccg ggacaacgcc    660

aagaacagcc tgtacctgca gatgaactcc ctgagagccg aggacaccgc catgtactat    720

tgcgccagag atgcccctga cctgctggct gtgcctaccg tgatctttag cggctaccac    780

tacggcgctg acgtttgggg acaaggcgcc acagtgacag tgtctagtgc ggccgcaacc    840

actactccgg cacctaggcc ccccactccg gcaccgacca ttgcatcaca accactgagt    900

cttagacctg aagcctgtcg acccgcagct ggggggcag tccacacacg gggattggat     960

ttcgcctgcg atatatacat ttgggcgcca ctggcaggca cctgcggggt cctgctcttg   1020

tcccttgtca tcaccctgta ctgtaagaga ggaagaaaga agttgttgta tattttcaaa   1080

cagccattca tgaggccggt ccagaccact caggaggagg atggatgcag ttgccgcttt   1140

ccggaagagg aagagggtgg gtgtgaactc cgagttaaat ttctcgcag tgctgatgcc    1200

ccagcgtata aacagggtca gaaccaactg tataatgaac tcaatttggg gaggcgagag   1260

gagtatgatg tattggacaa gcggcggggg cgggatcctg aaatgggcgg taagccaagg   1320

cgcaagaatc cacaggaggg tttgtataat gagttgcaga aggataaaat ggcggaagcg   1380

tattcagaaa tcggaatgaa gggagagcgc cgcagaggga aagggcatga tggcctctac   1440

caaggtttgt caacagcgac caaggatacc tatgacgcac ttcatatgca agcactgccc   1500

cccagg                                                              1506
```

```
<210> SEQ ID NO 182
<211> LENGTH: 502
<212> TYPE: PRT
<213> ORGANISM: Artificial Sequence
<220> FEATURE:
<223> OTHER INFORMATION: RJ149HL CAR (H4HL/CD8 TM/4-1BB/CD3zeta)

<400> SEQUENCE: 182

Met Leu Leu Leu Val Thr Ser Leu Leu Leu Cys Glu Leu Pro His Pro
1               5                   10                  15

Ala Phe Leu Leu Ile Pro Gln Val Gln Leu Val Glu Ser Gly Gly Gly
            20                  25                  30

Leu Val Lys Pro Gly Gly Ser Leu Arg Leu Ser Cys Ala Ala Ser Gly
        35                  40                  45

Phe Thr Phe Ser Asp Tyr Tyr Met Ser Trp Ile Arg Gln Ala Pro Gly
    50                  55                  60

Lys Gly Leu Glu Trp Val Ser Tyr Ile Ser Ser Ser Gly Ser Thr Ile
65                  70                  75                  80

Tyr Tyr Ala Asp Ser Val Lys Gly Arg Phe Thr Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Met Tyr Tyr Cys Ala Arg Asp Ala Pro Asp Leu Leu Ala Val
        115                 120                 125

Pro Thr Val Ile Phe Ser Gly Tyr His Tyr Gly Ala Asp Val Trp Gly
    130                 135                 140

Gln Gly Ala Thr Val Thr Val Ser Ser Gly Gly Gly Gly Ser Gly Gly
145                 150                 155                 160

Gly Gly Ser Gly Gly Gly Gly Ser Asp Ile Gln Met Thr Gln Ser Pro
                165                 170                 175

Ser Ser Leu Ser Ala Ser Val Gly Asp Arg Val Thr Ile Thr Cys Arg
            180                 185                 190
```

```
Ala Ser Gln Ser Ile Ser Ser Tyr Leu Asn Trp Tyr Gln Gln Lys Pro
        195                 200                 205

Gly Lys Ala Pro Lys Leu Leu Ile Tyr Ala Ala Ser Ser Leu Gln Ser
    210                 215                 220

Gly Val Pro Ser Arg Phe Ser Gly Ser Gly Ser Gly Thr Asp Phe Thr
225                 230                 235                 240

Leu Thr Ile Ser Ser Leu Gln Pro Glu Asp Val Gly Val Tyr Tyr Cys
                245                 250                 255

Leu Gln Ile Thr His Trp Pro His Thr Phe Gly Gln Gly Thr Lys Leu
            260                 265                 270

Glu Ile Lys Arg Ala Ala Ala Thr Thr Thr Pro Ala Pro Arg Pro Pro
        275                 280                 285

Thr Pro Ala Pro Thr Ile Ala Ser Gln Pro Leu Ser Leu Arg Pro Glu
    290                 295                 300

Ala Cys Arg Pro Ala Ala Gly Gly Ala Val His Thr Arg Gly Leu Asp
305                 310                 315                 320

Phe Ala Cys Asp Ile Tyr Ile Trp Ala Pro Leu Ala Gly Thr Cys Gly
                325                 330                 335

Val Leu Leu Leu Ser Leu Val Ile Thr Leu Tyr Cys Lys Arg Gly Arg
            340                 345                 350

Lys Lys Leu Leu Tyr Ile Phe Lys Gln Pro Phe Met Arg Pro Val Gln
        355                 360                 365

Thr Thr Gln Glu Glu Asp Gly Cys Ser Cys Arg Phe Pro Glu Glu Glu
    370                 375                 380

Glu Gly Gly Cys Glu Leu Arg Val Lys Phe Ser Arg Ser Ala Asp Ala
385                 390                 395                 400

Pro Ala Tyr Lys Gln Gly Gln Asn Gln Leu Tyr Asn Glu Leu Asn Leu
                405                 410                 415

Gly Arg Arg Glu Glu Tyr Asp Val Leu Asp Lys Arg Arg Gly Arg Asp
            420                 425                 430

Pro Glu Met Gly Gly Lys Pro Arg Arg Lys Asn Pro Gln Glu Gly Leu
        435                 440                 445

Tyr Asn Glu Leu Gln Lys Asp Lys Met Ala Glu Ala Tyr Ser Glu Ile
    450                 455                 460

Gly Met Lys Gly Glu Arg Arg Arg Gly Lys Gly His Asp Gly Leu Tyr
465                 470                 475                 480

Gln Gly Leu Ser Thr Ala Thr Lys Asp Thr Tyr Asp Ala Leu His Met
                485                 490                 495

Gln Ala Leu Pro Pro Arg
            500
```

<210> SEQ ID NO 183
<211> LENGTH: 1506
<212> TYPE: DNA
<213> ORGANISM: Artificial Sequence
<220> FEATURE:
<223> OTHER INFORMATION: RJ149HL CAR (H4HL/CD8 TM/4-1BB/CD3zeta)

<400> SEQUENCE: 183

```
atgcttctgc tcgtgacaag cctgctgctg tgcgagctgc cccaccctgc ctttctgctg      60

atccctcaag ttcagctggt tgaatctggc ggcggactgg ttaagcctgg cggttctctg     120

agactgagct gtgccgcctc cggcttcacc ttcagcgact actacatgag ctggatcaga     180

caggcccctg gcaaaggcct ggaatgggtg tcctacatca gctccagcgg cagcaccatc     240
```

```
tactacgccg atagcgtgaa gggcagattc accatcagcc gggacaacgc caagaacagc    300
ctgtacctgc agatgaactc cctgagagcc gaggacaccg ccatgtacta ttgcgccaga    360
gatgcccctg acctgctggc tgtgcctacc gtgatcttta gcggctacca ctacggcgct    420
gacgtttggg gacaaggcgc cacagtgaca gtgtctagtg gtggcggagg atctggcgga    480
ggtggaagcg gcggaggcgg atctgacatc cagatgacac agagccctag cagcctgtct    540
gccagcgtgg gagacagagt gaccatcacc tgtagagcca gccagagcat cagcagctac    600
ctgaactggt atcagcagaa gcccggcaag gcccctaaac tgctgatcta tgccgccagc    660
tctctgcagt ctggcgtgcc atctagattt tccggcagcg gctctggcac cgacttcacc    720
ctgaccatat ctagcctgca gcctgaggac gtgggcgtgt actactgcct gcagatcaca    780
cactggcccc acacatttgg ccagggcacc aagctggaaa tcaagagagc ggccgcaacc    840
actactccgg cacctaggcc ccccactccg gcaccgacca ttgcatcaca accactgagt    900
cttagacctg aagcctgtcg acccgcagct ggggggggcag tccacacacg gggattggat    960
ttcgcctgcg atatatacat ttgggcgcca ctggcaggca cctgcggggt cctgctcttg   1020
tcccttgtca tcaccctgta ctgtaagaga ggaagaaaga agttgttgta tattttcaaa   1080
cagccattca tgaggccggt ccagaccact caggaggagg atggatgcag ttgccgcttt   1140
ccggaagagg aagagggtgg gtgtgaactc cgagttaaat tttctcgcag tgctgatgcc   1200
ccagcgtata aacagggtca gaaccaactg tataatgaac tcaatttggg gaggcgagag   1260
gagtatgatg tattggacaa gcggcggggg cgggatcctg aaatgggcgg taagccaagg   1320
cgcaagaatc cacaggaggg tttgtataat gagttgcaga aggataaaat ggcggaagcg   1380
tattcagaaa tcggaatgaa gggagagcgc cgcagaggga aagggcatga tggcctctac   1440
caaggtttgt caacagcgac caaggatacc tatgacgcac ttcatatgca agcactgccc   1500
cccagg                                                              1506
```

<210> SEQ ID NO 184
<211> LENGTH: 104
<212> TYPE: PRT
<213> ORGANISM: Artificial Sequence
<220> FEATURE:
<223> OTHER INFORMATION: G6 L chain

<400> SEQUENCE: 184

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ala Ala Thr Tyr Tyr Cys Gln His Tyr Gly Thr Phe Gly Gln
                85                  90                  95

Gly Thr Lys Leu Glu Ile Lys Arg
            100
```

<210> SEQ ID NO 185
<211> LENGTH: 312
<212> TYPE: DNA

<213> ORGANISM: Artificial Sequence
<220> FEATURE:
<223> OTHER INFORMATION: G6 L chain

<400> SEQUENCE: 185
gacatccaga tgacacagag ccctagcagc ctgtctgcca gcgtgggaga cagagtgacc 60
atcacctgta gagccagcca gagcatcagc agctacctga actggtatca gcagaagccc 120
ggcaaggccc ctaaactgct gatctatgcc gccagctctc tgcagtctgg cgtgccatct 180
agattttccg gcagcggctc tggcaccgac ttcaccctga ccatatctag cctgcagcct 240
gaggatgccg ccacctacta ctgtcagcac tacggcacat ttggccaggg caccaagctg 300
gaaatcaaga ga 312

<210> SEQ ID NO 186
<211> LENGTH: 127
<212> TYPE: PRT
<213> ORGANISM: Artificial Sequence
<220> FEATURE:
<223> OTHER INFORMATION: G6 H chain

<400> SEQUENCE: 186

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp Tyr
20 25 30

Tyr Met Ser Trp Ile Arg Gln Ala Pro Gly Lys Gly Leu Glu Trp Val
35 40 45

Ser Tyr Ile Ser Ser Ser Gly Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg His Lys Thr Ser Leu Asn Asp Tyr Asp Phe Trp Ser Gly Tyr
100 105 110

Leu Leu Asp Tyr Trp Gly Gln Gly Thr Leu Val Thr Val Ser Ser
115 120 125

<210> SEQ ID NO 187
<211> LENGTH: 381
<212> TYPE: DNA
<213> ORGANISM: Artificial Sequence
<220> FEATURE:
<223> OTHER INFORMATION: G6 H chain

<400> SEQUENCE: 187
caagttcagc tggttgaatc tggcggcgga ctggttaagc ctggcggttc tctgagactg 60
agctgtgccg cctccggctt caccttcagc gactactaca tgagctggat cagacaggcc 120
cctggcaaag gcctggaatg ggtgtcctac atcagctcca gcggcagcac catctactac 180
gccgatagcg tgaagggcag attcaccatc agccgggaca acgccaagaa cagcctgtac 240
ctgcagatga actccctgag agccgaggac accgccgtgt actattgcgc cagacacaag 300
accagcctga acgactacga cttttggagc ggctacctgc tggactattg gggccaggga 360
acactggtca ccgtgtctag t 381

<210> SEQ ID NO 188
<211> LENGTH: 738

<212> TYPE: DNA
<213> ORGANISM: Artificial Sequence
<220> FEATURE:
<223> OTHER INFORMATION: G6LH binder

<400> SEQUENCE: 188
gacatccaga tgacacagag ccctagcagc ctgtctgcca gcgtgggaga cagagtgacc 60
atcacctgta gagccagcca gagcatcagc agctacctga actggtatca gcagaagccc 120
ggcaaggccc ctaaactgct gatctatgcc gccagctctc tgcagtctgg cgtgccatct 180
agattttccg gcagcggctc tggcaccgac ttcaccctga ccatatctag cctgcagcct 240
gaggatgccg ccacctacta ctgtcagcac tacggcacat ttggccaggg caccaagctg 300
gaaatcaaga gaggtggcgg aggatctggc ggaggtggaa gcggcggagg cggatctcaa 360
gttcagctgg ttgaatctgg cggcggactg gttaagcctg gcggttctct gagactgagc 420
tgtgccgcct ccggcttcac cttcagcgac tactacatga gctggatcag acaggcccct 480
ggcaaaggcc tggaatgggt gtcctacatc agctccagcg gcagcaccat ctactacgcc 540
gatagcgtga agggcagatt caccatcagc cgggacaacg ccaagaacag cctgtacctg 600
cagatgaact ccctgagagc cgaggacacc gccgtgtact attgcgccag acacaagacc 660
agcctgaacg actacgactt ttggagcggc tacctgctgg actattgggg ccagggaaca 720
ctggtcaccg tgtctagt 738

<210> SEQ ID NO 189
<211> LENGTH: 738
<212> TYPE: DNA
<213> ORGANISM: Artificial Sequence
<220> FEATURE:
<223> OTHER INFORMATION: G6HL binder

<400> SEQUENCE: 189
caagttcagc tggttgaatc tggcggcgga ctggttaagc ctggcggttc tctgagactg 60
agctgtgccg cctccggctt caccttcagc gactactaca tgagctggat cagacaggcc 120
cctggcaaag gcctggaatg ggtgtcctac atcagctcca gcggcagcac catctactac 180
gccgatagcg tgaagggcag attcaccatc agccgggaca acgccaagaa cagcctgtac 240
ctgcagatga actccctgag agccgaggac accgccgtgt actattgcgc cagacacaag 300
accagcctga acgactacga cttttggagc ggctacctgc tggactattg gggccaggga 360
acactggtca ccgtgtctag tggtggcgga ggatctggcg gaggtggaag cggcggaggc 420
ggatctgaca tccagatgac acagagccct agcagcctgt ctgccagcgt gggagacaga 480
gtgaccatca cctgtagagc cagccagagc atcagcagct acctgaactg gtatcagcag 540
aagcccggca aggcccctaa actgctgatc tatgccgcca gctctctgca gtctggcgtg 600
ccatctagat tttccggcag cggctctggc accgacttca ccctgaccat atctagcctg 660
cagcctgagg atgccgccac ctactactgt cagcactacg gcacatttgg ccagggcacc 720
aagctggaaa tcaagaga 738

<210> SEQ ID NO 190
<211> LENGTH: 494
<212> TYPE: PRT
<213> ORGANISM: Artificial Sequence
<220> FEATURE:
<223> OTHER INFORMATION: RJ150LH CAR (G6LH/CD8 TM/4-1BB/CD3zeta)

<400> SEQUENCE: 190

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Ser Ile Ser Ser Tyr Leu Asn Trp Tyr Gln Gln Lys Pro Gly Lys
    50                  55                  60

Ala Pro Lys Leu Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Ala Ala Thr Tyr Tyr Cys Gln His
            100                 105                 110

Tyr Gly Thr Phe Gly Gln Gly Thr Lys Leu Glu Ile Lys Arg Gly Gly
        115                 120                 125

Gly Gly Ser Gly Gly Gly Gly Ser Gly Gly Gly Gly Ser Gln Val Gln
    130                 135                 140

Leu Val Glu Ser Gly Gly Gly Leu Val Lys Pro Gly Gly Ser Leu Arg
145                 150                 155                 160

Leu Ser Cys Ala Ala Ser Gly Phe Thr Phe Ser Asp Tyr Tyr Met Ser
                165                 170                 175

Trp Ile Arg Gln Ala Pro Gly Lys Gly Leu Glu Trp Val Ser Tyr Ile
            180                 185                 190

Ser Ser Ser Gly Ser Thr Ile Tyr Tyr Ala Asp Ser Val Lys Gly Arg
        195                 200                 205

Phe Thr Ile Ser Arg Asp Asn Ala Lys Asn Ser Leu Tyr Leu Gln Met
    210                 215                 220

Asn Ser Leu Arg Ala Glu Asp Thr Ala Val Tyr Tyr Cys Ala Arg His
225                 230                 235                 240

Lys Thr Ser Leu Asn Asp Tyr Asp Phe Trp Ser Gly Tyr Leu Leu Asp
                245                 250                 255

Tyr Trp Gly Gln Gly Thr Leu Val Thr Val Ser Ser Ala Ala Ala Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Lys Arg Gly Arg Lys Lys Leu Leu Tyr Ile Phe Lys
            340                 345                 350

Gln Pro Phe Met Arg Pro Val Gln Thr Thr Gln Glu Glu Asp Gly Cys
        355                 360                 365

Ser Cys Arg Phe Pro Glu Glu Glu Glu Gly Gly Cys Glu Leu Arg Val
    370                 375                 380

Lys Phe Ser Arg Ser Ala Asp Ala Pro Ala Tyr Lys Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
```

```
            420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490
```

<210> SEQ ID NO 191
<211> LENGTH: 1482
<212> TYPE: DNA
<213> ORGANISM: Artificial Sequence
<220> FEATURE:
<223> OTHER INFORMATION: RJ150LH CAR (G6LH/CD8 TM/4-1BB/CD3zeta)

<400> SEQUENCE: 191

```
atgcttctgc tcgtgacaag cctgctgctg tgcgagctgc cccaccctgc ctttctgctg     60

atccctgaca tccagatgac acagagccct agcagcctgt ctgccagcgt gggagacaga    120

gtgaccatca cctgtagagc cagccagagc atcagcagct acctgaactg gtatcagcag    180

aagcccggca aggcccctaa actgctgatc tatgccgcca gctctctgca gtctggcgtg    240

ccatctagat tttccggcag cggctctggc accgacttca ccctgaccat atctagcctg    300

cagcctgagg atgccgccac ctactactgt cagcactacg gcacatttgg ccagggcacc    360

aagctggaaa tcaagagagg tggcggagga tctggcggag gtggaagcgg cggaggcgga    420

tctcaagttc agctggttga atctggcggc ggactggtta agcctggcgg ttctctgaga    480

ctgagctgtg ccgcctccgg cttcaccttc agcgactact acatgagctg gatcagacag    540

gcccctggca aaggcctgga atgggtgtcc tacatcagct ccagcggcag caccatctac    600

tacgccgata gcgtgaaggg cagattcacc atcagccggg acaacgccaa gaacagcctg    660

tacctgcaga tgaactccct gagagccgag gacaccgccg tgtactattg cgccagacac    720

aagaccagcc tgaacgacta cgacttttgg agcggctacc tgctggacta ttggggccag    780

ggaacactgg tcaccgtgtc tagtgcggcc gcaaccacta ctccggcacc taggcccccc    840

actccggcac cgaccattgc atcacaacca ctgagtctta gacctgaagc ctgtcgaccc    900

gcagctgggg gggcagtcca cacacgggga ttggatttcg cctgcgatat atacatttgg    960

gcgccactgg caggcacctg cggggtcctg ctcttgtccc ttgtcatcac cctgtactgt   1020

aagagaggaa gaaagaagtt gttgtatatt ttcaaacagc cattcatgag gccggtccag   1080

accactcagg aggaggatgg atgcagttgc cgctttccgg aagaggaaga gggtgggtgt   1140

gaactccgag ttaaatttc tcgcagtgct gatgccccag cgtataaaca gggtcagaac    1200

caactgtata atgaactcaa tttggggagg cgagaggagt atgatgtatt ggacaagcgg   1260

cgggggcggg atcctgaaat gggcggtaag ccaaggcgca agaatccaca ggagggtttg   1320

tataatgagt tgcagaagga taaaatggcg gaagcgtatt cagaaatcgg aatgaaggga   1380

gagcgccgca gagggaaagg gcatgatggc ctctaccaag gtttgtcaac agcgaccaag   1440

gatacctatg acgcacttca tatgcaagca ctgcccccca gg                      1482
```

<210> SEQ ID NO 192
<211> LENGTH: 494
<212> TYPE: PRT
<213> ORGANISM: Artificial Sequence
<220> FEATURE:
<223> OTHER INFORMATION: RJ150HL CAR (G6HL/CD8 TM/4-1BB/CD3zeta)

<400> SEQUENCE: 192

```
Met Leu Leu Leu Val Thr Ser Leu Leu Leu Cys Glu Leu Pro His Pro
1               5                   10                  15

Ala Phe Leu Leu Ile Pro Gln Val Gln Leu Val Glu Ser Gly Gly Gly
            20                  25                  30

Leu Val Lys Pro Gly Gly Ser Leu Arg Leu Ser Cys Ala Ala Ser Gly
        35                  40                  45

Phe Thr Phe Ser Asp Tyr Tyr Met Ser Trp Ile Arg Gln Ala Pro Gly
    50                  55                  60

Lys Gly Leu Glu Trp Val Ser Tyr Ile Ser Ser Ser Gly Ser Thr Ile
65                  70                  75                  80

Tyr Tyr Ala Asp Ser Val Lys Gly Arg Phe Thr Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg His Lys Thr Ser Leu Asn Asp Tyr
        115                 120                 125

Asp Phe Trp Ser Gly Tyr Leu Leu Asp Tyr Trp Gly Gln Gly Thr Leu
    130                 135                 140

Val Thr Val Ser Ser Gly Gly Gly Gly Ser Gly Gly Gly Gly Ser Gly
145                 150                 155                 160

Gly Gly Gly Ser Asp Ile Gln Met Thr Gln Ser Pro Ser Ser Leu Ser
                165                 170                 175

Ala Ser Val Gly Asp Arg Val Thr Ile Thr Cys Arg Ala Ser Gln Ser
            180                 185                 190

Ile Ser Ser Tyr Leu Asn Trp Tyr Gln Gln Lys Pro Gly Lys Ala Pro
        195                 200                 205

Lys Leu Leu Ile Tyr Ala Ala Ser Ser Leu Gln Ser Gly Val Pro Ser
    210                 215                 220

Arg Phe Ser Gly Ser Gly Ser Gly Thr Asp Phe Thr Leu Thr Ile Ser
225                 230                 235                 240

Ser Leu Gln Pro Glu Asp Ala Ala Thr Tyr Tyr Cys Gln His Tyr Gly
                245                 250                 255

Thr Phe Gly Gln Gly Thr Lys Leu Glu Ile Lys Arg Ala Ala Ala Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Lys Arg Gly Arg Lys Lys Leu Leu Tyr Ile Phe Lys
            340                 345                 350

Gln Pro Phe Met Arg Pro Val Gln Thr Thr Gln Glu Glu Asp Gly Cys
        355                 360                 365

Ser Cys Arg Phe Pro Glu Glu Glu Glu Gly Gly Cys Glu Leu Arg Val
    370                 375                 380

Lys Phe Ser Arg Ser Ala Asp Ala Pro Ala Tyr Lys Gln Gly Gln Asn
385                 390                 395                 400
```

```
Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490


<210> SEQ ID NO 193
<211> LENGTH: 1482
<212> TYPE: DNA
<213> ORGANISM: Artificial Sequence
<220> FEATURE:
<223> OTHER INFORMATION: RJ150HL CAR (G6HL/CD8 TM/4-1BB/CD3zeta)

<400> SEQUENCE: 193

atgcttctgc tcgtgacaag cctgctgctg tgcgagctgc cccaccctgc ctttctgctg     60

atccctcaag ttcagctggt tgaatctggc ggcggactgg ttaagcctgg cggttctctg    120

agactgagct gtgccgcctc cggcttcacc ttcagcgact actacatgag ctggatcaga    180

caggcccctg gcaaaggcct ggaatgggtg tcctacatca gctccagcgg cagcaccatc    240

tactacgccg atagcgtgaa gggcagattc accatcagcc gggacaacgc caagaacagc    300

ctgtacctgc agatgaactc cctgagagcc gaggacaccg ccgtgtacta ttgcgccaga    360

cacaagacca gcctgaacga ctacgacttt tggagcggct acctgctgga ctattggggc    420

cagggaacac tggtcaccgt gtctagtggt ggcggaggat ctggcggagg tggaagcggc    480

ggaggcggat ctgacatcca gatgacacag agccctagca gcctgtctgc cagcgtggga    540

gacagagtga ccatcacctg tagagccagc cagagcatca gcagctacct gaactggtat    600

cagcagaagc ccggcaaggc ccctaaactg ctgatctatg ccgccagctc tctgcagtct    660

ggcgtgccat ctagattttc cggcagcggc tctggcaccg acttcaccct gaccatatct    720

agcctgcagc ctgaggatgc cgccacctac tactgtcagc actacggcac atttggccag    780

ggcaccaagc tggaaatcaa gagagcggcc gcaaccacta ctccggcacc taggcccccc    840

actccggcac cgaccattgc atcacaacca ctgagtctta gacctgaagc ctgtcgaccc    900

gcagctgggg gggcagtcca cacacgggga ttggatttcg cctgcgatat atacatttgg    960

gcgccactgg caggcacctg cggggtcctg ctcttgtccc ttgtcatcac cctgtactgt   1020

aagagaggaa gaaagaagtt gttgtatatt ttcaaacagc cattcatgag gccggtccag   1080

accactcagg aggaggatgg atgcagttgc cgctttccgg aagaggaaga gggtgggtgt   1140

gaactccgag ttaaattttc tcgcagtgct gatgccccag cgtataaaca gggtcagaac   1200

caactgtata atgaactcaa tttggggagg cgagaggagt atgatgtatt ggacaagcgg   1260

cgggggcggg atcctgaaat gggcggtaag ccaaggcgca agaatccaca ggagggtttg   1320

tataatgagt tgcagaagga taaaatggcg gaagcgtatt cagaaatcgg aatgaaggga   1380

gagcgccgca gagggaaagg gcatgatggc ctctaccaag gtttgtcaac agcgaccaag   1440

gatacctatg acgcacttca tatgcaagca ctgcccccca gg                       1482
```

<210> SEQ ID NO 194
<211> LENGTH: 108
<212> TYPE: PRT
<213> ORGANISM: Artificial Sequence
<220> FEATURE:
<223> OTHER INFORMATION: C9 L chain

<400> SEQUENCE: 194

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Leu Glu Ile Lys Arg
            100                 105
```

<210> SEQ ID NO 195
<211> LENGTH: 324
<212> TYPE: DNA
<213> ORGANISM: Artificial Sequence
<220> FEATURE:
<223> OTHER INFORMATION: C9 L chain

<400> SEQUENCE: 195

```
gacatccaga tgacacagag ccctagcagc ctgtctgcca gcgtgggaga cagagtgacc     60

atcacctgta gagccagcca gagcatcagc agctacctga actggtatca gcagaagccc    120

ggcaaggccc ctaaactgct gatctatgcc gccagctctc tgcagtctgg cgtgccatct    180

agattttccg gcagcggctc tggcaccgac ttcaccctga ccatatctag cctgcagcct    240

gaggacttcg ccgtgtacta ctgccagcag agaagcaact ggcctcctac ctttggccag    300

ggcaccaagc tggaaatcaa gaga                                           324
```

<210> SEQ ID NO 196
<211> LENGTH: 125
<212> TYPE: PRT
<213> ORGANISM: Artificial Sequence
<220> FEATURE:
<223> OTHER INFORMATION: C9 H chain

<400> SEQUENCE: 196

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Lys Tyr Tyr Cys
```

```
                85                  90                  95

Ala Thr Ala Val Phe Ser Leu Gly Pro Glu Gly Tyr Tyr Tyr Tyr Met
            100                 105                 110

Asp Val Trp Gly Lys Gly Thr Thr Val Thr Val Ser Ser
        115                 120                 125


<210> SEQ ID NO 197
<211> LENGTH: 375
<212> TYPE: DNA
<213> ORGANISM: Artificial Sequence
<220> FEATURE:
<223> OTHER INFORMATION: C9 H chain

<400> SEQUENCE: 197

caagttcagc tggttgaatc tggcggcgga ctggttaagc ctggcggttc tctgagactg     60

agctgtgccg cctccggctt caccttcagc gactactaca tgagctggat cagacaggcc    120

cctggcaaag gcctggaatg ggtgtcctac atcagctcca gcggcagcac catctactac    180

gccgatagcg tgaagggcag attcaccatc agccgggaca acgccaagaa cagcctgtac    240

ctgcagatga actccctgag agccgaggat accgccaagt actactgtgc caccgccgtg    300

ttttctctgg gccctgaggg ctactactac tatatggacg tgtggggcaa gggcaccacc    360

gtgacagttt cttct                                                     375


<210> SEQ ID NO 198
<211> LENGTH: 744
<212> TYPE: DNA
<213> ORGANISM: Artificial Sequence
<220> FEATURE:
<223> OTHER INFORMATION: C9LH binder

<400> SEQUENCE: 198

gacatccaga tgacacagag ccctagcagc ctgtctgcca gcgtgggaga cagagtgacc     60

atcacctgta gagccagcca gagcatcagc agctacctga actggtatca gcagaagccc    120

ggcaaggccc ctaaactgct gatctatgcc gccagctctc tgcagtctgg cgtgccatct    180

agattttccg gcagcggctc tggcaccgac ttcaccctga ccatatctag cctgcagcct    240

gaggacttcg ccgtgtacta ctgccagcag agaagcaact ggcctcctac ctttggccag    300

ggcaccaagc tggaaatcaa gagaggtggc ggaggatctg gcggaggtgg aagcggcgga    360

ggcggatctc aagttcagct ggttgaatct ggcggcggac tggttaagcc tggcggttct    420

ctgagactga gctgtgccgc ctccggcttc accttcagcg actactacat gagctggatc    480

agacaggccc ctggcaaagg cctggaatgg gtgtcctaca tcagctccag cggcagcacc    540

atctactacg ccgatagcgt gaagggcaga ttcaccatca gccgggacaa cgccaagaac    600

agcctgtacc tgcagatgaa ctccctgaga gccgaggata ccgccaagta ctactgtgcc    660

accgccgtgt tttctctggg ccctgagggc tactactact atatggacgt gtggggcaag    720

ggcaccaccg tgacagtttc ttct                                           744


<210> SEQ ID NO 199
<211> LENGTH: 744
<212> TYPE: PRT
<213> ORGANISM: Artificial Sequence
<220> FEATURE:
<223> OTHER INFORMATION: C9HL binder

<400> SEQUENCE: 199

Cys Ala Ala Gly Thr Thr Cys Ala Gly Cys Thr Gly Gly Thr Thr Gly
```

```
1               5                   10                  15

Ala Ala Thr Cys Thr Gly Gly Cys Gly Gly Cys Gly Gly Ala Cys Thr
            20                  25                  30

Gly Gly Thr Thr Ala Ala Gly Cys Cys Thr Gly Gly Cys Gly Gly Thr
        35                  40                  45

Thr Cys Thr Cys Thr Gly Ala Gly Ala Cys Thr Gly Ala Gly Cys Thr
    50                  55                  60

Gly Thr Gly Cys Cys Gly Cys Cys Thr Cys Cys Gly Gly Cys Thr Thr
65                  70                  75                  80

Cys Ala Cys Cys Thr Thr Cys Ala Gly Cys Gly Ala Cys Thr Ala Cys
                85                  90                  95

Thr Ala Cys Ala Thr Gly Ala Gly Cys Thr Gly Gly Ala Thr Cys Ala
            100                 105                 110

Gly Ala Cys Ala Gly Gly Cys Cys Cys Cys Thr Gly Gly Cys Ala Ala
        115                 120                 125

Ala Gly Gly Cys Cys Thr Gly Gly Ala Ala Thr Gly Gly Gly Thr Gly
    130                 135                 140

Thr Cys Cys Thr Ala Cys Ala Thr Cys Ala Gly Cys Thr Cys Cys Ala
145                 150                 155                 160

Gly Cys Gly Gly Cys Ala Gly Cys Ala Cys Cys Ala Thr Cys Thr Ala
                165                 170                 175

Cys Thr Ala Cys Gly Cys Cys Gly Ala Thr Ala Gly Cys Gly Thr Gly
            180                 185                 190

Ala Ala Gly Gly Gly Cys Ala Gly Ala Thr Thr Cys Ala Cys Cys Ala
        195                 200                 205

Thr Cys Ala Gly Cys Cys Gly Gly Gly Ala Cys Ala Ala Cys Gly Cys
    210                 215                 220

Cys Ala Ala Gly Ala Ala Cys Ala Gly Cys Cys Thr Gly Thr Ala Cys
225                 230                 235                 240

Cys Thr Gly Cys Ala Gly Ala Thr Gly Ala Ala Cys Thr Cys Cys Cys
                245                 250                 255

Thr Gly Ala Gly Ala Gly Cys Cys Gly Ala Gly Gly Ala Thr Ala Cys
            260                 265                 270

Cys Gly Cys Cys Ala Ala Gly Thr Ala Cys Thr Ala Cys Thr Gly Thr
        275                 280                 285

Gly Cys Cys Ala Cys Cys Gly Cys Cys Gly Thr Gly Thr Thr Thr Thr
    290                 295                 300

Cys Thr Cys Thr Gly Gly Gly Cys Cys Cys Thr Gly Ala Gly Gly Gly
305                 310                 315                 320

Cys Thr Ala Cys Thr Ala Cys Thr Ala Cys Thr Ala Thr Ala Thr Gly
                325                 330                 335

Gly Ala Cys Gly Thr Gly Thr Gly Gly Gly Gly Cys Ala Ala Gly Gly
            340                 345                 350

Gly Cys Ala Cys Cys Ala Cys Cys Gly Thr Gly Ala Cys Ala Gly Thr
        355                 360                 365

Thr Thr Cys Thr Thr Cys Thr Gly Gly Thr Gly Gly Cys Gly Gly Ala
    370                 375                 380

Gly Gly Ala Thr Cys Thr Gly Gly Cys Gly Gly Ala Gly Gly Thr Gly
385                 390                 395                 400

Gly Ala Ala Gly Cys Gly Gly Cys Gly Gly Ala Gly Gly Cys Gly Gly
                405                 410                 415

Ala Thr Cys Thr Gly Ala Cys Ala Thr Cys Cys Ala Gly Ala Thr Gly
            420                 425                 430
```

Ala Cys Ala Cys Ala Gly Ala Gly Cys Cys Cys Thr Ala Gly Cys Ala
435 440 445

Gly Cys Cys Thr Gly Thr Cys Thr Gly Cys Cys Ala Gly Cys Gly Thr
450 455 460

Gly Gly Gly Ala Gly Ala Cys Ala Gly Ala Gly Thr Gly Ala Cys Cys
465 470 475 480

Ala Thr Cys Ala Cys Cys Thr Gly Thr Ala Gly Ala Gly Cys Cys Ala
485 490 495

Gly Cys Cys Ala Gly Ala Gly Cys Ala Thr Cys Ala Gly Cys Ala Gly
500 505 510

Cys Thr Ala Cys Cys Thr Gly Ala Ala Cys Thr Gly Gly Thr Ala Thr
515 520 525

Cys Ala Gly Cys Ala Gly Ala Ala Gly Cys Cys Cys Gly Gly Cys Ala
530 535 540

Ala Gly Gly Cys Cys Cys Cys Thr Ala Ala Ala Cys Thr Gly Cys Thr
545 550 555 560

Gly Ala Thr Cys Thr Ala Thr Gly Cys Cys Gly Cys Cys Ala Gly Cys
565 570 575

Thr Cys Thr Cys Thr Gly Cys Ala Gly Thr Cys Thr Gly Gly Cys Gly
580 585 590

Thr Gly Cys Cys Ala Thr Cys Thr Ala Gly Ala Thr Thr Thr Thr Cys
595 600 605

Cys Gly Gly Cys Ala Gly Cys Gly Gly Cys Thr Cys Thr Gly Gly Cys
610 615 620

Ala Cys Cys Gly Ala Cys Thr Thr Cys Ala Cys Cys Cys Thr Gly Ala
625 630 635 640

Cys Cys Ala Thr Ala Thr Cys Thr Ala Gly Cys Cys Thr Gly Cys Ala
645 650 655

Gly Cys Cys Thr Gly Ala Gly Gly Ala Cys Thr Thr Cys Gly Cys Cys
660 665 670

Gly Thr Gly Thr Ala Cys Thr Ala Cys Thr Gly Cys Cys Ala Gly Cys
675 680 685

Ala Gly Ala Gly Ala Ala Gly Cys Ala Ala Cys Thr Gly Gly Cys Cys
690 695 700

Thr Cys Cys Thr Ala Cys Cys Thr Thr Thr Gly Gly Cys Cys Ala Gly
705 710 715 720

Gly Gly Cys Ala Cys Cys Ala Ala Gly Cys Thr Gly Gly Ala Ala Ala
725 730 735

Thr Cys Ala Ala Gly Ala Gly Ala
740

<210> SEQ ID NO 200
<211> LENGTH: 496
<212> TYPE: PRT
<213> ORGANISM: Artificial Sequence
<220> FEATURE:
<223> OTHER INFORMATION: RJ151LH CAR (C9LH/CD8 TM/4-1BB/CD3zeta)

<400> SEQUENCE: 200

Met Leu Leu Leu Val Thr Ser Leu Leu Leu Cys Glu Leu Pro His Pro
1 5 10 15

Ala Phe Leu Leu Ile Pro Asp Ile Gln Met Thr Gln Ser Pro Ser Ser
20 25 30

Leu Ser Ala Ser Val Gly Asp Arg Val Thr Ile Thr Cys Arg Ala Ser
35 40 45

```
Gln Ser Ile Ser Ser Tyr Leu Asn Trp Tyr Gln Gln Lys Pro Gly Lys
    50                  55                  60

Ala Pro Lys Leu Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Val Tyr Tyr Cys Gln Gln
            100                 105                 110

Arg Ser Asn Trp Pro Pro Thr Phe Gly Gln Gly Thr Lys Leu Glu Ile
        115                 120                 125

Lys Arg Gly Gly Gly Gly Ser Gly Gly Gly Gly Ser Gly Gly Gly Gly
    130                 135                 140

Ser Gln Val Gln Leu Val Glu Ser Gly Gly Gly Leu Val Lys Pro Gly
145                 150                 155                 160

Gly Ser Leu Arg Leu Ser Cys Ala Ala Ser Gly Phe Thr Phe Ser Asp
                165                 170                 175

Tyr Tyr Met Ser Trp Ile Arg Gln Ala Pro Gly Lys Gly Leu Glu Trp
            180                 185                 190

Val Ser Tyr Ile Ser Ser Ser Gly Ser Thr Ile Tyr Tyr Ala Asp Ser
        195                 200                 205

Val Lys Gly Arg Phe Thr Ile Ser Arg Asp Asn Ala Lys Asn Ser Leu
    210                 215                 220

Tyr Leu Gln Met Asn Ser Leu Arg Ala Glu Asp Thr Ala Lys Tyr Tyr
225                 230                 235                 240

Cys Ala Thr Ala Val Phe Ser Leu Gly Pro Glu Gly Tyr Tyr Tyr Tyr
                245                 250                 255

Met Asp Val Trp Gly Lys Gly Thr Thr Val Thr Val Ser Ser Ala Ala
            260                 265                 270

Ala Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Lys Arg Gly Arg Lys Lys Leu Leu Tyr Ile
            340                 345                 350

Phe Lys Gln Pro Phe Met Arg Pro Val Gln Thr Thr Gln Glu Glu Asp
        355                 360                 365

Gly Cys Ser Cys Arg Phe Pro Glu Glu Glu Glu Gly Gly Cys Glu Leu
    370                 375                 380

Arg Val Lys Phe Ser Arg Ser Ala Asp Ala Pro Ala Tyr Lys Gln Gly
385                 390                 395                 400

Gln Asn Gln Leu Tyr Asn Glu Leu Asn Leu Gly Arg Arg Glu Glu Tyr
                405                 410                 415

Asp Val Leu Asp Lys Arg Arg Gly Arg Asp Pro Glu Met Gly Gly Lys
            420                 425                 430

Pro Arg Arg Lys Asn Pro Gln Glu Gly Leu Tyr Asn Glu Leu Gln Lys
        435                 440                 445

Asp Lys Met Ala Glu Ala Tyr Ser Glu Ile Gly Met Lys Gly Glu Arg
    450                 455                 460
```

```
Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
                485                 490                 495


<210> SEQ ID NO 201
<211> LENGTH: 1489
<212> TYPE: DNA
<213> ORGANISM: Artificial Sequence
<220> FEATURE:
<223> OTHER INFORMATION: RJ151LH CAR (C9LH/CD8 TM/4-1BB/CD3zeta)

<400> SEQUENCE: 201

atgcttctgc tcgtgacaag cctgctgctg tgcgagctgc cccaccctgc ctttctgctg     60

atccctgaca tccagatgac acagagccct agcagcctgt ctgccagcgt gggagacaga    120

gtgaccatca cctgtagagc cagccagagc atcagcagct acctgaactg gtatcagcag    180

aagcccggca aggcccctaa actgctgatc tatgccgcca gctctctgca gtctggcgtg    240

ccatctagat tttccggcag cggctctggc accgacttca ccctgaccat atctagcctg    300

cagcctgagg acttcgccgt gtactactgc cagcagagaa gcaactggcc tcctaccttt    360

ggccagggca ccaagctgga aatcaagaga ggtggcggag gatctggcgg aggtggaagc    420

ggcggaggcg gatctcaagt tcagctggtt gaatctggcg gcggactggt taagcctggc    480

ggttctctga gactgagctg tgccgcctcc ggcttcacct tcagcgacta ctacatgagc    540

tggatcagac aggcccctgg caaaggcctg gaatgggtgt cctacatcag ctccagcggc    600

agcaccatct actacgccga tagcgtgaag ggcagattca ccatcagccg ggacaacgcc    660

aagaacagcc tgtacctgca gatgaactcc ctgagagccg aggataccgc caagtactac    720

tgtgccaccg ccgtgttttc tctgggccct gagggctact actactatat ggacgtgtgg    780

ggcaagggca ccaccgtgac agtttcttct gcggccgcaa ccactactcc ggcacctagg    840

ccccccactc cggcaccgac cattgcatca caaccactga gtcttagacc tgaagcctgt    900

cgacccgcag ctgggggggc agtccacaca cggggattgg atttcgcctg cgatatatac    960

atttgggcgc cactggcagg cacctgcggg gtcctgctct tgtcccttgt catcaccctg   1020

tactgtaaga gaggaagaaa gaagttgttg tatattttca aacagccatt catgaggccg   1080

gtccagacca ctcaggagga ggatggatgc agttgccgct ttccggaaga ggaagagggt   1140

gggtgtgaac tccgagttaa attttctcgc agtgctgatg ccccagcgta taaacagggt   1200

cagaaccaac tgtataatga actcaatttg gggaggcgag aggagtatga tgtattggac   1260

aagcggcggg ggcgggatcc tgaaatgggc ggtaagccaa ggcgcaagaa tccacaggag   1320

ggtttgtata atgagttgca gaaggataaa atggcggaag cgtattcaga aatcggaatg   1380

aagggagagc gccgcagagg gaaagggcat gatggcctct accaaggttt gtcaacagcg   1440

accaaggata cctatgacgc acttcatatg caagcactgc cccccaggt               1489


<210> SEQ ID NO 202
<211> LENGTH: 496
<212> TYPE: PRT
<213> ORGANISM: Artificial Sequence
<220> FEATURE:
<223> OTHER INFORMATION: RJ151HL CAR (C9HL/CD8 TM/4-1BB/CD3zeta)

<400> SEQUENCE: 202

Met Leu Leu Leu Val Thr Ser Leu Leu Leu Cys Glu Leu Pro His Pro
1               5                   10                  15
```

```
Ala Phe Leu Leu Ile Pro Gln Val Gln Leu Val Glu Ser Gly Gly Gly
            20                  25                  30

Leu Val Lys Pro Gly Gly Ser Leu Arg Leu Ser Cys Ala Ala Ser Gly
        35                  40                  45

Phe Thr Phe Ser Asp Tyr Tyr Met Ser Trp Ile Arg Gln Ala Pro Gly
    50                  55                  60

Lys Gly Leu Glu Trp Val Ser Tyr Ile Ser Ser Ser Gly Ser Thr Ile
65                  70                  75                  80

Tyr Tyr Ala Asp Ser Val Lys Gly Arg Phe Thr Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Lys Tyr Tyr Cys Ala Thr Ala Val Phe Ser Leu Gly Pro Glu
        115                 120                 125

Gly Tyr Tyr Tyr Tyr Met Asp Val Trp Gly Lys Gly Thr Thr Val Thr
    130                 135                 140

Val Ser Ser Gly Gly Gly Gly Ser Gly Gly Gly Gly Ser Gly Gly Gly
145                 150                 155                 160

Gly Ser Asp Ile Gln Met Thr Gln Ser Pro Ser Ser Leu Ser Ala Ser
                165                 170                 175

Val Gly Asp Arg Val Thr Ile Thr Cys Arg Ala Ser Gln Ser Ile Ser
            180                 185                 190

Ser Tyr Leu Asn Trp Tyr Gln Gln Lys Pro Gly Lys Ala Pro Lys Leu
        195                 200                 205

Leu Ile Tyr Ala Ala Ser Ser Leu Gln Ser Gly Val Pro Ser Arg Phe
    210                 215                 220

Ser Gly Ser Gly Ser Gly Thr Asp Phe Thr Leu Thr Ile Ser Ser Leu
225                 230                 235                 240

Gln Pro Glu Asp Phe Ala Val Tyr Tyr Cys Gln Gln Arg Ser Asn Trp
                245                 250                 255

Pro Pro Thr Phe Gly Gln Gly Thr Lys Leu Glu Ile Lys Arg Ala Ala
            260                 265                 270

Ala Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Lys Arg Gly Arg Lys Lys Leu Leu Tyr Ile
            340                 345                 350

Phe Lys Gln Pro Phe Met Arg Pro Val Gln Thr Thr Gln Glu Glu Asp
        355                 360                 365

Gly Cys Ser Cys Arg Phe Pro Glu Glu Glu Glu Gly Gly Cys Glu Leu
    370                 375                 380

Arg Val Lys Phe Ser Arg Ser Ala Asp Ala Pro Ala Tyr Lys Gln Gly
385                 390                 395                 400

Gln Asn Gln Leu Tyr Asn Glu Leu Asn Leu Gly Arg Arg Glu Glu Tyr
                405                 410                 415

Asp Val Leu Asp Lys Arg Arg Gly Arg Asp Pro Glu Met Gly Gly Lys
            420                 425                 430

Pro Arg Arg Lys Asn Pro Gln Glu Gly Leu Tyr Asn Glu Leu Gln Lys
```

```
        435                 440                 445

Asp Lys Met Ala Glu Ala Tyr Ser Glu Ile Gly Met Lys Gly Glu Arg
    450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
                485                 490                 495


<210> SEQ ID NO 203
<211> LENGTH: 1488
<212> TYPE: DNA
<213> ORGANISM: Artificial Sequence
<220> FEATURE:
<223> OTHER INFORMATION: RJ151HL CAR (C9HL/CD8 TM/4-1BB/CD3zeta)

<400> SEQUENCE: 203

atgcttctgc tcgtgacaag cctgctgctg tgcgagctgc cccaccctgc ctttctgctg     60

atccctcaag ttcagctggt tgaatctggc ggcggactgg ttaagcctgg cggttctctg    120

agactgagct gtgccgcctc cggcttcacc ttcagcgact actacatgag ctggatcaga    180

caggcccctg gcaaaggcct ggaatgggtg tcctacatca gctccagcgg cagcaccatc    240

tactacgccg atagcgtgaa gggcagattc accatcagcc gggacaacgc caagaacagc    300

ctgtacctgc agatgaactc cctgagagcc gaggataccg ccaagtacta ctgtgccacc    360

gccgtgtttt ctctgggccc tgagggctac tactactata tggacgtgtg gggcaagggc    420

accaccgtga cagtttcttc tggtggcgga ggatctggcg gaggtggaag cggcggaggc    480

ggatctgaca tccagatgac acagagccct agcagcctgt ctgccagcgt gggagacaga    540

gtgaccatca cctgtagagc cagccagagc atcagcagct acctgaactg gtatcagcag    600

aagcccggca aggcccctaa actgctgatc tatgccgcca gctctctgca gtctggcgtg    660

ccatctagat tttccggcag cggctctggc accgacttca ccctgaccat atctagcctg    720

cagcctgagg acttcgccgt gtactactgc cagcagagaa gcaactggcc tcctaccttt    780

ggccagggca ccaagctgga aatcaagaga gcggccgcaa ccactactcc ggcacctagg    840

ccccccactc cggcaccgac cattgcatca caaccactga gtcttagacc tgaagcctgt    900

cgacccgcag ctgggggggc agtccacaca cggggattgg atttcgcctg cgatatatac    960

atttgggcgc cactggcagg cacctgcggg gtcctgctct tgtcccttgt catcaccctg   1020

tactgtaaga gaggaagaaa gaagttgttg tatattttca aacagccatt catgaggccg   1080

gtccagacca ctcaggagga ggatggatgc agttgccgct ttccggaaga ggaagagggt   1140

gggtgtgaac tccgagttaa attttctcgc agtgctgatg ccccagcgta taaacagggt   1200

cagaaccaac tgtataatga actcaatttg ggaggcgag aggagtatga tgtattggac    1260

aagcggcggg ggcgggatcc tgaaatgggc ggtaagccaa ggcgcaagaa tccacaggag   1320

ggtttgtata atgagttgca gaaggataaa atggcggaag cgtattcaga aatcggaatg   1380

aagggagagc gccgcagagg gaaagggcat gatggcctct accaaggttt gtcaacagcg   1440

accaaggata cctatgacgc acttcatatg caagcactgc cccccagg                1488


<210> SEQ ID NO 204
<211> LENGTH: 104
<212> TYPE: PRT
<213> ORGANISM: Artificial Sequence
<220> FEATURE:
<223> OTHER INFORMATION: D7 L chain
```

<400> SEQUENCE: 204

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Ala Tyr Tyr Cys Gln His Tyr Gly Thr Phe Gly Gln
                85                  90                  95

Gly Thr Lys Leu Glu Ile Lys Arg
            100
```

<210> SEQ ID NO 205
<211> LENGTH: 312
<212> TYPE: DNA
<213> ORGANISM: Artificial Sequence
<220> FEATURE:
<223> OTHER INFORMATION: D7 L chain

<400> SEQUENCE: 205

```
gacatccaga tgacacagag ccctagcagc ctgtctgcca gcgtgggaga cagagtgacc     60

atcacctgta gagccagcca gagcatcagc agctacctga actggtatca gcagaagccc    120

ggcaaggccc ctaaactgct gatctatgcc gccagctctc tgcagtctgg cgtgccatct    180

agattttccg gcagcggctc tggcaccgac ttcaccctga ccatatctag cctgcagcct    240

gaggatatcg ccgcctacta ctgtcagcac tacggcacat ttggccaggg caccaagctg    300

gaaatcaaga ga                                                        312
```

<210> SEQ ID NO 206
<211> LENGTH: 128
<212> TYPE: PRT
<213> ORGANISM: Artificial Sequence
<220> FEATURE:
<223> OTHER INFORMATION: D7 H chain

<400> SEQUENCE: 206

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Tyr Pro Leu Gly Gly Gly Tyr Asp Phe Trp Ser Gly
            100                 105                 110

Tyr Tyr Pro Asp Tyr Trp Gly Gln Gly Thr Leu Val Thr Val Ser Ser
        115                 120                 125
```

<210> SEQ ID NO 207
<211> LENGTH: 384
<212> TYPE: DNA
<213> ORGANISM: Artificial Sequence
<220> FEATURE:
<223> OTHER INFORMATION: D7 H chain

<400> SEQUENCE: 207
caagttcagc tggttgaatc tggcggcgga ctggttaagc ctggcggttc tctgagactg 60
agctgtgccg cctccggctt caccttcagc gactactaca tgagctggat cagacaggcc 120
cctggcaaag gcctggaatg ggtgtcctac atcagctcca gcggcagcac catctactac 180
gccgatagcg tgaagggcag attcaccatc agccgggaca acgccaagaa cagcctgtac 240
ctgcagatga actccctgag agccgaggac accgccgtgt actactgtgc cagagatggc 300
tatcctcttg gcggaggcta cgacttttgg agcggctact accccgatta ctggggccag 360
ggaacactgg tcacagtgtc tagt 384

<210> SEQ ID NO 208
<211> LENGTH: 741
<212> TYPE: DNA
<213> ORGANISM: Artificial Sequence
<220> FEATURE:
<223> OTHER INFORMATION: D7LH binder

<400> SEQUENCE: 208
gacatccaga tgacacagag ccctagcagc ctgtctgcca gcgtgggaga cagagtgacc 60
atcacctgta gagccagcca gagcatcagc agctacctga actggtatca gcagaagccc 120
ggcaaggccc ctaaactgct gatctatgcc gccagctctc tgcagtctgg cgtgccatct 180
agattttccg gcagcggctc tggcaccgac ttcaccctga ccatatctag cctgcagcct 240
gaggatatcg ccgcctacta ctgtcagcac tacggcacat ttggccaggg caccaagctg 300
gaaatcaaga gaggtggcgg aggatctggc ggaggtggaa gcggcggagg cggatctcaa 360
gttcagctgg ttgaatctgg cggcggactg gttaagcctg gcggttctct gagactgagc 420
tgtgccgcct ccggcttcac cttcagcgac tactacatga gctggatcag acaggcccct 480
ggcaaaggcc tggaatgggt gtcctacatc agctccagcg gcagcaccat ctactacgcc 540
gatagcgtga agggcagatt caccatcagc cgggacaacg ccaagaacag cctgtacctg 600
cagatgaact ccctgagagc cgaggacacc gccgtgtact actgtgccag agatggctat 660
cctcttggcg gaggctacga cttttggagc ggctactacc ccgattactg gggccaggga 720
acactggtca cagtgtctag t 741

<210> SEQ ID NO 209
<211> LENGTH: 741
<212> TYPE: DNA
<213> ORGANISM: Artificial Sequence
<220> FEATURE:
<223> OTHER INFORMATION: D7HL binder

<400> SEQUENCE: 209
caagttcagc tggttgaatc tggcggcgga ctggttaagc ctggcggttc tctgagactg 60
agctgtgccg cctccggctt caccttcagc gactactaca tgagctggat cagacaggcc 120
cctggcaaag gcctggaatg ggtgtcctac atcagctcca gcggcagcac catctactac 180
gccgatagcg tgaagggcag attcaccatc agccgggaca acgccaagaa cagcctgtac 240
ctgcagatga actccctgag agccgaggac accgccgtgt actactgtgc cagagatggc 300

```
tatcctcttg gcggaggcta cgacttttgg agcggctact accccgatta ctggggccag    360

ggaacactgg tcacagtgtc tagtggtggc ggaggatctg gcggaggtgg aagcggcgga    420

ggcggatctg acatccagat gacacagagc cctagcagcc tgtctgccag cgtgggagac    480

agagtgacca tcacctgtag agccagccag agcatcagca gctacctgaa ctggtatcag    540

cagaagcccg gcaaggcccc taaactgctg atctatgccg ccagctctct gcagtctggc    600

gtgccatcta gattttccgg cagcggctct ggcaccgact tcaccctgac catatctagc    660

ctgcagcctg aggatatcgc cgcctactac tgtcagcact acggcacatt tggccagggc    720

accaagctgg aaatcaagag a                                              741
```

```
<210> SEQ ID NO 210
<211> LENGTH: 495
<212> TYPE: PRT
<213> ORGANISM: Artificial Sequence
<220> FEATURE:
<223> OTHER INFORMATION: RJ152LH CAR (D7LH/CD8 TM/4-1BB/CD3zeta)

<400> SEQUENCE: 210

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Ser Ile Ser Ser Tyr Leu Asn Trp Tyr Gln Gln Lys Pro Gly Lys
    50                  55                  60

Ala Pro Lys Leu Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Ile Ala Ala Tyr Tyr Cys Gln His
            100                 105                 110

Tyr Gly Thr Phe Gly Gln Gly Thr Lys Leu Glu Ile Lys Arg Gly Gly
        115                 120                 125

Gly Gly Ser Gly Gly Gly Gly Ser Gly Gly Gly Gly Ser Gln Val Gln
    130                 135                 140

Leu Val Glu Ser Gly Gly Gly Leu Val Lys Pro Gly Gly Ser Leu Arg
145                 150                 155                 160

Leu Ser Cys Ala Ala Ser Gly Phe Thr Phe Ser Asp Tyr Tyr Met Ser
                165                 170                 175

Trp Ile Arg Gln Ala Pro Gly Lys Gly Leu Glu Trp Val Ser Tyr Ile
            180                 185                 190

Ser Ser Ser Gly Ser Thr Ile Tyr Tyr Ala Asp Ser Val Lys Gly Arg
        195                 200                 205

Phe Thr Ile Ser Arg Asp Asn Ala Lys Asn Ser Leu Tyr Leu Gln Met
    210                 215                 220

Asn Ser Leu Arg Ala Glu Asp Thr Ala Val Tyr Tyr Cys Ala Arg Asp
225                 230                 235                 240

Gly Tyr Pro Leu Gly Gly Gly Tyr Asp Phe Trp Ser Gly Tyr Tyr Pro
                245                 250                 255

Asp Tyr Trp Gly Gln Gly Thr Leu Val Thr Val Ser Ser Ala Ala Ala
            260                 265                 270

Thr Thr Thr Pro Ala Pro Arg Pro Pro Thr Pro Ala Pro Thr Ile Ala
```

```
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
        355                 360                 365

Cys Ser Cys Arg Phe Pro Glu Glu Glu Glu Gly Gly Cys Glu Leu Arg
    370                 375                 380

Val Lys Phe Ser Arg Ser Ala Asp Ala Pro Ala Tyr Lys Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495
```

<210> SEQ ID NO 211
<211> LENGTH: 1485
<212> TYPE: DNA
<213> ORGANISM: Artificial Sequence
<220> FEATURE:
<223> OTHER INFORMATION: RJ152LH CAR (D7LH/CD8 TM/4-1BB/CD3zeta)

<400> SEQUENCE: 211

```
atgcttctgc tcgtgacaag cctgctgctg tgcgagctgc cccaccctgc ctttctgctg      60

atccctgaca tccagatgac acagagccct agcagcctgt ctgccagcgt gggagacaga     120

gtgaccatca cctgtagagc cagccagagc atcagcagct acctgaactg gtatcagcag     180

aagcccggca aggcccctaa actgctgatc tatgccgcca gctctctgca gtctggcgtg     240

ccatctagat tttccggcag cggctctggc accgacttca ccctgaccat atctagcctg     300

cagcctgagg atatcgccgc ctactactgt cagcactacg gcacatttgg ccagggcacc     360

aagctggaaa tcaagagagg tggcggagga tctggcggag gtggaagcgg cggaggcgga     420

tctcaagttc agctggttga atctggcggc ggactggtta agcctggcgg ttctctgaga     480

ctgagctgtg ccgcctccgg cttcaccttc agcgactact acatgagctg gatcagacag     540

gcccctggca aaggcctgga atgggtgtcc tacatcagct ccagcggcag caccatctac     600

tacgccgata gcgtgaaggg cagattcacc atcagccggg acaacgccaa gaacagcctg     660

tacctgcaga tgaactccct gagagccgag gacaccgccg tgtactactg tgccagagat     720

ggctatcctc ttggcggagg ctacgacttt tggagcggct actaccccga ttactggggc     780

cagggaacac tggtcacagt gtctagtgcg gccgcaacca ctactccggc acctaggccc     840
```

```
cccactccgg caccgaccat tgcatcacaa ccactgagtc ttagacctga agcctgtcga    900

cccgcagctg ggggggcagt ccacacacgg ggattggatt tcgcctgcga tatatacatt    960

tgggcgccac tggcaggcac ctgcggggtc ctgctcttgt cccttgtcat caccctgtac   1020

tgtaagagag gaagaaagaa gttgttgtat attttcaaac agccattcat gaggccggtc   1080

cagaccactc aggaggagga tggatgcagt tgccgctttc cggaagagga agagggtggg   1140

tgtgaactcc gagttaaatt ttctcgcagt gctgatgccc cagcgtataa acagggtcag   1200

aaccaactgt ataatgaact caatttgggg aggcgagagg agtatgatgt attggacaag   1260

cggcgggggc gggatcctga aatgggcggt aagccaaggc gcaagaatcc acaggagggt   1320

ttgtataatg agttgcagaa ggataaaatg gcggaagcgt attcagaaat cggaatgaag   1380

ggagagcgcc gcagagggaa agggcatgat ggcctctacc aaggtttgtc aacagcgacc   1440

aaggatacct atgacgcact tcatatgcaa gcactgcccc ccagg                   1485
```

<210> SEQ ID NO 212
<211> LENGTH: 495
<212> TYPE: PRT
<213> ORGANISM: Artificial Sequence
<220> FEATURE:
<223> OTHER INFORMATION: RJ152HL (D7HL/CD8 TM/4-1BB/CD3zeta)

<400> SEQUENCE: 212

```
Met Leu Leu Leu Val Thr Ser Leu Leu Leu Cys Glu Leu Pro His Pro
1               5                   10                  15

Ala Phe Leu Leu Ile Pro Gln Val Gln Leu Val Glu Ser Gly Gly Gly
            20                  25                  30

Leu Val Lys Pro Gly Gly Ser Leu Arg Leu Ser Cys Ala Ala Ser Gly
        35                  40                  45

Phe Thr Phe Ser Asp Tyr Tyr Met Ser Trp Ile Arg Gln Ala Pro Gly
    50                  55                  60

Lys Gly Leu Glu Trp Val Ser Tyr Ile Ser Ser Ser Gly Ser Thr Ile
65                  70                  75                  80

Tyr Tyr Ala Asp Ser Val Lys Gly Arg Phe Thr Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Asp Gly Tyr Pro Leu Gly Gly Gly
        115                 120                 125

Tyr Asp Phe Trp Ser Gly Tyr Tyr Pro Asp Tyr Trp Gly Gln Gly Thr
    130                 135                 140

Leu Val Thr Val Ser Ser Gly Gly Gly Gly Ser Gly Gly Gly Gly Ser
145                 150                 155                 160

Gly Gly Gly Gly Ser Asp Ile Gln Met Thr Gln Ser Pro Ser Ser Leu
                165                 170                 175

Ser Ala Ser Val Gly Asp Arg Val Thr Ile Thr Cys Arg Ala Ser Gln
            180                 185                 190

Ser Ile Ser Ser Tyr Leu Asn Trp Tyr Gln Gln Lys Pro Gly Lys Ala
        195                 200                 205

Pro Lys Leu Leu Ile Tyr Ala Ala Ser Ser Leu Gln Ser Gly Val Pro
    210                 215                 220

Ser Arg Phe Ser Gly Ser Gly Ser Gly Thr Asp Phe Thr Leu Thr Ile
225                 230                 235                 240

Ser Ser Leu Gln Pro Glu Asp Ile Ala Ala Tyr Tyr Cys Gln His Tyr
                245                 250                 255
```

```
Gly Thr Phe Gly Gln Gly Thr Lys Leu Glu Ile Lys Arg Ala Ala Ala
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
        355                 360                 365

Cys Ser Cys Arg Phe Pro Glu Glu Glu Glu Gly Gly Cys Glu Leu Arg
    370                 375                 380

Val Lys Phe Ser Arg Ser Ala Asp Ala Pro Ala Tyr Lys Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495
```

```
<210> SEQ ID NO 213
<211> LENGTH: 1485
<212> TYPE: DNA
<213> ORGANISM: Artificial Sequence
<220> FEATURE:
<223> OTHER INFORMATION: RJ152HL (D7HL/CD8 TM/4-1BB/CD3zeta)

<400> SEQUENCE: 213

atgcttctgc tcgtgacaag cctgctgctg tgcgagctgc cccaccctgc ctttctgctg      60

atccctcaag ttcagctggt tgaatctggc ggcggactgg ttaagcctgg cggttctctg     120

agactgagct gtgccgcctc cggcttcacc ttcagcgact actacatgag ctggatcaga     180

caggcccctg gcaaaggcct ggaatgggtg tcctacatca gctccagcgg cagcaccatc     240

tactacgccg atagcgtgaa gggcagattc accatcagcc gggacaacgc caagaacagc     300

ctgtacctgc agatgaactc cctgagagcc gaggacaccg ccgtgtacta ctgtgccaga     360

gatggctatc ctcttggcgg aggctacgac ttttggagcg gctactaccc cgattactgg     420

ggccagggaa cactggtcac agtgtctagt ggtggcggag gatctggcgg aggtggaagc     480

ggcggaggcg gatctgacat ccagatgaca cagagcccta gcagcctgtc tgccagcgtg     540

ggagacagag tgaccatcac ctgtagagcc agccagagca tcagcagcta cctgaactgg     600

tatcagcaga agcccggcaa ggcccctaaa ctgctgatct atgccgccag ctctctgcag     660

tctggcgtgc catctagatt ttccggcagc ggctctggca ccgacttcac cctgaccata     720
```

```
tctagcctgc agcctgagga tatcgccgcc tactactgtc agcactacgg cacatttggc    780

cagggcacca agctggaaat caagagagcg gccgcaacca ctactccggc acctaggccc    840

cccactccgg caccgaccat tgcatcacaa ccactgagtc ttagacctga agcctgtcga    900

cccgcagctg ggggggcagt ccacacacgg ggattggatt tcgcctgcga tatatacatt    960

tgggcgccac tggcaggcac ctgcggggtc ctgctcttgt cccttgtcat caccctgtac   1020

tgtaagagag gaagaaagaa gttgttgtat attttcaaac agccattcat gaggccggtc   1080

cagaccactc aggaggagga tggatgcagt tgccgctttc cggaagagga agagggtggg   1140

tgtgaactcc gagttaaatt ttctcgcagt gctgatgccc cagcgtataa acagggtcag   1200

aaccaactgt ataatgaact caatttgggg aggcgagagg agtatgatgt attggacaag   1260

cggcgggggc gggatcctga aatgggcggt aagccaaggc gcaagaatcc acaggagggt   1320

ttgtataatg agttgcagaa ggataaaatg gcggaagcgt attcagaaat cggaatgaag   1380

ggagagcgcc gcagagggaa agggcatgat ggcctctacc aaggtttgtc aacagcgacc   1440

aaggatacct atgacgcact tcatatgcaa gcactgcccc ccagg                   1485
```

```
<210> SEQ ID NO 214
<211> LENGTH: 104
<212> TYPE: PRT
<213> ORGANISM: Artificial Sequence
<220> FEATURE:
<223> OTHER INFORMATION: B7 L chain

<400> SEQUENCE: 214

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln His Tyr Gly Thr Phe Gly Gln
                85                  90                  95

Gly Thr Lys Val Glu Ile Lys Arg
            100


<210> SEQ ID NO 215
<211> LENGTH: 312
<212> TYPE: DNA
<213> ORGANISM: Artificial Sequence
<220> FEATURE:
<223> OTHER INFORMATION: B7 L chain

<400> SEQUENCE: 215

gacatccaga tgacacagag ccctagcagc ctgtctgcca gcgtgggaga cagagtgacc     60

atcacctgta gagccagcca gagcatcagc agctacctga actggtatca gcagaagccc    120

ggcaaggccc ctaaactgct gatctatgcc gccagctctc tgcagtctgg cgtgccatct    180

agattttccg gcagcggctc tggcaccgac ttcaccctga ccatatctag cctgcagcct    240

gaggacttcg ccgtgtacta ctgtcagcac tacggcacct ttggccaggg caccaaggtg    300

gaaatcaaga ga                                                        312
```

<210> SEQ ID NO 216
<211> LENGTH: 127
<212> TYPE: PRT
<213> ORGANISM: Artificial Sequence
<220> FEATURE:
<223> OTHER INFORMATION: B7 H chain

<400> SEQUENCE: 216

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Met Tyr Tyr Cys
                85                  90                  95

Ala Arg His Lys Thr Ser Leu Asn Asp Tyr Asp Phe Trp Ser Gly Tyr
            100                 105                 110

Leu Leu Asp Tyr Trp Gly Gln Gly Thr Leu Val Thr Val Ser Ser
        115                 120                 125
```

<210> SEQ ID NO 217
<211> LENGTH: 381
<212> TYPE: DNA
<213> ORGANISM: Artificial Sequence
<220> FEATURE:
<223> OTHER INFORMATION: B7 H chain

<400> SEQUENCE: 217

```
caagttcagc tggttgaatc tggcggcgga ctggttaagc ctggcggttc tctgagactg     60

agctgtgccg cctccggctt caccttcagc gactactaca tgagctggat cagacaggcc    120

cctggcaaag gcctggaatg ggtgtcctac atcagctcca gcggcagcac catctactac    180

gccgatagcg tgaagggcag attcaccatc agccgggaca acgccaagaa cagcctgtac    240

ctgcagatga actccctgag agccgaggac acagccatgt actattgcgc cagacacaag    300

accagcctga acgactacga cttttggagc ggctacctgc tggactattg gggccaggga    360

acactggtca ccgtgtctag t                                              381
```

<210> SEQ ID NO 218
<211> LENGTH: 738
<212> TYPE: DNA
<213> ORGANISM: Artificial Sequence
<220> FEATURE:
<223> OTHER INFORMATION: B7LH binder

<400> SEQUENCE: 218

```
gacatccaga tgacacagag ccctagcagc ctgtctgcca gcgtgggaga cagagtgacc     60

atcacctgta gagccagcca gagcatcagc agctacctga actggtatca gcagaagccc    120

ggcaaggccc ctaaactgct gatctatgcc gccagctctc tgcagtctgg cgtgccatct    180

agattttccg gcagcggctc tggcaccgac ttcaccctga ccatatctag cctgcagcct    240

gaggacttcg ccgtgtacta ctgtcagcac tacggcacct ttggccaggg caccaaggtg    300
```

```
gaaatcaaga gaggtggcgg aggatctggc ggaggtggaa gcggcggagg cggatctcaa    360

gttcagctgg ttgaatctgg cggcggactg gttaagcctg gcggttctct gagactgagc    420

tgtgccgcct ccggcttcac cttcagcgac tactacatga gctggatcag acaggcccct    480

ggcaaaggcc tggaatgggt gtcctacatc agctccagcg gcagcaccat ctactacgcc    540

gatagcgtga agggcagatt caccatcagc cgggacaacg ccaagaacag cctgtacctg    600

cagatgaact ccctgagagc cgaggacaca gccatgtact attgcgccag acacaagacc    660

agcctgaacg actacgactt ttggagcggc tacctgctgg actattgggg ccagggaaca    720

ctggtcaccg tgtctagt                                                  738
```

<210> SEQ ID NO 219
<211> LENGTH: 738
<212> TYPE: DNA
<213> ORGANISM: Artificial Sequence
<220> FEATURE:
<223> OTHER INFORMATION: B7HL binder

<400> SEQUENCE: 219

```
caagttcagc tggttgaatc tggcggcgga ctggttaagc ctggcggttc tctgagactg     60

agctgtgccg cctccggctt caccttcagc gactactaca tgagctggat cagacaggcc    120

cctggcaaag gcctggaatg ggtgtcctac atcagctcca gcggcagcac catctactac    180

gccgatagcg tgaagggcag attcaccatc agccgggaca acgccaagaa cagcctgtac    240

ctgcagatga actccctgag agccgaggac acagccatgt actattgcgc cagacacaag    300

accagcctga acgactacga cttttggagc ggctacctgc tggactattg gggccaggga    360

acactggtca ccgtgtctag tggtggcgga ggatctggcg gaggtggaag cggcggaggc    420

ggatctgaca tccagatgac acagagccct agcagcctgt ctgccagcgt gggagacaga    480

gtgaccatca cctgtagagc cagccagagc atcagcagct acctgaactg gtatcagcag    540

aagcccggca aggcccctaa actgctgatc tatgccgcca gctctctgca gtctggcgtg    600

ccatctagat tttccggcag cggctctggc accgacttca ccctgaccat atctagcctg    660

cagcctgagg acttcgccgt gtactactgt cagcactacg gcacctttgg ccagggcacc    720

aaggtggaaa tcaagaga                                                  738
```

<210> SEQ ID NO 220
<211> LENGTH: 494
<212> TYPE: PRT
<213> ORGANISM: Artificial Sequence
<220> FEATURE:
<223> OTHER INFORMATION: RJ153LH CAR (B7LH/CD8 TM/4-1BB/CD3zeta)

<400> SEQUENCE: 220

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Ser Ile Ser Ser Tyr Leu Asn Trp Tyr Gln Gln Lys Pro Gly Lys
    50                  55                  60

Ala Pro Lys Leu Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95
```

```
Ile Ser Ser Leu Gln Pro Glu Asp Phe Ala Val Tyr Tyr Cys Gln His
            100                 105                 110

Tyr Gly Thr Phe Gly Gln Gly Thr Lys Val Glu Ile Lys Arg Gly Gly
        115                 120                 125

Gly Gly Ser Gly Gly Gly Gly Ser Gly Gly Gly Gly Ser Gln Val Gln
    130                 135                 140

Leu Val Glu Ser Gly Gly Gly Leu Val Lys Pro Gly Gly Ser Leu Arg
145                 150                 155                 160

Leu Ser Cys Ala Ala Ser Gly Phe Thr Phe Ser Asp Tyr Tyr Met Ser
                165                 170                 175

Trp Ile Arg Gln Ala Pro Gly Lys Gly Leu Glu Trp Val Ser Tyr Ile
            180                 185                 190

Ser Ser Ser Gly Ser Thr Ile Tyr Tyr Ala Asp Ser Val Lys Gly Arg
        195                 200                 205

Phe Thr Ile Ser Arg Asp Asn Ala Lys Asn Ser Leu Tyr Leu Gln Met
    210                 215                 220

Asn Ser Leu Arg Ala Glu Asp Thr Ala Met Tyr Tyr Cys Ala Arg His
225                 230                 235                 240

Lys Thr Ser Leu Asn Asp Tyr Asp Phe Trp Ser Gly Tyr Leu Leu Asp
                245                 250                 255

Tyr Trp Gly Gln Gly Thr Leu Val Thr Val Ser Ser Ala Ala Ala Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Lys Arg Gly Arg Lys Lys Leu Leu Tyr Ile Phe Lys
            340                 345                 350

Gln Pro Phe Met Arg Pro Val Gln Thr Thr Gln Glu Glu Asp Gly Cys
        355                 360                 365

Ser Cys Arg Phe Pro Glu Glu Glu Glu Gly Gly Cys Glu Leu Arg Val
    370                 375                 380

Lys Phe Ser Arg Ser Ala Asp Ala Pro Ala Tyr Lys Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490
```

<210> SEQ ID NO 221
<211> LENGTH: 1482

<212> TYPE: DNA
<213> ORGANISM: Artificial Sequence
<220> FEATURE:
<223> OTHER INFORMATION: RJ153LH CAR (B7LH/CD8 TM/4-1BB/CD3zeta)

<400> SEQUENCE: 221
atgcttctgc tcgtgacaag cctgctgctg tgcgagctgc cccaccctgc ctttctgctg 60
atccctgaca tccagatgac acagagccct agcagcctgt ctgccagcgt gggagacaga 120
gtgaccatca cctgtagagc cagccagagc atcagcagct acctgaactg gtatcagcag 180
aagcccggca aggcccctaa actgctgatc tatgccgcca gctctctgca gtctggcgtg 240
ccatctagat tttccggcag cggctctggc accgacttca ccctgaccat atctagcctg 300
cagcctgagg acttcgccgt gtactactgt cagcactacg gcacctttgg ccagggcacc 360
aaggtggaaa tcaagagagg tggcggagga tctggcggag gtggaagcgg cggaggcgga 420
tctcaagttc agctggttga atctggcggc ggactggtta agcctggcgg ttctctgaga 480
ctgagctgtg ccgcctccgg cttcaccttc agcgactact acatgagctg gatcagacag 540
gcccctggca aaggcctgga atgggtgtcc tacatcagct ccagcggcag caccatctac 600
tacgccgata gcgtgaaggg cagattcacc atcagccggg acaacgccaa gaacagcctg 660
tacctgcaga tgaactccct gagagccgag gacacagcca tgtactattg cgccagacac 720
aagaccagcc tgaacgacta cgacttttgg agcggctacc tgctggacta ttggggccag 780
ggaacactgg tcaccgtgtc tagtgcggcc gcaaccacta ctccggcacc taggcccccc 840
actccggcac cgaccattgc atcacaacca ctgagtctta gacctgaagc ctgtcgaccc 900
gcagctgggg gggcagtcca cacacgggga ttggatttcg cctgcgatat atacatttgg 960
gcgccactgg caggcacctg cggggtcctg ctcttgtccc ttgtcatcac cctgtactgt 1020
aagagaggaa gaaagaagtt gttgtatatt ttcaaacagc cattcatgag gccggtccag 1080
accactcagg aggaggatgg atgcagttgc cgctttccgg aagaggaaga gggtgggtgt 1140
gaactccgag ttaaattttc tcgcagtgct gatgccccag cgtataaaca gggtcagaac 1200
caactgtata atgaactcaa tttggggagg cgagaggagt atgatgtatt ggacaagcgg 1260
cgggggcggg atcctgaaat gggcggtaag ccaaggcgca agaatccaca ggagggtttg 1320
tataatgagt tgcagaagga taaaatggcg gaagcgtatt cagaaatcgg aatgaaggga 1380
gagcgccgca gagggaaagg gcatgatggc ctctaccaag gtttgtcaac agcgaccaag 1440
gatacctatg acgcacttca tatgcaagca ctgcccccca gg 1482

<210> SEQ ID NO 222
<211> LENGTH: 494
<212> TYPE: PRT
<213> ORGANISM: Artificial Sequence
<220> FEATURE:
<223> OTHER INFORMATION: RJ153HL CAR (B7HL/CD8 TM/4-1BB/CD3zeta)

<400> SEQUENCE: 222

Met Leu Leu Leu Val Thr Ser Leu Leu Leu Cys Glu Leu Pro His Pro
1               5                   10                  15

Ala Phe Leu Leu Ile Pro Gln Val Gln Leu Val Glu Ser Gly Gly Gly
            20                  25                  30

Leu Val Lys Pro Gly Gly Ser Leu Arg Leu Ser Cys Ala Ala Ser Gly
        35                  40                  45

Phe Thr Phe Ser Asp Tyr Tyr Met Ser Trp Ile Arg Gln Ala Pro Gly
    50                  55                  60

```
Lys Gly Leu Glu Trp Val Ser Tyr Ile Ser Ser Ser Gly Ser Thr Ile
65                  70                  75                  80

Tyr Tyr Ala Asp Ser Val Lys Gly Arg Phe Thr Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Met Tyr Tyr Cys Ala Arg His Lys Thr Ser Leu Asn Asp Tyr
        115                 120                 125

Asp Phe Trp Ser Gly Tyr Leu Leu Asp Tyr Trp Gly Gln Gly Thr Leu
    130                 135                 140

Val Thr Val Ser Ser Gly Gly Gly Gly Ser Gly Gly Gly Gly Ser Gly
145                 150                 155                 160

Gly Gly Gly Ser Asp Ile Gln Met Thr Gln Ser Pro Ser Ser Leu Ser
                165                 170                 175

Ala Ser Val Gly Asp Arg Val Thr Ile Thr Cys Arg Ala Ser Gln Ser
            180                 185                 190

Ile Ser Ser Tyr Leu Asn Trp Tyr Gln Gln Lys Pro Gly Lys Ala Pro
        195                 200                 205

Lys Leu Leu Ile Tyr Ala Ala Ser Ser Leu Gln Ser Gly Val Pro Ser
    210                 215                 220

Arg Phe Ser Gly Ser Gly Ser Gly Thr Asp Phe Thr Leu Thr Ile Ser
225                 230                 235                 240

Ser Leu Gln Pro Glu Asp Phe Ala Val Tyr Tyr Cys Gln His Tyr Gly
                245                 250                 255

Thr Phe Gly Gln Gly Thr Lys Val Glu Ile Lys Arg Ala Ala Ala Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Lys Arg Gly Arg Lys Lys Leu Leu Tyr Ile Phe Lys
            340                 345                 350

Gln Pro Phe Met Arg Pro Val Gln Thr Thr Gln Glu Glu Asp Gly Cys
        355                 360                 365

Ser Cys Arg Phe Pro Glu Glu Glu Glu Gly Gly Cys Glu Leu Arg Val
    370                 375                 380

Lys Phe Ser Arg Ser Ala Asp Ala Pro Ala Tyr Lys Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
```

485 490

<210> SEQ ID NO 223
<211> LENGTH: 1482
<212> TYPE: DNA
<213> ORGANISM: Artificial Sequence
<220> FEATURE:
<223> OTHER INFORMATION: RJ153HL CAR (B7HL/CD8 TM/4-1BB/CD3zeta)

<400> SEQUENCE: 223
atgcttctgc tcgtgacaag cctgctgctg tgcgagctgc cccaccctgc ctttctgctg 60
atccctcaag ttcagctggt tgaatctggc ggcggactgg ttaagcctgg cggttctctg 120
agactgagct gtgccgcctc cggcttcacc ttcagcgact actacatgag ctggatcaga 180
caggcccctg gcaaaggcct ggaatgggtg tcctacatca gctccagcgg cagcaccatc 240
tactacgccg atagcgtgaa gggcagattc accatcagcc gggacaacgc caagaacagc 300
ctgtacctgc agatgaactc cctgagagcc gaggacacag ccatgtacta ttgcgccaga 360
cacaagacca gcctgaacga ctacgacttt tggagcggct acctgctgga ctattggggc 420
cagggaacac tggtcaccgt gtctagtggt ggcggaggat ctggcggagg tggaagcggc 480
ggaggcggat ctgacatcca gatgacacag agccctagca gcctgtctgc cagcgtggga 540
gacagagtga ccatcacctg tagagccagc cagagcatca gcagctacct gaactggtat 600
cagcagaagc ccggcaaggc ccctaaactg ctgatctatg ccgccagctc tctgcagtct 660
ggcgtgccat ctagattttc cggcagcggc tctggcaccg acttcaccct gaccatatct 720
agcctgcagc ctgaggactt cgccgtgtac tactgtcagc actacggcac ctttggccag 780
ggcaccaagg tggaaatcaa gagagcggcc gcaaccacta ctccggcacc taggcccccc 840
actccggcac cgaccattgc atcacaacca ctgagtctta gacctgaagc ctgtcgaccc 900
gcagctgggg gggcagtcca cacacgggga ttggatttcg cctgcgatat atacatttgg 960
gcgccactgg caggcacctg cggggtcctg ctcttgtccc ttgtcatcac cctgtactgt 1020
aagagaggaa gaaagaagtt gttgtatatt ttcaaacagc cattcatgag gccggtccag 1080
accactcagg aggaggatgg atgcagttgc cgctttccgg aagaggaaga gggtgggtgt 1140
gaactccgag ttaaattttc tcgcagtgct gatgccccag cgtataaaca gggtcagaac 1200
caactgtata atgaactcaa tttggggagg cgagaggagt atgatgtatt ggacaagcgg 1260
cgggggcggg atcctgaaat gggcggtaag ccaaggcgca agaatccaca ggagggtttg 1320
tataatgagt tgcagaagga taaaatggcg gaagcgtatt cagaaatcgg aatgaaggga 1380
gagcgccgca gagggaaagg gcatgatggc ctctaccaag gtttgtcaac agcgaccaag 1440
gatacctatg acgcacttca tatgcaagca ctgcccccca gg 1482

<210> SEQ ID NO 224
<211> LENGTH: 104
<212> TYPE: PRT
<213> ORGANISM: Artificial Sequence
<220> FEATURE:
<223> OTHER INFORMATION: A6 L chain

<400> SEQUENCE: 224

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile

```
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ala Ala Thr Tyr Tyr Cys Gln Arg Tyr Gly Thr Phe Gly Gln
                85                  90                  95

Gly Thr Lys Val Asp Ile Lys Arg
            100


<210> SEQ ID NO 225
<211> LENGTH: 312
<212> TYPE: DNA
<213> ORGANISM: Artificial Sequence
<220> FEATURE:
<223> OTHER INFORMATION: A6 L chain

<400> SEQUENCE: 225

gacatccaga tgacacagag ccctagcagc ctgtctgcca gcgtgggaga cagagtgacc      60

atcacctgta gagccagcca gagcatcagc agctacctga actggtatca gcagaagccc     120

ggcaaggccc ctaaactgct gatctatgcc gccagctctc tgcagtctgg cgtgccatct     180

agattttccg gcagcggctc tggcaccgac ttcaccctga ccatatctag cctgcagcct     240

gaggatgccg ccacctacta ctgtcagaga tacggcacat tcggccaggg caccaaggtg     300

gacattaaga ga                                                         312


<210> SEQ ID NO 226
<211> LENGTH: 127
<212> TYPE: PRT
<213> ORGANISM: Artificial Sequence
<220> FEATURE:
<223> OTHER INFORMATION: A6 H chain

<400> SEQUENCE: 226

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Lys Thr Ser Leu Asn Asp Tyr Asp Phe Trp Ser Gly Tyr
            100                 105                 110

Leu Leu Asp Tyr Trp Gly Gln Gly Thr Leu Val Thr Val Ser Ser
        115                 120                 125


<210> SEQ ID NO 227
<211> LENGTH: 381
<212> TYPE: DNA
<213> ORGANISM: Artificial Sequence
<220> FEATURE:
<223> OTHER INFORMATION: A6 H chain

<400> SEQUENCE: 227
```

caagttcagc tggttgaatc tggcggcgga ctggttaagc ctggcggttc tctgagactg 60
agctgtgccg cctccggctt caccttcagc gactactaca tgagctggat cagacaggcc 120
cctggcaaag gcctggaatg ggtgtcctac atcagctcca gcggcagcac catctactac 180
gccgatagcg tgaagggcag attcaccatc agccgggaca acgccaagaa cagcctgtac 240
ctgcagatga actccctgag agccgaggac accgccgtgt actattgcgc cagacacaag 300
accagcctga acgactacga cttttggagc ggctacctgc tggactattg gggccaggga 360
acactggtca ccgtgtctag t 381

<210> SEQ ID NO 228
<211> LENGTH: 738
<212> TYPE: DNA
<213> ORGANISM: Artificial Sequence
<220> FEATURE:
<223> OTHER INFORMATION: A6LH binder

<400> SEQUENCE: 228
gacatccaga tgacacagag ccctagcagc ctgtctgcca gcgtgggaga cagagtgacc 60
atcacctgta gagccagcca gagcatcagc agctacctga actggtatca gcagaagccc 120
ggcaaggccc ctaaactgct gatctatgcc gccagctctc tgcagtctgg cgtgccatct 180
agattttccg gcagcggctc tggcaccgac ttcaccctga ccatatctag cctgcagcct 240
gaggatgccg ccacctacta ctgtcagaga tacggcacat tcggccaggg caccaaggtg 300
gacattaaga gaggtggcgg aggatctggc ggaggtggaa gcggcggagg cggatctcaa 360
gttcagctgg ttgaatctgg cggcggactg gttaagcctg gcggttctct gagactgagc 420
tgtgccgcct ccggcttcac cttcagcgac tactacatga gctggatcag acaggcccct 480
ggcaaaggcc tggaatgggt gtcctacatc agctccagcg gcagcaccat ctactacgcc 540
gatagcgtga agggcagatt caccatcagc cgggacaacg ccaagaacag cctgtacctg 600
cagatgaact ccctgagagc cgaggacacc gccgtgtact attgcgccag acacaagacc 660
agcctgaacg actacgactt ttggagcggc tacctgctgg actattgggg ccagggaaca 720
ctggtcaccg tgtctagt 738

<210> SEQ ID NO 229
<211> LENGTH: 738
<212> TYPE: DNA
<213> ORGANISM: Artificial Sequence
<220> FEATURE:
<223> OTHER INFORMATION: A6HL binder

<400> SEQUENCE: 229
caagttcagc tggttgaatc tggcggcgga ctggttaagc ctggcggttc tctgagactg 60
agctgtgccg cctccggctt caccttcagc gactactaca tgagctggat cagacaggcc 120
cctggcaaag gcctggaatg ggtgtcctac atcagctcca gcggcagcac catctactac 180
gccgatagcg tgaagggcag attcaccatc agccgggaca acgccaagaa cagcctgtac 240
ctgcagatga actccctgag agccgaggac accgccgtgt actattgcgc cagacacaag 300
accagcctga acgactacga cttttggagc ggctacctgc tggactattg gggccaggga 360
acactggtca ccgtgtctag tggtggcgga ggatctggcg gaggtggaag cggcggaggc 420
ggatctgaca tccagatgac acagagccct agcagcctgt ctgccagcgt gggagacaga 480
gtgaccatca cctgtagagc cagccagagc atcagcagct acctgaactg gtatcagcag 540

```
aagcccggca aggcccctaa actgctgatc tatgccgcca gctctctgca gtctggcgtg    600

ccatctagat tttccggcag cggctctggc accgacttca ccctgaccat atctagcctg    660

cagcctgagg atgccgccac ctactactgt cagagatacg gcacattcgg ccagggcacc    720

aaggtggaca ttaagaga                                                  738


<210> SEQ ID NO 230
<211> LENGTH: 494
<212> TYPE: PRT
<213> ORGANISM: Artificial Sequence
<220> FEATURE:
<223> OTHER INFORMATION: RJ154LH CAR (A6LH/CD8 TM/4-1BB/CD3zeta)

<400> SEQUENCE: 230

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Ser Ile Ser Ser Tyr Leu Asn Trp Tyr Gln Gln Lys Pro Gly Lys
    50                  55                  60

Ala Pro Lys Leu Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Ala Ala Thr Tyr Tyr Cys Gln Arg
            100                 105                 110

Tyr Gly Thr Phe Gly Gln Gly Thr Lys Val Asp Ile Lys Arg Gly Gly
        115                 120                 125

Gly Gly Ser Gly Gly Gly Gly Ser Gly Gly Gly Gly Ser Gln Val Gln
    130                 135                 140

Leu Val Glu Ser Gly Gly Gly Leu Val Lys Pro Gly Gly Ser Leu Arg
145                 150                 155                 160

Leu Ser Cys Ala Ala Ser Gly Phe Thr Phe Ser Asp Tyr Tyr Met Ser
                165                 170                 175

Trp Ile Arg Gln Ala Pro Gly Lys Gly Leu Glu Trp Val Ser Tyr Ile
            180                 185                 190

Ser Ser Ser Gly Ser Thr Ile Tyr Tyr Ala Asp Ser Val Lys Gly Arg
        195                 200                 205

Phe Thr Ile Ser Arg Asp Asn Ala Lys Asn Ser Leu Tyr Leu Gln Met
    210                 215                 220

Asn Ser Leu Arg Ala Glu Asp Thr Ala Val Tyr Tyr Cys Ala Arg His
225                 230                 235                 240

Lys Thr Ser Leu Asn Asp Tyr Asp Phe Trp Ser Gly Tyr Leu Leu Asp
                245                 250                 255

Tyr Trp Gly Gln Gly Thr Leu Val Thr Val Ser Ser Ala Ala Ala Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
```

```
                325                 330                 335

Thr Leu Tyr Cys Lys Arg Gly Arg Lys Lys Leu Leu Tyr Ile Phe Lys
            340                 345                 350

Gln Pro Phe Met Arg Pro Val Gln Thr Thr Gln Glu Glu Asp Gly Cys
        355                 360                 365

Ser Cys Arg Phe Pro Glu Glu Glu Glu Gly Gly Cys Glu Leu Arg Val
    370                 375                 380

Lys Phe Ser Arg Ser Ala Asp Ala Pro Ala Tyr Lys Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490


<210> SEQ ID NO 231
<211> LENGTH: 1482
<212> TYPE: DNA
<213> ORGANISM: art6ificial sequence
<220> FEATURE:
<223> OTHER INFORMATION: RJ154LH CAR (A6LH/CD8 TM/4-1BB/CD3zeta)

<400> SEQUENCE: 231

atgcttctgc tcgtgacaag cctgctgctg tgcgagctgc cccaccctgc ctttctgctg     60

atccctgaca tccagatgac acagagccct agcagcctgt ctgccagcgt gggagacaga    120

gtgaccatca cctgtagagc cagccagagc atcagcagct acctgaactg gtatcagcag    180

aagcccggca aggcccctaa actgctgatc tatgccgcca gctctctgca gtctggcgtg    240

ccatctagat tttccggcag cggctctggc accgacttca ccctgaccat atctagcctg    300

cagcctgagg atgccgccac ctactactgt cagagatacg gcacattcgg ccagggcacc    360

aaggtggaca ttaagagagg tggcggagga tctggcggag gtggaagcgg cggaggcgga    420

tctcaagttc agctggttga atctggcggc ggactggtta agcctggcgg ttctctgaga    480

ctgagctgtg ccgcctccgg cttcaccttc agcgactact acatgagctg gatcagacag    540

gcccctggca aaggcctgga atgggtgtcc tacatcagct ccagcggcag caccatctac    600

tacgccgata gcgtgaaggg cagattcacc atcagccggg acaacgccaa gaacagcctg    660

tacctgcaga tgaactccct gagagccgag gacaccgccg tgtactattg cgccagacac    720

aagaccagcc tgaacgacta cgacttttgg agcggctacc tgctggacta ttggggccag    780

ggaacactgg tcaccgtgtc tagtgcggcc gcaaccacta ctccggcacc taggcccccc    840

actccggcac cgaccattgc atcacaacca ctgagtctta gacctgaagc ctgtcgaccc    900

gcagctgggg gggcagtcca cacacgggga ttggatttcg cctgcgatat atacatttgg    960

gcgccactgg caggcacctg cggggtcctg ctcttgtccc ttgtcatcac cctgtactgt   1020

aagagaggaa gaaagaagtt gttgtatatt ttcaaacagc cattcatgag gccggtccag   1080

accactcagg aggaggatgg atgcagttgc cgctttccgg aagaggaaga gggtgggtgt   1140
```

```
gaactccgag ttaaatttc tcgcagtgct gatgccccag cgtataaaca gggtcagaac   1200

caactgtata atgaactcaa tttggggagg cgagaggagt atgatgtatt ggacaagcgg   1260

cgggggcggg atcctgaaat gggcggtaag ccaaggcgca agaatccaca ggagggtttg   1320

tataatgagt tgcagaagga taaaatggcg gaagcgtatt cagaaatcgg aatgaaggga   1380

gagcgccgca gagggaaagg gcatgatggc ctctaccaag gtttgtcaac agcgaccaag   1440

gatacctatg acgcacttca tatgcaagca ctgcccccca gg                     1482
```

<210> SEQ ID NO 232
<211> LENGTH: 494
<212> TYPE: PRT
<213> ORGANISM: Artificial Sequence
<220> FEATURE:
<223> OTHER INFORMATION: RJ154HL CAR (A6HL/CD8 TM/4-1BB/CD3zeta)

<400> SEQUENCE: 232

```
Met Leu Leu Leu Val Thr Ser Leu Leu Leu Cys Glu Leu Pro His Pro
1               5                   10                  15

Ala Phe Leu Leu Ile Pro Gln Val Gln Leu Val Glu Ser Gly Gly Gly
            20                  25                  30

Leu Val Lys Pro Gly Gly Ser Leu Arg Leu Ser Cys Ala Ala Ser Gly
        35                  40                  45

Phe Thr Phe Ser Asp Tyr Tyr Met Ser Trp Ile Arg Gln Ala Pro Gly
    50                  55                  60

Lys Gly Leu Glu Trp Val Ser Tyr Ile Ser Ser Ser Gly Ser Thr Ile
65                  70                  75                  80

Tyr Tyr Ala Asp Ser Val Lys Gly Arg Phe Thr Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg His Lys Thr Ser Leu Asn Asp Tyr
        115                 120                 125

Asp Phe Trp Ser Gly Tyr Leu Leu Asp Tyr Trp Gly Gln Gly Thr Leu
    130                 135                 140

Val Thr Val Ser Ser Gly Gly Gly Gly Ser Gly Gly Gly Gly Ser Gly
145                 150                 155                 160

Gly Gly Gly Ser Asp Ile Gln Met Thr Gln Ser Pro Ser Ser Leu Ser
                165                 170                 175

Ala Ser Val Gly Asp Arg Val Thr Ile Thr Cys Arg Ala Ser Gln Ser
            180                 185                 190

Ile Ser Ser Tyr Leu Asn Trp Tyr Gln Gln Lys Pro Gly Lys Ala Pro
        195                 200                 205

Lys Leu Leu Ile Tyr Ala Ala Ser Ser Leu Gln Ser Gly Val Pro Ser
    210                 215                 220

Arg Phe Ser Gly Ser Gly Ser Gly Thr Asp Phe Thr Leu Thr Ile Ser
225                 230                 235                 240

Ser Leu Gln Pro Glu Asp Ala Ala Thr Tyr Tyr Cys Gln Arg Tyr Gly
                245                 250                 255

Thr Phe Gly Gln Gly Thr Lys Val Asp Ile Lys Arg Ala Ala Ala Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300
```

```
Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Lys Arg Gly Arg Lys Lys Leu Leu Tyr Ile Phe Lys
            340                 345                 350

Gln Pro Phe Met Arg Pro Val Gln Thr Thr Gln Glu Glu Asp Gly Cys
        355                 360                 365

Ser Cys Arg Phe Pro Glu Glu Glu Glu Gly Gly Cys Glu Leu Arg Val
    370                 375                 380

Lys Phe Ser Arg Ser Ala Asp Ala Pro Ala Tyr Lys Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490
```

<210> SEQ ID NO 233
<211> LENGTH: 1482
<212> TYPE: DNA
<213> ORGANISM: Artificial Sequence
<220> FEATURE:
<223> OTHER INFORMATION: RJ154HL CAR (A6HL/CD8 TM/4-1BB/CD3zeta)

<400> SEQUENCE: 233

```
atgcttctgc tcgtgacaag cctgctgctg tgcgagctgc cccaccctgc ctttctgctg      60

atccctcaag ttcagctggt tgaatctggc ggcggactgg ttaagcctgg cggttctctg     120

agactgagct gtgccgcctc cggcttcacc ttcagcgact actacatgag ctggatcaga     180

caggcccctg gcaaaggcct ggaatgggtg tcctacatca gctccagcgg cagcaccatc     240

tactacgccg atagcgtgaa gggcagattc accatcagcc gggacaacgc caagaacagc     300

ctgtacctgc agatgaactc cctgagagcc gaggacaccg ccgtgtacta ttgcgccaga     360

cacaagacca gcctgaacga ctacgacttt tggagcggct acctgctgga ctattggggc     420

cagggaacac tggtcaccgt gtctagtggt ggcggaggat ctggcggagg tggaagcggc     480

ggaggcggat ctgacatcca gatgacacag agccctagca gcctgtctgc cagcgtggga     540

gacagagtga ccatcacctg tagagccagc cagagcatca gcagctacct gaactggtat     600

cagcagaagc ccggcaaggc ccctaaactg ctgatctatg ccgccagctc tctgcagtct     660

ggcgtgccat ctagattttc cggcagcggc tctggcaccg acttcaccct gaccatatct     720

agcctgcagc ctgaggatgc cgccacctac tactgtcaga gatacggcac attcggccag     780

ggcaccaagg tggacattaa gagagcggcc gcaaccacta ctccggcacc taggcccccc     840

actccggcac cgaccattgc atcacaacca ctgagtctta gacctgaagc ctgtcgaccc     900

gcagctgggg gggcagtcca cacacgggga ttggatttcg cctgcgatat atacatttgg     960
```

```
gcgccactgg caggcacctg cggggtcctg ctcttgtccc ttgtcatcac cctgtactgt   1020

aagagaggaa gaaagaagtt gttgtatatt ttcaaacagc cattcatgag gccggtccag   1080

accactcagg aggaggatgg atgcagttgc cgctttccgg aagaggaaga gggtgggtgt   1140

gaactccgag ttaaattttc tcgcagtgct gatgccccag cgtataaaca gggtcagaac   1200

caactgtata atgaactcaa tttggggagg cgagaggagt atgatgtatt ggacaagcgg   1260

cgggggcggg atcctgaaat gggcggtaag ccaaggcgca agaatccaca ggagggtttg   1320

tataatgagt tgcagaagga taaaatggcg gaagcgtatt cagaaatcgg aatgaaggga   1380

gagcgccgca gagggaaagg gcatgatggc ctctaccaag gtttgtcaac agcgaccaag   1440

gatacctatg acgcacttca tatgcaagca ctgcccccca gg                      1482
```

<210> SEQ ID NO 234
<211> LENGTH: 104
<212> TYPE: PRT
<213> ORGANISM: Artificial Sequence
<220> FEATURE:
<223> OTHER INFORMATION: C1 L chain

<400> SEQUENCE: 234

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ala Ala Thr Tyr Tyr Cys Gln His Tyr Gly Thr Phe Gly Gln
                85                  90                  95

Gly Thr Lys Val Glu Ile Lys Arg
            100
```

<210> SEQ ID NO 235
<211> LENGTH: 312
<212> TYPE: DNA
<213> ORGANISM: Artificial Sequence
<220> FEATURE:
<223> OTHER INFORMATION: C1 L chain

<400> SEQUENCE: 235

```
gacatccaga tgacacagag ccctagcagc ctgtctgcca gcgtgggaga cagagtgacc     60

atcacctgta gagccagcca gagcatcagc agctacctga actggtatca gcagaagccc    120

ggcaaggccc ctaaactgct gatctatgcc gccagctctc tgcagtctgg cgtgccatct    180

agattttccg gcagcggctc tggcaccgac ttcaccctga ccatatctag cctgcagcct    240

gaggatgccg ccacctacta ctgtcagcac tacggcacat ttggccaggg caccaaggtg    300

gaaatcaaga ga                                                        312
```

<210> SEQ ID NO 236
<211> LENGTH: 126
<212> TYPE: PRT
<213> ORGANISM: Artificial Sequence
<220> FEATURE:
<223> OTHER INFORMATION: C1 H chain

<400> SEQUENCE: 236

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Ala Pro His Lys His Tyr Asp Phe Trp Ser Gly Tyr Tyr
            100                 105                 110

Pro Asp Tyr Trp Gly Gln Gly Thr Leu Val Thr Val Ser Ser
        115                 120                 125

<210> SEQ ID NO 237
<211> LENGTH: 378
<212> TYPE: DNA
<213> ORGANISM: Artificial Sequence
<220> FEATURE:
<223> OTHER INFORMATION: C1 H chain

<400> SEQUENCE: 237
caagttcagc tggttgaatc tggcggcgga ctggttaagc ctggcggttc tctgagactg 60
agctgtgccg cctccggctt caccttcagc gactactaca tgagctggat cagacaggcc 120
cctggcaaag gcctggaatg ggtgtcctac atcagctcca gcggcagcac catctactac 180
gccgatagcg tgaagggcag attcaccatc agccgggaca acgccaagaa cagcctgtac 240
ctgcagatga actccctgag agccgaggac accgccgtgt actattgtgc cagacacgcc 300
cctcacaagc actacgactt ttggagcggc tactaccccg actattgggg ccagggaaca 360
ctggtcacag tgtcctct 378

<210> SEQ ID NO 238
<211> LENGTH: 735
<212> TYPE: DNA
<213> ORGANISM: Artificial Sequence
<220> FEATURE:
<223> OTHER INFORMATION: C1LH binder

<400> SEQUENCE: 238
gacatccaga tgacacagag ccctagcagc ctgtctgcca gcgtgggaga cagagtgacc 60
atcacctgta gagccagcca gagcatcagc agctacctga actggtatca gcagaagccc 120
ggcaaggccc ctaaactgct gatctatgcc gccagctctc tgcagtctgg cgtgccatct 180
agattttccg gcagcggctc tggcaccgac ttcaccctga ccatatctag cctgcagcct 240
gaggatgccg ccacctacta ctgtcagcac tacggcacat ttggccaggg caccaaggtg 300
gaaatcaaga gaggtggcgg aggatctggc ggaggtggaa gcggcggagg cggatctcaa 360
gttcagctgg ttgaatctgg cggcggactg gttaagcctg gcggttctct gagactgagc 420
tgtgccgcct ccggcttcac cttcagcgac tactacatga gctggatcag acaggcccct 480
ggcaaaggcc tggaatgggt gtcctacatc agctccagcg gcagcaccat ctactacgcc 540
gatagcgtga agggcagatt caccatcagc cgggacaacg ccaagaacag cctgtacctg 600

```
cagatgaact ccctgagagc cgaggacacc gccgtgtact attgtgccag acacgcccct    660

cacaagcact acgacttttg gagcggctac taccccgact attggggcca gggaacactg    720

gtcacagtgt cctct                                                     735


<210> SEQ ID NO 239
<211> LENGTH: 735
<212> TYPE: DNA
<213> ORGANISM: Artificial Sequence
<220> FEATURE:
<223> OTHER INFORMATION: C1HL binder

<400> SEQUENCE: 239

caagttcagc tggttgaatc tggcggcgga ctggttaagc ctggcggttc tctgagactg     60

agctgtgccg cctccggctt caccttcagc gactactaca tgagctggat cagacaggcc    120

cctggcaaag gcctggaatg ggtgtcctac atcagctcca gcggcagcac catctactac    180

gccgatagcg tgaagggcag attcaccatc agccgggaca acgccaagaa cagcctgtac    240

ctgcagatga actccctgag agccgaggac accgccgtgt actattgtgc cagacacgcc    300

cctcacaagc actacgactt ttggagcggc tactaccccg actattgggg ccagggaaca    360

ctggtcacag tgtcctctgg tggcggagga tctggcggag gtggaagcgg cggaggcgga    420

tctgacatcc agatgacaca gagccctagc agcctgtctg ccagcgtggg agacagagtg    480

accatcacct gtagagccag ccagagcatc agcagctacc tgaactggta tcagcagaag    540

cccggcaagg cccctaaact gctgatctat gccgccagct ctctgcagtc tggcgtgcca    600

tctagatttt ccggcagcgg ctctggcacc gacttcaccc tgaccatatc tagcctgcag    660

cctgaggatg ccgccaccta ctactgtcag cactacggca catttggcca gggcaccaag    720

gtggaaatca agaga                                                     735


<210> SEQ ID NO 240
<211> LENGTH: 493
<212> TYPE: PRT
<213> ORGANISM: Artificial Sequence
<220> FEATURE:
<223> OTHER INFORMATION: RJ155LH CAR (C1LH/CD8 TM/4-1BB/CD3zeta)

<400> SEQUENCE: 240

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Ser Ile Ser Ser Tyr Leu Asn Trp Tyr Gln Gln Lys Pro Gly Lys
    50                  55                  60

Ala Pro Lys Leu Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Ala Ala Thr Tyr Tyr Cys Gln His
            100                 105                 110

Tyr Gly Thr Phe Gly Gln Gly Thr Lys Val Glu Ile Lys Arg Gly Gly
        115                 120                 125

Gly Gly Ser Gly Gly Gly Gly Ser Gly Gly Gly Gly Ser Gln Val Gln
    130                 135                 140
```

```
Leu Val Glu Ser Gly Gly Gly Leu Val Lys Pro Gly Gly Ser Leu Arg
145                 150                 155                 160

Leu Ser Cys Ala Ala Ser Gly Phe Thr Phe Ser Asp Tyr Tyr Met Ser
                165                 170                 175

Trp Ile Arg Gln Ala Pro Gly Lys Gly Leu Glu Trp Val Ser Tyr Ile
            180                 185                 190

Ser Ser Ser Gly Ser Thr Ile Tyr Tyr Ala Asp Ser Val Lys Gly Arg
        195                 200                 205

Phe Thr Ile Ser Arg Asp Asn Ala Lys Asn Ser Leu Tyr Leu Gln Met
    210                 215                 220

Asn Ser Leu Arg Ala Glu Asp Thr Ala Val Tyr Tyr Cys Ala Arg His
225                 230                 235                 240

Ala Pro His Lys His Tyr Asp Phe Trp Ser Gly Tyr Tyr Pro Asp Tyr
                245                 250                 255

Trp Gly Gln Gly Thr Leu Val Thr Val Ser Ser Ala Ala Ala Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Lys Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```

```
<210> SEQ ID NO 241
<211> LENGTH: 1479
<212> TYPE: DNA
<213> ORGANISM: Artificial Sequence
<220> FEATURE:
<223> OTHER INFORMATION: RJ155LH CAR (C1LH/CD8 TM/4-1BB/CD3zeta)

<400> SEQUENCE: 241

atgcttctgc tcgtgacaag cctgctgctg tgcgagctgc cccaccctgc ctttctgctg      60
```

```
atccctgaca tccagatgac acagagccct agcagcctgt ctgccagcgt gggagacaga    120
gtgaccatca cctgtagagc cagccagagc atcagcagct acctgaactg gtatcagcag    180
aagcccggca aggcccctaa actgctgatc tatgccgcca gctctctgca gtctggcgtg    240
ccatctagat tttccggcag cggctctggc accgacttca ccctgaccat atctagcctg    300
cagcctgagg atgccgccac ctactactgt cagcactacg gcacatttgg ccagggcacc    360
aaggtggaaa tcaagagagg tggcggagga tctggcggag gtggaagcgg cggaggcgga    420
tctcaagttc agctggttga atctggcggc ggactggtta agcctggcgg ttctctgaga    480
ctgagctgtg ccgcctccgg cttcaccttc agcgactact acatgagctg gatcagacag    540
gcccctggca aaggcctgga atgggtgtcc tacatcagct ccagcggcag caccatctac    600
tacgccgata gcgtgaaggg cagattcacc atcagccggg acaacgccaa gaacagcctg    660
tacctgcaga tgaactccct gagagccgag gacaccgccg tgtactattg tgccagacac    720
gcccctcaca agcactacga cttttggagc ggctactacc ccgactattg gggccaggga    780
acactggtca cagtgtcctc tgcggccgca accactactc cggcacctag gcccccccact   840
ccggcaccga ccattgcatc acaaccactg agtcttagac ctgaagcctg tcgacccgca    900
gctgggggg cagtccacac acggggattg gatttcgcct gcgatatata catttgggcg    960
ccactggcag gcacctgcgg ggtcctgctc ttgtcccttg tcatcaccct gtactgtaag   1020
agaggaagaa agaagttgtt gtatattttc aaacagccat tcatgaggcc ggtccagacc   1080
actcaggagg aggatggatg cagttgccgc tttccggaag aggaagaggg tgggtgtgaa   1140
ctccgagtta aattttctcg cagtgctgat gccccagcgt ataaacaggg tcagaaccaa   1200
ctgtataatg aactcaattt ggggaggcga gaggagtatg atgtattgga caagcggcgg   1260
gggcgggatc ctgaaatggg cggtaagcca aggcgcaaga atccacagga gggtttgtat   1320
aatgagttgc agaaggataa aatggcggaa gcgtattcag aaatcggaat gaagggagag   1380
cgccgcagag ggaaagggca tgatggcctc taccaaggtt tgtcaacagc gaccaaggat   1440
acctatgacg cacttcatat gcaagcactg ccccccagg                           1479
```

<210> SEQ ID NO 242
<211> LENGTH: 493
<212> TYPE: PRT
<213> ORGANISM: Artificial Sequence
<220> FEATURE:
<223> OTHER INFORMATION: RJ155HL CAR (C1HL/CD8 TM/4-1BB/CD3zeta)

<400> SEQUENCE: 242

```
Met Leu Leu Leu Val Thr Ser Leu Leu Leu Cys Glu Leu Pro His Pro
1               5                   10                  15

Ala Phe Leu Leu Ile Pro Gln Val Gln Leu Val Glu Ser Gly Gly Gly
            20                  25                  30

Leu Val Lys Pro Gly Gly Ser Leu Arg Leu Ser Cys Ala Ala Ser Gly
        35                  40                  45

Phe Thr Phe Ser Asp Tyr Tyr Met Ser Trp Ile Arg Gln Ala Pro Gly
    50                  55                  60

Lys Gly Leu Glu Trp Val Ser Tyr Ile Ser Ser Ser Gly Ser Thr Ile
65                  70                  75                  80

Tyr Tyr Ala Asp Ser Val Lys Gly Arg Phe Thr Ile Ser Arg Asp Asn
                85                  90                  95

Ala Lys Asn Ser Leu Tyr Leu Gln Met Asn Ser Leu Arg Ala Glu Asp
            100                 105                 110
```

```
Thr Ala Val Tyr Tyr Cys Ala Arg His Ala Pro His Lys His Tyr Asp
        115                 120                 125

Phe Trp Ser Gly Tyr Tyr Pro Asp Tyr Trp Gly Gln Gly Thr Leu Val
    130                 135                 140

Thr Val Ser Ser Gly Gly Gly Gly Ser Gly Gly Gly Gly Ser Gly Gly
145                 150                 155                 160

Gly Gly Ser Asp Ile Gln Met Thr Gln Ser Pro Ser Ser Leu Ser Ala
                165                 170                 175

Ser Val Gly Asp Arg Val Thr Ile Thr Cys Arg Ala Ser Gln Ser Ile
            180                 185                 190

Ser Ser Tyr Leu Asn Trp Tyr Gln Gln Lys Pro Gly Lys Ala Pro Lys
        195                 200                 205

Leu Leu Ile Tyr Ala Ala Ser Ser Leu Gln Ser Gly Val Pro Ser Arg
    210                 215                 220

Phe Ser Gly Ser Gly Ser Gly Thr Asp Phe Thr Leu Thr Ile Ser Ser
225                 230                 235                 240

Leu Gln Pro Glu Asp Ala Ala Thr Tyr Tyr Cys Gln His Tyr Gly Thr
                245                 250                 255

Phe Gly Gln Gly Thr Lys Val Glu Ile Lys Arg Ala Ala Ala Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Lys Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```

<210> SEQ ID NO 243
<211> LENGTH: 1479
<212> TYPE: DNA
<213> ORGANISM: Artificial Sequence
<220> FEATURE:
<223> OTHER INFORMATION: RJ155HL CAR (C1HL/CD8 TM/4-1BB/CD3zeta)

<400> SEQUENCE: 243
atgcttctgc tcgtgacaag cctgctgctg tgcgagctgc cccaccctgc ctttctgctg 60
atccctcaag ttcagctggt tgaatctggc ggcggactgg ttaagcctgg cggttctctg 120
agactgagct gtgccgcctc cggcttcacc ttcagcgact actacatgag ctggatcaga 180
caggcccctg gcaaaggcct ggaatgggtg tcctacatca gctccagcgg cagcaccatc 240
tactacgccg atagcgtgaa gggcagattc accatcagcc gggacaacgc caagaacagc 300
ctgtacctgc agatgaactc cctgagagcc gaggacaccg ccgtgtacta ttgtgccaga 360
cacgcccctc acaagcacta cgacttttgg agcggctact accccgacta ttggggccag 420
ggaacactgg tcacagtgtc ctctggtggc ggaggatctg gcggaggtgg aagcggcgga 480
ggcggatctg acatccagat gacacagagc cctagcagcc tgtctgccag cgtgggagac 540
agagtgacca tcacctgtag agccagccag agcatcagca gctacctgaa ctggtatcag 600
cagaagcccg gcaaggcccc taaactgctg atctatgccg ccagctctct gcagtctggc 660
gtgccatcta gattttccgg cagcggctct ggcaccgact tcaccctgac catatctagc 720
ctgcagcctg aggatgccgc cacctactac tgtcagcact acggcacatt tggccagggc 780
accaaggtgg aaatcaagag agcggccgca accactactc cggcacctag gcccccccact 840 ccggcaccga ccattgcatc acaaccactg agtcttagac ctgaagcctg tcgacccgca 900 gctgggggg cagtccacac acggggattg gatttcgcct gcgatatata catttgggcg 960
ccactggcag gcacctgcgg ggtcctgctc ttgtcccttg tcatcaccct gtactgtaag 1020
agaggaagaa agaagttgtt gtatattttc aaacagccat tcatgaggcc ggtccagacc 1080
actcaggagg aggatggatg cagttgccgc tttccggaag aggaagaggg tgggtgtgaa 1140
ctccgagtta aattttctcg cagtgctgat gccccagcgt ataaacaggg tcagaaccaa 1200
ctgtataatg aactcaattt ggggaggcga gaggagtatg atgtattgga caagcggcgg 1260
gggcgggatc ctgaaatggg cggtaagcca aggcgcaaga atccacagga gggtttgtat 1320
aatgagttgc agaaggataa aatggcggaa gcgtattcag aaatcggaat gaagggagag 1380
cgccgcagag ggaaagggca tgatggcctc taccaaggtt tgtcaacagc gaccaaggat 1440
acctatgacg cacttcatat gcaagcactg ccccccagg 1479

<210> SEQ ID NO 244
<211> LENGTH: 15
<212> TYPE: PRT
<213> ORGANISM: Artificial Sequence
<220> FEATURE:
<223> OTHER INFORMATION: Exemplary Linker Sequences for scFv's, CARs, and/or cell engagers

<400> SEQUENCE: 244

Gly Gly Gly Gly Ser Gly Gly Ser Gly Ser Gly Gly Gly Gly Ser
1 5 10 15

<210> SEQ ID NO 245
<211> LENGTH: 15
<212> TYPE: PRT
<213> ORGANISM: Artificial Sequence
<220> FEATURE:
<223> OTHER INFORMATION: Exemplary Linker Sequences for scFv's, CARs, and/or cell engagers

<400> SEQUENCE: 245

Gly Gly Gly Gly Ser Gly Gly Ser Gly Ser Ser Gly Gly Gly Ser 1 5 10 15

<210> SEQ ID NO 246
<211> LENGTH: 15
<212> TYPE: PRT
<213> ORGANISM: Artificial Sequence
<220> FEATURE:
<223> OTHER INFORMATION: Exemplary Linker Sequences for scFv's, CARs, and/or cell engagers

<400> SEQUENCE: 246

Gly Gly Gly Gly Ser Gly Gly Gly Gly Ser Gly Gly Gly Gly Ser
1 5 10 15

<210> SEQ ID NO 247
<211> LENGTH: 15
<212> TYPE: PRT
<213> ORGANISM: Artificial Sequence
<220> FEATURE:
<223> OTHER INFORMATION: Exemplary Linker Sequences for scFv's, CARs, and/or cell engagers

<400> SEQUENCE: 247

Gly Gly Gly Gly Ser Gly Ser Gly Ala Ser Ser Gly Gly Gly Ser
1 5 10 15

<210> SEQ ID NO 248
<211> LENGTH: 15
<212> TYPE: PRT
<213> ORGANISM: Artificial Sequence
<220> FEATURE:
<223> OTHER INFORMATION: Exemplary Linker Sequences for scFv's, CARs, and/or cell engagers

<400> SEQUENCE: 248

Gly Gly Gly Gly Ser Gly Ser Gly Ala Ser Gly Gly Gly Gly Ser
1 5 10 15

<210> SEQ ID NO 249
<211> LENGTH: 15
<212> TYPE: PRT
<213> ORGANISM: Artificial Sequence
<220> FEATURE:
<223> OTHER INFORMATION: Exemplary Linker Sequences for scFv's, CARs, and/or cell engagers

<400> SEQUENCE: 249

Ser Gly Gly Gly Ser Gly Gly Gly Gly Ser Gly Gly Gly Gly Ser
1 5 10 15

<210> SEQ ID NO 250
<211> LENGTH: 18
<212> TYPE: PRT
<213> ORGANISM: Artificial Sequence
<220> FEATURE:
<223> OTHER INFORMATION: Exemplary Linker Sequences for scFv's, CARs, and/or cell engagers

<400> SEQUENCE: 250

Gly Ser Thr Ser Gly Ser Gly Lys Pro Gly Ser Gly Glu Gly Ser Thr
1 5 10 15

Lys Gly

<210> SEQ ID NO 251
<211> LENGTH: 19
<212> TYPE: PRT
<213> ORGANISM: Artificial Sequence
<220> FEATURE:
<223> OTHER INFORMATION: Exemplary Linker Sequences for scFv's, CARs, and/or cell engagers

<400> SEQUENCE: 251

Pro Asn Gly Ala Ser Gln Ser Ser Ser Ala Ser His Thr Gly Ser Ala
1 5 10 15

Pro Gly Ser

<210> SEQ ID NO 252
<211> LENGTH: 19
<212> TYPE: PRT
<213> ORGANISM: Artificial Sequence
<220> FEATURE:
<223> OTHER INFORMATION: Exemplary Linker Sequences for scFv's, CARs, and/or cell engagers

<400> SEQUENCE: 252

Pro Asn Gly Ala Ser Asn Ser Gly Ser Ala Pro Asp Thr Ser Ser Ala
1 5 10 15

Pro Gly Ser

<210> SEQ ID NO 253
<211> LENGTH: 19
<212> TYPE: PRT
<213> ORGANISM: Artificial Sequence
<220> FEATURE:
<223> OTHER INFORMATION: Exemplary Linker Sequences for scFv's, CARs, and/or cell engagers

<400> SEQUENCE: 253

Pro Asn Gly Ala Ser His Ser Gly Ser Ala Pro Asn Thr Ser Ser Ala
1 5 10 15

Pro Gly Ser

<210> SEQ ID NO 254
<211> LENGTH: 19
<212> TYPE: PRT
<213> ORGANISM: Artificial Sequence
<220> FEATURE:
<223> OTHER INFORMATION: Exemplary Linker Sequences for scFv's, CARs, and/or cell engagers

<400> SEQUENCE: 254

Pro Asn Gly Ala Ser Glu Ser Gly Ser Ala Ser Lys Thr Ser Ser Ala
1 5 10 15

Ser Gly Ser

<210> SEQ ID NO 255
<211> LENGTH: 19
<212> TYPE: PRT
<213> ORGANISM: Artificial Sequence
<220> FEATURE:
<223> OTHER INFORMATION: Exemplary Linker Sequences for scFv's, CARs, and/or cell engagers

<400> SEQUENCE: 255

Pro Asn Gly Ala Ser Asn Ser Gly Ser Ala Pro Lys Thr Gly Ser Ala
1 5 10 15

Ser Gly Ser

<210> SEQ ID NO 256
<211> LENGTH: 19
<212> TYPE: PRT

<213> ORGANISM: Artificial Sequence
<220> FEATURE:
<223> OTHER INFORMATION: Exemplary Linker Sequences for scFv's, CARs, and/or cell engagers

<400> SEQUENCE: 256

Pro Asn Gly Ala Ser Lys Ser Gly Ser Ala Ser Gln Thr Ser Ser Ala
1 5 10 15

Pro Gly Ser

<210> SEQ ID NO 257
<211> LENGTH: 19
<212> TYPE: PRT
<213> ORGANISM: Artificial Sequence
<220> FEATURE:
<223> OTHER INFORMATION: Exemplary Linker Sequences for scFv's, CARs, and/or cell engagers

<400> SEQUENCE: 257

Pro Asn Gly Ala Ser His Ser Ser Ser Ala Ser Gln Thr Gly Ser Ala
1 5 10 15

Pro Gly Ser

<210> SEQ ID NO 258
<211> LENGTH: 12
<212> TYPE: PRT
<213> ORGANISM: Artificial Sequence
<220> FEATURE:
<223> OTHER INFORMATION: Exemplary Linker Sequences for scFv's, CARs, and/or cell engagers

<400> SEQUENCE: 258

Pro Asn Gly Ala Ser Lys Arg Ser Ala Pro Gly Ser
1 5 10

<210> SEQ ID NO 259
<211> LENGTH: 19
<212> TYPE: PRT
<213> ORGANISM: Artificial Sequence
<220> FEATURE:
<223> OTHER INFORMATION: Exemplary Linker Sequences for scFv's, CARs, and/or cell engagers

<400> SEQUENCE: 259

Pro Asn Gly Ala Ser His Ser Gly Ser Ala Pro His Thr Ser Ser Ala
1 5 10 15

Ser Gly Ser

<210> SEQ ID NO 260
<211> LENGTH: 15
<212> TYPE: PRT
<213> ORGANISM: Artificial Sequence
<220> FEATURE:
<223> OTHER INFORMATION: Exemplary Linker Sequences for scFv's, CARs, and/or cell engagers

<400> SEQUENCE: 260

Arg Gly Arg Gly Arg Gly Arg Gly Arg Ser Arg Gly Gly Gly Ser
1 5 10 15

<210> SEQ ID NO 261
<211> LENGTH: 15
<212> TYPE: PRT
<213> ORGANISM: Artificial Sequence
<220> FEATURE:
<223> OTHER INFORMATION: Exemplary Linker Sequences for scFv's, CARs, and/or cell engagers

<400> SEQUENCE: 261

Ser His Gly Gly Ser His Gly Gly Gly Ser Gly Gly Gly Gly Ser
1 5 10 15

<210> SEQ ID NO 262
<211> LENGTH: 5
<212> TYPE: PRT
<213> ORGANISM: Artificial Sequence
<220> FEATURE:
<223> OTHER INFORMATION: Exemplary Linker Sequences for scFv's, CARs, and/or cell engagers

<400> SEQUENCE: 262

Gly Gln Ala Gly Arg
1 5

<210> SEQ ID NO 263
<211> LENGTH: 8
<212> TYPE: PRT
<213> ORGANISM: Artificial Sequence
<220> FEATURE:
<223> OTHER INFORMATION: Exemplary Linker Sequences for scFv's, CARs, and/or cell engagers

<400> SEQUENCE: 263

Gly Gly Gly Ser Gly Gly Gly Gly
1 5

<210> SEQ ID NO 264
<211> LENGTH: 5
<212> TYPE: PRT
<213> ORGANISM: Artificial Sequence
<220> FEATURE:
<223> OTHER INFORMATION: Exemplary Linker Sequences for scFv's, CARs, and/or cell engagers

<400> SEQUENCE: 264

Ser Gly Gly Gly Gly
1 5

<210> SEQ ID NO 265
<211> LENGTH: 5
<212> TYPE: PRT
<213> ORGANISM: Artificial Sequence
<220> FEATURE:
<223> OTHER INFORMATION: Exemplary Linker Sequences for scFv's, CARs, and/or cell engagers

<400> SEQUENCE: 265

Gly Gly Gly Gly Ser
1 5

<210> SEQ ID NO 266
<211> LENGTH: 30
<212> TYPE: PRT
<213> ORGANISM: Artificial Sequence
<220> FEATURE:
<223> OTHER INFORMATION: Exemplary Linker Sequences for scFv's, CARs, and/or cell engagers

<400> SEQUENCE: 266

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser
20 25 30

<210> SEQ ID NO 267
<211> LENGTH: 15
<212> TYPE: PRT
<213> ORGANISM: Artificial Sequence
<220> FEATURE:
<223> OTHER INFORMATION: Exemplary human IgG1-derived hinge

<400> SEQUENCE: 267

Glu Pro Lys Ser Cys Asp Lys Thr His Thr Cys Pro Pro Cys Pro
1               5                   10                  15

<210> SEQ ID NO 268
<211> LENGTH: 15
<212> TYPE: PRT
<213> ORGANISM: Artificial Sequence
<220> FEATURE:
<223> OTHER INFORMATION: Exemplary human IgG2-derived hinge

<400> SEQUENCE: 268

Asp Lys Thr His Thr Cys Pro Pro Cys Pro Ala Pro Pro Val Ala
1               5                   10                  15

<210> SEQ ID NO 269
<211> LENGTH: 12
<212> TYPE: PRT
<213> ORGANISM: Artificial Sequence
<220> FEATURE:
<223> OTHER INFORMATION: Exemplary human IgG4-derived hinge

<400> SEQUENCE: 269

Glu Ser Lys Tyr Gly Pro Pro Cys Pro Pro Cys Pro
1               5                   10

<210> SEQ ID NO 270
<211> LENGTH: 49
<212> TYPE: PRT
<213> ORGANISM: Artificial Sequence
<220> FEATURE:
<223> OTHER INFORMATION: Exemplary human CD8alpha-derived hinges

<400> SEQUENCE: 270

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Asp Ile
        35                  40                  45

Tyr

<210> SEQ ID NO 271
<211> LENGTH: 47
<212> TYPE: PRT
<213> ORGANISM: Artificial Sequence
<220> FEATURE:
<223> OTHER INFORMATION: Exemplary human CD8alpha-derived hinge

<400> SEQUENCE: 271

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr
        35                  40                  45

```
<210> SEQ ID NO 272
<211> LENGTH: 45
<212> TYPE: PRT
<213> ORGANISM: Artificial Sequence
<220> FEATURE:
<223> OTHER INFORMATION: Exemplary human CD8alpha-derived hinge

<400> SEQUENCE: 272

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45


<210> SEQ ID NO 273
<211> LENGTH: 39
<212> TYPE: PRT
<213> ORGANISM: Artificial Sequence
<220> FEATURE:
<223> OTHER INFORMATION: Exemplary human CD28-derived hinge

<400> SEQUENCE: 273

Ile Glu Val Met Tyr Pro Pro Pro Tyr Leu Asp Asn Glu Arg Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35


<210> SEQ ID NO 274
<211> LENGTH: 5
<212> TYPE: PRT
<213> ORGANISM: Artificial Sequence
<220> FEATURE:
<223> OTHER INFORMATION: Exemplary short hinges

<400> SEQUENCE: 274

Gly Gly Gly Gly Ser
1               5


<210> SEQ ID NO 275
<211> LENGTH: 3
<212> TYPE: PRT
<213> ORGANISM: Artificial Sequence
<220> FEATURE:
<223> OTHER INFORMATION: Exemplary short hinge

<400> SEQUENCE: 275

Ala Ala Ala
1


<210> SEQ ID NO 276
<211> LENGTH: 21
<212> TYPE: PRT
<213> ORGANISM: Artificial Sequence
<220> FEATURE:
<223> OTHER INFORMATION: Exemplary human CD3zeta transmembrane domain

<400> SEQUENCE: 276

Leu Cys Tyr Leu Leu Asp Gly Ile Leu Phe Ile Tyr Gly Val Ile Leu
1               5                   10                  15

Thr Ala Leu Phe Leu
```

20

<210> SEQ ID NO 277
<211> LENGTH: 22
<212> TYPE: PRT
<213> ORGANISM: Artificial Sequence
<220> FEATURE:
<223> OTHER INFORMATION: Exemplary human CD4 transmembrane domain

<400> SEQUENCE: 277

Met Ala Leu Ile Val Leu Gly Gly Val Ala Gly Leu Leu Leu Phe Ile
1               5                   10                  15

Gly Leu Gly Ile Phe Phe
            20

<210> SEQ ID NO 278
<211> LENGTH: 21
<212> TYPE: PRT
<213> ORGANISM: Artificial Sequence
<220> FEATURE:
<223> OTHER INFORMATION: Exemplary human CD8alpha transmembrane domain

<400> SEQUENCE: 278

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 279
<211> LENGTH: 24
<212> TYPE: PRT
<213> ORGANISM: Artificial Sequence
<220> FEATURE:
<223> OTHER INFORMATION: Exemplary human CD8alpha transmembrane domain

<400> SEQUENCE: 279

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 280
<211> LENGTH: 22
<212> TYPE: PRT
<213> ORGANISM: Artificial Sequence
<220> FEATURE:
<223> OTHER INFORMATION: Exemplary human CD8alpha transmembrane domain

<400> SEQUENCE: 280

Ile Trp Ala Pro Leu Ala Gly Thr Cys Gly Val Leu Leu Leu Ser Leu
1               5                   10                  15

Val Ile Thr Leu Tyr Cys
            20

<210> SEQ ID NO 281
<211> LENGTH: 19
<212> TYPE: PRT
<213> ORGANISM: Artificial Sequence
<220> FEATURE:
<223> OTHER INFORMATION: Exemplary human CD8alpha transmembrane domain

<400> SEQUENCE: 281

Ile Trp Ala Pro Leu Ala Gly Thr Cys Gly Val Leu Leu Leu Ser Leu
1               5                   10                  15

Val Ile Thr

<210> SEQ ID NO 282
<211> LENGTH: 27
<212> TYPE: PRT
<213> ORGANISM: Artificial Sequence
<220> FEATURE:
<223> OTHER INFORMATION: Exemplary human CD28 transmembrane domain

<400> SEQUENCE: 282

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 283
<211> LENGTH: 21
<212> TYPE: PRT
<213> ORGANISM: Artificial Sequence
<220> FEATURE:
<223> OTHER INFORMATION: Exemplary human CD278 transmembrane domain

<400> SEQUENCE: 283

Phe Trp Leu Pro Ile Gly Cys Ala Ala Phe Val Val Val Cys Ile Leu
1               5                   10                  15

Gly Cys Ile Leu Ile
            20

<210> SEQ ID NO 284
<211> LENGTH: 113
<212> TYPE: PRT
<213> ORGANISM: Artificial Sequence
<220> FEATURE:
<223> OTHER INFORMATION: Exemplary human CD3? intracellular signaling domain

<400> SEQUENCE: 284

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 285
<211> LENGTH: 42
<212> TYPE: PRT
<213> ORGANISM: Artificial Sequence
<220> FEATURE:
<223> OTHER INFORMATION: Exemplary human 4-1BB (CD137) intracellular signaling domain

<400> SEQUENCE: 285

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 286
<211> LENGTH: 41
<212> TYPE: PRT
<213> ORGANISM: Artificial Sequence
<220> FEATURE:
<223> OTHER INFORMATION: Exemplary human CD28 intracellular signaling
      domain

<400> SEQUENCE: 286

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40


<210> SEQ ID NO 287
<211> LENGTH: 42
<212> TYPE: PRT
<213> ORGANISM: Artificial Sequence
<220> FEATURE:
<223> OTHER INFORMATION: Exemplary human OX40 (CD134) intracellular
      signaling domain

<400> SEQUENCE: 287

Ala Leu Tyr Leu Leu Arg Arg Asp Gln Arg Leu Pro Pro Asp Ala His
1               5                   10                  15

Lys Pro Pro Gly Gly Gly Ser Phe Arg Thr Pro Ile Gln Glu Glu Gln
            20                  25                  30

Ala Asp Ala His Ser Thr Leu Ala Lys Ile
        35                  40


<210> SEQ ID NO 288
<211> LENGTH: 38
<212> TYPE: PRT
<213> ORGANISM: Artificial Sequence
<220> FEATURE:
<223> OTHER INFORMATION: Exemplary human CD278 intracellular signaling
      domain

<400> SEQUENCE: 288

Cys Trp Leu Thr Lys Lys Lys Tyr Ser Ser Ser Val His Asp Pro Asn
1               5                   10                  15

Gly Glu Tyr Met Phe Met Arg Ala Val Asn Thr Ala Lys Lys Ser Arg
            20                  25                  30

Leu Thr Asp Val Thr Leu
        35


<210> SEQ ID NO 289
<211> LENGTH: 24
<212> TYPE: PRT
<213> ORGANISM: Artificial Sequence
<220> FEATURE:
<223> OTHER INFORMATION: Exemplary human DAP10 intracellular signaling
      domain

<400> SEQUENCE: 289
```

```
Leu Cys Ala Arg Pro Arg Arg Ser Pro Ala Gln Glu Asp Gly Lys Val
1               5                   10                  15

Tyr Ile Asn Met Pro Gly Arg Gly
            20


<210> SEQ ID NO 290
<211> LENGTH: 52
<212> TYPE: PRT
<213> ORGANISM: Artificial Sequence
<220> FEATURE:
<223> OTHER INFORMATION: Exemplary human DAP12 intracellular signaling
      domain

<400> SEQUENCE: 290

Tyr Phe Leu Gly Arg Leu Val Pro Arg Gly Arg Gly Ala Ala Glu Ala
1               5                   10                  15

Ala Thr Arg Lys Gln Arg Ile Thr Glu Thr Glu Ser Pro Tyr Gln Glu
            20                  25                  30

Leu Gln Gly Gln Arg Ser Asp Val Tyr Ser Asp Leu Asn Thr Gln Arg
        35                  40                  45

Pro Tyr Tyr Lys
    50


<210> SEQ ID NO 291
<211> LENGTH: 48
<212> TYPE: PRT
<213> ORGANISM: Artificial Sequence
<220> FEATURE:
<223> OTHER INFORMATION: Exemplary human CD27 intracellular signaling
      domain

<400> SEQUENCE: 291

Gln Arg Arg Lys Tyr Arg Ser Asn Lys Gly Glu Ser Pro Val Glu Pro
1               5                   10                  15

Ala Glu Pro Cys His Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45


<210> SEQ ID NO 292
<211> LENGTH: 119
<212> TYPE: PRT
<213> ORGANISM: Artificial Sequence
<220> FEATURE:
<223> OTHER INFORMATION: Exemplary anti-human CD3 scFv (clone OKT3)
      (Heavy chain)

<400> SEQUENCE: 292

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95
```

Ala Arg Tyr Tyr Asp Asp His Tyr Cys Leu Asp Tyr Trp Gly Gln Gly
100 105 110

Thr Pro Val Thr Val Ser Ser
115

<210> SEQ ID NO 293
<211> LENGTH: 107
<212> TYPE: PRT
<213> ORGANISM: Artificial Sequence
<220> FEATURE:
<223> OTHER INFORMATION: Exemplary anti-human CD3 scFv (clone OKT3) (light chain)

<400> SEQUENCE: 293

Asp Ile Gln Met Thr Gln Ser Pro Ser Ser Leu Ser Ala Ser Val Gly
1 5 10 15

Asp Arg Val Thr Ile Thr Cys Ser Ala Ser Ser Ser Val Ser Tyr Met
20 25 30

Asn Trp Tyr Gln Gln Thr Pro Gly Lys Ala Pro Lys Arg Trp Ile Tyr
35 40 45

Asp Thr Ser Lys Leu Ala Ser Gly Val Pro Ser Arg Phe Ser Gly Ser
50 55 60

Gly Ser Gly Thr Asp Tyr Thr Phe Thr Ile Ser Ser Leu Gln Pro Glu
65 70 75 80

Asp Ile Ala Thr Tyr Tyr Cys Gln Gln Trp Ser Ser Asn Pro Phe Thr
85 90 95

Phe Gly Gln Gly Thr Lys Leu Gln Ile Thr Arg
100 105

<210> SEQ ID NO 294
<211> LENGTH: 122
<212> TYPE: PRT
<213> ORGANISM: Artificial Sequence
<220> FEATURE:
<223> OTHER INFORMATION: Exemplary anti-human CD3 scFv (clone UCHT1) (heavy chain)

<400> SEQUENCE: 294

Glu Val Gln Leu Gln Gln Ser Gly Pro Glu Leu Val Lys Pro Gly Ala
1 5 10 15

Ser Met Lys Ile Ser Cys Lys Ala Ser Gly Tyr Ser Phe Thr Gly Tyr
20 25 30

Thr Met Asn Trp Val Lys Gln Ser His Gly Lys Asn Leu Glu Trp Met
35 40 45

Gly Leu Ile Asn Pro Tyr Lys Gly Val Ser Thr Tyr Asn Gln Lys Phe
50 55 60

Lys Asp Lys Ala Thr Leu Thr Val Asp Lys Ser Ser Ser Thr Ala Tyr
65 70 75 80

Met Glu Leu Leu Ser Leu Thr Ser Glu Asp Ser Ala Val Tyr Tyr Cys
85 90 95

Ala Arg Ser Gly Tyr Tyr Gly Asp Ser Asp Trp Tyr Phe Asp Val Trp
100 105 110

Gly Gln Gly Thr Thr Leu Thr Val Phe Ser
115 120

<210> SEQ ID NO 295
<211> LENGTH: 108
<212> TYPE: PRT
<213> ORGANISM: Artificial Sequence
<220> FEATURE:

<223> OTHER INFORMATION: Exemplary anti-human CD3 scFv (clone UCHT1)
(light chain)

<400> SEQUENCE: 295

```
Met Asp Ile Gln Met Thr Gln Thr Thr Ser Ser Leu Ser Ala Ser Leu
1               5                   10                  15

Gly Asp Arg Val Thr Ile Ser Cys Arg Ala Ser Gln Asp Ile Arg Asn
            20                  25                  30

Tyr Leu Asn Trp Tyr Gln Gln Lys Pro Asp Gly Thr Val Lys Leu Leu
        35                  40                  45

Ile Tyr Tyr Thr Ser Arg Leu His Ser Gly Val Pro Ser Lys Phe Ser
    50                  55                  60

Gly Ser Gly Ser Gly Thr Asp Tyr Ser Leu Thr Ile Ser Asn Leu Glu
65                  70                  75                  80

Gln Glu Asp Ile Ala Thr Tyr Phe Cys Gln Gln Gly Asn Thr Leu Pro
                85                  90                  95

Trp Thr Phe Ala Gly Gly Thr Lys Leu Glu Ile Lys
            100                 105
```

<210> SEQ ID NO 296
<211> LENGTH: 124
<212> TYPE: PRT
<213> ORGANISM: Artificial Sequence
<220> FEATURE:
<223> OTHER INFORMATION: Exemplary anti-human CD16a scFv (heavy chain)

<400> SEQUENCE: 296

```
Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Phe Arg Cys Asp Arg Phe Arg Arg Phe Thr Ile Ser Arg Asp
65                  70                  75                  80

Asn Ala Lys Asn Ser Leu Tyr Leu Gln Met Asn Ser Leu Arg Ala Glu
                85                  90                  95

Asp Thr Ala Val Tyr Tyr Cys Ala Arg Gly Arg Ser Leu Leu Phe Asp
            100                 105                 110

Tyr Trp Gly Gln Gly Thr Leu Val Thr Val Ser Arg
        115                 120
```

<210> SEQ ID NO 297
<211> LENGTH: 108
<212> TYPE: PRT
<213> ORGANISM: Artificial Sequence
<220> FEATURE:
<223> OTHER INFORMATION: Exemplary anti-human CD16a scFv (light chain)

<400> SEQUENCE: 297

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45
```

Gly Lys Asn Asn Arg Pro Ser Gly Ile Pro Asp Arg Phe Ser Gly Ser
50 55 60

Ser Ser Gly Asn Thr Ala Ser Leu Thr Ile Thr Gly Ala Gln Ala Glu
65 70 75 80

Asp Glu Ala Asp Tyr Tyr Cys Asn Ser Arg Asp Ser Ser Gly Asn His
85 90 95

Val Val Phe Gly Gly Gly Thr Lys Leu Thr Val Gly
100 105

<210> SEQ ID NO 298
<211> LENGTH: 119
<212> TYPE: PRT
<213> ORGANISM: Artificial Sequence
<220> FEATURE:
<223> OTHER INFORMATION: Exemplary anti-human NKG2A scFv (Heavy chain)

<400> SEQUENCE: 298

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Glu Ile Ser Ser Gly Gly Ser Tyr Thr Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg His Gly Asp Tyr Pro Arg Phe Phe Asp Val Trp Gly Gln Gly
100 105 110

Thr Thr Val Thr Val Ser Ser
115

<210> SEQ ID NO 299
<211> LENGTH: 107
<212> TYPE: PRT
<213> ORGANISM: Artificial Sequence
<220> FEATURE:
<223> OTHER INFORMATION: Exemplary anti-human NKG2A scFv (light chain)

<400> SEQUENCE: 299

Glu Ile Val Leu Thr Gln Ser Pro Ala Thr Leu Ser Leu Ser Pro Gly
1 5 10 15

Glu Arg Ala Thr Leu Ser Cys Ser Ala Ser Ser Ser Val Ser Ser Tyr
20 25 30

Ile Tyr Trp Tyr Gln Gln Lys Pro Gly Gln Ala Pro Arg Leu Leu Ile
35 40 45

Tyr Leu Thr Ser Asn Leu Ala Ser Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Trp Ser Gly Asn Pro Tyr
85 90 95

Thr Phe Gly Gln Gly Thr Lys Leu Glu Ile Lys
100 105

<210> SEQ ID NO 300

<211> LENGTH: 121
<212> TYPE: PRT
<213> ORGANISM: Artificial Sequence
<220> FEATURE:
<223> OTHER INFORMATION: Exemplary anti-human NKG2D scFv (Heavy chain)

<400> SEQUENCE: 300

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Phe Ile Arg Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Arg Gly Leu Gly Asp Gly Thr Tyr Phe Asp Tyr Trp Gly
100 105 110

Gln Gly Thr Thr Val Thr Val Ser Ser
115 120

<210> SEQ ID NO 301
<211> LENGTH: 110
<212> TYPE: PRT
<213> ORGANISM: Artificial Sequence
<220> FEATURE:
<223> OTHER INFORMATION: Exemplary anti-human NKG2D scFv (light chain)

<400> SEQUENCE: 301

Gln Ser Ala Leu Thr Gln Pro Ala Ser Val Ser Gly Ser Pro Gly Gln
1 5 10 15

Ser Ile Thr Ile Ser Cys Ser Gly Ser Ser Ser Asn Ile Gly Asn Asn
20 25 30

Ala Val Asn Trp Tyr Gln Gln Leu Pro Gly Lys Ala Pro Lys Leu Leu
35 40 45

Ile Tyr Tyr Asp Asp Leu Leu Pro Ser Gly Val Ser Asp Arg Phe Ser
50 55 60

Gly Ser Lys Ser Gly Thr Ser Ala Phe Leu Ala Ile Ser Gly Leu Gln
65 70 75 80

Ser Glu Asp Glu Ala Asp Tyr Tyr Cys Ala Ala Trp Asp Asp Ser Leu
85 90 95

Asn Gly Pro Val Phe Gly Gly Gly Thr Lys Leu Thr Val Leu
100 105 110

<210> SEQ ID NO 302
<211> LENGTH: 114
<212> TYPE: PRT
<213> ORGANISM: Artificial Sequence
<220> FEATURE:
<223> OTHER INFORMATION: Exemplary anti-human NKp30 scFv (heavy chain)

<400> SEQUENCE: 302

Gln Val Gln Leu Val Gln Ser Gly Ala Glu Val Lys Lys Pro Gly Ala
1 5 10 15

Ser Val Lys Val Ser Cys Lys Ala Ser Gly His Thr Phe Thr Ser Tyr
20 25 30

```
Phe Met His Trp Val Arg Gln Ala Pro Gly Gln Gly Leu Glu Trp Met
        35                  40                  45

Gly Ile Ile Asn Pro Ser Asp Asp Tyr Ala Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Ala Ile Phe Asp Tyr Trp Gly Gln Gly Thr Leu Val Thr Val
            100                 105                 110

Ser Ser


<210> SEQ ID NO 303
<211> LENGTH: 114
<212> TYPE: PRT
<213> ORGANISM: Artificial Sequence
<220> FEATURE:
<223> OTHER INFORMATION: Exemplary anti-human NKp30 scFv (heavy chain)

<400> SEQUENCE: 303

Gln Val Gln Leu Val Gln Ser Gly Ala Glu Val Lys Lys Pro Gly Ala
1               5                   10                  15

Ser Val Lys Val Ser Cys Lys Ala Ser Gly His Thr Phe Thr Ser Tyr
            20                  25                  30

Phe Met His Trp Val Arg Gln Ala Pro Gly Gln Gly Leu Glu Trp Met
        35                  40                  45

Gly Ile Ile Asn Pro Ser Asp Asp Tyr Ala Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Ala Ile Phe Asp Tyr Trp Gly Gln Gly Thr Pro Val Thr Val
            100                 105                 110

Ser Ser


<210> SEQ ID NO 304
<211> LENGTH: 107
<212> TYPE: PRT
<213> ORGANISM: Artificial Sequence
<220> FEATURE:
<223> OTHER INFORMATION: Exemplary anti-human NKp30 scFv (light chain)

<400> SEQUENCE: 304

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
```

100 105

<210> SEQ ID NO 305
<211> LENGTH: 114
<212> TYPE: PRT
<213> ORGANISM: Artificial Sequence
<220> FEATURE:
<223> OTHER INFORMATION: Exemplary anti-human NKp46 scFv (Heavy chain)

<400> SEQUENCE: 305

Glu Ile Gln Leu Gln Gln Ser Gly Ala Glu Leu Val Lys Pro Gly Ala
1 5 10 15

Ser Val Lys Leu Ser Cys Thr Ala Ser Gly Phe Asn Ile Lys Asp Thr
20 25 30

Tyr Phe His Trp Val Lys Gln Arg Pro Glu Gln Gly Leu Glu Trp Ile
35 40 45

Gly Arg Ile Asp Pro Ala Asn Gly Asn Thr Lys Tyr Asp Pro Lys Phe
50 55 60

His Asp Lys Ala Thr Ile Ile Ala Asp Ile Ser Ser Asn Thr Ala Tyr
65 70 75 80

Leu Gln Phe Ser Ser Leu Thr Ser Glu Asp Thr Ala Val Tyr Tyr Cys
85 90 95

Ala Ala Asn Arg Tyr Gly Tyr Trp Gly Gln Gly Thr Thr Leu Thr Val
100 105 110

Ser Ser

<210> SEQ ID NO 306
<211> LENGTH: 111
<212> TYPE: PRT
<213> ORGANISM: Artificial Sequence
<220> FEATURE:
<223> OTHER INFORMATION: Exemplary anti-human NKp46 scFv (light chain)

<400> SEQUENCE: 306

Asp Ile Val Met Thr Gln Ala Ala Pro Ser Ile Pro Val Thr Pro Gly
1 5 10 15

Glu Ser Val Ser Ile Ser Cys Arg Ser Ser Lys Ser Leu Leu Tyr Ile
20 25 30

Asn Gly Asn Thr His Leu Phe Trp Phe Leu Gln Arg Pro Gly Gln Ser
35 40 45

Pro Gln Leu Leu Ile Tyr Arg Met Ser Asn Leu Ala Ser Gly Val Pro
50 55 60

Asp Arg Phe Ser Gly Ser Gly Ser Gly Thr Ala Phe Thr Leu Arg Ile
65 70 75 80

Ser Arg Val Glu Ala Glu Asp Val Gly Val Tyr Tyr Cys Met Gln His
85 90 95

Leu Glu Tyr Pro Phe Thr Phe Gly Ser Gly Thr Lys Leu Glu Ile
100 105 110

<210> SEQ ID NO 307
<211> LENGTH: 120
<212> TYPE: PRT
<213> ORGANISM: Artificial Sequence
<220> FEATURE:
<223> OTHER INFORMATION: Exemplary anti-human NKp46 scFv (Heavy chain)

<400> SEQUENCE: 307

Gln Val Gln Leu Gln Gln Ser Gly Pro Glu Leu Val Lys Pro Gly Ala
1 5 10 15

```
Ser Val Lys Met Ser Cys Lys Ala Ser Gly Tyr Thr Phe Thr Asp Tyr
            20                  25                  30

Val Ile Asn Trp Gly Lys Gln Arg Ser Gly Gln Gly Leu Glu Trp Ile
        35                  40                  45

Gly Glu Ile Tyr Pro Gly Ser Gly Thr Asn Tyr Tyr Asn Glu Lys Phe
    50                  55                  60

Lys Ala Lys Ala Thr Leu Thr Ala Asp Lys Ser Ser Asn Ile Ala Tyr
65                  70                  75                  80

Met Gln Leu Ser Ser Leu Thr Ser Glu Asp Ser Ala Val Tyr Phe Cys
                85                  90                  95

Ala Arg Arg Gly Arg Tyr Gly Leu Tyr Ala Met Asp Tyr Trp Gly Gln
            100                 105                 110

Gly Thr Ser Val Thr Val Ser Ser
        115                 120
```

<210> SEQ ID NO 308
<211> LENGTH: 120
<212> TYPE: PRT
<213> ORGANISM: Artificial Sequence
<220> FEATURE:
<223> OTHER INFORMATION: Exemplary anti-human NKp46 scFv (light chain)

<400> SEQUENCE: 308

```
Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Val Ile Asn Trp Gly Lys Gln Arg Ser Gly Gln Gly Leu Glu Trp Ile
        35                  40                  45

Gly Glu Ile Tyr Pro Gly Ser Gly Thr Asn Tyr Tyr Asn Glu Lys Phe
    50                  55                  60

Lys Ala Lys Ala Thr Leu Thr Ala Asp Lys Ser Ser Asn Ile Ala Tyr
65                  70                  75                  80

Met Gln Leu Ser Ser Leu Thr Ser Glu Asp Ser Ala Val Tyr Phe Cys
                85                  90                  95

Ala Arg Arg Gly Arg Tyr Gly Leu Tyr Ala Met Asp Tyr Trp Gly Gln
            100                 105                 110

Gly Thr Ser Val Thr Val Ser Ser
        115                 120
```

<210> SEQ ID NO 309
<211> LENGTH: 113
<212> TYPE: PRT
<213> ORGANISM: Artificial Sequence
<220> FEATURE:
<223> OTHER INFORMATION: Exemplary anti-human CD16a VH domain

<400> SEQUENCE: 309

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Ile
        35                  40                  45

Gly Ser Ile Tyr Tyr Ser Gly Ser Thr Asn Tyr Asn Pro Ser Leu Lys
    50                  55                  60

Ser Leu Val Thr Ile Ser Arg Asp Asn Ser Lys Asn Thr Leu Tyr Leu
65                  70                  75                  80
```

```
Gln Met Asn Ser Leu Arg Ala Glu Asp Thr Ala Thr Tyr Tyr Cys Ala
                85                  90                  95

Arg Glu Ser Ile Asp Tyr Trp Gly Gln Gly Thr Leu Val Thr Val Ser
            100                 105                 110

Ser


<210> SEQ ID NO 310
<211> LENGTH: 271
<212> TYPE: PRT
<213> ORGANISM: Artificial Sequence
<220> FEATURE:
<223> OTHER INFORMATION: Linker + gOKT3-7 (anti-CD3 scFv)

<400> SEQUENCE: 310

Gly Gly Gly Gly Ser Gly Gly Gly Gly Ser Gly Gly Gly Gly Ser Gln
1               5                   10                  15

Val Gln Leu Val Gln Ser Gly Gly Gly Val Val Gln Pro Gly Arg Ser
            20                  25                  30

Leu Arg Leu Ser Cys Lys Ala Ser Gly Tyr Thr Phe Thr Arg Tyr Thr
        35                  40                  45

Met His Trp Val Arg Gln Ala Pro Gly Lys Gly Leu Glu Trp Ile Gly
    50                  55                  60

Tyr Ile Asn Pro Ser Arg Gly Tyr Thr Asn Tyr Asn Gln Lys Val Lys
65                  70                  75                  80

Asp Arg Phe Thr Ile Ser Arg Asp Asn Ser Lys Asn Thr Ala Phe Leu
                85                  90                  95

Gln Met Asp Ser Leu Arg Pro Glu Asp Thr Gly Val Tyr Phe Cys Ala
            100                 105                 110

Arg Tyr Tyr Asp Asp His Tyr Cys Leu Asp Tyr Trp Gly Gln Gly Thr
        115                 120                 125

Pro Val Thr Val Ser Ser Gly Gly Gly Gly Ser Gly Gly Gly Gly Ser
    130                 135                 140

Gly Gly Gly Gly Ser Gly Gly Gly Gly Ser Gly Gly Gly Gly Ser Gly
145                 150                 155                 160

Gly Gly Gly Ser Asp Ile Gln Met Thr Gln Ser Pro Ser Ser Leu Ser
                165                 170                 175

Ala Ser Val Gly Asp Arg Val Thr Ile Thr Cys Ser Ala Ser Ser Ser
            180                 185                 190

Val Ser Tyr Met Asn Trp Tyr Gln Gln Thr Pro Gly Lys Ala Pro Lys
        195                 200                 205

Arg Trp Ile Tyr Asp Thr Ser Lys Leu Ala Ser Gly Val Pro Ser Arg
    210                 215                 220

Phe Ser Gly Ser Gly Ser Gly Thr Asp Tyr Thr Phe Thr Ile Ser Ser
225                 230                 235                 240

Leu Gln Pro Glu Asp Ile Ala Thr Tyr Tyr Cys Gln Gln Trp Ser Ser
                245                 250                 255

Asn Pro Phe Thr Phe Gly Gln Gly Thr Lys Leu Gln Ile Thr Arg
            260                 265                 270


<210> SEQ ID NO 311
<211> LENGTH: 813
<212> TYPE: DNA
<213> ORGANISM: Artificial Sequence
<220> FEATURE:
<223> OTHER INFORMATION: Linker + gOKT3-7 (anti-CD3 scFv)

<400> SEQUENCE: 311
```

-continued

```
ggaggtggcg ggtctggtgg aggcggaagc ggtggtggcg gatcccaggt ccaactggtg     60

caaagtggag gcggcgtagt acagcccggt cggtccctgc ggctcagctg taaagcaagt    120

gggtacactt tcaccagata tacaatgcac tgggttagac aggcccccgg caagggtctt    180

gaatggatag gatatatcaa cccatcccgc ggatatacaa actacaatca gaaggtgaag    240

gaccggttca cgattagtag agacaactcc aaaaacactg cgttccttca aatggactca    300

ttgcgacccg aggacactgg agtgtatttc tgtgccaggt attatgacga ccattattgc    360

ctggactact gggggcaagg cacaccggtt acggtatctt ccggaggtgg cgggtctggt    420

ggaggcggaa gcggtggtgg cggatccggg ggaggaggct ctggcggagg cggatcaggg    480

ggtggaggtt ccgacattca aatgacacaa tcccctagtt ctttgtctgc gtccgtgggg    540

gatcgggtaa caatcacttg ctctgcatca agcagtgttt cttatatgaa ctggtatcag    600

cagacacccg gtaaggcccc aaaacgatgg atttatgaca cgagtaaact cgcatccggg    660

gtgccttcac gcttctccgg ttctggttcc ggcacggatt acactttcac catcagtagc    720

ctgcaacctg aggacattgc aacttattac tgtcaacaat ggagcagtaa tccattcacg    780

ttcggccaag ggacaaaact gcagattact agg                                 813
```

BINDERS AND CHIMERIC ANTIGEN RECEPTORS WHICH SPECIFICALLY BIND FIBROBLAST GROWTH FACTOR RECEPTOR 4

CROSS-REFERENCE TO RELATED APPLICATIONS

This application is a U.S. National Phase Application of PCT International Application Number PCT/US2021/054287, filed on Oct. 8, 2021, designating the United States of America and published in the English language, which is an International Application of and claims the benefit of priority to U.S. Provisional Application No. 63/089,985, filed on Oct. 9, 2020. The disclosures of the above-referenced applications are hereby expressly incorporated by reference in their entireties.

STATEMENT REGARDING FEDERALLY SPONSORED R & D

This invention was made with government support under Grant No. CA CA241023 awarded by the National Institutes of Health. The government has certain rights in the invention.

REFERENCE TO SEQUENCE LISTING

The present application is being filed along with a Sequence Listing in electronic format. The Sequence Listing is provided as a file entitled SeqList-SCRI-335NP, created Mar. 20, 2023, which is approximately 282,112 bytes in size. The information in the electronic format of the Sequence Listing is incorporated herein by reference in its entirety.

FIELD OF THE INVENTION

Some embodiments of the methods and compositions provided herein relate to chimeric antigen receptors (CARs), which specifically bind to fibroblast growth factor receptor 4 (FGFR4). Some embodiments concern nucleic acids encoding such CARs, and cells containing such CARs. Some embodiments include the use of such CARs in therapies for a cancer, such as an FGFR4-expressing cancer, including but not limited to rhabdomyosarcomas.

Some embodiments include methods and materials involved in binding a molecule, such as an antibody, a fragment of an antibody, an antibody domain, a chimeric antigen receptor (CAR), a cell engager, or an antibody-drug conjugate (ADC) to FGFR4. For example, Some embodiments include binders (e.g., antibodies, antigen binding fragments, antibody domains, CARs, cell engagers, or ADCs) that bind to an FGFR4 polypeptide and methods and materials for using such binders to treat cancer. Some embodiments include cells (e.g., host cells) designed to express one or more binders (e.g., antibodies, antigen binding fragments, antibody domains, CARs, or cell engagers) having the ability to bind to an FGFR4 polypeptide and methods and materials for using such cells to treat or inhibit a cancer, including but not limited to rhabdomyosarcomas.

BACKGROUND OF THE INVENTION

Rhabdomyosarcoma (RMS) is one of the most prevalent extracranial solid tumor of childhood, behind neuroblastoma and Wilms tumor (Shern J F, et al., 2015, Crit Rev Oncogenesis 20:227-243). Although significant advances have been made through the optimization of chemotherapy for early-stage disease, patients with high-risk or recurrent disease have a 5-year survival rate of <30% and 17%, respectively. Key genetic alterations seen in this disease include: a characteristic PAX3-FOXO1 or PAX7-FOXO1 fusion gene product; mutations in TP53, RAS, PI3K3CA, CTNNB1 (beta-catenin), FGFR4 (fibroblast growth factor receptor 4); and loss of heterozygosity at 11p15.5 (Li F P, et al., 1969, J Natl Cancer Inst 43:1365-1373; Steenman M, et al., 2000, Gene Chromosome Cancer 28:1-13; Barr F G, et al., 1993, Nat Genet 3:113-117; Taylor A C, et al., 2000, Med Pediatr Oncol 35:96-103; Stratton M R, et al., 1989, Cancer Res 49:6324-6327; Shukla M, et al., 2012, Clin Canc Res 18:748-757; Taylor J G et al., 2009, J Clin Invest 119:3395-3407). Historically RMS was defined by lesion morphology (alveolar, ARMS, versus embryonal, ERMS), but it has now become clear that the biology of the disease is closely associated with genotype. RMS is now defined by the presence or absence of PAX3/7 fusion genes (Shern J F, et al., 2014, Cancer Disc 4:216-231; Chen X, et al., 2013, Cancer Cell 24:710-724; Kohsaka S, et al., 2014, Nat Genet 46:595-600). Clinical studies have established that fusion gene status is more relevant to outcome in low and intermediate risk disease, than traditional pathological classification as ERMS or ARMS (Skapek S X, et al., 2013, Pediatr Blood Cancer 60:1411-1417). However, clinical studies have also established that in advanced metastatic disease, standard clinical risk factors, such as the degree of dissemination, better define outcome, which is uniformly poor and unimproved in decades (Rudzinski E R, et al., 2017, Pediatr Blood Cancer, 64:e26645).

The recent success of using immune checkpoint inhibitors to treat melanoma and lung cancer has had little impact in pediatric cancer because of the low mutational rate of pediatric tumors (Alexandrov B, et al., 2013, Nature 500:415-421). In fact, PAX gene translocation-expressing RMS has a remarkably low mutation rate, 0.1 protein coding mutations per Mb, with no recurring point mutations. Therefore, there is a need for additional improved therapies to treat or inhibit the progressions of cancers, such as RMS.

SUMMARY OF THE INVENTION

Some embodiments provided herein include methods and materials involved in binding a molecule (e.g., an antibody, an antigen binding fragment, an antibody domain, a CAR, a cell engager, or an ADC) to an FGFR4 polypeptide. For example, some embodiments include binders (e.g., antibodies, antigen binding fragments, antibody domains, CARs, cell engagers, or ADCs) that bind to an FGFR4 polypeptide and methods and materials for using one or more such binders in a therapy for a mammal (e.g., a human) having cancer, including but not limited to rhabdomyosarcomas.

Some embodiments include cells (e.g., host cells) designed to express one or more binders (e.g., antibodies, antigen binding fragments, antibody domains, CARs, or cell engagers) having the ability to bind to an FGFR4 polypeptide and methods and materials for using such cells to treat or inhibit a cancer, including but not limited to rhabdomyosarcomas.

As described herein, binders (e.g., one or more antibodies, one or more antigen binding fragments, one or more antibody domains, one or more CARs, one or more cell engagers, and/or one or more ADCs) can be designed to have the ability to bind to an FGFR4 polypeptide. For example, a binder (e.g., an antibody, an antigen binding fragment, an antibody domain, a CAR, a cell engager, or an ADC)

provided herein can have the ability to bind to a polypeptide comprising, consisting essentially of, or consisting of the amino acid sequence of a human FGFR4.

In some cases, a single set of three complementarity-determining regions (CDRs) of an antibody domain (e.g., a VH domain) provided herein, for example, such as in TABLE 3 and TABLE 4, or two sets of three CDRs of an antibody (e.g., scFc) provided herein, for example, such as in TABLE 3 and TABLE 4, can be engineered into a CAR to create $CAR^+$ cells (e.g., $CAR^+$ T cells, $CAR^+$ stem cells such as $CAR^+$ induced pluripotent stem cells, or $CAR^+$ natural killer (NK) cells) having the ability to target $FGFR4^+$ cells (e.g., $FGFR4^+$ tumor cells and/or $FGFR4^+$ tumor vasculature), can be engineered into an antibody structure that includes an Fc region to create antibodies having the ability to target $FGFR4^+$ cells (e.g., $FGFR4^+$ tumor cells and/or $FGFR4^+$ tumor vasculature) and induce antibody-dependent cell-mediated cytotoxicity (ADCC) against the target FGFR4 cells, and/or can be engineered into a cell engager such as a bi-specific T cell engager (e.g., a BiTE), a bi-specific killer engager (e.g., a BiKE), and/or a tri-specific killer engager (e.g., a TriKE) to create cell engagers having the ability to target $FGFR4^+$ cells (e.g., $FGFR4^+$ tumor cells and/or $FGFR4^+$ tumor vasculature) and induce one or more immune responses (e.g., T cell immune responses and/or ADCC using a cell engager in the absence of an Fc-containing antibody) against the target $FGFR4^+$ cells. It is noted that BiKE- and TriKE-mediated killing can be referred to ADCC even though it is not initiated by an Fc domain.

In addition, as described herein, binders (e.g., one or more antibodies, one or more antigen binding fragments, and/or one or more antibody domains) provided herein can be used to create conjugates that include the binder and a drug. For example, ADCs such as full antibody-drug conjugates, Fab-drug conjugates, and/or antibody domain-drug conjugates can be designed to include an appropriate binder provided herein to create the conjugate. Such conjugates can be used to deliver the drug payload to target cells such as cancer cells (e.g., $FGFR4^+$ cancer cells) or cancer vasculature (e.g., $FGFR4^+$ cancer vasculature).

As also described herein, binders (e.g., one or more antibodies, one or more antigen binding fragments, one or more antibody domains, one or more cell engagers, and/or one or more ADCs) provided herein can be used in a therapy for a mammal (e.g., a human) having cancer, including but not limited to rhabdomyosarcomas. For example, a mammal (e.g., a human) having cancer (e.g., an $FGFR4^+$ cancer, including but not limited to rhabdomyosarcomas) can be administered a composition comprising one or more binders (e.g., one or more antibodies, one or more antigen binding fragments, one or more antibody domains, one or more cell engagers, and/or one or more ADCs) described herein to reduce the number of cancer cells within the mammal, to induce ADCC against cancer cells within the mammal, and/or to increase the survival duration of the mammal from the cancer.

As also described herein, cells (e.g., host cells) can be designed to express one or more binders (e.g., antibodies, antigen binding fragments, antibody domains, CARs, or cell engagers) having the ability to bind to an FGFR4 polypeptide. For example, cells such as T cells (e.g., CTLs), stem cells (e.g., induced pluripotent stem cells), or NK cells can be engineered to express one or more CARs having the ability to bind to an FGFR4 polypeptide. Such cells (e.g., FGFR4-specific $CAR^+$ T cells or NK cells) can be used to treat or inhibit a cancer, including but not limited to rhabdomyosarcomas.

In some embodiments, a binder (e.g., an antibody, antigen binding fragment, and/or antibody domain) provided herein can be used to detect the presence or absence of an FGFR4 polypeptide. For example, a binder (e.g., an antibody, antigen binding fragment, and/or antibody domain) provided herein can be used to determine whether or not a sample (e.g., a biological sample such tumor biopsy) obtained from a mammal (e.g., a human) contains $FGFR4^+$ cells (e.g., $FGFR4^+$ cancer cells). Having the ability to detect the presence or absence of an FGFR4 polypeptide (e.g., $FGFR4^+$ cancer cells) can allow clinicians, health professionals, and patients to make better decisions about possible treatment options. For example, detection of $FGFR4^+$ cancer cells within a mammal can allow clinicians, health professionals, and patients to select an appropriate anti-cancer treatment that targets the FGFR4 cancer cells. Such therapies that target the $FGFR4^+$ cancer cells can include administration of an anti-FGFR4 antibody such as U3-1784 and/or one or more of the binders described herein having the ability to bind to an FGFR4 polypeptide and/or administration of one or more cells (e.g., FGFR4-specific $CAR^+$ T cells or NK cells) designed to express a binder described herein.

Some embodiments of the methods and compositions provided herein include a nucleic acid comprising a polynucleotide encoding a chimeric antigen receptor (CAR), wherein the CAR comprises: a ligand binding domain capable of specifically binding or configured to specifically bind to an IgM membrane-proximal domain of a fibroblast growth factor receptor 4 (FGFR4) protein; a transmembrane domain; and an intracellular signalling domain.

In some embodiments, the ligand binding domain comprises a complementarity-determining region (CDR). In some embodiments, the ligand binding domain comprises a heavy chain complementarity-determining region (CDR). In some embodiments, the ligand binding domain comprises a first additional heavy chain CDR. In some embodiments, the ligand binding domain comprises a second additional heavy chain CDR. In some embodiments, the ligand binding domain comprises a light chain CDR.

In some embodiments, the CDR comprises an amino acid sequence having 0-4 conservative amino acid substitutions of an amino acid sequence of any one of SEQ ID NOs:42-149. In some embodiments, the CDR comprises an amino acid sequence having 0-4 conservative amino acid substitutions of an amino acid sequence of any one of SEQ ID NOs:41-53, 57-62, 78-101, 114-125 and 132-137. In some embodiments, the CDR comprises an amino acid sequence having 0-4 conservative amino acid substitutions of an amino acid sequence of any one of SEQ ID NOs:57-59.

In some embodiments, the ligand binding domain comprises an amino acid sequence having at least 95% sequence identity to any one of SEQ ID NOs:01-22. In some embodiments, the ligand binding domain comprises an amino acid sequence having at least 95% sequence identity to any one of SEQ ID NOs:01-04, 06, 07, 11-14, 17, 18 and 20. In some embodiments, the ligand binding domain comprises an amino acid sequence having at least 95% sequence identity to SEQ ID NO:06. In some embodiments, the ligand binding domain comprises the amino acid sequence of SEQ ID NO:06.

In some embodiments, the ligand binding domain comprises, consists essentially of, or consists of a variable heavy chain (VH) domain. In some embodiments, the ligand binding domain lacks a variable light chain (VL) domain.

In some embodiments, the transmembrane domain comprises a domain selected from a CD8 transmembrane domain or a CD28 transmembrane domain. In some embodiments, the transmembrane domain comprises a CD8 transmembrane domain. In some embodiments, the CD8 transmembrane domain comprises an amino acid sequence having at least 95% sequence identity to SEQ ID NO:24.

In some embodiments, the intracellular signalling domain comprises a costimulatory domain selected from the group consisting of CD27, CD28, 4-1BB, OX-40, CD30, CD40, PD-1, ICOS, LFA-1, CD2, CD7, NKG2C, B7-H3, and CD3-zeta. In some embodiments, the intracellular signalling domain comprises a 4-1BB costimulatory domain in combination with a CD3-zeta domain. In some embodiments, the 4-1BB costimulatory domain comprises an amino acid sequence having at least 95% sequence identity to SEQ ID NO:29. In some embodiments, the CD3-zeta domain comprises an amino acid sequence having at least 95% sequence identity to SEQ ID NO:31.

In some embodiments, the CAR comprises an amino acid sequence having at least 95% sequence identity to SEQ ID NO:41. In some embodiments, the CAR comprises the amino acid sequence of SEQ ID NO:41.

In some embodiments, the CAR further comprises a spacer located between the ligand binding domain and the transmembrane domain.

Some embodiments also include a constitutive promoter operably linked to the polynucleotide encoding the CAR. In some embodiments, the constitutive promoter comprises an EF1α promoter.

Some embodiments also include an inducible promoter operably linked to the polynucleotide encoding the CAR Some embodiments also include a polynucleotide encoding a cell-surface selectable marker. In some embodiments, the cell-surface selectable marker is selected from a truncated EGFR polypeptide (EGFRt) or a truncated Her2 polypeptide (Her2t).

Some embodiments also include a ribosome skip sequence located between a polynucleotide encoding the intracellular signalling domain and the polynucleotide encoding a cell-surface selectable marker. In some embodiments, the ribosome skip sequence is selected from the group consisting of a P2A sequence, a T2A sequence, an E2A sequence, and an F2A sequence.

Some embodiments also include a polynucleotide encoding a suicide gene system. In some embodiments, the suicide gene system is selected from a herpes simplex virus thymidine kinase/ganciclovir (HSVTK/GCV) suicide gene system, or an inducible caspase suicide gene system.

Some embodiments include a polypeptide encoded by any one of the foregoing nucleic acids.

Some embodiments include a vector comprising any one of the foregoing nucleic acids. In some embodiments, the vector is selected from the group consisting of a viral vector, a transposon vector, an integrase vector, and an mRNA vector. In some embodiments, the viral vector is selected from the group consisting of a lentiviral vector, an adeno-associated virus, a foamy viral vector, a retroviral vector, and a gamma retroviral vector. In some embodiments, the viral vector is a lentiviral vector.

Some embodiments include a host cell comprising any one of the foregoing nucleic acids. In some embodiments, the host cell is a T cell. In some embodiments, the host cell is a CD4+ T-cell or a CD8+ T-cell. In some embodiments, the host cell is a CD8+ cytotoxic T-cell selected from the group consisting of a naïve CD8+ T-cell, a CD8+ memory T-cell, a central memory CD8+ T-cell, a regulatory CD8+ T-cell, an IPS derived CD8+ T-cell, an effector memory CD8+ T-cell, and a bulk CD8+ T-cell.

In some embodiments, the host cell is a CD4+ T helper cell selected from the group consisting of a naïve CD4+ T-cell, a CD4+ memory T-cell, a central memory CD4+ T-cell, a regulatory CD4+ T-cell, an IPS derived CD4+ T-cell, an effector memory CD4+ T-cell, and a bulk CD4+ T-cell. In some embodiments, the host cell is a precursor T-cell, or a hematopoietic stem cell. In some embodiments, the cell is allogenic to a subject. In some embodiments, the cell is human.

Some embodiments include a pharmaceutical composition comprising any one of the foregoing host cells and a pharmaceutically acceptable excipient.

Some embodiments include a method for preparing a population of cells, comprising: (a) introducing any one of the foregoing nucleic acids into an isolated population of cells; and (b) culturing the population of cells in the presence of an agent selected from an anti-CD3, an anti-CD28, and a cytokine such as IL-2. In some embodiments, the population of cells comprises a CD4+ T-cell or a CD8+ T-cell. In some embodiments, the population of cells comprises a CD8+ cytotoxic T-cell selected from the group consisting of a naïve CD8+ T-cell, a CD8+ memory T-cell, a central memory CD8+ T-cell, a regulatory CD8+ T-cell, an IPS derived CD8+ T-cell, an effector memory CD8+ T-cell, and a bulk CD8+ T-cell. In some embodiments, the population of cells comprises a CD4+ T helper cell selected from the group consisting of a naïve CD4+ T-cell, a CD4+ memory T-cell, a central memory CD4+ T-cell, a regulatory CD4+ T-cell, an IPS derived CD4+ T-cell, an effector memory CD4+ T-cell, and a bulk CD4+ T-cell. In some embodiments, the population of cells comprises a precursor T-cell, or a hematopoietic stem cell.

Some embodiments include a method of treating, inhibiting or ameliorating a cancer, including but not limited to rhabdomyosarcomas, in a subject, comprising: administering any one of the foregoing host cells to the subject.

In some embodiments, the cancer comprises an FGFR4-expressing cell. In some embodiments, the cancer comprises a solid tumor. In some embodiments, the cancer comprises a cell expressing a protein selected from a PAX3-FOXO1 fusion gene product, and a PAX7-FOXO1 fusion gene product. In some embodiments, the cancer comprises a cell comprising a mutation in a gene selected from TP53, RAS, PI3K3CA, CTNNB1, and FGFR4. In some embodiments, the cancer comprises a rhabdomyosarcoma. In some embodiments, the subject is human.

Some embodiments include any one of the foregoing host cells for use in treating, inhibiting or ameliorating a cancer in a subject.

Some embodiments include use of any one of the host cells in the manufacture of a medicament for treating, inhibiting or ameliorating a cancer in a subject.

Some embodiments include any one of the foregoing host cells for use as a medicament.

BRIEF DESCRIPTION OF THE DRAWINGS

FIG. 9 depicts exemplary linker amino acid sequences for scFv's, CARs, and/or cell engagers, including SEQ ID NOS:244-266.

FIG. 10 depicts the amino acid sequences of exemplary hinges that can be used to design a CAR, including SEQ ID NOS:267-275.

FIG. 11 depicts the amino acid sequences of exemplary transmembrane domains that can be used to design a CAR, including SEQ ID NOS:276-283.

FIG. 12 depicts the amino acid sequences of exemplary intracellular signaling domains that can be used to design a CAR, including SEQ ID NOS:284-291.

FIG. 13 depicts the amino acid sequences of exemplary antigen binding domains that can be used to design cell engagers that bind to T cells, including SEQ ID NOS:292-295.

FIG. 14 depicts the amino acid sequences of exemplary antigen binding domains that can be used to design cell engagers that bind to NK cells, including SEQ ID NOS: 296-309.

FIG. 15B depicts an amino acid of a linker sequence (SEQ ID NO:310) followed by an gOKT3-7 scFv sequence (SEQ ID NO:311), which can be attached to a VH domain as shown in FIG. 15A. FIG. 15B also depicts a nucleic acid sequence encoding that linker and gOKT3-7 scFv.

DETAILED DESCRIPTION

Figure 1:
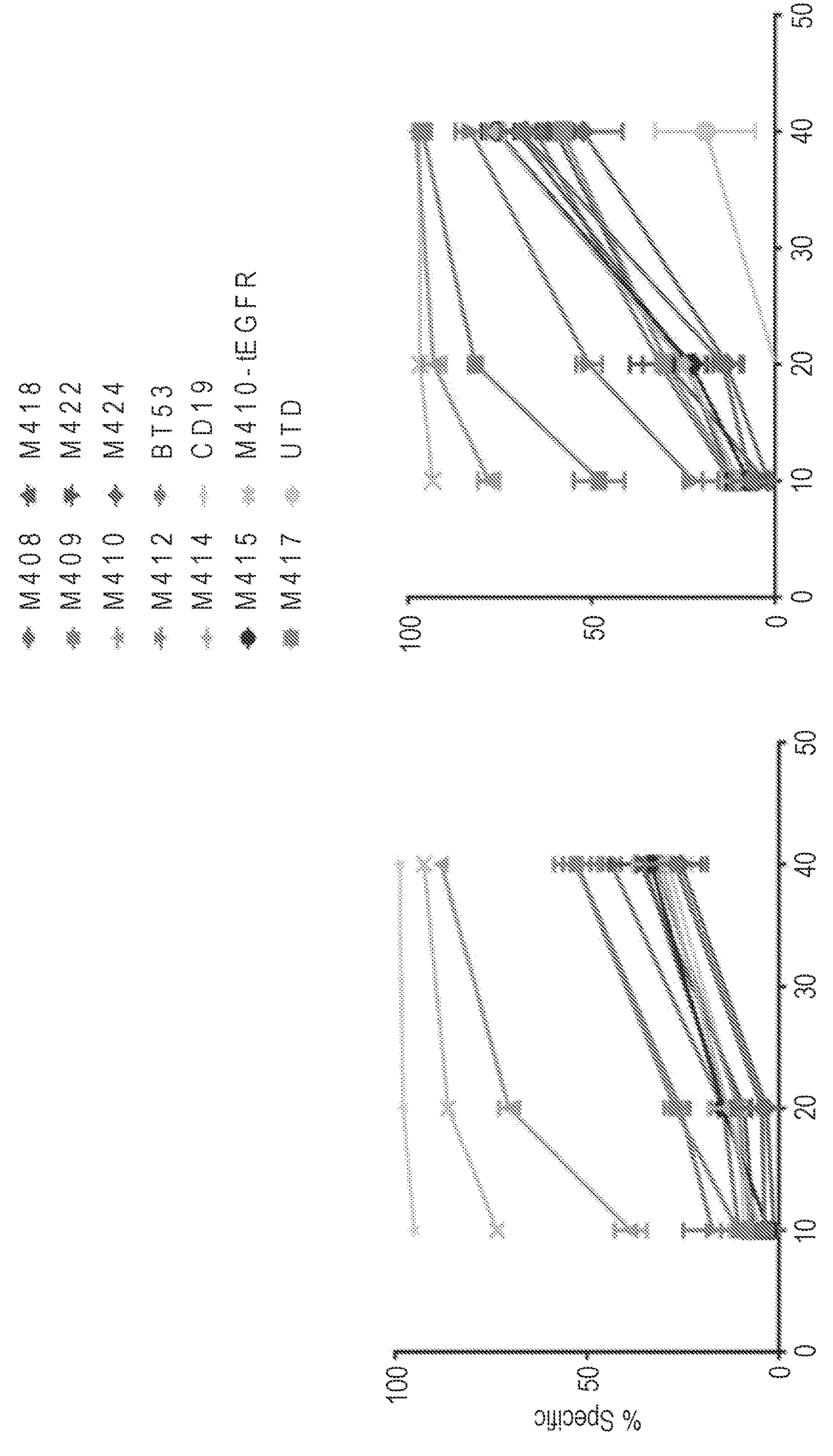
FIG. 1 depicts graphs for cytolytic activity in T cells expressing anti-FGFR4 CARs. T cells containing anti-FGFR4 CARs were tested against a CD19+/FGFR4$^+$ cell line, RH30_19 (left panel), or a CD19(−)/FGFR4$^+$ cell line, RMS559 (right panel). Specific lysis and E:T ratios are listed on the axes. Test anti-FGFR4 CARs and a control murine MAb-derived binder BT53-CAR are listed in the legend.

Some embodiments provided herein include binders (e.g., antibodies, antigen binding fragments, antibody domains, CARs, cell engagers, and ADCs) that bind (e.g., specifically bind) to an FGFR4 polypeptide (e.g., a human FGFR4 polypeptide). For example, some embodiments include binders (e.g., antibodies, antigen binding fragments, antibody domains, CARs, cell engagers, and ADCs) that bind (e.g., specifically bind) to a polypeptide comprising, consisting essentially of, or consisting of the amino acid of human FGFR4. In some cases, a binder (e.g., an antibody, an antigen binding fragment, an antibody domain, a CAR, a cell engager, or an ADC) provided herein can have the ability to bind to an FGFR4 polypeptide. For example, a binder (e.g., an antibody, an antigen binding fragment, an antibody domain, a CAR, a cell engager, or an ADC) provided herein can have the ability to bind to a human FGFR4 polypeptide.

The term "antibody" as used herein includes polyclonal antibodies, monoclonal antibodies, recombinant antibodies, humanized antibodies, human antibodies, chimeric antibodies, multi-specific antibodies (e.g., bispecific antibodies) formed from at least two antibodies, diabodies, single-chain variable fragment antibodies (e.g., scFv antibodies), and tandem single-chain variable fragments antibody (e.g., taFv). A diabody can include two chains, each having a heavy chain variable domain and a light chain variable domain, either from the same or from different antibodies (see, e.g., Hornig and Farber-Schwarz, *Methods Mol. Biol.,* 907:713-27 (2012); and Brinkmann and Kontermann, *MAbs.,* 9(2):182-212(2017)). The two variable regions can be connected by a polypeptide linker (e.g., a polypeptide linker having five to ten residues in length or a polypeptide linker as set forth in FIG. 9). In some cases, an interdomain disulfide bond can be present in one or both of the heavy chain variable domain and light chain variable domain pairs of the diabody. A scFv is a single-chain polypeptide antibody in which the heavy chain variable domain and the light chain variable domain are directly connected or connected via a polypeptide linker (e.g., a polypeptide linker having eight to 18 residues in length or a polypeptide linker as set forth in FIG. 9). See, also, Chen et al., *Adv. Drug Deliv. Rev.,* 65(10):1357-1369 (2013). A scFv can be designed to have an orientation with the heavy chain variable domain being followed by the light chain variable domain or can be designed to have an orientation with the light chain variable domain being followed by the heavy chain variable domain. In both cases, the optional linker can be located between the two domains.

An antibody provided herein can include the CDRs as described herein (e.g., as described in TABLE 3 or 4) and can be configured to be a human antibody, a humanized antibody, or a chimeric antibody. In some cases, an antibody provided herein can include the CDRs as described herein (e.g., as described in TABLE 3 or 4) and can be a monoclonal antibody. In some cases, an antibody provided herein can include the CDRs as described herein (e.g., as described in TABLE 3 or 4) and can be configured as a scFv antibody.

The term "antigen binding fragment" as used herein refers to a fragment of an antibody (e.g., a fragment of a humanized antibody, a fragment of a human antibody, or a fragment of a chimeric antibody) having the ability to bind to an antigen. Examples of antigen binding fragments include, without limitation, Fab, Fab', or $F(ab')_2$ antigen binding fragments. An antigen binding fragment provided herein can include the CDRs as described herein (e.g., as described in TABLE 3 or 4) and can be configured to be a human antigen binding fragment, a humanized antigen binding fragment, or a chimeric antigen binding fragment. In some cases, an antigen binding fragment provided herein can include the CDRs as described herein (e.g., as described in TABLE 3 or 4) and can be a monoclonal antigen binding fragment. In some cases, an antigen binding fragment provided herein can include the CDRs as described herein (e.g., as described in TABLE 3 or 4) and can be configured as a Fab antibody.

The term "antibody domain" as used herein refers to a domain of an antibody such as a heavy chain variable domain (VH domain) or a light chain variable domain (VL domain) in the absence of one or more other domains of an antibody. In some cases, an antibody domain can be a single antibody domain (e.g., a VH domain or a VL domain) having the ability to bind to an antigen. An antibody domain provided herein can include the CDRs as described herein (e.g., as described in TABLE 3 or 4) and can be a human antibody domain (e.g., a human VH domain), a humanized antibody domain (e.g., a humanized VH domain), or a chimeric antibody domain (e.g., a chimeric VH domain). In some cases, an antibody domain provided herein can include the CDRs as described herein (e.g., as described in TABLE 3 or 4) and can be a monoclonal antibody domain. In some cases, an antibody domain provided herein can include the CDRs as described herein (e.g., as described in TABLE 3 or 4) and can be engineered as a single VH domain or a single VL domain.

An anti-FGFR4 antibody, anti-FGFR4 antigen binding fragment, or anti-FGFR4 antibody domain provided herein can be of the IgA-, IgD-, IgE-, IgG-, or IgM-type, including IgG- or IgM-types such as, without limitation, $IgG_1$-, $IgG_2$-, $IgG_3$-, $IgG_4$-, $IgM_1$-, and $IgM_2$-types. In some cases, an antibody provided herein (e.g., an anti-FGFR4 antibody) can be a scFv antibody. In some cases, an antigen binding fragment provided herein (e.g., an anti-FGFR4 antibody fragment) can be a Fab. In some cases, an antibody provided herein (e.g., an anti-FGFR4 antibody) can be a fully intact antibody consisting of both VH and VL. In some cases, an antibody domain provided herein (e.g., an anti-FGFR4 antibody domain) can be a VH domain.

As described herein, a chimeric antigen receptor can refer to a chimeric polypeptide that is designed to include an antigen binding domain, an optional hinge, a transmembrane domain, and one or more intracellular signaling domains. As described herein, the antigen binding domain of a CAR provided herein can be designed to bind to an FGFR4 polypeptide (e.g., a human FGFR4 polypeptide). For example, a CAR provided herein can be designed to include the components of an antibody, antigen binding fragment, and/or antibody domain described herein (e.g., a combination of CDRs) as an antigen binding domain provided that that antigen binding domain has the ability to bind to an FGFR4 polypeptide (e.g., a human FGFR4 polypeptide). In some examples, a CAR provided herein can be designed to include an antigen binding domain that includes a single set of three CDRs (e.g., a CDR1, CDR2, and CDR3) of an antibody domain (e.g., a VH domain) provided herein (see, e.g., TABLE 3 and TABLE 4). In some examples, a CAR provided herein can be designed to include an antigen binding domain that includes a first set of three CDRs (e.g., a CDR1, CDR2, and CDR3 of a heavy chain) and a second set of CDRs (e.g., a CDR1, CDR2, and CDR3 of a light chain) of an antibody (e.g., a Fab) provided herein (see, e.g., TABLE 3 and TABLE 4). In some cases, an antigen binding domain of a CAR targeting an FGFR4 polypeptide can be designed to include a VH domain described herein or a scFv antibody described herein.

In some cases, a CAR provided herein can be designed to include a hinge. Any appropriate hinge can be used to design a CAR described herein. Examples of hinges that can be used to make a CAR described herein include, without limitation, Ig-derived hinges (e.g., an IgG1-derived hinge, an IgG2-derived hinge, or an IgG4-derived hinge), Ig-derived hinges containing a CD2 domain and a CD3 domain, Ig-derived hinges containing a CD2 domain and lacking a CD3 domain, Ig-derived hinges containing a CD3 domain and lacking a CD2 domain, Ig-derived hinges lacking a CD2 domain and lacking a CD3 domain, CD8α-derived hinges, CD28-derived hinges, and CD3ζ-derived hinges. A CAR provided herein can be designed to include a hinge of any appropriate length. For example, a CAR provided herein can be designed to include a hinge that is from about 3 to about 75 (e.g., from about 3 to about 65, from about 3 to about 50, from about 5 to about 75, from about 10 to about 75, from about 5 to about 50, from about 10 to about 50, from about 10 to about 40, or from about 10 to about 30) amino acid residues in length. In some cases, a linker sequence can be used as hinge to make a CAR described herein. For example, any one of the linker sequences set forth in FIG. 9 can be used as a hinge of a CAR described herein.

In some cases, a CAR provided herein can be designed to include a hinge that comprises, consists essentially of, or consists of one of the amino acid sequences set forth in FIG. 9 or FIG. 10. In some cases, a CAR provided herein can be designed to include a hinge that comprises, consists essentially of, or consists of one of the amino acid sequences set forth in FIG. 9 or FIG. 10 with one, two, three, four, five, six, seven, eight, nine, or ten amino acid deletions, additions, substitutions, or combinations thereof. In some cases, a CAR provided herein can be designed to include a hinge that comprises, consists essentially of, or consists of one of the amino acid sequences set forth in FIG. 9 or FIG. 10 with two or less, three or less, four or less, five or less, six or less, seven or less, eight or less, nine or less, or ten or less amino acid deletions, additions, substitutions, or combinations thereof.

A CAR provided herein can be designed to include any appropriate transmembrane domain. For example, the transmembrane domain of a CAR provided herein can be, without limitation, a CD3ζ transmembrane domain, a CD4 transmembrane domain, a CD8a transmembrane domain, a CD28 transmembrane domain, and a 4-1BB transmembrane domain. In some cases, a CAR provided herein can be designed to include a transmembrane domain that comprises, consists essentially of, or consists of one of the amino acid sequences set forth in FIG. 11. In some cases, a CAR provided herein can be designed to include a transmembrane domain that comprises, consists essentially of, or consists of one of the amino acid sequences set forth in FIG. 11 with one, two, three, four, five, six, seven, eight, nine, or ten amino acid deletions, additions, substitutions, or combinations thereof. In some cases, a CAR provided herein can be designed to include a transmembrane domain that comprises, consists essentially of, or consists of one of the amino acid sequences set forth in FIG. 11 with two or less, three or less, four or less, five or less, six or less, seven or less, eight or less, nine or less, or ten or less amino acid deletions, additions, substitutions, or combinations thereof.

A CAR provided herein can be designed to include one or more intracellular signaling domains. For example, a CAR provided herein can be designed to include one, two, three, or four intracellular signaling domains. Any appropriate intracellular signaling domain or combination of intracellular signaling domains can be used to make a CAR described herein. Examples of intracellular signaling domains that can be used to make a CAR described herein include, without limitation, CD3ζ intracellular signaling domains, CD27 intracellular signaling domains, CD28 intracellular signaling domains, OX40 (CD134) intracellular signaling domains, 4-1BB (CD137) intracellular signaling domains, CD278 intracellular signaling domains, DAP10 intracellular signaling domains, and DAP12 intracellular signaling domains. In some cases, a CAR described herein can be designed to be a first-generation CAR having a CD3ζ intracellular signaling domain. In some cases, a CAR described herein can be designed to be a second-generation CAR having a CD28 intracellular signaling domain followed by a CD3ζ intracellular signaling domain. In some cases, a CAR described herein can be designed to be a third generation CAR having (a) a CD28 intracellular signaling domain followed by (b) a CD27 intracellular signaling domain, an OX40 intracellular signaling domains, or a 4-1BB intracellular signaling domain followed by (c) a CD3ζ intracellular signaling domain. In some cases, a CAR provided herein can be designed to include at least one intracellular signaling domain that comprises, consists essentially of, or consists of one of the amino acid sequences set forth in FIG. 12. In some cases, a CAR provided herein can be designed to include at least one intracellular signaling domain that comprises, consists essentially of, or consists of one of the amino acid sequences set forth in FIG. 12 with one, two, three, four, five, six, seven, eight, nine, or ten amino acid deletions, additions, substitutions, or combinations thereof, provided that that intracellular signaling domain has at least some activity to activate intracellular signaling. In some cases, a CAR provided herein can be designed to include at least one intracellular signaling domain that comprises, consists essentially of, or consists of one of the amino acid sequences set forth in FIG. 12 with two or less, three or less, four or less, five or less, six or less, seven or less, eight or less, nine or less, or ten or less amino acid deletions, additions, substitutions, or combinations thereof, provided that that intracellular signaling domain has at least some activity to activate intracellular signaling.

The term "cell engager" as used herein refers to a polypeptide that includes two or more antigen binding domains (e.g., two, three, or four antigen binding domains) and has the ability to link two cells together. Examples of cell engagers include, without limitation, BiTEs, BiKEs, and TriKEs. In general, a cell engager provided herein can be designed to include at least one antigen binding domain having the ability to bind to an FGFR4 polypeptide (e.g., a human FGFR4 polypeptide) and at least one antigen binding domain having the ability to bind to an antigen expressed on the surface of a cell (e.g., a T cell or an NK cell). In some cases, a cell engager described herein can link an $FGFR4^+$ cell (e.g., an $FGFR4^+$ cancer cell) to another cell (e.g., a T cell or an NK cell) via the two or more antigen binding domains of the cell engager.

When a cell engager includes an antigen binding domain having the ability to bind to an FGFR4 polypeptide (e.g., a human FGFR4 polypeptide) and two or more other antigen binding domains (e.g., two, three, or four other antigen binding domains), each of those other antigen binding domains can bind to different antigens expressed on the surface of different cell types or can bind to different antigens expressed on the surface of the same cell type. For example, a TriKE can be designed to have a first antigen binding domain having the ability to bind to an FGFR4 polypeptide (e.g., a human FGFR4 polypeptide), a second antigen binding domain having the ability to bind to a first antigen expressed on the surface of an NK cell (e.g., a CD16 polypeptide such as a CD16a polypeptide), and a third antigen binding domain having the ability to bind to a second antigen expressed on the surface of an NK cell (e.g., an NKG2A polypeptide).

As described herein, at least one antigen binding domain of a cell engager provided herein can be designed to bind to an FGFR4 polypeptide (e.g., a human FGFR4 polypeptide). For example, a cell engager provided herein can be designed to include the components of an antibody, antigen binding fragment, and/or antibody domain described herein (e.g., a combination of CDRs) as an antigen binding domain provided that that antigen binding domain has the ability to bind to an FGFR4 polypeptide (e.g., a human FGFR4 polypeptide). In some examples, a cell engager provided herein can be designed to include an antigen binding domain that includes a single set of three CDRs (e.g., a CDR1, CDR2, and CDR3) of an antibody domain (e.g., a VH domain) provided herein (see, e.g., TABLE 3 or 4). In some examples, a cell engager provided herein can be designed to include an antigen binding domain that includes a first set of three CDRs (e.g., a CDR1, CDR2, and CDR3 of a heavy chain) of an antibody domain (e.g., a Fab) provided herein and a second set of three CDRs (e.g., a CDR1, CDR2, and CDR3 of a light chain) of an antibody domain (e.g., a Fab) provided herein (see, e.g., TABLE 3 or 4). In some cases, an antigen binding domain of a cell engager targeting an FGFR4 polypeptide can be designed to include a VH domain described herein. In some cases, an antigen binding domain of a CAR described herein that has the ability to bind to an FGFR4 polypeptide (e.g., a human FGFR4 polypeptide) can be used as an antigen binding domain of a cell engager that targets $FGFR4^+$ cells.

Figure 15A:
FIG. 15A is a schematic of an exemplary BiTE designed using CDR1, CDR2, and CDR3 of a VH domain provided herein. A humanized anti-CD3 scFv (e.g., an gOKT3-7 scFv set forth in U.S. Pat. No. 6,750,325, herein expressly incorporated by reference in its entirety) can be linked to the C-terminus of the VH domain via a linker (e.g., a (G4S)3 linker).

As described herein, a cell engager can be designed to include at least one antigen binding domain having the ability to bind to an FGFR4 polypeptide (e.g., a human FGFR4 polypeptide) and at least one other antigen binding domain. That at least one other antigen binding domain can have the ability to bind to any appropriate antigen expressed on the surface of a cell. For example, when designing a cell engager such as a BiTE to link an $FGFR4^+$ cell and a T cell, the cell engager can include an antigen binding domain having the ability to bind to an FGFR4 polypeptide (e.g., a human FGFR4 polypeptide) and an antigen binding domain having the ability to bind to a polypeptide expressed on the surface of a T cell. Examples of polypeptides expressed on the surface of a T cell that can be targeted by an antigen binding domain of a cell engager provided herein include, without limitation, CD3 polypeptides. Examples of antigen binding domains having the ability to bind to a polypeptide expressed on the surface of a T cell that can be used to make a cell engager provided herein (e.g., a BiTE) include, without limitation, anti-CD3 scFvs and anti-CD3 VH domains. Additional examples of amino acid sequences that can be used as antigen binding domains having the ability to bind to a polypeptide expressed on the surface of a T cell (e.g., CD3) are described in U.S. Pat. No. 6,750,325, herein expressly incorporated by reference (see, e.g., the sequence listing of U.S. Pat. No. 6,750,325). In some cases, a cell engagers designed to have the ability to bind to an FGFR4 polypeptide and a T cell can have the structure as shown in FIGS. 15A and 15B.

In some cases, a cell engager provided herein can be designed to include an antigen binding domain that comprises, consists essentially of, or consists of one of the amino acid sequences set forth in FIG. 13. In some cases, a cell engager provided herein can be designed to include an antigen binding domain that comprises, consists essentially of, or consists of one of the amino acid sequences set forth in FIG. 13 with one, two, three, four, five, six, seven, eight, nine, or ten amino acid deletions, additions, substitutions, or combinations thereof, provided that the antigen binding domain has the ability to bind to a polypeptide expressed on the surface of a T cell. In some cases, a cell engager provided herein can be designed to include an antigen binding domain that comprises, consists essentially of, or consists of one of the amino acid sequences set forth in FIG. 13 with two or less, three or less, four or less, five or less, six or less, seven or less, eight or less, nine or less, or ten or less amino acid deletions, additions, substitutions, or combinations thereof, provided that the antigen binding domain has the ability to bind to a polypeptide expressed on the surface of a T cell.

When designing a cell engager such as a BiKE or a TriKE to link an $FGFR4^{+}$ cell and an NK cell, the cell engager can include an antigen binding domain having the ability to bind to an FGFR4 polypeptide (e.g., a human FGFR4 polypeptide) and one or more (e.g., one, two, or three) antigen binding domains having the ability to bind to a polypeptide expressed on the surface of an NK cell. Examples of polypeptides expressed on the surface of an NK cell that can be targeted by an antigen binding domain of a cell engager provided herein include, without limitation, CD16 polypeptides (e.g., CD16a polypeptides), NKG2A polypeptides, NKG2D polypeptides, NKp30 polypeptides, NKp44 polypeptides, and NKp46 polypeptides. Examples of antigen binding domains having the ability to bind to a polypeptide expressed on the surface of an NK cell that can be used to make a cell engager provided herein (e.g., a BiKE or TriKE) include, without limitation, anti-CD16a scFvs, anti-NKG2A scFvs, anti-NKG2D scFvs, anti-NKp30 scFvs (see, e.g., BioLegend Catalog #325207), anti-NKp44 scFvs, anti-NKp46 scFvs, anti-CD16a VH domains, anti-NKG2A VH domains, anti-NKG2D VH domains, anti-NKp30 VH domains, anti-NKp44 VH domains, or anti-NKp46 VH domains. Additional examples of amino acid sequences that can be used as antigen binding domains having the ability to bind to a polypeptide expressed on the surface of an NK cell (e.g., CD16, NKG2A, NKG2D, or NKp46) are described in McCall et al. (Mol. Immunol., 36(7):433-445 (1999); see, e.g., anti-CD16 scFv sequences); International Patent Application Publication No. PCT/US2017/048721 (see, e.g., the CDRs and sequence listing for anti-CD16a binding domains); U.S. Patent Application Publication No. 2011/0052606 (see, e.g., the CDRs and the sequence listing for anti-NKG2A antibodies such as Z199); U.S. Patent Application Publication No. 2011/0150870 (see, e.g., the CDRs and sequence listing for anti-NKG2D antibodies); U.S. Patent Application Publication No. 2018/0369373 (see, e.g., the CDRs and sequence listing for anti-NKp46 antibodies); and U.S. Patent Application Publication No. 2017/0368169 (see, e.g., the CDRs and sequence listing for anti-NKp46 antibodies), all of which are expressly incorporated by reference in their entireties.

In some cases, a cell engager provided herein can be designed to include an antigen binding domain (e.g., a scFv or VH) that comprises, consists essentially of, or consists of one or more of the amino acid sequences set forth in FIG. 14. In some cases, a cell engager provided herein can be designed to include an antigen binding domain (e.g., a scFv or VH) that comprises, consists essentially of, or consists of one of the amino acid sequences set forth in FIG. 14 with one, two, three, four, five, six, seven, eight, nine, or ten amino acid deletions, additions, substitutions, or combinations thereof, provided that the antigen binding domain has the ability to bind to a polypeptide expressed on the surface of an NK cell. In some cases, a cell engager provided herein can be designed to include an antigen binding domain (e.g., a scFv or VH) that comprises, consists essentially of, or consists of one of the amino acid sequences set forth in FIG. 14 with two or less, three or less, four or less, five or less, six or less, seven or less, eight or less, nine or less, or ten or less amino acid deletions, additions, substitutions, or combinations thereof, provided that the antigen binding domain has the ability to bind to a polypeptide expressed on the surface of an NK cell.

In some cases, a cell engager provided herein can be designed to include a linker located between each antigen binding domain. Any appropriate linker can be used to design a cell engager provided herein. Examples of linkers that can be used to make a cell engager described herein include, without limitation, the linker sequences set forth in FIG. 9. A cell engager provided herein can be designed to include a linker of any appropriate length. For example, a cell engager provided herein can be designed to include a linker that is from about 3 to about 100 (e.g., from about 3 to about 90, from about 3 to about 80, from about 3 to about 70, from about 3 to about 60, from about 3 to about 50, from about 3 to about 40, from about 3 to about 30, from about 3 to about 20, from about 3 to about 15, from about 5 to about 100, from about 10 to about 100, from about 20 to about 100, from about 30 to about 100, from about 40 to about 100, from about 50 to about 100, from about 60 to about 100, from about 70 to about 100, from about 10 to about 50, from about 10 to about 40, from about 10 to about 30, from about 10 to about 20, or from about 12 to about 17) amino acid residues in length. In some cases, a cell engager provided herein (e.g., a BiTE) can be designed to include a GGGGSGGGGSGGGGS linker. In some cases, a hinge of a CAR described herein can be used as a linker to make a cell engager described herein. For example, any one of the sequences set forth in FIG. 10 can be used as a linker of a cell engager described herein.

In some cases, a cell engager provided herein can be designed to include a linker that comprises, consists essentially of, or consists of one of the amino acid sequences set forth in FIG. 9 or FIG. 10. In some cases, a cell engager provided herein can be designed to include a linker that comprises, consists essentially of, or consists of one of the amino acid sequences set forth in FIG. 9 or FIG. 10 with one, two, three, four, five, six, seven, eight, nine, or ten amino acid deletions, additions, substitutions, or combinations thereof. In some cases, a cell engager provided herein can be designed to include a linker that comprises, consists essentially of, or consists of one of the amino acid sequences set forth in FIG. 9 or FIG. 10 with two or less, three or less, four or less, five or less, six or less, seven or less, eight or less, nine or less, or ten or less amino acid deletions, additions, substitutions, or combinations thereof.

In one embodiment, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain having a CDR1 having the amino acid sequence set forth in SEQ ID NO:42 (or a variant of SEQ ID NO:42 with one or two amino acid modifications), a CDR2 having the amino acid sequence set forth in SEQ ID NO:43 (or a variant of SEQ ID NO:43 with one or two amino acid modifications), and a CDR3 having the amino acid sequence set forth in SEQ ID NO:44 (or a variant of SEQ ID NO:44 with one or two amino acid modifications). An example of such an antibody domain having these CDRs and the ability to bind to an FGFR4 polypeptide (e.g., a human FGFR4 polypeptide) includes, without limitation, the VH domain set forth in TABLE 3.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) and having a heavy chain variable domain having a CDR1 having the amino acid sequence set forth in SEQ ID NO:42 (or a variant of SEQ ID NO:42 with one or two amino acid modifications), a CDR2 having the amino acid sequence set forth in SEQ ID NO:43 (or a variant of SEQ ID NO:43 with one or two amino acid modifications), and a CDR3 having the amino acid sequence set forth in SEQ ID NO:44 (or a variant of SEQ ID NO:44 with one or two amino acid modifications) can include any appropriate framework regions (see, e.g., TABLE 3).

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain that includes an amino acid sequence having at least 90% sequence identity to the amino acid sequence set forth in SEQ ID NO:01. For example, a binder (e.g., an antibody, antigen binding fragment, antibody domain, a CAR, a cell engager, and/or an ADC) provided herein can include a heavy chain variable domain that includes an amino acid sequence having at least 90, 91, 92, 93, 94, 95, 96, 97, 98, or 99% sequence identity to the amino acid sequence set forth in SEQ ID NO:01. In some cases, a binder (e.g., an antibody, antigen binding fragment, antibody domain, a CAR, a cell engager, and/or an ADC) provided herein can include (a) a heavy chain variable domain that includes an amino acid sequence having 100% identity to the amino acid sequence set forth in SEQ ID NO:01.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain that includes an amino acid sequence having at least 90% sequence identity to the amino acid sequence set forth in SEQ ID NO:01, provided that the heavy chain variable domain includes the amino acid sequences set forth in SEQ ID NOs:42, 43, and 44. For example, a binder (e.g., an antibody, antigen binding fragment, antibody domain, a CAR, a cell engager, and/or an ADC) provided herein can include a heavy chain variable domain that includes an amino acid sequence having at least 90, 91, 92, 93, 94, 95, 96, 97, 98, or 99% sequence identity to the amino acid sequence set forth in SEQ ID NO:01, provided that the heavy chain variable domain includes the amino acid sequences set forth in SEQ ID NOs:42, 43, and 44.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain having the amino acid sequence set forth in SEQ ID NO:01 or the amino acid set forth in SEQ ID NO:01 with one, two, three, four, five, six, seven, eight, nine, or 10 amino acid modifications (e.g., amino acid substitutions, amino acid deletions, and/or amino acid additions). For example, antibody domain (e.g., a VH domain) provided herein can have the ability to bind to an FGFR4 polypeptide (e.g., a human FGFR4 polypeptide) and can include a heavy chain variable domain having the amino acid sequence set forth in SEQ ID NO:01 with one, two, three, four, five, six, seven, eight, nine, or 10 amino acid modifications (e.g., amino acid substitutions, amino acid deletions, and/or amino acid additions), provided that the heavy chain variable domain includes the amino acid sequences set forth in SEQ ID NOs:42, 43, and 44.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain comprising (i) a CDR1 that comprises, consists essentially of, or consists of the amino acid sequence set forth in SEQ ID NO:42, (ii) a CDR2 that comprises, consists essentially of, or consists of the amino acid sequence set forth in SEQ ID NO:43, and (iii) a CDR3 that comprises, consists essentially of, or consists of the amino acid sequence set forth in SEQ ID NO:44.

As used herein, a "CDR1 that consists essentially of the amino acid sequence set forth in SEQ ID NO:42" is a CDR1 that has zero, one, or two amino acid substitutions within SEQ ID NO:42, that has zero, one, two, three, four, or five amino acid residues directly preceding SEQ ID NO:42, and/or that has zero, one, two, three, four, or five amino acid residues directly following SEQ ID NO:42, provided that the binder (e.g., an antibody, antigen binding fragment, antibody domain, a CAR, a cell engager, and/or an ADC) maintains its basic ability to bind to an FGFR4 polypeptide (e.g., a human FGFR4 polypeptide).

As used herein, a "CDR2 that consists essentially of the amino acid sequence set forth in SEQ ID NO:43" is a CDR2 that has zero, one, or two amino acid substitutions within SEQ ID NO:43, that has zero, one, two, three, four, or five amino acid residues directly preceding SEQ ID NO:43, and/or that has zero, one, two, three, four, or five amino acid residues directly following SEQ ID NO:43, provided that the binder (e.g., an antibody, antigen binding fragment, antibody domain, a CAR, a cell engager, and/or an ADC) maintains its basic ability to bind to an FGFR4 polypeptide (e.g., a human FGFR4 polypeptide).

As used herein, a "CDR3 that consists essentially of the amino acid sequence set forth in SEQ ID NO:44" is a CDR3 that has zero, one, or two amino acid substitutions within SEQ ID NO. 44, that has zero, one, two, three, four, or five amino acid residues directly preceding SEQ ID NO:44, and/or that has zero, one, two, three, four, or five amino acid residues directly following SEQ ID NO:44, provided that the binder (e.g., an antibody, antigen binding fragment, antibody domain, a CAR, a cell engager, and/or an ADC) maintains its basic ability to bind to an FGFR4 polypeptide (e.g., a human FGFR4 polypeptide).

In another embodiment, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain having a CDR1 having the amino acid sequence set forth in SEQ ID NO:45 (or a variant of SEQ ID NO:45 with one or two amino acid modifications), a CDR2 having the amino acid sequence set forth in SEQ ID NO:46 (or a variant of SEQ ID NO:46 with one or two amino acid modifications), and a CDR3 having the amino acid sequence set forth in SEQ ID NO:47 (or a variant of SEQ ID NO:47 with one or two amino acid modifications). An example of such an antibody domain having these CDRs and the ability to bind to an FGFR4 polypeptide (e.g., a human FGFR4 polypeptide) includes, without limitation, the VH domain set forth in TABLE 3.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) and having a heavy chain variable domain having a CDR1 having the amino acid sequence set forth in SEQ ID NO:45 (or a variant of SEQ ID NO:45 with one or two amino acid modifications), a CDR2 having the amino acid sequence set forth in SEQ ID NO:46 (or a variant of SEQ ID NO:46 with one or two amino acid modifications), and a CDR3 having the amino acid sequence set forth in SEQ ID NO:47 (or a variant of SEQ ID NO:47 with one or two amino acid modifications) can include any appropriate framework regions (see, e.g., TABLE 3).

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain that includes an amino acid sequence having at least 90% sequence identity to the amino acid sequence set forth in SEQ ID NO:02. For example, a binder (e.g., an antibody, antigen binding fragment, antibody domain, a CAR, a cell engager, and/or an ADC) provided herein can include a heavy chain variable domain that includes an amino acid sequence having at least 90, 91, 92, 93, 94, 95, 96, 97, 98, or 99% sequence identity to the amino acid sequence set forth in SEQ ID NO:02. In some cases, a binder (e.g., an antibody, antigen binding fragment, antibody domain, a CAR, a cell engager, and/or an ADC) provided herein can include (a) a heavy chain variable domain that includes an amino acid sequence having 100% identity to the amino acid sequence set forth in SEQ ID NO:02.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain that includes an amino acid sequence having at least 90% sequence identity to the amino acid sequence set forth in SEQ ID NO:02, provided that the heavy chain variable domain includes the amino acid sequences set forth in SEQ ID NOs:45, 46, and 47. For example, a binder (e.g., an antibody, antigen binding fragment, antibody domain, a CAR, a cell engager, and/or an ADC) provided herein can include a heavy chain variable domain that includes an amino acid sequence having at least 90, 91, 92, 93, 94, 95, 96, 97, 98, or 99% sequence identity to the amino acid sequence set forth in SEQ ID NO:02, provided that the heavy chain variable domain includes the amino acid sequences set forth in SEQ ID NOs:45, 46, and 47.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain having the amino acid sequence set forth in SEQ ID NO:02 or the amino acid set forth in SEQ ID NO:02 with one, two, three, four, five, six, seven, eight, nine, or 10 amino acid modifications (e.g., amino acid substitutions, amino acid deletions, and/or amino acid additions). For example, antibody domain (e.g., a VH domain) provided herein can have the ability to bind to an FGFR4 polypeptide (e.g., a human FGFR4 polypeptide) and can include a heavy chain variable domain having the amino acid sequence set forth in SEQ ID NO:02 with one, two, three, four, five, six, seven, eight, nine, or 10 amino acid modifications (e.g., amino acid substitutions, amino acid deletions, and/or amino acid additions), provided that the heavy chain variable domain includes the amino acid sequences set forth in SEQ ID NOs:45, 46, and 47.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain comprising (i) a CDR1 that comprises, consists essentially of, or consists of the amino acid sequence set forth in SEQ ID NO:45, (ii) a CDR2 that comprises, consists essentially of, or consists of the amino acid sequence set forth in SEQ ID NO:46, and (iii) a CDR3 that comprises, consists essentially of, or consists of the amino acid sequence set forth in SEQ ID NO:47. As used herein, a "CDR1 that consists essentially of the amino acid sequence set forth in SEQ ID NO:45" is a CDR1 that has zero, one, or two amino acid substitutions within SEQ ID NO:45, that has zero, one, two, three, four, or five amino acid residues directly preceding SEQ ID NO. 45, and/or that has zero, one, two, three, four, or five amino acid residues directly following SEQ ID NO:45, provided that the binder (e.g., an antibody, antigen binding fragment, antibody domain, a CAR, a cell engager, and/or an ADC) maintains its basic ability to bind to an FGFR4 polypeptide (e.g., a human FGFR4 polypeptide).

As used herein, a "CDR2 that consists essentially of the amino acid sequence set forth in SEQ ID NO:46" is a CDR2 that has zero, one, or two amino acid substitutions within SEQ ID NO:46, that has zero, one, two, three, four, or five amino acid residues directly preceding SEQ ID NO:46, and/or that has zero, one, two, three, four, or five amino acid residues directly following SEQ ID NO:46, provided that the binder (e.g., an antibody, antigen binding fragment, antibody domain, a CAR, a cell engager, and/or an ADC) maintains its basic ability to bind to an FGFR4 polypeptide (e.g., a human FGFR4 polypeptide).

As used herein, a "CDR3 that consists essentially of the amino acid sequence set forth in SEQ ID NO:47" is a CDR3 that has zero, one, or two amino acid substitutions within SEQ ID NO. 47, that has zero, one, two, three, four, or five amino acid residues directly preceding SEQ ID NO:47, and/or that has zero, one, two, three, four, or five amino acid residues directly following SEQ ID NO:47, provided that the binder (e.g., an antibody, antigen binding fragment, antibody domain, a CAR, a cell engager, and/or an ADC) maintains its basic ability to bind to an FGFR4 polypeptide (e.g., a human FGFR4 polypeptide).

In another embodiment, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain having a CDR1 having the amino acid sequence set forth in SEQ ID NO:48 (or a variant of SEQ ID NO:48 with one or two amino acid modifications), a CDR2 having the amino acid sequence set forth in SEQ ID NO:49 (or a variant of SEQ ID NO:49 with one or two amino acid modifications), and a CDR3 having the amino acid sequence set forth in SEQ ID NO:50 (or a variant of SEQ ID NO:50 with one or two amino acid modifications). An example of such an antibody domain having these CDRs and the ability to bind to an FGFR4 polypeptide (e.g., a human FGFR4 polypeptide) includes, without limitation, the VH domain set forth in TABLE 3.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) and having a heavy chain variable domain having a CDR1 having the amino acid sequence set forth in SEQ ID NO:48 (or a variant of SEQ ID NO:48 with one or two amino acid modifications), a CDR2 having the amino acid sequence set forth in SEQ ID NO:49 (or a variant of SEQ ID NO:49 with one or two amino acid modifications), and a CDR3 having the amino acid sequence set forth in SEQ ID NO:50 (or a variant of SEQ ID NO:50 with one or two amino acid modifications) can include any appropriate framework regions (see, e.g., TABLE 3).

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain that includes an amino acid sequence having at least 90% sequence identity to the amino acid sequence set forth in SEQ ID NO:03. For example, a binder (e.g., an antibody, antigen binding fragment, antibody domain, a CAR, a cell engager, and/or an ADC) provided herein can include a heavy chain variable domain that includes an amino acid sequence having at least 90, 91, 92, 93, 94, 95, 96, 97, 98, or 99% sequence identity to the amino acid sequence set forth in SEQ ID NO:03. In some cases, a binder (e.g., an antibody, antigen binding fragment, antibody domain, a CAR, a cell engager, and/or an ADC) provided herein can include (a) a heavy chain variable domain that includes an amino acid sequence having 100% identity to the amino acid sequence set forth in SEQ ID NO:03.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain that includes an amino acid sequence having at least 90% sequence identity to the amino acid sequence set forth in SEQ ID NO:03, provided that the heavy chain variable domain includes the amino acid sequences set forth in SEQ ID NOs:48, 49, and 50. For example, a binder (e.g., an antibody, antigen binding fragment, antibody domain, a CAR, a cell engager, and/or an ADC) provided herein can include a heavy chain variable domain that includes an amino acid sequence having at least 90, 91, 92, 93, 94, 95, 96, 97, 98, or 99% sequence identity to the amino acid sequence set forth in SEQ ID NO:03, provided that the heavy chain variable domain includes the amino acid sequences set forth in SEQ ID NOs:48, 49, and 50.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain having the amino acid sequence set forth in SEQ ID NO:03 or the amino acid set forth in SEQ ID NO:03 with one, two, three, four, five, six, seven, eight, nine, or 10 amino acid modifications (e.g., amino acid substitutions, amino acid deletions, and/or amino acid additions). For example, antibody domain (e.g., a VH domain) provided herein can have the ability to bind to an FGFR4 polypeptide (e.g., a human FGFR4 polypeptide) and can include a heavy chain variable domain having the amino acid sequence set forth in SEQ ID NO:03 with one, two, three, four, five, six, seven, eight, nine, or 10 amino acid modifications (e.g., amino acid substitutions, amino acid deletions, and/or amino acid additions), provided that the heavy chain variable domain includes the amino acid sequences set forth in SEQ ID NOs:48, 49, and 50.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain comprising (i) a CDR1 that comprises, consists essentially of, or consists of the amino acid sequence set forth in SEQ ID NO:48, (ii) a CDR2 that comprises, consists essentially of, or consists of the amino acid sequence set forth in SEQ ID NO:49, and (iii) a CDR3 that comprises, consists essentially of, or consists of the amino acid sequence set forth in SEQ ID NO:50.

As used herein, a "CDR1 that consists essentially of the amino acid sequence set forth in SEQ ID NO:48" is a CDR1 that has zero, one, or two amino acid substitutions within SEQ ID NO:48, that has zero, one, two, three, four, or five amino acid residues directly preceding SEQ ID NO:48, and/or that has zero, one, two, three, four, or five amino acid residues directly following SEQ ID NO:48, provided that the binder (e.g., an antibody, antigen binding fragment, antibody domain, a CAR, a cell engager, and/or an ADC) maintains its basic ability to bind to an FGFR4 polypeptide (e.g., a human FGFR4 polypeptide).

As used herein, a "CDR2 that consists essentially of the amino acid sequence set forth in SEQ ID NO:49" is a CDR2 that has zero, one, or two amino acid substitutions within SEQ ID NO:49, that has zero, one, two, three, four, or five amino acid residues directly preceding SEQ ID NO:49, and/or that has zero, one, two, three, four, or five amino acid residues directly following SEQ ID NO:49, provided that the binder (e.g., an antibody, antigen binding fragment, antibody domain, a CAR, a cell engager, and/or an ADC) maintains its basic ability to bind to an FGFR4 polypeptide (e.g., a human FGFR4 polypeptide).

As used herein, a "CDR3 that consists essentially of the amino acid sequence set forth in SEQ ID NO:50" is a CDR3 that has zero, one, or two amino acid substitutions within SEQ ID NO:50, that has zero, one, two, three, four, or five amino acid residues directly preceding SEQ ID NO:50, and/or that has zero, one, two, three, four, or five amino acid residues directly following SEQ ID NO:50, provided that the binder (e.g., an antibody, antigen binding fragment, antibody domain, a CAR, a cell engager, and/or an ADC) maintains its basic ability to bind to an FGFR4 polypeptide (e.g., a human FGFR4 polypeptide).

In another embodiment, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain having a CDR1 having the amino acid sequence set forth in SEQ ID NO:51 (or a variant of SEQ ID NO:51 with one or two amino acid modifications), a CDR2 having the amino acid sequence set forth in SEQ ID NO:52 (or a variant of SEQ ID NO:52 with one or two amino acid modifications), and a CDR3 having the amino acid sequence set forth in SEQ ID NO:53 (or a variant of SEQ ID NO:53 with one or two amino acid modifications). An example of such an antibody domain having these CDRs and the ability to bind to an FGFR4 polypeptide (e.g., a human FGFR4 polypeptide) includes, without limitation, the VH domain set forth in TABLE 3.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) and having a heavy chain variable domain having a CDR1 having the amino acid sequence set forth in SEQ ID NO:51 (or a variant of SEQ ID NO:51 with one or two amino acid modifications), a CDR2 having the amino acid sequence set forth in SEQ ID NO:52 (or a variant of SEQ ID NO:52 with one or two amino acid modifications), and a CDR3 having the amino acid sequence set forth in SEQ ID NO:53 (or a variant of SEQ ID NO:53 with one or two amino acid modifications) can include any appropriate framework regions (see, e.g., TABLE 3).

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain that includes an amino acid sequence having at least 90% sequence identity to the amino acid sequence set forth in SEQ ID NO:04. For example, a binder (e.g., an antibody, antigen binding fragment, antibody domain, a CAR, a cell engager, and/or an ADC) provided herein can include a heavy chain variable domain that includes an amino acid sequence having at least 90, 91, 92, 93, 94, 95, 96, 97, 98, or 99% sequence identity to the amino acid sequence set forth in SEQ ID NO:04. In some cases, a binder (e.g., an antibody, antigen binding fragment, antibody domain, a CAR, a cell engager, and/or an ADC) provided herein can include (a) a heavy chain variable domain that includes an amino acid sequence having 100% identity to the amino acid sequence set forth in SEQ ID NO:04.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain that includes an amino acid sequence having at least 90% sequence identity to the amino acid sequence set forth in SEQ ID NO:04, provided that the heavy chain variable domain includes the amino acid sequences set forth in SEQ ID NOs:51, 52, and 53. For example, a binder (e.g., an antibody, antigen binding fragment, antibody domain, a CAR, a cell engager, and/or an ADC) provided herein can include a heavy chain variable domain that includes an amino acid sequence having at least 90, 91, 92, 93, 94, 95, 96, 97, 98, or 99% sequence identity to the amino acid sequence set forth in SEQ ID NO:04, provided that the heavy chain variable domain includes the amino acid sequences set forth in SEQ ID NOs:51, 52, and 53.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain having the amino acid sequence set forth in SEQ ID NO:04 or the amino acid set forth in SEQ ID NO:04 with one, two, three, four, five, six, seven, eight, nine, or 10 amino acid modifications (e.g., amino acid substitutions, amino acid deletions, and/or amino acid additions). For example, an antibody domain (e.g., a VH domain) provided herein can have the ability to bind to an FGFR4 polypeptide (e.g., a human FGFR4 polypeptide) and can include a heavy chain variable domain having the amino acid sequence set forth in SEQ ID NO:04 with one, two, three, four, five, six, seven, eight, nine, or 10 amino acid modifications (e.g., amino acid substitutions, amino acid deletions, and/or amino acid additions), provided that the heavy chain variable domain includes the amino acid sequences set forth in SEQ ID NOs:51, 52, and 53.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain comprising (i) a CDR1 that comprises, consists essentially of, or consists of the amino acid sequence set forth in SEQ ID NO:51, (ii) a CDR2 that comprises, consists essentially of, or consists of the amino acid sequence set forth in SEQ ID NO:52, and (iii) a CDR3 that comprises, consists essentially of, or consists of the amino acid sequence set forth in SEQ ID NO:53.

As used herein, a "CDR1 that consists essentially of the amino acid sequence set forth in SEQ ID NO:51" is a CDR1 that has zero, one, or two amino acid substitutions within SEQ ID NO. 51, that has zero, one, two, three, four, or five amino acid residues directly preceding SEQ ID NO:51, and/or that has zero, one, two, three, four, or five amino acid residues directly following SEQ ID NO:51, provided that the binder (e.g., an antibody, antigen binding fragment, antibody domain, a CAR, a cell engager, and/or an ADC) maintains its basic ability to bind to an FGFR4 polypeptide (e.g., a human FGFR4 polypeptide).

As used herein, a "CDR2 that consists essentially of the amino acid sequence set forth in SEQ ID NO:52" is a CDR2 that has zero, one, or two amino acid substitutions within SEQ ID NO:52, that has zero, one, two, three, four, or five amino acid residues directly preceding SEQ ID NO:52, and/or that has zero, one, two, three, four, or five amino acid residues directly following SEQ ID NO:52, provided that the binder (e.g., an antibody, antigen binding fragment, antibody domain, a CAR, a cell engager, and/or an ADC) maintains its basic ability to bind to an FGFR4 polypeptide (e.g., a human FGFR4 polypeptide).

As used herein, a "CDR3 that consists essentially of the amino acid sequence set forth in SEQ ID NO:53" is a CDR3 that has zero, one, or two amino acid substitutions within SEQ ID NO:53, that has zero, one, two, three, four, or five amino acid residues directly preceding SEQ ID NO:53, and/or that has zero, one, two, three, four, or five amino acid residues directly following SEQ ID NO:53, provided that the binder (e.g., an antibody, antigen binding fragment, antibody domain, a CAR, a cell engager, and/or an ADC) maintains its basic ability to bind to an FGFR4 polypeptide (e.g., a human FGFR4 polypeptide).

In another embodiment, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain having a CDR1 having the amino acid sequence set forth in SEQ ID NO:54 (or a variant of SEQ ID NO:54 with one or two amino acid modifications), a CDR2 having the amino acid sequence set forth in SEQ ID NO:55 (or a variant of SEQ ID NO. 55 with one or two amino acid modifications), and a CDR3 having the amino acid sequence set forth in SEQ ID NO:56 (or a variant of SEQ ID NO:56 with one or two amino acid modifications). An example of such an antibody domain having these CDRs and the ability to bind to an FGFR4 polypeptide (e.g., a human FGFR4 polypeptide) includes, without limitation, the VH domain set forth in TABLE 3.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) and having a heavy chain variable domain having a CDR1 having the amino acid sequence set forth in SEQ ID NO:54 (or a variant of SEQ ID NO:54 with one or two amino acid modifications), a CDR2 having the amino acid sequence set forth in SEQ ID NO:55 (or a variant of SEQ ID NO:55 with one or two amino acid modifications), and a CDR3 having the amino acid sequence set forth in SEQ ID NO:56 (or a variant of SEQ ID NO:56 with one or two amino acid modifications) can include any appropriate framework regions (see, e.g., TABLE 3).

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain that includes an amino acid sequence having at least 90% sequence identity to the amino acid sequence set forth in SEQ ID NO:05. For example, a binder (e.g., an antibody, antigen binding fragment, antibody domain, a CAR, a cell engager, and/or an ADC) provided herein can include a heavy chain variable domain that includes an amino acid sequence having at least 90, 91, 92, 93, 94, 95, 96, 97, 98, or 99% sequence identity to the amino acid sequence set forth in SEQ ID NO:05. In some cases, a binder (e.g., an antibody, antigen binding fragment, antibody domain, a CAR, a cell engager, and/or an ADC) provided herein can include (a) a heavy chain variable domain that includes an amino acid sequence having 100% identity to the amino acid sequence set forth in SEQ ID NO:05.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain that includes an amino acid sequence having at least 90% sequence identity to the amino acid sequence set forth in SEQ ID NO:05, provided that the heavy chain variable domain includes the amino acid sequences set forth in SEQ ID NOs:54, 55, and 56. For example, a binder (e.g., an antibody, antigen binding fragment, antibody domain, a CAR, a cell engager, and/or an ADC) provided herein can include a heavy chain variable domain that includes an amino acid sequence having at least 90, 91, 92, 93, 94, 95, 96, 97, 98, or 99% sequence identity to the amino acid sequence set forth in SEQ ID NO:05, provided that the heavy chain variable domain includes the amino acid sequences set forth in SEQ ID NOs:54, 55, and 56.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain having the amino acid sequence set forth in SEQ ID NO:05 or the amino acid set forth in SEQ ID NO:05 with one, two, three, four, five, six, seven, eight, nine, or 10 amino acid modifications (e.g., amino acid substitutions, amino acid deletions, and/or amino acid additions). For example, an antibody domain (e.g., a VH domain) provided herein can have the ability to bind to an FGFR4 polypeptide (e.g., a human FGFR4 polypeptide) and can include a heavy chain variable domain having the amino acid sequence set forth in SEQ ID NO:05 with one, two, three, four, five, six, seven, eight, nine, or 10 amino acid modifications (e.g., amino acid substitutions, amino acid deletions, and/or amino acid additions), provided that the heavy chain variable domain includes the amino acid sequences set forth in SEQ ID NOs:54, 55, and 56.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain comprising (i) a CDR1 that comprises, consists essentially of, or consists of the amino acid sequence set forth in SEQ ID NO:54, (ii) a CDR2 that comprises, consists essentially of, or consists of the amino acid sequence set forth in SEQ ID NO:55, and (iii) a CDR3 that comprises, consists essentially of, or consists of the amino acid sequence set forth in SEQ ID NO:56.

As used herein, a "CDR1 that consists essentially of the amino acid sequence set forth in SEQ ID NO:54" is a CDR1 that has zero, one, or two amino acid substitutions within SEQ ID NO:54, that has zero, one, two, three, four, or five amino acid residues directly preceding SEQ ID NO:54, and/or that has zero, one, two, three, four, or five amino acid residues directly following SEQ ID NO:54, provided that the binder (e.g., an antibody, antigen binding fragment, antibody domain, a CAR, a cell engager, and/or an ADC) maintains its basic ability to bind to an FGFR4 polypeptide (e.g., a human FGFR4 polypeptide).

As used herein, a "CDR2 that consists essentially of the amino acid sequence set forth in SEQ ID NO:55" is a CDR2 that has zero, one, or two amino acid substitutions within SEQ ID NO:55, that has zero, one, two, three, four, or five amino acid residues directly preceding SEQ ID NO:55, and/or that has zero, one, two, three, four, or five amino acid residues directly following SEQ ID NO:55, provided that the binder (e.g., an antibody, antigen binding fragment, antibody domain, a CAR, a cell engager, and/or an ADC) maintains its basic ability to bind to an FGFR4 polypeptide (e.g., a human FGFR4 polypeptide).

As used herein, a "CDR3 that consists essentially of the amino acid sequence set forth in SEQ ID NO:56" is a CDR3 that has zero, one, or two amino acid substitutions within SEQ ID NO:56, that has zero, one, two, three, four, or five amino acid residues directly preceding SEQ ID NO:56, and/or that has zero, one, two, three, four, or five amino acid residues directly following SEQ ID NO:56, provided that the binder (e.g., an antibody, antigen binding fragment, antibody domain, a CAR, a cell engager, and/or an ADC) maintains its basic ability to bind to an FGFR4 polypeptide (e.g., a human FGFR4 polypeptide).

In another embodiment, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain having a CDR1 having the amino acid sequence set forth in SEQ ID NO:57 (or a variant of SEQ ID NO:57 with one or two amino acid modifications), a CDR2 having the amino acid sequence set forth in SEQ ID NO:58 (or a variant of SEQ ID NO:58 with one or two amino acid modifications), and a CDR3 having the amino acid sequence set forth in SEQ ID NO:59 (or a variant of SEQ ID NO:59 with one or two amino acid modifications). An example of such an antibody domain having these CDRs and the ability to bind to an FGFR4 polypeptide (e.g., a human FGFR4 polypeptide) includes, without limitation, the VH domain set forth in TABLE 3.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) and having a heavy chain variable domain having a CDR1 having the amino acid sequence set forth in SEQ ID NO:57 (or a variant of SEQ ID NO:57 with one or two amino acid modifications), a CDR2 having the amino acid sequence set forth in SEQ ID NO:58 (or a variant of SEQ ID NO:58 with one or two amino acid modifications), and a CDR3 having the amino acid sequence set forth in SEQ ID NO:59 (or a variant of SEQ ID NO:59 with one or two amino acid modifications) can include any appropriate framework regions (see, e.g., TABLE 3).

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain that includes an amino acid sequence having at least 90% sequence identity to the amino acid sequence set forth in SEQ ID NO:06. For example, a binder (e.g., an antibody, antigen binding fragment, antibody domain, a CAR, a cell engager, and/or an ADC) provided herein can include a heavy chain variable domain that includes an amino acid sequence having at least 90, 91, 92, 93, 94, 95, 96, 97, 98, or 99% sequence identity to the amino acid sequence set forth in SEQ ID NO:06. In some cases, a binder (e.g., an antibody, antigen binding fragment, antibody domain, a CAR, a cell engager, and/or an ADC) provided herein can include (a) a heavy chain variable domain that includes an amino acid sequence having 100% identity to the amino acid sequence set forth in SEQ ID NO:06.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain that includes an amino acid sequence having at least 90% sequence identity to the amino acid sequence set forth in SEQ ID NO:06, provided that the heavy chain variable domain includes the amino acid sequences set forth in SEQ ID NOs:57, 58, and 59. For example, a binder (e.g., an antibody, antigen binding fragment, antibody domain, a CAR, a cell engager, and/or an ADC) provided herein can include a heavy chain variable domain that includes an amino acid sequence having at least 90, 91, 92, 93, 94, 95, 96, 97, 98, or 99% sequence identity to the amino acid sequence set forth in SEQ ID NO:06, provided that the heavy chain variable domain includes the amino acid sequences set forth in SEQ ID NOs:57, 58, and 59.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain having the amino acid sequence set forth in SEQ ID NO:06 or the amino acid set forth in SEQ ID NO:06 with one, two, three, four, five, six, seven, eight, nine, or 10 amino acid modifications (e.g., amino acid substitutions, amino acid deletions, and/or amino acid additions). For example, an antibody domain (e.g., a VH domain) provided herein can have the ability to bind to an FGFR4 polypeptide (e.g., a human FGFR4 polypeptide) and can include a heavy chain variable domain having the amino acid sequence set forth in SEQ ID NO:06 with one, two, three, four, five, six, seven, eight, nine, or 10 amino acid modifications (e.g., amino acid substitutions, amino acid deletions, and/or amino acid additions), provided that the heavy chain variable domain includes the amino acid sequences set forth in SEQ ID NOs:57, 58, and 59.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain comprising (i) a CDR1 that comprises, consists essentially of, or consists of the amino acid sequence set forth in SEQ ID NO:57, (ii) a CDR2 that comprises, consists essentially of, or consists of the amino acid sequence set forth in SEQ ID NO:58, and (iii) a CDR3 that comprises, consists essentially of, or consists of the amino acid sequence set forth in SEQ ID NO:59.

As used herein, a "CDR1 that consists essentially of the amino acid sequence set forth in SEQ ID NO:57" is a CDR1 that has zero, one, or two amino acid substitutions within SEQ ID NO:57, that has zero, one, two, three, four, or five amino acid residues directly preceding SEQ ID NO:57, and/or that has zero, one, two, three, four, or five amino acid residues directly following SEQ ID NO:57, provided that the binder (e.g., an antibody, antigen binding fragment, antibody domain, a CAR, a cell engager, and/or an ADC) maintains its basic ability to bind to an FGFR4 polypeptide (e.g., a human FGFR4 polypeptide).

As used herein, a "CDR2 that consists essentially of the amino acid sequence set forth in SEQ ID NO:58" is a CDR2 that has zero, one, or two amino acid substitutions within SEQ ID NO:58, that has zero, one, two, three, four, or five amino acid residues directly preceding SEQ ID NO:58, and/or that has zero, one, two, three, four, or five amino acid residues directly following SEQ ID NO:58, provided that the binder (e.g., an antibody, antigen binding fragment, antibody domain, a CAR, a cell engager, and/or an ADC) maintains its basic ability to bind to an FGFR4 polypeptide (e.g., a human FGFR4 polypeptide).

As used herein, a "CDR3 that consists essentially of the amino acid sequence set forth in SEQ ID NO:59" is a CDR3 that has zero, one, or two amino acid substitutions within SEQ ID NO:59, that has zero, one, two, three, four, or five amino acid residues directly preceding SEQ ID NO:59, and/or that has zero, one, two, three, four, or five amino acid residues directly following SEQ ID NO:59, provided that the binder (e.g., an antibody, antigen binding fragment, antibody domain, a CAR, a cell engager, and/or an ADC) maintains its basic ability to bind to an FGFR4 polypeptide (e.g., a human FGFR4 polypeptide).

In another embodiment, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain having a CDR1 having the amino acid sequence set forth in SEQ ID NO:60 (or a variant of SEQ ID NO:60 with one or two amino acid modifications), a CDR2 having the amino acid sequence set forth in SEQ ID NO:61 (or a variant of SEQ ID NO:61 with one or two amino acid modifications), and a CDR3 having the amino acid sequence set forth in SEQ ID NO:62 (or a variant of SEQ ID NO:62 with one or two amino acid modifications). An example of such an antibody domain having these CDRs and the ability to bind to an FGFR4 polypeptide (e.g., a human FGFR4 polypeptide) includes, without limitation, the VH domain set forth in TABLE 3.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) and having a heavy chain variable domain having a CDR1 having the amino acid sequence set forth in SEQ ID NO:60 (or a variant of SEQ ID NO:60 with one or two amino acid modifications), a CDR2 having the amino acid sequence set forth in SEQ ID NO:61 (or a variant of SEQ ID NO:61 with one or two amino acid modifications), and a CDR3 having the amino acid sequence set forth in SEQ ID NO:62 (or a variant of SEQ ID NO:62 with one or two amino acid modifications) can include any appropriate framework regions (see, e.g., TABLE 3).

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain that includes an amino acid sequence having at least 90% sequence identity to the amino acid sequence set forth in SEQ ID NO:07. For example, a binder (e.g., an antibody, antigen binding fragment, antibody domain, a CAR, a cell engager, and/or an ADC) provided herein can include a heavy chain variable domain that includes an amino acid sequence having at least 90, 91, 92, 93, 94, 95, 96, 97, 98, or 99% sequence identity to the amino acid sequence set forth in SEQ ID NO:07. In some cases, a binder (e.g., an antibody, antigen binding fragment, antibody domain, a CAR, a cell engager, and/or an ADC) provided herein can include (a) a heavy chain variable domain that includes an amino acid sequence having 100% identity to the amino acid sequence set forth in SEQ ID NO:07.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain that includes an amino acid sequence having at least 90% sequence identity to the amino acid sequence set forth in SEQ ID NO:07, provided that the heavy chain variable domain includes the amino acid sequences set forth in SEQ ID NOs:60, 61, and 62. For example, a binder (e.g., an antibody, antigen binding fragment, antibody domain, a CAR, a cell engager, and/or an ADC) provided herein can include a heavy chain variable domain that includes an amino acid sequence having at least 90, 91, 92, 93, 94, 95, 96, 97, 98, or 99/a sequence identity to the amino acid sequence set forth in SEQ ID NO:07, provided that the heavy chain variable domain includes the amino acid sequences set forth in SEQ ID NOs:60, 61, and 62.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain having the amino acid sequence set forth in SEQ ID NO:07 or the amino acid set forth in SEQ ID NO:07 with one, two, three, four, five, six, seven, eight, nine, or 10 amino acid modifications (e.g., amino acid substitutions, amino acid deletions, and/or amino acid additions). For example, an antibody domain (e.g., a VH domain) provided herein can have the ability to bind to an FGFR4 polypeptide (e.g., a human FGFR4 polypeptide) and can include a heavy chain variable domain having the amino acid sequence set forth in SEQ ID NO:07 with one, two, three, four, five, six, seven, eight, nine, or 10 amino acid modifications (e.g., amino acid substitutions, amino acid deletions, and/or amino acid additions), provided that the heavy chain variable domain includes the amino acid sequences set forth in SEQ ID NOs:60, 61, and 62.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain comprising (i) a CDR1 that comprises, consists essentially of, or consists of the amino acid sequence set forth in SEQ ID NO:60, (ii) a CDR2 that comprises, consists essentially of, or consists of the amino acid sequence set forth in SEQ ID NO:61, and (iii) a CDR3 that comprises, consists essentially of, or consists of the amino acid sequence set forth in SEQ ID NO:62.

As used herein, a "CDR1 that consists essentially of the amino acid sequence set forth in SEQ ID NO:60" is a CDR1 that has zero, one, or two amino acid substitutions within SEQ ID NO:60, that has zero, one, two, three, four, or five amino acid residues directly preceding SEQ ID NO:60, and/or that has zero, one, two, three, four, or five amino acid residues directly following SEQ ID NO:60, provided that the binder (e.g., an antibody, antigen binding fragment, antibody domain, a CAR, a cell engager, and/or an ADC) maintains its basic ability to bind to an FGFR4 polypeptide (e.g., a human FGFR4 polypeptide).

As used herein, a "CDR2 that consists essentially of the amino acid sequence set forth in SEQ ID NO:61" is a CDR2 that has zero, one, or two amino acid substitutions within SEQ ID NO:61, that has zero, one, two, three, four, or five amino acid residues directly preceding SEQ ID NO:61, and/or that has zero, one, two, three, four, or five amino acid residues directly following SEQ ID NO:61, provided that the binder (e.g., an antibody, antigen binding fragment, antibody domain, a CAR, a cell engager, and/or an ADC) maintains its basic ability to bind to an FGFR4 polypeptide (e.g., a human FGFR4 polypeptide).

As used herein, a "CDR3 that consists essentially of the amino acid sequence set forth in SEQ ID NO:62" is a CDR3 that has zero, one, or two amino acid substitutions within SEQ ID NO:62, that has zero, one, two, three, four, or five amino acid residues directly preceding SEQ ID NO:62, and/or that has zero, one, two, three, four, or five amino acid residues directly following SEQ ID NO:62, provided that the binder (e.g., an antibody, antigen binding fragment, antibody domain, a CAR, a cell engager, and/or an ADC) maintains its basic ability to bind to an FGFR4 polypeptide (e.g., a human FGFR4 polypeptide).

In another embodiment, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain having a CDR1 having the amino acid sequence set forth in SEQ ID NO:63 (or a variant of SEQ ID NO:63 with one or two amino acid modifications), a CDR2 having the amino acid sequence set forth in SEQ ID NO:64 (or a variant of SEQ ID NO:64 with one or two amino acid modifications), and a CDR3 having the amino acid sequence set forth in SEQ ID NO:65 (or a variant of SEQ ID NO:65 with one or two amino acid modifications). An example of such an antibody domain having these CDRs and the ability to bind to an FGFR4 polypeptide (e.g., a human FGFR4 polypeptide) includes, without limitation, the VH domain set forth in TABLE 3.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) and having a heavy chain variable domain having a CDR1 having the amino acid sequence set forth in SEQ ID NO:63 (or a variant of SEQ ID NO:63 with one or two amino acid modifications), a CDR2 having the amino acid sequence set forth in SEQ ID NO:64 (or a variant of SEQ ID NO:64 with one or two amino acid modifications), and a CDR3 having the amino acid sequence set forth in SEQ ID NO:65 (or a variant of SEQ ID NO:65 with one or two amino acid modifications) can include any appropriate framework regions (see, e.g., TABLE 3).

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain that includes an amino acid sequence having at least 90% sequence identity to the amino acid sequence set forth in SEQ ID NO:08. For example, a binder (e.g., an antibody, antigen binding fragment, antibody domain, a CAR, a cell engager, and/or an ADC) provided herein can include a heavy chain variable domain that includes an amino acid sequence having at least 90, 91, 92, 93, 94, 95, 96, 97, 98, or 99% sequence identity to the amino acid sequence set forth in SEQ ID NO:08. In some cases, a binder (e.g., an antibody, antigen binding fragment, antibody domain, a CAR, a cell engager, and/or an ADC) provided herein can include (a) a heavy chain variable domain that includes an amino acid sequence having 100% identity to the amino acid sequence set forth in SEQ ID NO:08.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain that includes an amino acid sequence having at least 90% sequence identity to the amino acid sequence set forth in SEQ ID NO:08, provided that the heavy chain variable domain includes the amino acid sequences set forth in SEQ ID NOs:63, 64, and 65. For example, a binder (e.g., an antibody, antigen binding fragment, antibody domain, a CAR, a cell engager, and/or an ADC) provided herein can include a heavy chain variable domain that includes an amino acid sequence having at least 90, 91, 92, 93, 94, 95, 96, 97, 98, or 99% sequence identity to the amino acid sequence set forth in SEQ ID NO:08, provided that the heavy chain variable domain includes the amino acid sequences set forth in SEQ ID NOs:63, 64, and 65.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain having the amino acid sequence set forth in SEQ ID NO:08 or the amino acid set forth in SEQ ID NO:08 with one, two, three, four, five, six, seven, eight, nine, or 10 amino acid modifications (e.g., amino acid substitutions, amino acid deletions, and/or amino acid additions). For example, an antibody domain (e.g., a VH domain) provided herein can have the ability to bind to an FGFR4 polypeptide (e.g., a human FGFR4 polypeptide) and can include a heavy chain variable domain having the amino acid sequence set forth in SEQ ID NO:08 with one, two, three, four, five, six, seven, eight, nine, or 10 amino acid modifications (e.g., amino acid substitutions, amino acid deletions, and/or amino acid additions), provided that the heavy chain variable domain includes the amino acid sequences set forth in SEQ ID NOs:63, 64, and 65.

In some cases, a binder (e.g., an antibody, antigen binding fragment, antibody domain, a CAR, a cell engager, and/or an ADC) provided herein having the ability to bind to an FGFR4 polypeptide (e.g., a human FGFR4 polypeptide) can include a heavy chain variable domain comprising (i) a CDR1 that comprises, consists essentially of, or consists of the amino acid sequence set forth in SEQ ID NO:63, (ii) a CDR2 that comprises, consists essentially of, or consists of the amino acid sequence set forth in SEQ ID NO:64, and (iii) a CDR3 that comprises, consists essentially of, or consists of the amino acid sequence set forth in SEQ ID NO:65.

As used herein, a "CDR1 that consists essentially of the amino acid sequence set forth in SEQ ID NO:63" is a CDR1 that has zero, one, or two amino acid substitutions within SEQ ID NO:63, that has zero, one, two, three, four, or five amino acid residues directly preceding SEQ ID NO:63, and/or that has zero, one, two, three, four, or five amino acid residues directly following SEQ ID NO:63, provided that the binder (e.g., an antibody, antigen binding fragment, antibody domain, a CAR, a cell engager, and/or an ADC) maintains its basic ability to bind to an FGFR4 polypeptide (e.g., a human FGFR4 polypeptide).

As used herein, a "CDR2 that consists essentially of the amino acid sequence set forth in SEQ ID NO:64" is a CDR2 that has zero, one, or two amino acid substitutions within SEQ ID NO:64, that has zero, one, two, three, four, or five amino acid residues directly preceding SEQ ID NO:64, and/or that has zero, one, two, three, four, or five amino acid residues directly following SEQ ID NO:64, provided that the binder (e.g., an antibody, antigen binding fragment, antibody domain, a CAR, a cell engager, and/or an ADC) maintains its basic ability to bind to an FGFR4 polypeptide (e.g., a human FGFR4 polypeptide).

As used herein, a "CDR3 that consists essentially of the amino acid sequence set forth in SEQ ID NO:65" is a CDR3 that has zero, one, or two amino acid substitutions within SEQ ID NO:65, that has zero, one, two, three, four, or five amino acid residues directly preceding SEQ ID NO:65, and/or that has zero, one, two, three, four, or five amino acid residues directly following SEQ ID NO:65, provided that the binder (e.g., an antibody, antigen binding fragment, antibody domain, a CAR, a cell engager, and/or an ADC) maintains its basic ability to bind to an FGFR4 polypeptide (e.g., a human FGFR4 polypeptide).

As indicated herein, the amino acid sequences described herein can include amino acid modifications (e.g., the articulated number of amino acid modifications). Such amino acid modifications can include, without limitation, amino acid substitutions, amino acid deletions, amino acid additions, and combinations. In some cases, an amino acid modification can be made to improve the binding and/or contact with an antigen and/or to improve a functional activity of a binder (e.g., an antibody, antigen binding fragment, antibody domain, a CAR, a cell engager, and/or an ADC) provided herein. In some cases, an amino acid substitution within an articulated sequence identifier can be a conservative amino acid substitution. For example, conservative amino acid substitutions can be made by substituting one amino acid residue for another amino acid residue having a similar side chain. Families of amino acid residues having similar side chains can include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine).

In some cases, an amino acid substitution within an articulated sequence identifier can be a non-conservative amino acid substitution. Non-conservative amino acid substitutions can be made by substituting one amino acid residue for another amino acid residue having a dissimilar side chain. Examples of non-conservative substitutions include, without limitation, substituting (a) a hydrophilic residue (e.g., serine or threonine) for a hydrophobic residue (e.g., leucine, isoleucine, phenylalanine, valine, or alanine); (b) a cysteine or proline for any other residue; (c) a residue having a basic side chain (e.g., lysine, arginine, or histidine) for a residue having an acidic side chain (e.g., aspartic acid or glutamic acid); and (d) a residue having a bulky side chain (e.g., phenylalanine) for glycine or other residue having a small side chain.

Methods for generating an amino acid sequence variant (e.g., an amino acid sequence that includes one or more modifications with respect to an articulated sequence identifier) can include site-specific mutagenesis or random mutagenesis (e.g., by PCR) of a nucleic acid encoding the antibody or fragment thereof. See, for example, Zoller, *Curr. Opin. Biotechnol.* 3: 348-354 (1992). Both naturally occurring and non-naturally occurring amino acids (e.g., artificially-derivatized amino acids) can be used to generate an amino acid sequence variant provided herein.

When designing a single chain antibody (e.g., a scFv) having a heavy chain variable domain and a light chain variable domain, the two regions can be directly connected or can be connected using any appropriate linker sequence. For example, a heavy chain variable domain having the CDRs of TABLE 4 can be directly connected to a light chain variable domain via a linker sequence. Examples of linker sequences that can be used to connect a heavy chain variable domain and a light chain variable domain to create a scFv include, without limitation, those linkers set forth in FIG. 9 or FIG. 10.

The binders (e.g., antibodies, antigen binding fragments, antibody domains, CARs, cell engagers, and/or ADCs) provided herein can be produced using any appropriate method. For example, the binders (e.g., antibodies, antigen binding fragments, antibody domains, CARs, and/or cell engagers) provided herein can be produced in recombinant host cells. For example, a nucleic acid encoding a binder (e.g., an antibody, antigen binding fragment, antibody domain, CAR, and/or cell engager) provided herein can be constructed, introduced into an expression vector, and expressed in suitable host cells. TABLE 6 includes examples of nucleic acid sequences that encode exemplary binders (e.g., antibody domains) described herein. In some cases, a binder (e.g., an antibody, antigen binding fragment, antibody domain, CAR, and/or cell engager) provided herein can be recombinantly produced in prokaryotic hosts such as *E. coli, Bacillus brews, Bacillus subtilis, Bacillus megateriurn, Lactobacillus zeae/casei*, or *Lactobacillus paracasei*. A binder (e.g., an antibody, antigen binding fragment, antibody domain, CAR, and/or cell engager) provided herein also can be recombinantly produced in eukaryotic hosts such as yeast (e.g., *Pichia pastoris. Saccharomyces cerevisiae, Hansenula polymorpha, Schizosaccharomyces pombe, Schwanniomyces occidentalis, Kluyveromyces lactis*, or *Yarrowia lipolytica*), filamentous fungi of the genera *Trichoderma* (e.g., *T. reesei*) and *Aspergillus* (e.g., *A. niger* and *A. oryzae*), protozoa such as *Leishmania tarentolae*, insect cells, or mammalian cells (e.g., mammalian cell lines such as Chinese hamster ovary (CHO) cells, Per.C6 cells, mouse myeloma NS0 cells, baby hamster kidney (BHK) cells, or human embryonic kidney cell line HEK293). See, for example, the Frenzel et al. reference (*Front Immunol.,* 4:217 (2013)).

In some cases, an antigen binding fragment or antibody domain provided herein can be produced by proteolytic digestion of an intact antibody. For example, an antigen binding fragment can be obtained by treating an antibody with an enzyme such as papain or pepsin. Papain digestion of whole antibodies can be used to produce $F(ab)_2$ or Fab fragments, while pepsin digestion of whole antibodies can be used to produce $F(ab')_2$ or Fab' fragments.

In some cases, a binder (e.g., an antibody, antigen binding fragment, antibody domain, CAR, cell engager, and/or ADC) provided herein can be substantially pure. The term "substantially pure" as used herein with reference to a binder (e.g., an antibody, antigen binding fragment, antibody domain, CAR, cell engager, and/or ADC) refers to the binder (e.g., an antibody, antigen binding fragment, antibody domain, CAR, cell engager, and/or ADC) as being substantially free of other polypeptides, lipids, carbohydrates, and nucleic acid with which it is naturally associated. Thus, a substantially pure binder (e.g., an antibody, antigen binding fragment, antibody domain, CAR, cell engager, and/or ADC) provided herein is any binder (e.g., an antibody, antigen binding fragment, antibody domain, CAR, cell engager, and/or ADC) that is removed from its natural environment and is at least 60% pure. A substantially pure binder (e.g., an antibody, antigen binding fragment, antibody domain, CAR, cell engager, and/or ADC) provided herein can be at least about 65, 70, 75, 80, 85, 90, 95, or 99% pure.

This document also provides bispecific binders (e.g., bispecific antibodies, bispecific antigen binding fragments, and/or bispecific antibody domains) that bind to two different epitopes with at least one being an epitope of an FGFR4 polypeptide (e.g., a human FGFR4 polypeptide). In some cases, a bispecific binder provided herein can be designed to bind to two different epitopes of the same FGFR4 polypeptide (e.g., a human FGFR4 polypeptide). In some cases, a bispecific binder provided herein can bind to an FGFR4 polypeptide (e.g., a human FGFR4 polypeptide) and to an epitope on a different polypeptide (e.g., a CD3 polypeptide). Bispecific binders can be produced by chemically conjugating two different binders (e.g., antibodies, antigen binding fragments, and/or antibody domains) together. Bispecific binders also can be produced by fusing two antibody-producing cells, e.g., hybridomas, to make a hybrid cell line that produces two different heavy and two different light chains within the same cell, which can result in, for example, bispecific IgG molecules. See, Brinkmann and Kontermann, *MAbs.,* 9(2):182-212 (2017).

In some cases, a binder (e.g., an antibody, antigen binding fragment, antibody domain, CAR, and/or cell engager) provided herein can be fused or conjugated (e.g., covalently or non-covalently attached) to another polypeptide or other moiety to provide a fusion protein or conjugate. For example, a binder (e.g., an antibody, antigen binding fragment, antibody domain, CAR, and/or cell engager) provided herein can be conjugated (e.g., covalently or non-covalently attached) to a polymer (e.g., polyethylene glycol (PEG), polyethylenimine (PEI) modified with PEG (PEI-PEG), and/or polyglutamic acid (PGA) (N-(2-Hydroxypropyl) methacrylamide (HPMA) copolymers), hyaluronic acid, a fluorescent substance, a luminescent substance, a hapten, an enzyme, a metal chelate, a drug, a radioisotope, and/or a cytotoxic agent. Any appropriate method can be used to conjugate (e.g., covalently or non-covalently attach) another polypeptide or other moiety to a binder (e.g., an antibody, antigen binding fragment, antibody domain, CAR, and/or cell engager) provided herein. For example, another polypeptide or other moiety can be conjugated to a binder (e.g., an antibody, antigen binding fragment, antibody domain, CAR, and/or cell engager) provided herein using the methods described in U.S. Pat. No. 8,021,661.

In some cases, a binder (e.g., an antibody, antigen binding fragment, antibody domain, CAR, cell engager, and/or ADC) provided herein can be modified with a moiety that improves its stabilization and/or retention in circulation, for example, in blood, serum, or other tissues by, for example, at least 1.5-, 2-, 5-, 10-, or 50-fold. For example, a binder (e.g., an antibody, antigen binding fragment, antibody domain, CAR, cell engager, and/or ADC) provided herein can be attached (e.g., covalently or non-covalently attached) to a polymer such as a substantially non-antigenic polymer. Examples of substantially non-antigenic polymers that can be used as described herein include, without limitation, polyalkylene oxides and polyethylene oxides. In some cases, a polymer used herein can have any appropriate molecule weight. For example, a polymer having an average molecular weight from about 200 Daltons to about 35,000 Daltons (e.g., from about 1,000 to about 15,000 Daltons or from about 2,000 to about 12,500 Daltons) can be used. In some cases, a binder (e.g., an antibody, antigen binding fragment, antibody domain, CAR, cell engager, and/or ADC) provided herein can be attached (e.g., covalently or non-covalently) to a water-soluble polymer. Examples of water-soluble polymers that can be used as described herein include, without limitation, hydrophilic polyvinyl polymers, polyvinylalcohol, polyvinylpyrrolidone, polyalkylene oxide homopolymers, polyethylene glycol (PEG), polypropylene glycols, polyoxyethylenated polyols, and copolymers thereof and/or block copolymers thereof provided that the water solubility of the copolymer or block copolymers is maintained.

In some cases, a binder (e.g., an antibody, antigen binding fragment, antibody domain, CAR, cell engager, and/or ADC) provided herein can be attached (e.g., covalently or non-covalently attached) to one or more polyoxyalkylenes (e.g., polyoxyethylene, polyoxypropylene, or block copolymers of polyoxyethylene and polyoxypropylene), polymethacrylates, carbomers, branched or unbranched polysaccharides, or combinations thereof. For example, a binder (e.g., an antibody, antigen binding fragment, antibody domain, CAR, cell engager, and/or ADC) provided herein can be covalently attached to polyoxyethylene.

This document also provides ADCs. The term "ADC" as used herein refers to a conjugate that includes (a) an antigen binding domain and (b) at least one drug covalently linked directly or indirectly to that antigen binding domain. In some cases, an ADC described herein can include (a) an antigen binding domain having the ability to bind to an FGFR4 polypeptide (e.g., a human FGFR4 polypeptide) and (b) at least one drug covalently linked directly or indirectly to that antigen binding domain. Any appropriate binder (e.g., an antibody, antigen binding fragment, and/or antibody domain) provided herein and having the ability to bind to an FGFR4 polypeptide (e.g., a human FGFR4 polypeptide) can be used as an antigen binding domain to make an ADC described herein. For example, any of the binders set forth in TABLE 3 can be used to make an ADC having the ability to bind to an FGFR4 polypeptide (e.g., a human FGFR4 polypeptide). Examples of drugs that can be used to make an ADC described herein include, without limitation, auristatins (e.g., monomethyl auristatin E (MMAE)), mertansine (DM-1), and pyrrolobenzodiazepine (PBD) dimers. Any appropriate ADC linker can be used to covalently attach one or more drugs to an antigen binding domain having the ability to bind to an FGFR4 polypeptide (e.g., a human FGFR4 polypeptide) to form an ADC provided herein. For example, cleavable or non-cleavable ADC linkers can be used to covalently attach one or more drugs to an antigen binding domain having the ability to bind to an FGFR4 polypeptide (e.g., a human FGFR4 polypeptide) to form an ADC provided herein. Examples of ADC linkers can be used to covalently attach one or more drugs to an antigen binding domain having the ability to bind to an FGFR4 polypeptide (e.g., a human FGFR4 polypeptide) to form an ADC provided herein include, without limitation, ADC disulfide linkers, ADC hydrazone linkers, ADC peptide linkers, ADC thioether linkers, and ADC PEG-containing linkers.

This document also provides nucleic acid molecules (e.g., isolated nucleic acid molecules) having a nucleic acid sequence encoding at least part of a binder (e.g., an antibody, antigen binding fragment, antibody domain, CAR, and/or cell engager) provided herein. For example, an isolated nucleic acid molecule provided herein can include a nucleic acid sequence encoding a VH domain set forth in TABLE 3. A nucleic acid provided herein (e.g., an isolated nucleic acid molecule) can be single stranded or double stranded nucleic acid of any appropriate type (e.g., DNA, RNA, or DNA/RNA hybrids).

This document also provides vectors (e.g., plasmid vectors or viral vectors) containing one or more nucleic acids provided herein. An example of a plasmid vector that can be designed to include one or more nucleic acids having a nucleic acid sequence encoding at least part of a binder (e.g., an antibody, antigen binding fragment, antibody domain, CAR, and/or cell engager) provided herein includes, without limitation, phagemids. Examples of viral vectors that can be designed to include one or more nucleic acids having a nucleic acid sequence encoding at least part of a binder (e.g., an antibody, antigen binding fragment, antibody domain, CAR, and/or cell engager) provided herein include, without limitation, retroviral vectors, parvovirus-based vectors (e.g., adenoviral-based vectors and adeno-associated virus (AAV)-based vectors), lentiviral vectors (e.g., herpes simplex (HSV)-based vectors), poxviral vectors (e.g., vaccinia virus-based vectors and fowlpox virus-based vectors), and hybrid or chimeric viral vectors. For example, a viral vector having an adenoviral backbone with lentiviral components such as those described elsewhere (Zheng et al., *Nat. Biotech.,* 18(2): 176-80 (2000); WO 98/22143; WO 98/46778; and WO 00/17376) or viral vectors having an adenoviral backbone with AAV components such as those described elsewhere (Fisher et al., *Hum. Gene Ther.,* 7:2079-2087 (1996)) can be designed to include one or more nucleic acids having a nucleic acid sequence encoding at least part of a binder (e.g., an antibody, antigen binding fragment, antibody domain, CAR, and/or cell engager) provided herein.

In some cases, a vector (e.g., a plasmid vector or a viral vector) provided herein can include a nucleic acid sequence encoding scFv or antibody domain (e.g., a VH domain) provided herein. In some cases, a vector (e.g., a plasmid vector or a viral vector) provided herein can include a nucleic acid sequence encoding CAR provided herein. In some cases, a vector (e.g., a plasmid vector or a viral vector) provided herein can include a nucleic acid sequence encoding cell engager provided herein.

A vector provided herein (e.g., a plasmid vector or viral vector provided herein) can include any appropriate promoter and other regulatory sequence (e.g., transcription and translation initiation and termination codons) operably linked the nucleic acid sequence encoding at least part of a binder (e.g., an antibody, antigen binding fragment, antibody domain, CAR, and/or cell engager) provided herein. In some cases, a promoter used to drive expression can be a constitutive promotor or a regulatable promotor. Examples of regulatable promoters that can be used as described herein include, without limitation, inducible promotors, repressible promotors, and tissue-specific promoters. Examples of viral promotors that can be used as described herein include, without limitation, adenoviral promotors, vaccinia virus promotors, CMV promotors (e.g., immediate early CMV promotors) and AAV promoters.

Any appropriate method can be used to make a nucleic acid molecule (or vector such as a plasmid vector or viral vector) having a nucleic acid sequence encoding at least part of a binder (e.g., an antibody, antigen binding fragment, antibody domain, CAR, and/or cell engager) provided herein. For example, molecule cloning techniques can be used to make a nucleic acid molecule (or vector such as a plasmid vector or viral vector) having a nucleic acid sequence encoding at least part of a binder (e.g., an antibody, antigen binding fragment, antibody domain, CAR, and/or cell engager) provided herein as described elsewhere (see, e.g., Sambrook et al., Molecular Cloning: A Laboratory Manual, 2nd edition, Cold Spring Harbor Laboratory, N Y (1989); and Ausubel et al., Current Protocols in Molecular Biology, Green Publishing Associates and John Wiley & Sons, New York, N.Y. (1994)).

This document also provides host cells that include a nucleic acid provided herein (e.g., a nucleic acid having a nucleic acid sequence encoding at least part of a binder (e.g., an antibody, antigen binding fragment, antibody domain, CAR, and/or cell engager) provided herein). Host cells that can be designed to include one or more nucleic acids provided herein can be prokaryotic cells or eukaryotic cells. Examples of prokaryotic cells that can be designed to include a nucleic acid provided herein include, without limitation, *E. coli*(e.g., Tb-1, TG-1, DH5α, XL-Blue MRF (Stratagene), SA2821, or Y1090 cells), *Bacillus subtilis, Salmonella typhimurium, Serratia marcescens*, or *Pseudomonas* (e.g., *P. aeruginosa*) cells. Examples of eukaryotic cells that can be designed to include a nucleic acid provided herein include, without limitation, insect cells (e.g., Sf9 or Ea4 cells), yeast cells (e.g., *S. cerevisiae* cells), and mammalian cells (e.g., mouse, rat, hamster, monkey, or human cells). For example, VERO cells, HeLa cells, 3T3 cells, chinese hamster ovary (CHO) cells, W138 BHK cells, COS-7 cells, and MDCK cells can be designed to include a nucleic acid provided herein. Any appropriate method can be used to introduce one or more nucleic acids provided herein (e.g., a vector such as a plasmid vector or viral vector having a nucleic acid sequence encoding at least part of a binder provided herein) into a host cell. For example, calcium chloride-mediated transformation, transduction, conjugation, triparental mating, DEAE, dextran-mediated transfection, infection, membrane fusion with liposomes, high velocity bombardment with DNA-coated microprojectiles, direct microinjection into single cells, electroporation, or combinations thereof can be used to introduce a nucleic acid provided herein into a host cell (see, e.g., Sambrook et al., Molecular Biology: A Laboratory Manual, Cold Spring Harbor Laboratory, N Y (1989); Davis et al., Basic Methods in Molecular Biology (1986); and Neumann et al., *EMBO J.,* 1:841 (1982)).

In some cases, cells such as T cells, stem cells (e.g., induced pluripotent stem cells or mesenchymal stem cells), or NK cells can be designed to express one or more nucleic acids encoding a CAR described herein. For example, a population of T cells can be infected with viral vectors designed to express nucleic acid encoding a CAR described herein (e.g., a CAR having the ability to bind to an FGFR4 polypeptide).

In some cases, cells such as T cells, stem cells (e.g., induced pluripotent stem cells or mesenchymal stem cells), or NK cells can be designed to express one or more nucleic acids encoding a cell engager described herein. For example, a population of T cells can be infected with viral vectors designed to express nucleic acid encoding a cell engager described herein (e.g., a cell engager having the ability to bind to an FGFR4 polypeptide).

In some cases, a binder (e.g., an antibody, antigen binding fragment, antibody domain, CAR, and/or cell engager) provided herein can be produced using a method that includes (a) introducing nucleic acid encoding the polypeptide into a host cell; (b) culturing the host cell in culture medium under conditions sufficient to express the polypeptide; (c) harvesting the polypeptide from the cell or culture medium; and (d) purifying the polypeptide (e.g., to reach at least 50, 60, 70, 80, 90, 95, 97, 98, or 99% purity).

In some cases, a binder (e.g., an antibody, antigen binding fragment, antibody domain, cell engager, and/or ADC) provided herein, a nucleic acid provided herein (e.g., nucleic acid encoding an antibody, antigen binding fragment, antibody domain, CAR, and/or cell engager provided herein), a vector provided herein (e.g., a viral vector designed to express an antibody, antigen binding fragment, antibody domain, CAR, and/or cell engager provided herein), and/or a host cell provided herein (e.g., a host cell designed to express an antibody, antigen binding fragment, antibody domain, CAR, and/or cell engager provided herein) can be formulated as a pharmaceutical composition for administration to a mammal (e.g. a human) having a cancer including but not limited to rhabdomyosarcomas, as a therapy for that mammal. In some cases, a binder (e.g., an antibody, antigen binding fragment, antibody domain, cell engager, and/or ADC) provided herein, a nucleic acid provided herein (e.g., nucleic acid encoding an antibody, antigen binding fragment, antibody domain, CAR, and/or cell engager provided herein), a vector provided herein (e.g., a viral vector designed to express an antibody, antigen binding fragment, antibody domain, CAR, and/or cell engager provided herein), and/or a host cell provided herein (e.g., a host cell designed to express an antibody, antigen binding fragment, antibody domain, CAR, and/or cell engager provided herein) can be formulated as a pharmaceutical composition for administration to a mammal (e.g. a human) to reduce the number of cancer cells within the mammal and/or to increase the survival of the mammal suffering from cancer. For example, a binder (e.g., an antibody, antigen binding fragment, antibody domain, cell engager, and/or ADC) provided herein having the ability to bind to an FGFR4 polypeptide (e.g., a human FGFR4 polypeptide) can be formulated as a pharmaceutical composition for administration to a mammal (e.g. a human). In some cases, a pharmaceutical composition provided herein can include a pharmaceutically acceptable carrier such as a buffer, a salt, a surfactant, a sugar, a tonicity modifier, or combinations thereof as, for example, described elsewhere (Gervasi, et al., *Eur. J. Pharmaceutics and Biopharmaceutics,* 131:8-24 (2018)). Examples of pharmaceutically acceptable carriers that can be used to make a pharmaceutical composition provided herein include, without limitation, water, lactic acid, citric acid, sodium chloride, sodium citrate, sodium succinate, sodium phosphate, a surfactant (e.g., polysorbate 20, polysorbate 80, or poloxamer 188), dextran 40, a sugar (e.g., sorbitol, mannitol, sucrose, dextrose, or trehalose), or combinations thereof. For example, a pharmaceutical composition designed to include a binder (e.g., an antibody, antigen binding fragment, antibody domain, CAR, cell engager, and/or ADC) provided herein (or a nucleic acid, a vector, or a host cell provided herein) can be formulated to include a buffer (e.g., an acetate, citrate, histidine, succinate, phosphate, or hydroxymethylaminomethane (Tris) buffer), a surfactant (e.g., polysorbate 20, polysorbate 80, or poloxamer 188), and a sugar such as sucrose. Other ingredients that can be included within a pharmaceutical composition provided herein include, without limitation, amino acids such as glycine or arginine, antioxidants such as ascorbic acid, methionine, or ethylenediaminetetraacetic acid (EDTA), anticancer agents such as enzalutamide, imatinib, gefitinib, erlotinib, sunitinib, lapatinib, nilotinib, sorafenib, temsirolimus, everolimus, pazopanib, crizotinib, ruxolitinib, axitinib, bosutinib, cabozantinib, ponatinib, regorafenib, ibrutinib, trametinib, perifosine, bortezomib, carfilzomib, batimastat, ganetespib, obatoclax, navitoclax, taxol, paclitaxel, or bevacizumab, or combinations thereof. For example, a pharmaceutical composition provided herein can be formulated to include one or more binders (e.g., one or more antibodies, one or more antigen binding fragments, one or more antibody domains, one or more cells designed to express a CAR having the ability to bind to an FGFR4 polypeptide, one or more cell engagers, and/or one or more ADCs) provided herein in combination with one or more checkpoint inhibitors such as anti-PD-1 antibodies or PD-1 inhibitors (e.g., cemiplimab, nivolumab, pembrolizumab, JTX-4014, spartalizumab, camrelizumab, sintilimab, tislelizumab, toripalimab, dostarlimab, INCMGA00012, AMP-224, or AMP-514), anti-PD-L1 antibodies or PD-L1 inhibitors (e.g., avelumab, durvalumab, atezolizumab, KN035, CK-301, AUNP12, CA-170, or BMS-986189), and/or anti-CTLA-4 antibodies (e.g., ipilimumab).

In some cases, when a pharmaceutical composition is formulated to include one or more binders (e.g., one or more antibodies, one or more antigen binding fragments, one or more antibody domains, one or more cells designed to express a CAR having the ability to bind to an FGFR4 polypeptide, one or more cell engagers, and/or one or more ADCs) provided herein, any appropriate concentration of the binder can be used. For example, a pharmaceutical composition provided herein can be formulated to be a liquid that includes from about 1 mg to about 500 mg (e.g., from about 1 mg to about 500 mg, from about 10 mg to about 500 mg, from about 50 mg to about 500 mg, from about 100 mg to about 500 mg, from about 0.5 mg to about 250 mg, from about 0.5 mg to about 150 mg, from about 0.5 mg to about 100 mg, from about 0.5 mg to about 50 mg, from about 1 mg to about 300 mg, from about 2 mg to about 200 mg, from about 10 mg to about 300 mg, from about 25 mg to about 300 mg, from about 50 mg to about 150 mg, or from about 150 mg to about 300 mg) of a binder (e.g., an antibody, antigen binding fragment, antibody domain, $CAR^+$ cell population, cell engager, and/or ADC) provided herein per mL. In another example, a pharmaceutical composition provided herein can be formulated to be a solid or semi-solid that includes from about 0.5 mg to about 500 mg (e.g., from about 1 mg to about 500 mg, from about 10 mg to about 500 mg, from about 50 mg to about 500 mg, from about 100 mg to about 500 mg, from about 0.5 mg to about 250 mg, from about 0.5 mg to about 150 mg, from about 0.5 mg to about 100 mg, from about 0.5 mg to about 50 mg, from about 1 mg to about 300 mg, from about 10 mg to about 300 mg, from about 25 mg to about 300 mg, from about 50 mg to about 150 mg, or from about 150 mg to about 300 mg) of a binder (e.g., an antibody, antigen binding fragment, antibody domain, cell engager, and/or ADC) provided herein. In some cases, a pharmaceutical composition containing a binder (e.g., an antibody, antigen binding fragment, and/or antibody domain) provided herein can be formulated as a dosage form with a titer of the binder being from about $1\times10^5$ to about $1\times10^{12}$ (e.g., from about $1\times10^5$ to about $1\times10^{10}$, from about $1\times10^5$ to about $1\times10^8$, from about $1\times10^6$ to about $1\times10^{12}$, from about $1\times10^6$ to about $1\times10^{12}$, from about $1\times10^8$ to about $1\times10^{12}$, from about $1\times10^9$ to about $1\times10^{12}$, from about $1\times10^6$ to about $1\times10^{11}$, or from about $1\times10^7$ to about $1\times10^{10}$).

In some cases, when a pharmaceutical composition is formulated to include one or more nucleic acids (e.g., vectors such as viral vectors) encoding at least part of a binder (e.g., an antibody, antigen binding fragment, antibody domain, CAR, and/or cell engager) provided herein, any appropriate concentration of the nucleic acid can be used. For example, a pharmaceutical composition provided herein can be formulated to be a liquid that includes from about 0.5 mg to about 500 mg (e.g., from about 1 mg to about 500 mg, from about 10 mg to about 500 mg, from about 50 mg to about 500 mg, from about 100 mg to about 500 mg, from about 0.5 mg to about 250 mg, from about 0.5 mg to about 150 mg, from about 0.5 mg to about 100 mg, from about 0.5 mg to about 50 mg, from about 1 mg to about 300 mg, from about 2 mg to about 200 mg, from about 10 mg to about 300 mg, from about 25 mg to about 300 mg, from about 50 mg to about 150 mg, or from about 150 mg to about 300 mg) of a nucleic acid provided herein per mL. In another example, a pharmaceutical composition provided herein can be formulated to be a solid or semi-solid that includes from about 0.5 mg to about 500 mg (e.g., from about 1 mg to about 500 mg, from about 10 mg to about 500 mg, from about 50 mg to about 500 mg, from about 100 mg to about 500 mg, from about 0.5 mg to about 250 mg, from about 0.5 mg to about 150 mg, from about 0.5 mg to about 100 mg, from about 0.5 mg to about 50 mg, from about 1 mg to about 300 mg, from about 10 mg to about 300 mg, from about 25 mg to about 300 mg, from about 50 mg to about 150 mg, or from about 150 mg to about 300 mg) of a nucleic acid provided herein.

In some cases, a pharmaceutical composition designed to include a binder (e.g., an antibody, antigen binding fragment, antibody domain, cell engager, and/or ADC) provided herein can be formulated to include one or more agents capable of reducing aggregation of the binder when formulated. Examples of such agents that can be used as described herein include, without limitation, methionine, arginine, lysine, aspartic acid, glycine, or glutamic acid, and combinations thereof. In some cases, one or more of these amino acids can be included within the formulation at a concentration from about 0.5 mM to about 145 mM (e.g., from about 1 mM to about 145 mM, from about 10 mM to about 145 mM, from about 100 mM to about 145 mM, from about 0.5 mM to about 125 mM, from about 0.5 mM to about 100 mM, from about 0.5 mM to about 75 mM, or from about 10 mM to about 100 mM).

A pharmaceutical composition provided herein can be in any appropriate form. For example, a pharmaceutical composition provided herein can designed to be a liquid, a semi-solid, or a solid. In some cases, a pharmaceutical composition provided herein can be a liquid solution (e.g., an injectable and/or infusible solution), a dispersion, a suspension, a tablet, a pill, a powder, a microemulsion, a liposome, or a suppository. In some cases, a pharmaceutical composition provided herein can be lyophilized. In some cases, a pharmaceutical composition provided herein (e.g., a pharmaceutical composition that includes one or more binders (e.g., one or more antibodies, one or more antigen binding fragments, one or more antibody domains, one or more cell engagers, and/or one or more ADCs) provided herein can be formulated with a carrier or coating designed to protect against rapid release. For example, a pharmaceutical composition provided herein can be formulated as a controlled release formulation or as a regulated release formulation as described elsewhere (U.S. Patent Application Publication Nos. 2019/0241667; 2019/0233522; and 2019/0233498, all of which are expressly incorporated by reference in their entireties).

This document also provides methods for administering a composition (e.g., a pharmaceutical composition provided herein) containing one or more binders (e.g., one or more antibodies, one or more antigen binding fragments, one or more antibody domains, one or more cell engagers, and/or one or more ADCs) provided herein (or a nucleic acid, vector, or host cell (e.g., $CAR^+$ cells) provided herein) to a mammal (e.g., a human). For example, a composition (e.g., a pharmaceutical composition provided herein) containing one or more binders (e.g., one or more antibodies, one or more antigen binding fragments, one or more antibody domains, one or more cell engagers, and/or one or more ADCs) provided herein (or a nucleic acid, vector, and/or host cell (e.g., CAR cells) provided herein) can be administered to a mammal (e.g., a human) having cancer including but not limited to rhabdomyosarcomas, as a therapy for that mammal. In some cases, a composition (e.g., a pharmaceutical composition provided herein) containing one or more binders (e.g., one or more antibodies, one or more antigen binding fragments, one or more antibody domains, one or more cell engagers, and/or one or more ADCs) provided herein (or a nucleic acid, vector, and/or host cell (e.g., $CAR^+$ cells) provided herein) can be administered to a mammal (e.g. a human) to reduce the number of cancer cells within the mammal and/or to increase the survival of the mammal suffering from a cancer, including but not limited to rhabdomyosarcomas.

Any appropriate cancer can be treated or inhibited using a composition (e.g., a pharmaceutical composition provided herein) containing one or more binders (e.g., one or more antibodies, one or more antigen binding fragments, one or more antibody domains, one or more cell engagers, and/or one or more ADCs) provided herein (or a nucleic acid, vector, or host cell (e.g., $CAR^+$ cells) provided herein). For example, a mammal (e.g., a human) having cancer, including but not limited to rhabdomyosarcomas, can be treated or inhibited by administering a composition (e.g., a pharmaceutical composition) containing one or more binders (e.g., one or more antibodies, one or more antigen binding fragments, one or more antibody domains, one or more cell engagers, and/or one or more ADCs) provided herein to that mammal. Examples of cancers that can be treated or inhibited as described herein include, without limitation, Ewing's sarcoma, acute myeloid leukemia (AML), liver cancer, colorectal cancer, brain cancer, skin cancer (e.g., melanoma), lung cancer, prostate cancer, breast cancer (e.g., PR positive breast cancer, ER positive breast cancer, HER2 positive breast cancer, or triple negative breast cancer), ovarian cancer, cervical cancer, esophageal cancer, glioma, kidney cancer, mesothelioma, and pancreatic cancer. In some cases, a solid cancer such as liver cancer, colorectal cancer, brain cancer, skin cancer (e.g., melanoma), lung cancer, prostate cancer, breast cancer (e.g., PR positive breast cancer, ER positive breast cancer, HER2 positive breast cancer, or triple negative breast cancer), ovarian cancer, cervical cancer, esophageal cancer, glioma, kidney cancer, mesothelioma, or pancreatic cancer can be treated as described herein. In some cases, cancer such as lymphoma (e.g., B cell lymphomas such as diffuse large cell lymphoma (DLBCL)), leukemia (e.g., chronic lymphocytic leukemia (CLL) and acute lymphoblastic leukemia (ALL)), or acute myeloid leukemia can be treated as described herein. In some cases, a mammal (e.g., a human) having an FGFR4 cancer (e.g., an $FGFR4^+$ Ewing's sarcoma, an $FGFR4^+$ AML, an $FGFR4^+$ liver cancer, $FGFR4^+$ colorectal cancer, $FGFR4^+$ brain cancer, $FGFR4^+$ skin cancer (e.g., $FGFR4^+$ melanoma), $FGFR4^+$ lung cancer, $FGFR4^+$ prostate cancer, $FGFR4^+$ breast cancer (e.g., $FGFR4^+$ PR positive breast cancer, FGFR4 ER positive breast cancer, $FGFR4^+$ HER2 positive breast cancer, or $FGFR4^+$ triple negative breast cancer), $FGFR4^+$ ovarian cancer, $FGFR4^+$ cervical cancer, $FGFR4^+$ esophageal cancer, $FGFR4^+$ glioma, $FGFR4^+$ kidney cancer, $FGFR4^+$ mesothelioma, or $FGFR4^+$ pancreatic cancer) can be administered a composition (e.g., a pharmaceutical composition) containing one or more binders (e.g., one or more antibodies, one or more antigen binding fragments, one or more antibody domains, one or more cell engagers, and/or one or more ADCs) provided herein to treat that mammal or inhibit the cancer (e.g., to reduce the number of cancer cells within the mammal).

Any appropriate method can be used to administer a composition (e.g., a pharmaceutical composition) provided herein to a mammal (e.g., a human). For example, a composition provided herein (e.g., a pharmaceutical composition containing one or more binders provided herein such as one or more antibodies, one or more antigen binding fragments, one or more antibody domains, one or more cell engagers, and/or one or more ADCs provided herein) can be administered to a mammal (e.g., a human) intravenously (e.g., via an intravenous injection or infusion), subcutaneously (e.g., via a subcutaneous injection), intraperitoneally (e.g., via an intraperitoneal injection), orally, via inhalation, or intramuscularly (e.g., via intramuscular injection). In some cases, the route and/or mode of administration of a composition (e.g., a pharmaceutical composition provided herein) can be adjusted for the mammal being treated.

In some cases, an effective amount of a composition containing one or more binders (e.g., one or more antibodies, one or more antigen binding fragments, one or more antibody domains, one or more cell engagers, and/or one or more ADCs) provided herein (or a nucleic acid, vector, or host cell (e.g., $CAR^+$ cells) provided herein) (e.g., a pharmaceutical composition provided herein) can be an amount that reduces the number of cancer cells within a mammal having cancer without producing significant toxicity to the mammal. In some cases, an effective amount of a composition containing one or more binders (e.g., one or more antibodies, one or more antigen binding fragments, one or more antibody domains, one or more cell engagers, and/or one or more ADCs) provided herein (or a nucleic acid, vector, or host cell (e.g., $CAR^+$ cells) provided herein) (e.g., a pharmaceutical composition provided herein) can be an amount that increases the survival time of a mammal having cancer as compared to a control mammal having comparable cancer and not treated with the composition. For example, an effective amount of a binder (e.g., an antibody, antigen binding fragment, antibody domain, cell engager, and/or ADC) provided herein can be from about 0.001 mg/kg to about 100 mg/kg (e.g., from about 0.001 mg/kg to about 90 mg/kg, from about 0.001 mg/kg to about 80 mg/kg, from about 0.001 mg/kg to about 70 mg/kg, from about 0.001 mg/kg to about 60 mg/kg, from about 0.001 mg/kg to about 50 mg/kg, from about 0.001 mg/kg to about 40 mg/kg, from about 0.001 mg/kg to about 30 mg/kg, from about 0.005 mg/kg to about 100 mg/kg, from about 0.01 mg/kg to about 100 mg/kg, from about 0.05 mg/kg to about 100 mg/kg, from about 0.1 mg/kg to about 100 mg/kg, from about 0.5 mg/kg to about 100 mg/kg, from about 1 mg/kg to about 100 mg/kg, from about 5 mg/kg to about 100 mg/kg, from about 0.01 mg/kg to about 25 mg/kg, from about 0.1 mg/kg to about 30 mg/kg, from about 0.15 mg/kg to about 25 mg/kg, from about 0.2 mg/kg to about 20 mg/kg, from about 0.5 mg/kg to about 20 mg/kg, from about 1 mg/kg to about 30 mg/kg, from about 1 mg/kg to about 25 mg/kg, from about 1 mg/kg to about 20 mg/kg, from about 2 mg/kg to about 20 mg/kg, from about 5 mg/kg to about 30 mg/kg, from about 10 mg/kg to about 30 mg/kg, from about 15 mg/kg to about 30 mg/kg, from about 20 mg/kg to about 30 mg/kg, from about 3 mg/kg to about 30 mg/kg, from about 0.5 mg/kg to about 10 mg/kg, from about 1 mg/kg to about 10 mg/kg, from about 1 mg/kg to about 5 mg/kg, or from about 1 mg/kg to about 3 mg/kg). The effective amount can remain constant or can be adjusted as a sliding scale or variable dose depending on the mammal's response to treatment. Various factors can influence the actual effective amount used for a particular application. For example, the severity of cancer when treating a mammal having cancer, the route of administration, the age and general health condition of the mammal, excipient usage, the possibility of co-usage with other therapeutic or prophylactic treatments such as use of other agents (e.g., checkpoint inhibitors), and the judgment of the treating physician may require an increase or decrease in the actual effective amount of a composition provided herein (e.g., a pharmaceutical composition containing one or more binders provided herein) that is administered.

In some cases, an effective frequency of administration of a composition containing one or more binders (e.g., one or more antibodies, one or more antigen binding fragments, one or more antibody domains, one or more cell engagers, and/or one or more ADCs) provided herein (or a nucleic acid, vector, or host cell (e.g., $CAR^+$ cells) provided herein) (e.g., a pharmaceutical composition provided herein) can be a frequency that reduces the number of cancer cells within a mammal having cancer without producing significant toxicity to the mammal. In some cases, an effective frequency of administration of a composition containing one or more binders (e.g., one or more antibodies, one or more antigen binding fragments, one or more antibody domains, one or more cell engagers, and/or one or more ADCs) provided herein (or a nucleic acid, vector, or host cell (e.g., $CAR^+$ cells) provided herein) (e.g., a pharmaceutical composition provided herein) can be a frequency that increases the survival time of a mammal having a cancer, including but not limited to rhabdomyosarcomas, as compared to a control mammal having a comparable cancer and not administered the composition. For example, an effective frequency of administration of a pharmaceutical composition provided herein such as a pharmaceutical composition containing one or more binders provided herein can be from about twice daily to about once a year (e.g., from about twice daily to about once a month, from about twice daily to about once a week, from about once daily to about once a month, or from one once daily to about once a week). In some cases, the frequency of administration of a pharmaceutical composition provided herein such as a pharmaceutical composition containing one or more binders provided herein can be daily. The frequency of administration of a pharmaceutical composition provided herein such as a pharmaceutical composition containing one or more binders provided herein can remain constant or can be variable during the duration of treatment. Various factors can influence the actual effective frequency used for a particular application. For example, the severity of the cancer, the route of administration, the age and general health condition of the mammal, excipient usage, the possibility of co-usage with other therapeutic or prophylactic treatments such as use of other agents (e.g., checkpoint inhibitors), and the judgment of the treating physician may require an increase or decrease in the actual effective frequency of administration of a composition provided herein (e.g., a pharmaceutical composition containing one or more binders provided herein).

In some cases, an effective duration of administration of a composition containing one or more binders (e.g., one or more antibodies, one or more antigen binding fragments, one or more antibody domains, one or more cell engagers, and/or one or more ADCs) provided herein (or a nucleic acid, vector, or host cell (e.g., $CAR^+$ cells) provided herein) (e.g., a pharmaceutical composition provided herein) can be a duration that reduces the number of cancer cells within a mammal without producing significant toxicity to the mammal. In some cases, an effective duration of administration of a composition containing one or more binders (e.g., one or more antibodies, one or more antigen binding fragments, one or more antibody domains, one or more cell engagers, and/or one or more ADCs) provided herein (or a nucleic acid, vector, or host cell (e.g., $CAR^+$ cells) provided herein) (e.g., a pharmaceutical composition provided herein) can be a duration that increases the survival time of a mammal having cancer as compared to a control mammal having comparable cancer and not treated with the composition. For example, an effective duration of administration of a pharmaceutical composition provided herein such as a pharmaceutical composition containing one or more binders provided herein can vary from a single time point of administration to several weeks to several months (e.g., 4 to 12 weeks). Multiple factors can influence the actual effective duration used for a particular application. For example, the severity of the cancer, the route of administration, the age and general health condition of the mammal, excipient usage, the possibility of co-usage with other therapeutic or prophylactic treatments such as use of other agents (e.g., checkpoint inhibitors), and the judgment of the treating physician may require an increase or decrease in the actual effective duration of administration of a composition provided herein (e.g., a pharmaceutical composition containing one or more binders provided herein).

In some cases, a binder (e.g., an antibody, antigen binding fragment, and/or antibody domain) provided herein can be used to detect the presence or absence of an FGFR4 polypeptide (e.g., a human FGFR4 polypeptide) in vitro, in situ, or in vivo (e.g., in vivo imaging within a mammal such as a human). For example, a binder (e.g., an antibody, antigen binding fragment, and/or antibody domain) provided herein can be designed to include a label (e.g., a covalently attached radioactive, enzymatic, colorimetric, or fluorescent label). The labelled binder can be used to detect the presence or absence of an FGFR4 polypeptide (e.g., a human FGFR4 polypeptide) within a biological sample in vitro. Examples of biological samples that can be assessed using a binder (e.g., an antibody, antigen binding fragment, and/or antibody domain) provided herein include, without limitation, serum samples, plasma samples, tissue samples, biopsy samples, cell line samples, and tissue culture samples. In some cases, a biological sample that can be assessed as described herein can include mammalian body tissues and/or cells such as leukocytes, ovary tissue or cells, prostate tissue or cells, heart tissue or cells, placenta tissue or cells, pancreas tissue or cells, liver tissue or cells, spleen tissue or cells, lung tissue or cells, breast tissue or cells, head and neck tissue or cells, endometrium tissue or cells, colon tissue or cells, colorectal tissue or cells, cervix tissue or cells, stomach tissue or cells, or umbilical tissue or cells that may express an FGFR4 polypeptide (e.g., a human FGFR4 polypeptide). In some cases, a binder (e.g., an antibody, antigen binding fragment, and/or antibody domain) provided herein can be immobilized, e.g., on a support, and retention of an FGFR4 polypeptide (e.g., a human FGFR4 polypeptide) from a biological sample on the support can be detected, and/or vice versa. In some cases, a binder (e.g., an antibody, antigen binding fragment, and/or antibody domain) provided herein can be used in applications such as fluorescence polarization, microscopy, ELISA, centrifugation, chromatography, and/or cell sorting (e.g., fluorescence activated cell sorting).

antibody, antigen binding fragment, and/or antibody domain) provided herein that is labelled (e.g., covalently labelled) with a radiolabel or an MRI detectable label can be administered to a mammal (e.g., a human), and that mammal can be assessed by detecting the detectable label. In some cases, a mammal can be scanned to evaluate the location(s) of a labelled binder provided herein within the mammal. For example, the mammal can be imaged using NMR or other tomographic techniques.

Examples of labels that can be attached (e.g., covalently or non-covalently attached) to a binder (e.g., an antibody, antigen binding fragment, and/or antibody domain) provided herein include, without limitation, radiolabels such as $^{131}I$, $^{111}In$, $^{123}I$, $^{99m}Tc$, $^{32}P$, $^{33}P$, $^{125}I$, $^{3}H$, $^{14}C$, or $^{188}Rh$, fluorescent labels such as fluorescein and rhodamine, nuclear magnetic resonance active labels, positron emitting isotopes detectable by a positron emission tomography ("PET") scanner, chemiluminescers such as luciferin, or enzymatic markers such as a peroxidase or a phosphatase. In some cases, short-range radiation emitters such as isotopes detectable by short-range detector probes can be used.

Some embodiments of the methods and compositions provided herein include chimeric antigen receptors (CARs), which specifically bind to fibroblast growth factor receptor 4 (FGFR4). Some embodiments include nucleic acids encoding such CARs, and cells containing such CARs. Some embodiments include the use of such CARs therapies for a cancer, such as an FGFR4-expressing cancer, such as a rhabdomyosarcoma.

Genomics can be used to design CARs for CAR T-cell immunotherapy (Orentas R J, et al., 2012, Front Oncol 2:194). Affymetrix-based expression analysis of ARMS and ERMS patient samples, comparing tumor to normal gene expression demonstrated that even though a number of transcripts were shared between disease types, fusion positive (ARMS) samples alone identified FGFR4 as a favorable target. TABLE 1 lists transcripts overexpressed in ARMS in comparison to normal tissue and shows the top 12 transcripts ranked by difference from averaged normal tissue by T statistic. The broad distribution of MCAM/CD146 and the potential toxicity of targeting CHRNA1 makes FGFR4 a target.

TABLE 1

| Rank | Gene ID | T value | P value | |
|---|---|---|---|---|
| 1 | CD146/MCAM* | 27.68 | 2.8 × 10E−20 | Melanoma cell adhesion molecule (MUC18) |
| 2 | CHRNA1* | 24.21 | 7.2 × 10E−19 | Cholinergic R, nicotinic, alpha 1 subunit (muscle) |
| 3 | CD334/FGFR4* | 19.67 | 1.0 × 10E−16 | Fibroblast growth factor receptor 4 |
| 4 | MEGF10* | 19.19 | 1.8 × 10E−16 | Multiple EGF-like-domains 10 |
| 5 | ACVR2A* | 14.78 | 7.3 × 10E−14 | Activin A receptor, type IIA |
| 6 | KCNN3 | 14.00 | 2.5 × 10E−13 | K+, Ca-activ. channel subfam N, 3 |
| 7 | CDH15/MCAD | 13.85 | 3.1 × 10E−13 | Cadherin 15, M-cadherin (myotubule) |
| 8 | SEMA6B* | 12.15 | 5.5 × 10E−12 | Semaphorin 6B |
| 9 | GPC2* | 11.89 | 8.7 × 10E−12 | Glypican 2 (cerebroglycan) |
| 10 | CD271/NGFR | 11.43 | 2.0 × 10E−11 | NGFR, nerve growth factor receptor |
| 11 | CACNA1I | 11.30 | 2.6 × 10E−11 | Ca channel, voltage-dep., alpha1 subunit |
| 12 | MET | 11.07 | 4.0 × 10E−11 | Met proto-oncogene |

*Transcripts shared by both ARMS and ERMS.
FGFR4 is the highest ranked target that can be safely approached in ARMS, and is not expressed in ERMS.

In some cases, a binder (e.g., an antibody, antigen binding fragment, and/or antibody domain) provided herein containing a label (e.g., a covalently attached radioactive label) can be used to detect the presence or absence of an FGFR4 polypeptide (e.g., a human FGFR4 polypeptide) within a mammal (e.g., a human). For example, a binder (e.g., an Studies have shown a role of FGFR4 in RMS tumor biology demonstrating that FGFR4 expression is associated with advanced stage RMS and poor survival, and that FGFR4 knockdown in a human RMS cell line led to decreased pathogenicity in a mouse model of disease (Taylor J G el al., 2009, J Clin Invest 119-3395-3407). A mutated tyrosine kinase receptor in RMS has been identified. In 7 of 94 primary RMS tumors, FGFR4 tyrosine kinase mutations were identified, which served to increase autophosphorylation, Stat3 signaling, tumor proliferation, and metastatic potential. The function of FGFR4 as an oncogenic driver has been documented, for example, a mouse model expressing the common FGFR4$^{V550E}$ mutation was used to demonstrate that the dual PI3K/mTOR inhibitor omipalisib was able to impact tumor progression by blocking these down-stream FGFR4 signals (McKinnon T, et al., 2018, Oncogene 37:2630-2644). Other studies have shown that FGFR4 overexpression leads to resistance to chemotherapy and the induction of an anti-apoptotic state (Roidl A., et al., 2009, Clin Cancer Res 15:2058-2066).

GD2-specific CARs were developed for the treatment of pediatric solid tumors (Long A H, et al., 2016, Cancer Immunol Res 4:869-880). In looking at GD2 expression, all osteosarcomas (n=18), 13% of RMS (ARMS, n=14, ERMS, n=1), and 20% of Ewing sarcomas (n-=35), were positive. The ability of a GD2-CAR to control tumor xenografts in vivo was tested. Although GD2-CARs, especially in the 4-1BB-zeta chain format, were effective against a Kelly neuroblastoma cell line in vivo in NSG mice, GD2-CARs were ineffective against the 143b osteosarcoma cell line. Despite this ineffectiveness, and low incidence on RMS, these studies established that the GD2-CAR self-associated on the T cell surface leading to target cell-independent metabolic exhaustion, and that this was partially rescued by the inclusion of a CD137/4-1BB signaling domain in the CAR construct (Long A H, et al., 2015, Nat Med 21:581-590). This optimized 4-1BBz CAR was still poorly effective, unless mice were also treated with all-trans retinoic acid (ATRA). ATRA inhibited the accumulation of monocytic myeloid derived suppressor cells (mMDSCs) in the tumor lesion and diminished their inhibitory effect on T cell proliferation.

The cell surface protein FGFR4 is expressed during development, however expression on normal tissue is low to non-existent in mature tissues. Nevertheless, FGFR4 is highly overexpressed in certain human tumors, including rhabdomyosarcoma. Disclosed herein are a series of binding moieties identified through screening methods and used to generate polynucleotides encoding CARs.

Certain embodiments of the methods and compositions provided herein can include aspects disclosed in Lang L, et al., 2019, Cells 8:3.1; Chen C, et al., 2005, Hybridoma, 24(3):152-159; U.S. Pat. Nos. 9,266,955; 8,394,927; 10,358,498; and 11,078,286, which are each expressly incorporated by reference in its entirety.

Certain Definitions

Unless defined otherwise, all technical and scientific terms used herein have the same meaning as commonly understood by one of ordinary skill in the art to which the invention pertains.

As used herein, "a" or "an" may mean one or more than one.

"About" as used herein when referring to a measurable value is meant to encompass variations of ±20% or ±10%, more preferably ±5%, even more preferably ±1%, and still more preferably ±0.1% from the specified value.

As used herein, "nucleic acid" or "nucleic acid molecule" have their plain and ordinary meaning in view of the whole specification and may to refer to, for example, polynucleotides, such as deoxyribonucleic acid (DNA) or ribonucleic acid (RNA), oligonucleotides, fragments generated by the polymerase chain reaction (PCR), or fragments generated by any of ligation, scission, endonuclease action, or exonuclease action. Nucleic acid molecules can be composed of monomers that are naturally occurring nucleotides (such as DNA or RNA), or analogs of naturally occurring nucleotides (e.g., enantiomeric forms of naturally occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, or azido groups, or sugars can be functionalized as ethers or esters. Moreover, the entire sugar moiety can be replaced with sterically and electronically similar structures, such as aza-sugars or carbocyclic sugar analogs. Examples of modifications in a base moiety include alkylated purines or pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, or phosphoramidate, and the like. The term "nucleic acid molecule" also includes so-called "peptide nucleic acids," which comprise naturally occurring or modified nucleic acid bases attached to a polyamide backbone. Nucleic acids can be either single stranded or double stranded. In some embodiments, a nucleic acid sequence encoding a fusion protein is provided. In some embodiments, the nucleic acid encoding the chimeric antigen receptor specific for FGFR4.

As used herein, "coding for" or "encoding" has its plain and ordinary meaning when read in light of the specification, and includes, for example, the property of specific sequences of nucleotides in a polynucleotide, such as a gene, a cDNA, or an mRNA, to serve as templates for synthesis of other macromolecules such as a defined sequence of amino acids. Thus, a gene codes for a protein if transcription and translation of mRNA corresponding to that gene produces the protein in a cell or other biological system.

As used herein, "chimeric antigen receptor" has its plain and ordinary meaning when read in light of the specification, and may include but is not limited to, for example, a synthetically designed receptor comprising a ligand binding domain of an antibody or other protein sequence that binds to a molecule associated with a disease or disorder and is, preferably, linked via a spacer domain to one or more intracellular signaling domains of a cell, such as a T cell, or other receptors, such as one or more costimulatory domains. Chimeric receptor can also be referred to as artificial cell receptors or T cell receptors, chimeric cell receptors or T cell receptors, chimeric immunoreceptors, or CARs. These receptors can be used to graft the specificity of a monoclonal antibody or binding fragment thereof onto a cell, preferably a T-cell, with transfer of their coding sequence facilitated by viral vectors, such as a retroviral vector or a lentiviral vector. CARs can be, in some instances, genetically engineered T cell receptors designed to redirect T cells to target cells that express specific cell-surface antigens. T cells can be removed from a subject and modified so that they can express receptors that can be specific for an antigen by a process called adoptive cell transfer. The T cells are reintroduced into the patient where they can then recognize and target an antigen. CARs are also engineered receptors that can graft an arbitrary specificity onto an immune receptor cell. CARs are considered by some investigators to include the antibody or antibody fragment, preferably an antigen binding fragment of an antibody, the spacer, signaling domain, and transmembrane region. Due to the surprising effects of modifying the different components or domains of the CAR described herein, such as the epitope binding region (for example, antibody fragment, scFv, or portion thereof), spacer, transmembrane domain, and/or signaling domain), the components of the CAR are frequently distinguished throughout this disclosure in terms of independent elements. The variation of the different elements of the CAR can, for example, lead to stronger binding affinity for a specific epitope or antigen.

The CARs graft the specificity of a monoclonal antibody or binding fragment thereof or scFv onto a T cell, with the transfer of their coding sequence facilitated by vectors. In order to use CARs as a therapy for a subject in need, a technique called adoptive cell transfer is used in which T cells are removed from a subject and modified so that they can express the CARs that are specific for an antigen. The T cells, which can then recognize and target an antigen, are reintroduced into the patient.

As used herein, an "antibody" has its plain and ordinary meaning when read in light of the specification, and includes, for example, a large Y-shape protein produced by plasma cells that is used by the immune system to identify and neutralize foreign objects such as bacteria and viruses. The antibody protein can comprise four polypeptide chains, two identical heavy chains and two identical light chains connected by disulfide bonds. Each chain is composed of structural domains called immunoglobulin domains. These domains can contain about 70, 80, 90, 100, 110, 120, 130, 140, or 150 amino acids or any number of amino acids in between in a range defined by any two of these values and are classified into different categories according to their size and function. In some embodiments, the ligand binding domain comprises a CDR, an antibody or binding fragment thereof or scFv, a receptor ligand or mutants thereof, peptide, and/or polypeptide affinity molecule or binding partner. In some embodiments, the ligand binding domain is an antibody fragment, desirably, a binding portion thereof. In some embodiments, the antibody fragment or binding portion thereof present on a CAR is specific for a ligand on a B-cell. In some embodiments, the antibody fragment or binding portion thereof present on a CAR or TcR is specific for a ligand. In some embodiments, the antibody fragment or binding portion thereof present on a CAR is specific for FGFR4. In some embodiments, the ligand binding domain is an antibody fragment or a binding portion thereof, such as a VH domain, or a single chain variable fragment (scFv) containing VH and VL domains. In some embodiments, the antibody fragment or binding portion thereof present on a CAR comprises one or more domains from a humanized antibody, or binding portion thereof.

As used herein, "complementarity-determining regions" or "CDR" includes certain portions of the variable region in an antibody or antigen binding fragment thereof, which forms the binding and specificity of various specific antibodies to their particular antigen. Variability is not uniformly distributed throughout an antibody variable region, and may be focused concentrated in three segments called complementarity-determining regions (CDRs) or hypervariable regions in the variable regions of the light and heavy chain. The more conserved part of the variable region is called the framework region (FR). The variable regions of the natural heavy and light chains each contain four FR regions, which are substantially in a β-folded configuration, joined by three CDRs which form a linking loop, and in some cases can form a partially s-folded structure. The CDRs in each chain are closely adjacent to the others by the FR regions and form an antigen-binding site of the antibody with the CDRs of the other chain. The constant regions are not directly involved in the binding of the antibody to the antigen, but they exhibit different effects or functions, for example, involving in antibody-dependent cytotoxicity of the antibodies. In some embodiments, a CDR can be found within antibody region as numbered by Kabat as follows: for the light chain, CDR1 at amino acids 24-34; CDR2 at amino acids 50-56; CDR3 at amino acids 89-97; for the heavy chain, CDR1 at amino acids 31-35; CDR2 at amino acids 50-65; and CDR3 at amino acids 95-102. CDR regions in antibodies and antigen fragments thereof, such as scFVs, can be readily determined.

As used herein, a "single chain variable fragment" or "scFv" has its plain and ordinary meaning when read in light of the specification, and includes, for example, a fusion protein of the variable regions of the heavy (VH) and light chains (VL) of immunoglobulins, connected with a short linker peptide of ten to 25 amino acids or about 25 amino acids. In some embodiments, a CAR is provided, wherein the CAR comprises a ScFv or a VH domain specific for FGFR4.

The strength of binding of a ligand is referred to as the binding affinity and can be determined by direct interactions and solvent effects. A ligand can be bound by a "ligand binding domain." A ligand binding domain, for example, can refer to a conserved sequence in a structure that can bind a specific ligand or a specific epitope on a protein. The ligand binding domain or ligand binding portion can comprise an antibody or binding fragment thereof or scFv, a VH domain, a receptor ligand or mutants thereof, peptide, and/or polypeptide affinity molecule or binding partner. Without being limiting, a ligand binding domain can be a specific protein domain or an epitope on a protein that is specific for a ligand or ligands.

Some embodiments include a spacer. In some embodiments, the peptide spacer is 15 amino acids or less but not less than 1 or 2 amino acids. In some embodiments, the spacer is a polypeptide chain. In some aspects, the polypeptide chain may range in length, such as from 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239 or 240 amino acids or a length within a range defined by any two of the aforementioned lengths. A spacer can comprise any 20 amino acids, for example, in any order to create a desirable length of polypeptide chain in a CAR, which includes the amino acids arginine, histidine, lysine, aspartic acid, glutamic acid, serine, threonine, asparagine, glutamine, cysteine, glycine, proline, alanine, valine, isoleucine, methionine, phenylalanine, tyrosine or tryptophan. A spacer sequence can be a linker between the ligand binding domain and the transmembrane domain of the CAR. In some embodiments, the chimeric antigen receptor further comprises a sequence encoding a spacer. In some embodiments, the spacer comprises a sequence with a length of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239 or 240 amino acids or a length within a range defined by any two of the aforementioned lengths. In some embodiments, the spacer resides between the ligand binding domain and the transmembrane region of the CAR. In some embodiments, the spacer resides between the ligand binding domain of the CAR and the transmembrane region of the CAR.

A spacer may also be customized, selected, or optimized for a desired length so as to improve or modulate binding of the ligand binding domain to the target cell, which may increase cytotoxic efficacy. In some embodiments, the linker or spacer between the ligand binding domain and the transmembrane can be 25 to 55 amino acids in length (e.g., at least, equal to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 amino acids or a length within a range defined by any two of the aforementioned lengths).

In some embodiments, the spacer comprises a CD8 hinge. In some embodiments, the spacer comprises a hinge region of a human antibody. In some embodiments, the spacer comprises an IgG4 hinge. In some embodiments, the IgG4 hinge region is a modified IgG4 hinge. A "modified IgG4 hinge" as described herein can refer to a hinge region that can have at least 90%/6, 91%, 92%, 93%, 94% 95%, 96%, 97%, 98%, 99%/6, or 100% sequence identity or a sequence identity within a range defined by any two of the aforementioned percentages, with a hinge region amino acid sequence as set forth in a spacer, such as a spacer listed in TABLE 5. In some embodiments, the CAR comprises an S spacer, M spacer or an L spacer. Example sequences are listed in TABLE 5.

As used herein, a "de-immunized spacer" has its plain and ordinary meaning when read in light of the specification, and includes, for example, a spacer that induces little to no immune response or a diminished or reduced immune response from a patient. In some embodiments, the CAR comprises a spacer, wherein the spacer does not induce an immune response in a subject, such as a human. It is important that the spacer does not induce an immune response or induces a reduced or diminished or low immune response in a subject, such as a human, in order to prevent or reduce the ability of the immune system to attack the chimeric antigen receptor.

In some embodiments, the transmembrane domain is a region of a membrane-spanning protein that is hydrophobic that can reside in the bilayer of a cell to anchor a protein that is embedded to the biological membrane. Without being limiting, the topology of the transmembrane domain can be a transmembrane alpha helix. In some embodiments, a CAR comprises a sequence encoding a transmembrane domain. In some embodiments, the transmembrane domain comprises a CD8 transmembrane sequence or a fragment thereof or a CD28 transmembrane sequence or a fragment thereof that is a length of 10, 11, 12, 13, 14, 15, 16, 17, 18, 19, 20, 21, 22, 23, 24, 25, 26, 27, or 28 amino acids or a length within a range defined by any two of the aforementioned lengths. In some embodiments, the CD8 transmembrane sequence or a fragment thereof or the CD28 transmembrane sequence or fragment thereof comprises 28 amino acids in length.

In some embodiments, the signaling domains, such as primary signaling domains or costimulatory domains, include an intracellular or cytoplasmic domain of a protein or a receptor protein that interacts with components within the interior of the cells and is capable of or configured to relay or participate in the relaying of a signal. Such interactions in some aspects can occur through the intracellular domain communicating via specific protein-protein or protein-ligand interactions with an effector molecule or an effector protein, which in turn can send the signal along a signal chain to its destination. In some embodiments, the signaling domain includes one or more co-stimulatory domains. In some embodiments, the one or more costimulatory domains include a signaling moiety that provides a T-cell with a signal, which, in addition to the primary signal provided by for instance the CD3 zeta chain of the TCR/CD3 complex, enhances a response such as a T-cell effector response, such as, for example, an immune response, activation, proliferation, differentiation, cytokine secretion, cytolytic activity, perforin or granzyme activity or any combination thereof. In some embodiments, the intracellular signaling domain or the co-stimulatory domain can include all or a portion of CD27, CD28, 4-1BB, OX40, CD30, CD40, ICOS, lymphocyte function-associated antigen-1 (LFA-1), CD2, CD7, LIGHT, NKG2C, or B7-H3, or a ligand that specifically binds with CD83 or any combination thereof.

As used herein, a "ribosome skip sequence" has its plain and ordinary meaning when read in light of the specification, and includes, for example, a sequence that during translation, forces the ribosome to "skip" the ribosome skip sequence and translate the region after the ribosome skip sequence without formation of a peptide bond. Several viruses, for example, have ribosome skip sequences that allow sequential translation of several proteins on a single nucleic acid without having the proteins linked via a peptide bond. As described herein, this is the "linker" sequence. In some embodiments of the nucleic acids provided herein, the nucleic acids comprise a ribosome skip sequence between the sequence for the chimeric antigen receptor and the sequence of the marker protein, such that the proteins are co-expressed and not linked by a peptide bond. In some embodiments, the ribosome skip sequence is a P2A, T2A, E2A or F2A sequence.

As used herein, a "marker sequence," has its plain and ordinary meaning when read in light of the specification, and includes, for example, a protein that is used for selecting or tracking a protein or cell that has a protein of interest. In the embodiments described herein, the fusion protein provided can comprise a marker sequence that can be selected in experiments, such as flow cytometry. In some embodiments, the marker is a truncated EGFR polypeptide (EGFRt), or a truncated HER2 polypeptide (HER2t).

As used herein, "signal sequence" for secretion, can also be referred to as a "signal peptide." The signal peptide can be used for secretion efficiency and in some systems it is recognized by a signal recognition particle, which halts translation and directs the signal sequence to a SRP receptor for secretion. In some embodiments of the CARs provided herein, the CARs further comprise a signal sequence. In some embodiments, of the nucleic acid encoding a CAR, the nucleic acid comprises a sequence encoding a signal sequence. In some embodiments, the signal sequence is for targeting a protein to a cell membrane following translation of the protein.

As used herein, "vector" or "construct" has its plain and ordinary meaning when read in light of the specification, and includes, for example, a nucleic acid used to introduce heterologous nucleic acids into a cell that has regulatory elements to provide expression of the heterologous nucleic acids in the cell. Vectors include but are not limited to plasmid, minicircles, yeast, viral genomes, lentiviral vector, foamy viral vector, retroviral vector or gammaretroviral vector. The vector may be DNA or RNA, such as mRNA.

As used herein, "T-cells" or "T lymphocytes" can be from any mammal, preferably a primate, including monkeys or humans, a companion animal such as a dog, cat, or horse, or a domestic animal, such as a sheep, goat, or cattle. In some embodiments the T-cells are allogeneic (from the same species but different donor) as the recipient subject; in some embodiments the T-cells are autologous (the donor and the recipient are the same); in some embodiments the T-cells are syngeneic (the donor and the recipients are different but are identical twins).

As used herein, "T cell precursors" refer to lymphoid precursor cells that can migrate to the thymus and become T cell precursors, which do not express a T cell receptor. All T cells originate from hematopoietic stem cells in the bone marrow. Hematopoietic progenitors (lymphoid progenitor cells) from hematopoietic stem cells populate the thymus and expand by cell division to generate a large population of immature thymocytes. The earliest thymocytes express neither CD4 nor CD8 and are therefore classed as double-negative (CD4-CD8−) cells. As they progress through their development, they become double-positive thymocytes (CD4+ CD8+), and finally mature to single-positive (CD4+ CD8− or CD4-CD8+) thymocytes that are then released from the thymus to peripheral tissues.

As used herein, "hematopoietic stem cells" or "HSC" are precursor cells that can give rise to myeloid cells such as, for example, macrophages, monocytes, macrophages, neutrophils, basophils, eosinophils, erythrocytes, megakaryocytes/platelets, dendritic cells and/or lymphoid lineages (such as, for example, T-cells, B-cells, or NK-cells). HSCs have a heterogeneous population in which three classes of stem cells exist, which are distinguished by their ratio of lymphoid to myeloid progeny in the blood (L/M).

As used herein, "CD4+ expressing T-cell," or "CD4+ T-cell," are used synonymously throughout, is also known as T helper cells, which play an important role in the immune system, and in the adaptive immune system. CD4+ T-cells also help the activity of other immune cells by releasing T-cell cytokines. These cells help, suppress or regulate immune responses. They are essential in B cell antibody class switching, in the activation and growth of cytotoxic T-cells, and in maximizing bactericidal activity of phagocytes, such as macrophages. CD4+ expressing T-cells have the ability to make some cytokines, however the amounts of cytokines made by CD4+ T-cells are not at a concentration that promotes, improves, contributes to, or induces engraftment fitness. As described herein, "CD4+ T-cells" are mature T helper-cells that play a role in the adaptive immune system.

As used herein, "CD8+ expressing T-cell" or "CD8+ T-cell," are used synonymously throughout, is also known as a TC, cytotoxic T lymphocyte, CTL, T-killer cell, cytolytic T-cell or killer T-cell. As described herein, CD8+ T-cells are T-lymphocytes that can kill cancer cells, virally infected cells, or damaged cells. CD8+ T-cells express T-cell receptors (TCRs) that can recognize a specific antigen. CD8+ T-cells express CD8 on the surface. CD8+ expressing T-cells have the ability to make some cytokines, however the amounts of cytokines made by CD8+ T-cells are not at a concentration that promotes, improves, contributes to, or induces engraftment fitness. "CD8 T-cells" or "killer T-cells" are T-lymphocytes that can kill cancer cells, cells that are infected with viruses or cells that are damaged.

Mature T cells express the surface protein CD4 and are referred to as CD4+ T-cells. CD4+ T-cells are generally treated as having a pre-defined role as helper T-cells within the immune system. For example, when an antigen-presenting cell expresses an antigen on MHC class II, a CD4+ cell will aid those cells through a combination of cell to cell interactions (e.g. CD40 and CD40L) and through cytokines. Nevertheless, there are rare exceptions; for example, subgroups of regulatory T-cells, natural killer cells, and cytotoxic T-cells express CD4. All of the latter CD4+ expressing T-cell groups are not considered T helper cells.

As used herein, "central memory" T-cell (or "TCM") refers to an antigen experienced CTL that expresses CD62L or CCR-7 and CD45RO on the surface thereof, and does not express or has decreased expression of CD45RA, as compared to naïve cells. In some embodiments, central memory cells are positive for expression of CD62L, CCR7, CD28, CD127, CD45RO, and/or CD95, and have decreased expression of CD54RA, as compared to naïve cells.

As used herein, "effector memory" T-cell (or "TEM") refers to an antigen experienced T-cell that does not express or has decreased expression of CD62L on the surface thereof as compared to central memory cells, and does not express or has decreased expression of CD45RA as compared to naïve cell. In some embodiments, effector memory cells are negative for expression of CD62L and/or CCR7, as compared to naïve cells or central memory cells, and have variable expression of CD28 and/or CD45RA.

As used herein, "naïve" T-cells refers to a non-antigen experienced T lymphocyte that expresses CD62L and/or CD45RA, and/or does not express CD45RO− as compared to central or effector memory cells. In some embodiments, naïve CD8+ T lymphocytes are characterized by the expression of phenotypic markers of naïve T-cells including CD62L, CCR7, CD28, CD127, or CD45RA.

As used herein, "effector" "TE" T-cells refers to a antigen experienced cytotoxic T lymphocyte cells that do not express or have decreased expression of CD62L, CCR7, CD28, and are positive for granzyme B or perforin or both, as compared to central memory or naïve T-cells.

As used herein, "cytokines" has its plain and ordinary meaning when read in light of the specification, and includes, for example, small proteins (5-25 kDa) that are important in cell signaling. Cytokines are released by cells and affect the behavior of other cells, and sometimes the releasing cell itself, such as a T-cell. Cytokines can include, for example, chemokines, interferons, interleukins, lymphokines, or tumor necrosis factor or any combination thereof. Cytokines can be produced by a broad range of cells, which can include, for example, immune cells like macrophages, B lymphocytes, T lymphocytes, mast cells, as well as, endothelial cells, fibroblasts, or various stromal cells.

Cytokines can act through receptors and are important in the immune system as the cytokines can modulate the balance between humoral and cell-based immune responses, and they can regulate the maturation, growth, and responsiveness of particular cell populations. Some cytokines enhance or inhibit the action of other cytokines in complex ways. Without being limiting, cytokines can include, for example, Acylation stimulating protein, Adipokine, Albinterferon, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL5, CCL6, CCL7, CCL8, CCL9, Chemokine, Colony-stimulating factor, CX3CL1, CX3CR1, CXCL1, CXCL10, CXCL11, CXCL13, CXCL14, CXCL15, CXCL16, CXCL17, CXCL2, CXCL3, CXCL5, CXCL6, CXCL7, CXCL9, Erythropoietin, Gc-MAF, Granulocyte colony-stimulating factor, Granulocyte macrophage colony-stimulating factor, Hepatocyte growth factor, IL 10 family of cytokines, IL 17 family of cytokines, IL1A, IL1B, Inflammasome, Interferome, Interferon, Interferon beta 1a, Interferon beta 1b, Interferon gamma, Interferon type I, Interferon type II, Interferon type III, Interleukin, Interleukin 1 family, Interleukin 1 receptor antagonist, Interleukin 10, Interleukin 12, Interleukin 12 subunit beta, Interleukin 13, Interleukin 15, Interleukin 16, Interleukin 2, Interleukin 23, Interleukin 23 subunit alpha, Interleukin 34, Interleukin 35, Interleukin 6, Interleukin 7, Interleukin 8, Interleukin 36, Leukemia inhibitory factor, Leukocyte-promoting factor, Lymphokine, Lymphotoxin, Lymphotoxin alpha, Lymphotoxin beta, Macrophage colony-stimulating factor, Macrophage inflammatory protein, Macrophage-activating factor, Monokine, Myokine, Myonectin, Nicotinamide phosphoribosyltransferase, Oncostatin M, Oprelvekin, Platelet factor 4, Proinflammatory cytokine, Promegapoietin, RANKL, Stromal cell-derived factor 1, Talimogene laherparepvec, Tumor necrosis factor alpha, Tumor necrosis factors, XCL1, XCL2, GM-CSF, or XCR1 or any combination thereof. In some embodiments of the methods of making genetically modified T-cells, a transduced population of CD8+ expressing T-cells and/or CD4+ expressing T-cells is contacted with at least one cytokine so as to generate a transduced, cytokine-stimulated population of CD8+ T-cells and/or CD4+ T-cells. In some embodiments, the at least one cytokine utilized comprises GM-CSF, IL-7, IL-12, IL-15, IL-18, IL-2 or IL-21 or any combination thereof. In some embodiments, the period of contact with the cytokine is at least one day, such as for at least 1, 2, 3, 4, 5, 6, 7, 8, 9, 10, 11, 12, 13, 14, 15, 16, 17, 18, 19, or 20 days or any time that is within a range of times defined by any two of the aforementioned time points.

As used herein, "interleukins" or IL are cytokines that the immune system depends largely upon. Examples of interleukins, which can be utilized herein, for example, include IL-1, IL-2, IL-3, IL-4, IL-5, IL-6, IL-7, IL-8/CXCL8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, or IL-36 or any combination thereof. Contacting T-cells with interleukins can have effects that promote, support, induce, or improve engraftment fitness of the cells. IL-1, for example can function in the maturation & proliferation of T-cells. IL-2, for example, can stimulate growth and differentiation of T-cell response. IL-3, for example, can promote differentiation and proliferation of myeloid progenitor cells. IL-4, for example, can promote proliferation and differentiation. IL-7, for example, can promote differentiation and proliferation of lymphoid progenitor cells, involved in B, T, and NK cell survival, development, and homeostasis. IL-15, for example, can induce production of natural killer cells. IL-21, for example, co-stimulates activation and proliferation of CD8+ T-cells, augments NK cytotoxicity, augments CD40-driven B cell proliferation, differentiation and isotype switching, and/or promotes differentiation of Th17 cells.

As used herein, "propagating cells" or propagation refers to steps to allow proliferation, expansion, growth and reproduction of cells. For example, cultures of CD8+ T-cells and CD4+ T-cells can typically be incubated under conditions that are suitable for the growth and proliferation of T lymphocytes. In some embodiments of the method of making genetically modified T-cells, which have a chimeric antigen receptor, the CD4+ expressing T-cells are propagated for at least 1 day and may be propagated for 20 days, such as 1, 2, 3, 4, 5, 6, 7, 8, 9, 10, 11, 12, 13, 14, 15, 16, 17, 18, 19, or 20 days or for a period that is within a range defined by any two of the aforementioned time periods. In some embodiments of the method of making genetically modified T-cells, which have a chimeric antigen receptor, the CD8+ expressing T-cells are propagated for at least 1 day and may be propagated for 20 days, such as 1, 2, 3, 4, 5, 6, 7, 8, 9, 10, 11, 12, 13, 14, 15, 16, 17, 18, 19, or 20 days or for a period that is within a range defined by any two of the aforementioned time periods.

In another alternative, the expansion method or propagation can further comprise adding anti-CD3 and/or anti CD28 antibody to the culture medium (e.g., at a concentration of at least 0.5 ng/ml). In another alternative, the method of making genetically modified T-cells, which have a chimeric antigen receptor method can further comprise adding IL-2, IL-15, or IL-21 or any combination thereof to the culture medium (e.g., wherein the concentration of IL-2 is at least 10 units/mL). In another alternative, the method of making genetically modified T-cells, which have a chimeric antigen receptor method can further comprise adding IL-7, IL-15, or IL21 or any combination thereof to the culture medium (e.g., wherein the concentration of IL-2 is at least 10 units/mL). After isolation of T lymphocytes, both cytotoxic and helper T lymphocytes can be sorted into naïve, memory, and effector T-cell subpopulations either before or after expansion.

As used herein, "genetically modified immune cells" or "Genetically engineered cells" are made by a process called genetic engineering, which can include but is not limited to manipulating a cell's own genome or inserting a new nucleic acid into a cell. In some embodiments, these cells can be macrophages and can also be referred to as genetically engineered macrophages (GEMs). These techniques can be used to change the genetic makeup of the cell, and can include inserting a vector encoding a gene of interest into a cell, and genome editing using RNAi systems, meganucleases, zinc finger nucleases, transcription activator like effector nucleases (TALENS), or CRISPRs. Without being limiting, the vectors encoding the gene of interest can be a viral vector, DNA or an mRNA. In some embodiments, described herein, genetically modified immune cells are provided. In some embodiments, the genetically modified immune cells are made using genome editing proteins or systems, such as for example, meganucleases, zinc finger nucleases, transcription activator like effector nucleases (TALENS), CRISPR/VP64-Cas9 systems or CRISPR/CAS9 systems.

Some embodiments include polypeptide sequences or conservative variations thereof, such as conservative substitutions in a polypeptide sequence. In some embodiments, "conservative amino acid substitution" refers to amino acid substitutions that substitute functionally-equivalent amino acids. Conservative amino acid changes result in silent changes in the amino acid sequence of the resulting peptide. For example, one or more amino acids of a similar polarity act as functional equivalents and result in a silent alteration within the amino acid sequence of the peptide. Substitutions that are charge neutral and which replace a residue with a smaller residue may also be considered "conservative substitutions" even if the residues are in different groups (e.g., replacement of phenylalanine with the smaller isoleucine). Families of amino acid residues having similar side chains have been defined in the art. Several families of conservative amino acid substitutions are shown in TABLE 2.

TABLE 2

| Family | Amino Acids |
|---|---|
| non-polar | Trp, Phe, Met, Leu, Ile, Val, Ala, Pro |
| uncharged polar | Gly, Ser, Thr, Asn, Gln, Tyr, Cys |
| acidic/negatively charged | Asp, Glu |
| basic/positively charged | Arg, Lys, His |
| Beta-branched | Thr, Val, Ile |
| residues that influence chain orientation | Gly, Pro |
| aromatic | Trp, Tyr, Phe, His |

Certain Nucleic Acids

Some embodiments the methods and compositions provided herein include one or more nucleic acids encoding a CAR capable of specifically binding to a FGFR4 protein, such as an extracellular domain of a FGFR4 protein, such as an IgIII membrane-proximal domain of a FGFR4 protein. In some embodiments, the CAR comprises a ligand binding domain capable of specifically binding to a FGFR4 protein; a transmembrane domain; and an intracellular signalling domain.

In some embodiments, the ligand binding domain comprises a complementarity-determining region (CDR) derived from a binding moiety polypeptide, such as a binding moiety polypeptide capable of specifically binding to a FGFR4 protein, such as an extracellular domain of a FGFR4 protein, such as an IgIII membrane-proximal domain of a FGFR4 protein. In some embodiments, the ligand binding domain comprises an antigen-binding fragment of an antibody, an scFv, or a variable heavy chain (VH) domain and a variable heavy chain (VL) domain. In some embodiments, the VH domain and the VL domain are linked via a linker, such as a triple repeat of the amino acid sequence "GGGGS". In some embodiments, the ligand binding domain comprises a VH-VL domains in which the VH domain precedes the VL domain in the polypeptide. In some embodiments, the ligand binding domain comprises a VL-VH domains in which the VL domain precedes the VH domain in the polypeptide.

In some embodiments, the ligand binding domain comprises, consists essentially of, or consists of a VH domain. In some embodiments, the ligand binding domain lacks a VL domain. In some embodiments, the ligand binding domain can consist essentially of a VH domain and no more than 10 other amino acids. In some embodiments, the ligand binding domain can consist essentially of a VH domain and no more than 5 other amino acids. In some embodiments, the ligand binding domain can consist essentially of a VH domain and no more than 3 other amino acids.

In some embodiments, the ligand binding domain comprises an amino acid sequence having at least or equal to 90%, 91%, 92%, 93%, 94% 95%, 96% 97%, 98%, 99%, or 100% sequence identity to the amino acid sequence of any one of SEQ ID NOs:01-22. In some embodiments, the ligand binding domain comprises an amino acid sequence having at least or equal to 90%, 91%, 92%, 93%, 94% 95%, 96% 97%, 98%, 99%, or 100% sequence identity to the amino acid sequence of any one of SEQ ID NOs:01-04, 06, 07, 11-14, 17, 18 and 20. In some embodiments, the ligand binding domain comprises an amino acid sequence having at least or equal to 90%, 91%, 92%, 93%, 94% 95%, 96% 97%, 98%, 99%, or 100% sequence identity to the amino acid sequence of SEQ ID NO:06. In some embodiments, the ligand binding domain comprises the amino acid sequence of SEQ ID NO:06.

In some embodiments, the ligand binding domain comprises a CDR of a binding moiety polypeptide, such as a binding moiety polypeptide which specifically binds to a FGFR4 protein, such as an extracellular domain of a FGFR4 protein, such as an IgM membrane-proximal domain of a FGFR4 protein. In some embodiments, the ligand binding domain can include a heavy chain CDR. In some embodiments, the ligand binding domain can include two heavy chain CDRs. In some embodiments, the ligand binding domain can include three heavy chain CDRs. In some embodiments, the ligand binding domain can include a light chain CDR. In some embodiments, the ligand binding domain can include two light chain CDRs. In some embodiments, the ligand binding domain can include three light chain CDRs. In some embodiments, the ligand binding domain can include a heavy chain CDR1, a heavy chain CDR2, a heavy chain CDR3, a light chain CDR1, a light chain CDR2, and/or a light chain CDR3, derived from a binding moiety polypeptide which specifically binds to a FGFR4 protein, such as an extracellular domain of a FGFR4 protein, such as an IgIII membrane-proximal domain of a FGFR4 protein. In some embodiments, the ligand binding domain comprises a CDR domain comprising or consisting of a CDR sequence comprising an amino acid sequence having 0-4 conservative amino acid substitutions of an amino acid sequence of any one of SEQ ID NOs:42-149. In some embodiments, the ligand binding domain comprises a CDR domain comprising or consisting of a CDR sequence comprising an amino acid sequence having 0-4 conservative amino acid substitutions of an amino acid sequence of any one of SEQ ID NOs:41-53, 57-62, 78-101, 114-125 and 132-137. In some embodiments, the ligand binding domain comprises a CDR domain comprising or consisting of a CDR sequence comprising an amino acid sequence having 0-4 conservative amino acid substitutions of an amino acid sequence of any one of SEQ ID NOs:57-59.

In some embodiments, the transmembrane domain comprises a domain selected from a CD8 transmembrane domain and a CD28 transmembrane domain. In some embodiments, the transmembrane domain comprises a CD8 transmembrane domain. In some embodiments, the CD8 transmembrane domain comprises an amino acid sequence having at least or equal to 90%, 91%, 92%, 93%, 94% 95%, 96% 97%, 98%, 99%, or 100% sequence identity to the amino acid sequence of SEQ ID NO:24.

In some embodiments, the intracellular signalling domain comprises a costimulatory domain selected from the group consisting of CD27, CD28, 4-1BB, OX-40, CD30, CD40, PD-1, ICOS, LFA-1, CD2, CD7, NKG2C, B7-H3, and CD3-zeta. In some embodiments, the intracellular signalling domain comprises a costimulatory domain selected from the group consisting of CD27, CD28, 4-1BB, OX-40, CD30, CD40, PD-1, ICOS, LFA-1, CD2, CD7, NKG2C, and B7-H3 in combination with a CD3-zeta domain. In some embodiments, the intracellular signalling domain comprises a 4-1BB costimulatory domain in combination with a CD3-zeta domain. In some embodiments, the 4-1BB costimulatory domain comprises an amino acid sequence having at least or equal to 90%, 91%, 92%, 93%, 94% 95%, 96% 97%, 98%, 99%, or 100% sequence identity to the amino acid sequence of SEQ ID NO:29. In some embodiments, the CD3-zeta domain comprises an amino acid sequence having at least or equal to 90%, 91%, 92%, 93%, 94% 95%, 96% 97%, 98%, 99%, or 100% sequence identity to the amino acid sequence of SEQ ID NO:31.

In some embodiments, the CAR comprises an amino acid sequence having at least or equal to 90%, 91%, 92%, 93%, 94% 95%, 96% 97%, 98%, 99%, or 100% sequence identity to the amino acid sequence of a CAR listed in TABLE 5 or TABLE 6. In some embodiments, the CAR comprises an amino acid sequence having at least or equal to 90%, 91%, 92%, 93%, 94% 95%, 96% 97%, 98%, 99%, or 100% sequence identity to the amino acid sequence of SEQ ID NO:41. In some embodiments, the CAR comprises the amino acid sequence of SEQ ID NO:41.

In some embodiments, the CAR also includes a spacer located between the ligand binding domain and the transmembrane domain. In some embodiments, the spacer comprises a short (S), medium (M), or long (L) spacer. Examples of spacers are listed in TABLE 5.

In some embodiments, the nucleic acid also includes a promoter operably linked to the polynucleotide encoding a chimeric antigen receptor. In some embodiments, the promoter comprises a constitutive promoter. In some embodiments, the constitutive promoter comprises an EF1α promoter. In some embodiments, the promoter comprises an inducible promoter.

In some embodiments, the nucleic acid also includes a polynucleotide encoding a cell-surface selectable marker. In some embodiments, the cell-surface selectable marker is selected from a truncated EGFR polypeptide (EGFRt) or a truncated Her2 polypeptide (Her2t). In some embodiments, the nucleic acid also includes a ribosome skip sequence located between a polynucleotide encoding the intracellular signalling domain and the polynucleotide encoding a cell-surface selectable marker. In some embodiments, the ribosome skip sequence is selected from the group consisting of a P2A sequence, a T2A sequence, an E2A sequence, and an F2A sequence.

In some embodiments, the nucleic acid also includes a polynucleotide encoding a suicide gene system. In some embodiments, the suicide gene system is selected from a herpes simplex virus thymidine kinase/ganciclovir (HSVTK/GCV) suicide gene system, or an inducible caspase suicide gene system.

Some embodiments of the methods and compositions provided herein include a vector comprising any one of the nucleic acids provided herein. In some embodiments, the vector is a viral vector. In some embodiments, the vector is a lentiviral vector, foamy viral vector, retroviral vector, an adenoviral vector, or an adenovirus associated viral vector. In some embodiments, the vector is a transposon, integrase vector system, or an mRNA vector.

Certain sequences useful with embodiments provided herein are listed in TABLE 3, TABLE 4, TABLE 5 or TABLE 6. In TABLE 3, CDR sequences within the listed binding polypeptide sequences are underlined. Heavy chain CDRs and light chain CDRs can be readily determined from TABLE 3. For example, sequences of screen 'VH domain only' include heavy chain CDR1, CDR2, and CDR3; a binder 'VLVH' includes a first three light chain CDRs, and a second three heavy chain CDRs; and a binder 'VHVL' includes a first three heavy chain CDRs, and a second three light chain CDRs. TABLE 4 lists CDR sequences from TABLE 3.

TABLE 3

| FGFR4 binding poly-peptide (binder) | Screen | SEQ ID NO: | Sequence |
|---|---|---|---|
| E9 | VH domain only | SEQ ID NO: 01 | EVQLVESGGGLVQPGGSLRLSCTVSGFTFSSYA<br>LGWVRQAPGKGLEWIGYIYHKGDTNYNPSLKS<br>LVTISRDNSKNTLYLQMNSLRAEDTALYYCAK<br>VRWVSSTSTLGFDYWGQGTLVTVSS |
| A4 | VH domain only | SEQ ID NO: 02 | EVQLVESGGGLVQPGGSLRLSCVASGFTFISYA<br>MSWVRQAPGKGLEWMAIIYPDDAGTMYSPSF<br>QGQVTISRDNSKNTLYLQMNSLRAEDTALYYC<br>ARVTMVRGVIGFDPWGQGTLVTVSS |
| E61 | VH domain only | SEQ ID NO: 03 | EVQLVESGGGLVQPGGSLRLSCTFSGFTFSSYA<br>MSWVRQAPGKGLEWMGIIYPGDSNTIYSPSFQ<br>GQVTISRDNSKNTLYLQMNSLRAEDTATYYCA<br>RSGAYDGRIWFDPWGQGTLVTVSS |
| A7 | VH domain only | SEQ ID NO: 04 | EVQLVESGGGLVQPGGSLRLSCAASGFTFSNY<br>GMSWVRQAPGKGLEWIGYIYHTGNTYYNPSL<br>KSRVTISRDNSKNTLYLQMNSLRAEDTAIYYC<br>AREGVMGGYHTDPNYYYYGMDVWGQGTTVT<br>VSS |
| D92 | VH domain only | SEQ ID NO: 05 | EVQLVESGGGLVQPGGSLRLSCVASGFTFSSYG<br>MHWVRQAPGKGLEWIGYSYYSGSTYYNPSLK<br>SLVTISRDNSKNTLYLQMNSLRAEDTATYYCA<br>RDGSSWYSFPYYYGMDVWGQGTTVTVSS |

TABLE 3-continued

| FGFR4 binding poly-peptide (binder) | Screen | SEQ ID NO: | Sequence |
|---|---|---|---|
| D8 | VH domain only | SEQ ID NO: 06 | EVQLVESGGGLVQPGGSLRLSCAASGFTFSNYGMSWVRQAPGKALEWIGEINHSGSTNYNPSLKSRVTISRDNSKNTLYLQMNSLRAEDTAIYYCRGGWVGYWGQGTLVTVSS |
| F11 | VH domain only | SEQ ID NO: 07 | EVQLVESGGGLVQPGGSLRLSCAASGFTFSNYGMSWVRQAPGQGLEWVSYISNGGGTMYYADSVKGRFTISRDNSKNTLYLQMNSLRAEDTATYYCTRAPYCSGGDCYPMSTHELDSWGQGTLVTVSS |
| C52 | VH domain only | SEQ ID NO: 08 | EVQLVESGGGLVQPGGSLRLSCAASGFTLSSYWMSWVRQAPGKGLEWIGVIYYSGATYYNPSLKSLVTISRDNSKNTLYLQMNSLRAEDTAVYYCARGALDYFDLWGQGALVTVSS |
| H4-VLVH | F(ab) screen | SEQ ID NO: 09 | DIQMTQSPSSLSASVGDRVTITCRASQSISSYLNWYQQKPGKAPKLLIYAASSLQSGVPSRFSGSGSGTDFTLTISSLQPEDVGVYYCLQITHWPHTFGQGTKLEIKRGGGGSGGGGSGGGGSQVQLVESGGGLVKPGGSLRLSCAASGFTFSDYYMSWIRQAPGKGLEWVSYISSSGSTIYYADSVKGRFTISRDNAKNSLYLQMNSLRAEDTAMYYCARDAPDLLAVPTVIFSGYHYGADVWGQGATVTVSS |
| H4-VHVL | — | SEQ ID NO: 10 | QVQLVESGGGLVKPGGSLRLSCAASGFTFSDYYMSWIRQAPGKGLEWVSYISSSGSTIYYADSVKGRFTISRDNAKNSLYLQMNSLRAEDTAMYYCARDAPDLLAVPTVIFSGYHYGADVWGQGATVTVSSGGGGSGGGGSGGGGSDIQMTQSPSSLSASVGDRVTITCRASQSISSYLNWYQQKPGKAPKLLIYAASSLQSGVPSRFSGSGSGTDFTLTISSLQPEDVGVYYCLQITHWPHTFGQGTKLEIKR |
| G6-VLVH | F(ab) screen | SEQ ID NO: 11 | DIQMTQSPSSLSASVGDRVTITCRASQSISSYLNWYQQKPGKAPKLLIYAASSLQSGVPSRFSGSGSGTDFTLTISSLQPEDAATYYCQHYGTFGQGTKLEIKRGGGGSGGGGSGGGGSQVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARHKTSLNDYDFWSGYLLDYWGQGTLVTVSS |
| G6-VHVL | — | SEQ ID NO: 12 | QVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARHKTSLNDYDFWSGYLLDYWGQGTLVTVSSGGGGSGGGGSGGGGSDIQMTQSPSSLSASVGDRVTITCRASQSISSYLNWYQQKPGKAPKLLIYAASSLQSGVPSRFSGSGSGTDFTLTISSLQPEDAATYYCQHYGTFGQGTKLEIKR |
| C9-VLVH | F(ab) screen | SEQ ID NO: 13 | DIQMTQSPSSLSASVGDRVTITCRASQSISSYLNWYQQKPGKAPKLLIYAASSLQSGVPSRFSGSGSGTDFTLTISSLQPEDFAVYYCQQRSNWPPTFGQGTKLEIKRGGGGSGGGGSGGGGSQVQLVESGGGLVKPGGSLRLSCAASGFTFSDYYMSWIRQAPGKGLEWVSYISSSGSTIYYADSVKGRFTISRDNAKNSLYLQMNSLRAEDTAKYYCATAVFSLGPEGYYYYMDVWGKGTTVTVSS |
| C9-VHVLH | — | SEQ ID NO: 14 | QVQLVESGGGLVKPGGSLRLSCAASGFTFSDYYMSWIRQAPGKGLEWVSYISSSGSTIYYADSVKGRFTISRDNAKNSLYLQMNSLRAEDTAKYYCATAVFSLGPEGYYYYMDVWGKGTTVTVSSGGGGSGGGGSGGGGSDIQMTQSPSSLSASVGDRVTITCRASQSISSYLNWYQQKPGKAPKLLIYAASSLQSGVPSRFSGSGSGTDFTLTISSLQPEDFAVYYCQQRSNWPPTFGQGTKLEIKR |

TABLE 3-continued

| FGFR4 binding poly-peptide (binder) | Screen | SEQ ID NO: | Sequence |
|---|---|---|---|
| D7-VLVH | F(ab) screen | SEQ ID NO: 15 | DIQMTQSPSSLSASVGDRVTITCRASQSISSYLNWYQQKPGKAPKLLIYAASSLQSGVPSRFSGSGSGTDFTLTISSLQPEDIAAYYCQHYGTFGQGTKLEIKRGGGGSGGGGSGGGGSQVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARDGYPLGGGYDFWSGYYPDYWGQGTLVTVSS |
| D7-VHVL | — | SEQ ID NO: 16 | QVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARDGYPLGGGYDFWSGYYPDYWGQGTLVTVSSGGGGSGGGGSGGGGSDIQMTQSPSSLSASVGDRVTITCRASQSISSYLNWYQQKPGKAPKLLIYAASSLQSGVPSRFSGSGSGTDFTLTISSLQPEDIAAYYCQHYGTFGQGTKLEIKR |
| B7-VLVH | F(ab) screen | SEQ ID NO: 17 | DIQMTQSPSSLSASVGDRVTITCRASQSISSYLNWYQQKPGKAPKLLIYAASSLQSGVPSRFSGSGSGTDFTLTISSLQPEDFAVYYCQHYGTFGQGTKVEIKRGGGGSGGGGSGGGGSQVQLVESGGGLVKPGGSLRLSCAASGFTFSDYYMSWIRQAPGKGLEWVSYISSSGSTIYYADSVKGRFTISRDNAKNSLYLQMNSLRAEDTAMYYCARHKTSLNDYDFWSGYLLDYWGQGTLVTVSS |
| B7-VHVL | — | SEQ ID NO: 18 | QVQLVESGGGLVKPGGSLRLSCAASGFTFSDYYMSWIRQAPGKGLEWVSYISSSGSTIYYADSVKGRFTISRDNAKNSLYLQMNSLRAEDTAMYYCARHKTSLNDYDFWSGYLLDYWGQGTLVTVSSGGGGSGGGGSGGGGSDIQMTQSPSSLSASVGDRVTITCRASQSISSYLNWYQQKPGKAPKLLIYAASSLQSGVPSRFSGSGSGTDFTLTISSLQPEDFAVYYCQHYGTFGQGTKVEIKR |
| A6-VLVH | F(ab) screen | SEQ ID NO: 19 | DIQMTQSPSSLSASVGDRVTITCRASQSISSYLNWYQQKPGKAPKLLIYAASSLQSGVPSRFSGSGSGTDFTLTISSLQPEDAATYYCQRYGTFGQGTKVDIKRGGGGSGGGGSGGGGSQVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARHKTSLNDYDFWSGYLLDYWGQGTLVTVSS |
| A6-VHVL | — | SEQ ID NO: 20 | QVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARHKTSLNDYDFWSGYLLDYWGQGTLVTVSSGGGGSGGGGSGGGGSDIQMTQSPSSLSASVGDRVTITCRASQSISSYLNWYQQKPGKAPKLLIYAASSLQSGVPSRFSGSGSGTDFTLTISSLQPEDAATYYCQRYGTFGQGTKVDIKR |
| C1-VLVH | F(ab) screen | SEQ ID NO: 21 | DIQMTQSPSSLSASVGDRVTITCRASQSISSYLNWYQQKPGKAPKLLIYAASSLQSGVPSRFSGSGSGTDFTLTISSLQPEDAATYYCQHYGTFGQGTKVEIKRGGGGSGGGGSGGGGSQVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARHAPHKHYDFWSGYYPDYWGQGTLVTVSS |
| C1-VHVL | — | SEQ ID NO: 22 | QVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARHAPHKHYDFWSGYYPDYWGQGTLVTVSSGGGGSGGGGSGGGGSDIQMTQSPSSLSASVGDRVTITCRASQSISSYLNWYQQKPGKAPKLLIYAASSLQSGVPSRFSGSGSGTDFTLTISSLQPEDAATYYCQHYGTFGQGTKVEIKR |

TABLE 4

| FGFR4 binding poly-peptide (binder) | SEQ ID NO | CDR Sequences |
|---|---|---|
| E9 | SEQ ID NO: 42 | SYALG |
| | SEQ ID NO: 43 | YIYHKGDTNYNPSLKS |
| | SEQ ID NO: 44 | VRWVSSTSTLGFDY |
| A4 | SEQ ID NO: 45 | SYAMS |
| | SEQ ID NO: 46 | IIYPDDAGTMYSPSFQG |
| | SEQ ID NO: 47 | VTMVRGVIGFDP |
| E61 | SEQ ID NO: 48 | SYAMS |
| | SEQ ID NO: 49 | MGIIYPGDSNTIYSPSFQG |
| | SEQ ID NO: 50 | SGAYDGRIWFDP |
| A7 | SEQ ID NO: 51 | NYGMS |
| | SEQ ID NO: 52 | YIYHTGNTYYNPSLKS |
| | SEQ ID NO: 53 | EGVMGGYHTDPNYYYYGMDV |
| D92 | SEQ ID NO: 54 | SYGMH |
| | SEQ ID NO: 55 | YSYYSGSTYYNPSLKS |
| | SEQ ID NO: 56 | DGSSWYSFPYYYGMDV |
| D8 | SEQ ID NO: 57 | NYGMS |
| | SEQ ID NO: 58 | EINHSGSTNYNPSLKS |
| | SEQ ID NO: 59 | RGGWVGY |
| F11 | SEQ ID NO: 60 | NYGMS |
| | SEQ ID NO: 61 | YISNGGGTMYYADSVKG |
| | SEQ ID NO: 62 | TRAPYCSGGDCYPMSTHELDS |
| C52 | SEQ ID NO: 63 | SYWMS |
| | SEQ ID NO: 64 | VIYYSGATYYNPSLKS |
| | SEQ ID NO: 65 | GALDYFDL |
| H4-VLVH | SEQ ID NO: 66 | RASQSISSYLN |
| | SEQ ID NO: 67 | AASSLQS |
| | SEQ ID NO: 68 | LQITHWPHT |
| | SEQ ID NO: 69 | DYYMS |
| | SEQ ID NO: 70 | YISSSGSTIYYADSVKG |
| | SEQ ID NO: 71 | DAPDLLAVPTVIFSGYHYGADV |
| H4-VHVL | SEQ ID NO: 72 | DYYMS |
| | SEQ ID NO: 73 | YISSSGSTIYYADSVKG |
| | SEQ ID NO: 74 | DAPDLLAVPTVIFSGYHYGADV |
| | SEQ ID NO: 75 | RASQSISSYLN |
| | SEQ ID NO: 76 | AASSLQS |
| | SEQ ID NO: 77 | LQITHWPHT |
| G6-VLVH | SEQ ID NO: 78 | RASQSISSYLN |
| | SEQ ID NO: 79 | AASSLQS |
| | SEQ ID NO: 80 | QHYGT |
| | SEQ ID NO: 81 | DYYMS |
| | SEQ ID NO: 82 | YISSSGSTIYYADSVKG |
| | SEQ ID NO: 83 | HKTSLNDYDFWSGYLLDY |
| G6-VHVL | SEQ ID NO: 84 | DYYMS |
| | SEQ ID NO: 85 | YISSSGSTIYYADSVKG |
| | SEQ ID NO: 86 | HKTSLNDYDFWSGYLLDY |
| | SEQ ID NO: 87 | RASQSISSYLN |
| | SEQ ID NO: 88 | AASSLQS |
| | SEQ ID NO: 89 | QHYGT |
| C9-VLVH | SEQ ID NO: 90 | RASQSISSYLN |
| | SEQ ID NO: 91 | AASSLQS |
| | SEQ ID NO: 92 | QQRSNWPPT |
| | SEQ ID NO: 93 | DYYMS |
| | SEQ ID NO: 94 | YISSSGSTIYYADSVKG |
| | SEQ ID NO: 95 | AVFSLGPEGYYYYMDV |

TABLE 4-continued

| FGFR4 binding poly-peptide (binder) | SEQ ID NO | CDR Sequences |
|---|---|---|
| C9-VHVLH | SEQ ID NO: 96 | DYYMS |
| | SEQ ID NO: 97 | YISSSGSTIYYADSVKG |
| | SEQ ID NO: 98 | AVFSLGPEGYYYYMDV |
| | SEQ ID NO: 99 | RASQSISSYLN |
| | SEQ ID NO: 100 | AASSLQS |
| | SEQ ID NO: 101 | QQRSNWPPT |
| D7-VLVH | SEQ ID NO: 102 | RASQSISSYLN |
| | SEQ ID NO: 103 | AASSLQS |
| | SEQ ID NO: 104 | QHYGT |
| | SEQ ID NO: 105 | DYYMS |
| | SEQ ID NO: 106 | YISSSGSTIYYADSVKG |
| | SEQ ID NO: 107 | DGYPLGGGYDFWSGYYPDY |
| D7-VHVL | SEQ ID NO: 108 | DYYMS |
| | SEQ ID NO: 109 | YISSSGSTIYYADSVKG |
| | SEQ ID NO: 110 | DGYPLGGGYDFWSGYYPDY |
| | SEQ ID NO: 111 | RASQSISSYLN |
| | SEQ ID NO: 112 | AASSLQS |
| | SEQ ID NO: 113 | QHYGT |
| B7-VLVH | SEQ ID NO: 114 | RASQSISSYLN |
| | SEQ ID NO: 115 | AASSLQS |
| | SEQ ID NO: 116 | QHYGT |
| | SEQ ID NO: 117 | DYYMS |
| | SEQ ID NO: 118 | YISSSGSTIYYADSVKG |
| | SEQ ID NO: 119 | HKTSLNDYDFWSGYLLDY |
| B7-VHVL | SEQ ID NO: 120 | DYYMS |
| | SEQ ID NO: 121 | YISSSGSTIYYADSVKG |
| | SEQ ID NO: 122 | HKTSLNDYDFWSGYLLDY |
| | SEQ ID NO: 123 | RASQSISSYLN |
| | SEQ ID NO: 124 | AASSLQS |
| | SEQ ID NO: 125 | QHYGT |
| A6-VLVH | SEQ ID NO: 126 | RASQSISSYLN |
| | SEQ ID NO: 127 | AASSLQS |
| | SEQ ID NO: 128 | QRYGT |
| | SEQ ID NO: 129 | DYYMS |
| | SEQ ID NO: 130 | YISSSGSTIYYADSVKG |
| | SEQ ID NO: 131 | HKTSLNDYDFWSGYLLDY |
| A6-VHVL | SEQ ID NO: 132 | DYYMS |
| | SEQ ID NO: 133 | YISSSGSTIYYADSVKG |
| | SEQ ID NO: 134 | HKTSLNDYDFWSGYLLDY |
| | SEQ ID NO: 135 | RASQSISSYLN |
| | SEQ ID NO: 136 | AASSLQS |
| | SEQ ID NO: 137 | QRYGT |
| C1-VLVH | SEQ ID NO: 138 | RASQSISSYLN |
| | SEQ ID NO: 139 | AASSLQS |
| | SEQ ID NO: 140 | QHYGT |
| | SEQ ID NO: 141 | DYYMS |
| | SEQ ID NO: 142 | YISSSGSTIYYADSVKG |
| | SEQ ID NO: 143 | HAPHKHYDFWSGYYPDY |
| C1-VHVL | SEQ ID NO: 144 | DYYMS |
| | SEQ ID NO: 145 | YISSSGSTIYYADSVKG |
| | SEQ ID NO: 146 | HAPHKHYDFWSGYYPDY |
| | SEQ ID NO: 147 | RASQSISSYLN |
| | SEQ ID NO: 148 | AASSLQS |
| | SEQ ID NO: 149 | QHYGT |

TABLE 5

| Feature SEQ ID NO | Sequence |
| --- | --- |
| Leader peptide SEQ ID NO: 23 | MLLLVTSLLLCELPHPAFLLIP |
| CD8 linker and transmembrane domains SEQ ID NO: 24 | TTTPAPRPPTPAPTIASQPLSLRPEACRPAAGGAVHTRGLDFAC DIYIWAPLAGTCGVLLLSLVITLYC |
| CD8 linker and transmembrane domains SEQ ID NO: 25 | ACCACTACTCCGGCACCTAGGCCCCCCACTCCGGCACCGACC ATTGCATCACAACCACTGAGTCTTAGACCTGAAGCCTGTCGA CCCGCAGCTGGGGGGGCAGTCCACACACGGGGATTGGATTT CGCCTGCGATATATACATTTGGGCGCCACTGGCAGGCACCTG CGGGGTCCTGCTCTTGTCCCTTGTCATCACCCTGTACTGT |
| CD28tm SEQ ID NO: 26 | MFWVLVVVGGVLACYSLLVTVAFIIFWV |
| CD28tm SEQ ID NO: 27 | ATGTTCTGGGTGCTGGTGGTGGTCGGAGGCGTGCTGGCCTGC TACAGCCTGCTGGTCACCGTGGCCTTCATCATCTTTTGGGTG |
| CD28 cytoplasmic SEQ ID NO: 28 | RSKRSRLLHSDYMNMTPRRPGPTRKHYQPYAPPRDFAAYRS |
| 4-1BB signaling domain SEQ ID NO: 29 | KRGRKKLLYIFKQPFMRPVQTTQEEDGCSCRFPEEEEGGCEL |
| 4-1BB signaling domain SEQ ID NO: 30 | AAGAGAGGAAGAAAGAAGTTGTTGTATATTTTCAAACAGCC ATTCATGAGGCCGGTCCAGACCACTCAGGAGGAGGATGGAT GCAGTTGCCGCTTTCCGGAAGAGGAAGAGGGTGGGTGTGAA CTC |
| CD3-zeta chain signaling domain SEQ ID NO: 31 | RVKFSRSADAPAYKQGQNQLYNELNLGRREEYDVLDKRRGRD PEMGGKPRRKNPQEGLYNELQKDKMAEAYSEIGMKGERRRGK GHDGLYQGLSTATKDTYDALHMQALPPR |
| CD3-zeta chain signaling domain SEQ ID NO: 32 | CGAGTTAAATTTTCTCGCAGTGCTGATGCCCCAGCGTATAAA CAGGGTCAGAACCAACTGTATAATGAACTCAATTTGGGGAG GCGAGAGGAGTATGATGTATTGGACAAGCGGCGGGGGCGGG ATCCTGAAATGGGCGGTAAGCCAAGGCGCAAGAATCCACAG GAGGGTTTGTATAATGAGTTGCAGAAGGATAAAATGGCGGA AGCGTATTCAGAAATCGGAATGAAGGGAGAGCGCCGCAGAG GGAAAGGGCATGATGGCCTCTACCAAGGTTTGTCAACAGCG ACCAAGGATACCTATGACGCACTTCATATGCAAGCACTGCC CCCCAGG |
| T2A SEQ ID NO: 33 | CTCGAGGGCGGCGGAGAGGGCAGAGGAAGTCTTCTAACATG CGGTGACGTGGAGGAGAATCCCGGCCCTAGG |
| EGFRt SEQ ID NO: 34 | CGCAAAGTGTGTAACGGAATAGGTATTGGTGAATTTAAAGA CTCACTCTCCATAAATGCTACGAATATTAAACACTTCAAAAA CTGCACCTCCATCAGTGGCGATCTCCACATCCTGCCGGTGGC ATTTAGGGGTGACTCCTTCACACATACTCCTCCTCTGGATCC ACAGGAACTGGATATTCTGAAAACCGTAAAGGAAATCACAG GGTTTTTGCTGATTCAGGCTTGGCCTGAAAACAGGACGGACC TCCATGCCTTTGAGAACCTAGAAATCATACGCGGCAGGACC AAGCAACATGGTCAGTTTTCTCTTGCAGTCGTCAGCCTGAAC ATAACATCCTTGGGATTACGCTCCCTCAAGGAGATAAGTGAT GGAGATGTGATAATTTCAGGAAACAAAAATTTGTGCTATGC AAATACAATAAACTGGAAAAAACTGTTTGGGACCTCCGGTC AGAAAACCAAAATTATAAGCAACAGAGGTGAAAACAGCTGC AAGGCCACAGGCCAGGTCTGCCATGCCTTGTGCTCCCCCGA GGGCTGCTGGGGCCCGGAGCCCAGGGACTGCGTCTCTTGCC GGAATGTCAGCCGAGGCAGGGAATGCGTGGACAAGTGCAAC CTTCTGGAGGGTGAGCCAAGGGAGTTTGTGGAGAACTCTGA GTGCATACAGTGCCACCCAGAGTGCCTGCCTCAGGCCATGA ACATCACCTGCACAGGACGGGGACCAGACAACTGTATCCAG TGTGCCCACTACATTGACGGCCCCCACTGCGTCAAGACCTGC CCGGCAGGAGTCATGGGAGAAAACAACACCCTGGTCTGGAA GTACGCAGACGCCGGCCATGTGTGCCACCTGTGCCATCCAA ACTGCACCTACGGATGCACTGGGCCAGGTCTTGAAGGCTGT CCAACGAATGGGCCTAAGATCCCGTCCATCGCCACTGGGAT GGTGGGGGCCCTCCTCTTGCTGCTGGTGGTGGCCCTGGGGAT CGGCCTCTTCATG |

TABLE 5-continued

| Feature SEQ ID NO | Sequence |
|---|---|
| S (small) spacer SEQ ID NO: 35 | ESKYGPPCPPCP |
| S (small) spacer SEQ ID NO: 36 | GAATCTAAGTACGGACCGCCCTGCCCCCCTTGCCCT |
| M (medium) spacer SEQ ID NO: 37 | ESKYGPPCPPCPGQPREPQVYTLPPSQEEMTKNQVSLTCLVKGF YPSDIAVEWESNGQPENNYKTTPPVLDSDGSFFLYSRLTVDKSR WQEGNVFSCSVMHEALHNHYTQKSLSLSLGK |
| M (medium) spacer SEQ ID NO: 38 | GAATCTAAGTACGGACCGCCCTGCCCCCCTTGCCCTGGCCAG CCTAGAGAACCCCAGGTGTACACCCTGCCTCCCAGCCAGGA AGAGATGACCAAGAACCAGGTGTCCCTGACCTGCCTGGTCA AAGGCTTCTACCCCAGCGATATCGCCGTGGAATGGGAGAGC AACGGCCAGCCCGAGAACAACTACAAGACCACCCCCCCTGT GCTGGACAGCGACGGCAGCTTCTTCCTGTACTCCCGGCTGAC CGTGGACAAGAGCCGGTGGCAGGAAGGCAACGTCTTCAGCT GCAGCGTGATGCACGAGGCCCTGCACAACCACTACACCCAG AAGTCCCTGAGCCTGAGCCTGGGCAAG |
| L (long) spacer SEQ ID NO: 39 | ESKYGPPCPPCPAPEFLGGPSVFLFPPKPKDTLMISRTPEVTCVV VDVSQEDPEVQFNWYVDGVEVHNAKTKPREEQFNSTYRVVSV LTVLHQDWLNGKEYKCKVSNKGLPSSIEKTISKAKGQPREPQV YTLPPSQEEMTKNQVSLTCLVKGFYPSDIAVEWESNGQPENNY KTTPPVLDSDGSFFLYSRLTVDKSRWQEGNVFSCSVMHEALHN HYTQKSLSLSLGK |
| L (long) spacer SEQ ID NO: 40 | GAATCTAAGTACGGACCGCCCTGCCCCCCTTGCCCTGCCCCC GAGTTCGACGGCGGACCCAGCGTGTTCCTGTTCCCCCCCAAG CCCAAGGACACCCTGATGATCAGCCGGACCCCCGAGGTGAC CTGCGTGGTGGTGGACGTGAGCCAGGAAGATCCCGAGGTCC AGTTCAATTGGTACGTGGACGGCGTGGAAGTGCACAACGCC AAGACCAAGCCCAGAGAGGAACAGTTCCAGAGCACCTACCG GGTGGTGTCTGTGCTGACCGTGCTGCACCAGGACTGGCTGAA CGGCAAAGAATACAAGTGCAAGGTGTCCAACAAGGGCCTGC CCAGCAGCATCGAAAAGACCATCAGCAAGGCCAAGGGCCA GCCTCGCGAGCCCCAGGTGTACACCCTGCCTCCCTCCCAGGA AGAGATGACCAAGAACCAGGTGTCCCTGACCTGCCTGGTGA AGGGCTTCTACCCCAGCGACATCGCCGTGGAGTGGGAGAGC AACGGCCAGCCTGAGAACAACTACAAGACCACCCCTCCCGT GCTGGACAGCGACGGCAGCTTCTTCCTGTACAGCCGGCTGA CCGTGGACAAGAGCCGGTGGCAGGAAGGCAACGTCTTTAGC TGCAGCGTGATGCACGAGGCCCTGCACAACCACTACACCCA GAAGAGCCTGAGCCTGTCCCTGGGCAAG |
| RJ146 CAR (D8/CD8 TM/ 4-1BB/CD3zeta) SEQ ID NO: 41 | MLLLVTSLLLCELPHPAFLLIPEVQLVESGGGLVQPGGSLRLSC AASGFTFSNYGMSWVRQAPGKALEWIGEINHSGSTNYNPSLKS RVTISRDNSKNTLYLQMNSLRAEDTAIYYCRGGWVGYWGQGT LVTVSSAAATTTPAPRPPTPAPTIASQPLSLRPEACRPAAGGAVH TRGLDFACDIYIWAPLAGTCGVLLLSLVITLYCKRGRKKLLYIF KQPFMRPVQTTQEEDGCSCRFPEEEEGGCELRVKFSRSADAPA YKQGQNQLYNELNLGRREEYDVLDKRRGRDPEMGGKPRRKN PQEGLYNELQKDKMAEAYSEIGMKGERRRGKGHDGLYQGLST ATKDTYDALHMQALPPR |

Certain CARs Specific for FGFR4

Some embodiments of the methods and compositions provided herein include a CAR specific for FGFR4. In some such embodiments, the CAR is encoded by a nucleic acid provided herein. The CAR can be encoded by the nucleic acid of any one of the embodiments herein or the vector of any one of the embodiments herein.

Certain Cells for CAR T Cell Expression and Therapy

Some embodiments of the methods and compositions provided herein include a cell comprising a CAR specific for FGFR4, as described in any one of the embodiments herein, or a nucleic acid encoding a CAR specific for FGFR4, as described in any one of the embodiments herein. In some embodiments, the cell is from a donor that is the same as the recipient of the therapy (e.g., autologous CAR T cell therapy), or related or unrelated to the subject in need of CAR T cell therapy. In some embodiments, the cell is from the subject in need of CAR T cell therapy. In some embodiments, the cell is allogeneic to a subject in need of CAR T cell therapy. In some embodiments, the cell is human.

In some embodiments, the cell is a T cell. In some embodiments, the cell is a CD4+ T-cell or a CD8+ T-cell. In some embodiments, the cell is a CD8+ cytotoxic T-cell selected from the group consisting of a naïve CD8+ T-cell, a CD8+ memory T-cell, a central memory CD8+ T-cell, a regulatory CD8+ T-cell, an IPS derived CD8+ T-cell, an effector memory CD8+ T-cell, and a bulk CD8+ T-cell. In some embodiments, the cell is a CD4+ T helper cell selected from the group consisting of a naïve CD4+ T-cell, a CD4+ memory T-cell, a central memory CD4+ T-cell, a regulatory CD4+ T-cell, an IPS derived CD4+ T-cell, an effector memory CD4+ T-cell, and a bulk CD4+ T-cell. In some embodiments, the cell is a precursor T-cell, or a hematopoietic stem cell.

Some embodiments of the methods and compositions provided herein include a pharmaceutical composition comprising a cell comprising a CAR specific for FGFR4 as described in any one of the embodiments herein, or a nucleic acid encoding a CAR specific for FGFR4 as described in any one of the embodiments herein, and a pharmaceutically acceptable excipient.

Certain Methods of Preparing Donor Cells

Some embodiments of the methods and compositions provided herein include methods of preparing a population of cells comprising a CAR specific for FGFR4, such as a population of cells for an infusion. Some embodiments include obtaining a cell from a subject, or a cell from another matched to be compatible to the subject for cellular therapy. Some embodiments also include introducing any one of the vectors providing herein containing a CAR specific for FGFR4 into the cell. Some embodiments also include expanding the cell and isolating the cell. Some embodiments include culturing the cell in the presence of an agent selected from an anti-CD3, an anti-CD28, or a cytokine, such as IL-2.

Certain Methods of Therapy

Some embodiments of the methods and compositions provided herein include methods of therapy, such as methods of treating, inhibiting or ameliorating a cancer in a subject. In some embodiments, the cancer comprises a cancer cell expressing FGFR4. In some embodiments, the cancer comprises a solid tumor. In some embodiments, the cancer comprises a cell expressing a protein selected from a PAX3-FOXO1 fusion gene product, and a PAX7-FOXO1 fusion gene product. In some embodiments, the cancer comprises a cell comprising a mutation in a gene selected from TP53, RAS, PI3K3CA, CTNNB1, or FGFR4. In some embodiments, the cancer comprises a rhabdomyosarcoma. In some embodiments, the subject is human.

Certain sequences useful with embodiments provided herein are listed in TABLE 6.

TABLE 6

| Feature SEQ ID NO | Sequence |
|---|---|
| E9 binder SEQ ID NO: 150 | GAGGTGCAGCTGGTTGAATCTGGCGGAGGACTGGTTCAGCC TGGCGGATCTCTGAGACTGAGCTGTACCGTGTCCGGCTTCAC CTTCAGCTCTTATGCCCTCGGCTGGGTCCGACAGGCTCCTGG AAAAGGACTGGAATGGATCGGCTACATCTACCACAAGGGCG ACACCAACTACAACCCCAGCCTGAAGTCCCTGGTCACCATC AGCAGAGACAACAGCAAGAACACCCTGTACCTGCAGATGAA CAGCCTGAGAGCCGAGGACACAGCCCTGTACTACTGCGCCA AAGTCCGCTGGGTGTCCAGCACAAGCACCCTGGGCTTTGATT ATTGGGGCCAGGGCACACTGGTCACCGTGTCATCT |
| RJ141 CAR: (E9/CD8 TM/ 4-1BB/CD3zeta) SEQ ID NO: 151 | MLLLVTSLLLCELPHPAFLLIPEVQLVESGGGLVQPGGSLRLSCT VSGFTFSSYALGWVRQAPGKGLEWIGYIYHKGDTNYNPSLKSL VTISRDNSKNTLYLQMNSLRAEDTALYYCAKVRWVSSTSTLGF DYWGQGTLVTVSSAAATTTPAPRPPTPAPTIASQPLSLRPEACR PAAGGAVHTRGLDFACDIYIWAPLAGTCGVLLLSLVITLYCKR GRKKLLYIFKQPFMRPVQTTQEEDGCSCRFPEEEEGGCELRVKF SRSADAPAYKQGQNQLYNELNLGRREEYDVLDKRRGRDPEMG GKPRRKNPQEGLYNELQKDKMAEAYSEIGMKGERRRGKGHD GLYQGLSTATKDTYDALHMQALPPR |
| RJ141 CAR: (B9/CD8 TM/ 4-1BB/CD3zeta) SEQ ID NO: 152 | ATGCTTCTGCTCGTGACAAGCCTGCTGCTGTGCGAGCTGCCC CACCCTGCCTTTCTGCTGATCCCTGAGGTGCAGCTGGTTGAA TCTGGCGGAGGACTGGTTCAGCCTGGCGGATCTCTGAGACTG AGCTGTACCGTGTCCGGCTTCACCTTCAGCTCTTATGCCCTC GGCTGGGTCCGACAGGCTCCTGGAAAAGGACTGGAATGGAT CGGCTACATCTACCACAAGGGCGACACCAACTACAACCCCA GCCTGAAGTCCCTGGTCACCATCAGCAGAGACAACAGCAAG AACACCCTGTACCTGCAGATGAACAGCCTGAGAGCCGAGGA CACAGCCCTGTACTACTGCGCCAAAGTCCGCTGGGTGTCCAG CACAAGCACCCTGGGCTTTGATTATTGGGGCCAGGGCACAC TGGTCACCGTGTCATCTGCGGCCGCAACCACTACTCCGGCAC CTAGGCCCCCCACTCCGGCACCGACCATTGCATCACAACCAC TGAGTCTTAGACCTGAAGCCTGTCGACCCGCAGCTGGGGGG GCAGTCCACACACGGGGATTGGATTTCGCCTGCGATATATAC ATTTGGGCGCCACTGGCAGGCACCTGCGGGGTCCTGCTCTTG TCCCTTGTCATCACCCTGTACTGTAAGAGAGGAAGAAAGAA GTTGTTGTATATTTTCAAACAGCCATTCATGAGGCCGGTCCA GACCACTCAGGAGGAGGATGGATGCAGTTGCCGCTTTCCGG AAGAGGAAGAGGGTGGGTGTGAACTCCGAGTTAAATTTTCT CGCAGTGCTGATGCCCCAGCGTATAAACAGGGTCAGAACCA ACTGTATAATGAACTCAATTTGGGGAGGCGAGAGGAGTATG ATGTATTGGACAAGCGGCGGGGGCGGGATCCTGAAATGGGC GGTAAGCCAAGGCGCAAGAATCCACAGGAGGGTTTGTATAA TGAGTTGCAGAAGGATAAAATGGCGGAAGCGTATTCAGAAA TCGGAATGAAGGGAGAGCGCCGCAGAGGGAAAGGGCATGA TGGCCTCTACCAAGGTTTGTCAACAGCGACCAAGGATACCT ATGACGCACTTCATATGCAAGCACTGCCCCCCAGG |
| A4 binder SEQ ID NO: 153 | GAGGTGCAGCTGGTTGAATCTGGCGGAGGACTGGTTCAGCC TGGCGGATCTCTGAGACTGAGCTGTGTGGCCAGCGGCTTCAC CTTCATCAGCTACGCCATGAGCTGGGTCCGACAGGCCCCTGG AAAAGGCCTTGAGTGGATGGCCATTATCTACCCCGATGACG CCGGCACCATGTACAGCCCTAGCTTTCAGGGCCAAGTGACC ATCAGCCGGGACAACAGCAAGAACACCCTGTACCTGCAGAT |

TABLE 6-continued

| Feature SEQ ID NO | Sequence |
|---|---|
| | GAACAGCCTGAGAGCCGAGGACACAGCCCTGTACTACTGTG CCAGAGTGACAATGGTCCGAGGCGTGATCGGCTTCGATCCTT GGGGACAGGGAACCCTGGTCACCGTTTCTTCT |
| RJ142 CAR (A4/CD8 TM/ 4-1BB/CD3zeta) SEQ ID NO: 154 | MLLLVTSLLLCELPHPAFLLIPEVQLVESGGGLVQPGGSLRLSC VASGFTFISYAMSWVRQAPGKGLEWMAIIYPDDAGTMYSPSFQ GQVTISRDNSKNTLYLQMNSLRAEDTALYYCARVTMVRGVIG FDPWGQGTLVTVSSAAATTTPAPRPPTPAPTIASQPLSLRPEACR PAAGGAVHTRGLDFACDIYIWAPLAGTCGVLLLSLVITLYCKR GRKKLLYIFKQPFMRPVQTTQEEDGCRFPEEEEGGCELRVKF SRSADAPAYKQGQNQLYNELNLGRREEYDVLDKRRGRDPEMG GKPRRKNPQEGLYNELQKDKMAEAYSEIGMKGERRRGKGHD GLYQGLSTATKDTYDALHMQALPPR |
| RJ142 CAR (A4/CD8 TM/ 4-1BB/CD3zeta) SEQ ID NO: 155 | ATGCTTCTGCTCGTGACAAGCCTGCTGCTGTGCGAGCTGCCC CACCCTGCCTTTCTGCTGATCCCTGAGGTGCAGCTGGTTGAA TCTGGCGGAGGACTGGTTCAGCCTGGCGGATCTCTGAGACTG AGCTGTGTGGCCAGCGGCTTCACCTTCATCAGCTACGCCATG AGCTGGGTCCGACAGGCCCCTGGAAAAGGCCTTGAGTGGAT GGCCATTATCTACCCCGATGACGCCGGCACCATGTACAGCCC TAGCTTTCAGGGCCAAGTGACCATCAGCCGGGACAACAGCA AGAACACCCTGTACCTGCAGATGAACAGCCTGAGAGCCGAG GACACAGCCCTGTACTACTGTGCCAGAGTGACAATGGTCCG AGGCGTGATCGGCTTCGATCCTTGGGGACAGGGAACCCTGG TCACCGTTTCTTCTGCGGCCGCAACCACTACTCCGGCACCTA GGCCCCCCACTCCGGCACCGACCATTGCATCACAACCACTG AGTCTTAGACCTGAAGCCTGTCGACCCGCAGCTGGGGGGGC AGTCCACACACGGGGATTGGATTTCGCCTGCGATATATACAT TTGGGCGCCACTGGCAGGCACCTGCGGGGTCCTGCTCTTGTC CCTTGTCATCACCCTGTACTGTAAGAGAGGAAGAAAGAAGT TGTTGTATATTTTCAAACAGCCATTCATGAGGCCGGTCCAGA CCACTCAGGAGGAGGATGGATGCAGTTGCCGCTTTCCGGAA GAGGAAGAGGGTGGGTGTGAACTCCGAGTTAAATTTTCTCG CAGTGCTGATGCCCCAGCGTATAAACAGGGTCAGAACCAAC TGTATAATGAACTCAATTTGGGGAGGCGAGAGGAGTATGAT GTATTGGACAAGCGGCGGGGGGGGGATCCTGAAATGGGCGG TAAGCCAAGGCGCAAGAATCCACAGGAGGGTTTGTATAATG AGTTGCAGAAGGATAAAATGGCGGAAGCGTATTCAGAAATC GGAATGAAGGGAGAGCGCCGCAGAGGGAAAGGGCATGATG GCCTCTACCAAGGTTTGTCAACAGCGACCAAGGATACCTAT GACGCACTTCATATGCAAGCACTGCCCCCCAGG |
| B61 binder SEQ ID NO: 156 | GAGGTGCAGCTGGTTGAATCTGGCGGAGGACTGGTTCAGCC TGGCGGATCTCTGAGACTGTCCTGCACCTTCAGCGGCTTCAC CTTCTCCAGCTACGCCATGAGCTGGGTCCGACAGGCTCCTGG CAAAGGCCTTGAGTGGATGGGCATCATCTACCCCGGCGACA GCAACACCATCTACAGCCCTAGCTTCCAGGGCCAAGTGACC ATCAGCCGGGACAACAGCAAGAACACCCTGTACCTGCAGAT GAACAGCCTGAGAGCCGAGGACACCGCCACCTACTACTGTG CTAGAAGCGGCGCCTACGACGGCCGGATTTGGTTTGATCCTT GGGGCCAGGGCACCCTGGTCACAGTTTCTTCT |
| RJ143 CAR (B61/CD8TM/ 4-1BB/CD3zeta) SEQ ID NO: 157 | MLLLVTSLLLCELPHPAFLLIPEVQLVESGGGLVQPGGSLRLSCT FSGFTFSSYAMSWVRQAPGKGLEWMGIIYPGDSNTIYSPSFQGQ VTISRDNSKNTLYLQMNSLRAEDTATYYCARSGAYDGRIWFDP WGQGTLVTVSSAAATTTPAPRPPTPAPTIASQPLSLRPEACRPA AGGAVHTRGLDFACDIYIWAPLAGTCGVLLLSLVITLYCKRGR KKLLYIFKQPFMRPVQTTQEEDGCSCRFPEEEEGGCELRVKFSR SADAPAYKQGQNQLYNELNLGRREEYDVLDKRRGRDPEMGG KPRRKNPQEGLYNELQKDKMAEAYSEIGMKGERRRGKGHDGL YQGLSTATKDTYDALHMQALPPR |
| RJ143 CAR (E61/CD8TM/ 4-1BB/CD3zeta) SEQ ID NO: 158 | ATGCTTCTGCTCGTGACAAGCCTGCTGCTGTGCGAGCTGCCC CACCCTGCCTTTCTGCTGATCCCTGAGGTGCAGCTGGTTGAA TCTGGCGGAGGACTGGTTCAGCCTGGCGGATCTCTGAGACTG TCCTGCACCTTCAGCGGCTTCACCTTCTCCAGCTACGCCATG AGCTGGGTCCGACAGGCTCCTGGCAAAGGCCTTGAGTGGAT GGGCATCATCTACCCCGGCGACAGCAACACCATCTACAGCC CTAGCTTCCAGGGCCAAGTGACCATCAGCCGGGACAACAGC AAGAACACCCTGTACCTGCAGATGAACAGCCTGAGAGCCGA GGACACCGCCACCTACTACTGTGCTAGAAGCGGCGCCTACG ACGGCCGGATTTGGTTTGATCCTTGGGGCCAGGGCACCCTGG TCACAGTTTCTTCTGCGGCCGCAACCACTACTCCGGCACCTA GGCCCCCCACTCCGGCACCGACCATTGCATCACAACCACTG AGTCTTAGACCTGAAGCCTGTCGACCCGCAGCTGGGGGGGC AGTCCACACACGGGGATTGGATTTCGCCTGCGATATATACAT TTGGGCGCCACTGGCAGGCACCTGCGGGGTCCTGCTCTTGTC |

TABLE 6-continued

| Feature SEQ ID NO | Sequence |
|---|---|
| | CCTTGTCATCACCCTGTACTGTAAGAGAGGAAGAAAGAAGT TGTTGTATATTTTCAAACAGCCATTCATGAGGCCGGTCCAGA CCACTCAGGAGGAGGATGGATGCAGTTGCCGCTTTCCGGAA GAGGAAGAGGGTGGGTGTGAACTCCGAGTTAAATTTTCTCG CAGTGCTGATGCCCCAGCGTATAAACAGGGTCAGAACCAAC TGTATAATGAACTCAATTTGGGGAGGCGAGAGGAGTATGAT GTATTGGACAAGCGGCGGGGGCGGGATCCTGAAATGGGCGG TAAGCCAAGGCGCAAGAATCCACAGGAGGGTTTGTATAATG AGTTGCAGAAGGATAAAATGGCGGAAGCGTATTCAGAAATC GGAATGAAGGGAGAGCGCCGCAGAGGGAAAGGGCATGATG GCCTCTACCAAGGTTTGTCAACAGCGACCAAGGATACCTAT GACGCACTTCATATGCAAGCACTGCCCCCCAGG |
| A7 binder SEQ ID NO: 159 | GAGGTGCAGCTGGTTGAATCTGGCGGAGGACTGGTTCAGCC TGGCGGATCTCTGAGACTGTCTTGTGCCGCCAGCGGCTTCAC CTTCAGCAACTACGGCATGAGCTGGGTCCGACAGGCCCCTG GAAAAGGCCTTGAGTGGATCGGCTACATCTACCACACCGGC AACACCTACTACAACCCCAGCCTGAAGTCCAGAGTGACCAT CAGCCGGGACAACAGCAAGAACACCCTGTACCTGCAGATGA ACAGCCTGAGAGCCGAGGACACCGCCATCTACTACTGTGCC AGAGAAGGCGTGATGGGCGGCTACCACACAGACCCCAATTA CTACTACTATGGCATGGACGTGTGGGGCCAGGGCACCACAG TGACAGTTTCTTCT |
| RJ144 CAR (A7/CD8 TM/ 4-1BB/CD3zeta) SEQ ID NO: 160 | MLLLVTSLLLCELPHPAFLLIPEVQLVESGGGLVQPGGSLRLSC AASGFTFSNYGMSWVRQAPGKGLEWIGYIYHTGNTYYNPSLK SRVTISRDNSKNTLYLQMNSLRAEDTAIYYCAREGVMGGYHT DPNYYYYGMDVWGQGTTVTVSSAAATTTPAPRPPTPAPTIASQ PLSLRPEACRPAAGGAVHTRGLDFACDIYIWAPLAGTCGVLLLS LVITLYCKRGRKKLLYIFKQPFMRPVQTTQEEDGCSCRFPEEEE GGCELRVKFSRSADAPAYKQGQNQLYNELNLGRREEYDVLDK RRGRDPEMGGKPRRKNPQEGLYNELQKDKMAEAYSEIGMKGE RRRGKGHDGLYQGLSTATKDTYDALHMQALPPR |
| RJ144 CAR (A7/CD8 TM/ 4-1BB/CD3zeta) SEQ ID NO: 161 | ATGCTTCTGCTCGTGACAAGCCTGCTGCTGTGCGAGCTGCCC CACCCTGCCTTTCTGCTGATCCCTGAGGTGCAGCTGGTTGAA TCTGGCGGAGGACTGGTTCAGCCTGGCGGATCTCTGAGACTG TCTTGTGCCGCCAGCGGCTTCACCTTCAGCAACTACGGCATG AGCTGGGTCCGACAGGCCCCTGGAAAAGGCCTTGAGTGGAT CGGCTACATCTACCACACCGGCAACACCTACTACAACCCCA GCCTGAAGTCCAGAGTGACCATCAGCCGGGACAACAGCAAG AACACCCTGTACCTGCAGATGAACAGCCTGAGAGCCGAGGA CACCGCCATCTACTACTGTGCCAGAGAAGGCGTGATGGGCG GCTACCACACAGACCCCAATTACTACTACTATGGCATGGAC GTGTGGGGCCAGGGCACCACAGTGACAGTTTCTTCTGCGGC CGCAACCACTACTCCGGCACCTAGGCCCCCCACTCCGGCACC GACCATTGCATCACAACCACTGAGTCTTAGACCTGAAGCCTG TCGACCCGCAGCTGGGGGGGCAGTCCACACACGGGGATTGG ATTTCGCCTGCGATATATACATTTGGGCGCCACTGGCAGGCA CCTGCGGGGTCCTGCTCTTGTCCCTTGTCATCACCCTGTACTG TAAGAGAGGAAGAAAGAAGTTGTTGTATATTTTCAAACAGC CATTCATGAGGCCGGTCCAGACCACTCAGGAGGAGGATGGA TGCAGTTGCCGCTTTCCGGAAGAGGAAGAGGGTGGGTGTGA ACTCCGAGTTAAATTTTCTCGCAGTGCTGATGCCCCAGCGTA TAAACAGGGTCAGAACCAACTGTATAATGAACTCAATTTGG GGAGGCGAGAGGAGTATGATGTATTGGACAAGCGGCGGGG GCGGGATCCTGAAATGGGCGGTAAGCCAAGGCGCAAGAATC CACAGGAGGGTTTGTATAATGAGTTGCAGAAGGATAAAATG GCGGAAGCGTATTCAGAAATCGGAATGAAGGGAGAGCGCCG CAGAGGGAAAGGGCATGATGGCCTCTACCAAGGTTTGTCAA CAGCGACCAAGGATACCTATGACGCACTTCATATGCAAGCA CTGCCCCCCAGG |
| D92 binder SEQ ID NO: 162 | GAGGTGCAGCTGGTTGAATCTGGCGGAGGACTGGTTCAGCC TGGCGGATCTCTGAGACTGAGCTGTGTGGCCAGCGGCTTCAC CTTTAGCAGCTACGGCATGCACTGGGTCCGACAGGCACCTG GCAAAGGCCTGGAATGGATCGGCTACAGCTACTACAGCGGC AGCACCTACTACAACCCCAGCCTGAAGTCCCTGGTCACCATC AGCAGAGACAACAGCAAGAACACCCTGTACCTGCAGATGAA CAGCCTGAGAGCCGAGGACACCGCCACCTACTATTGTGCCA GAGATGGCAGCAGCTGGTACAGCTTCCCCTACTACTATGGC ATGGACGTGTGGGGCCAGGGCACCACAGTGACAGTTTCTTCT |

TABLE 6-continued

| Feature SEQ ID NO | Sequence |
|---|---|
| RJ145 CAR (D92/CD8TM/ 4-1BB/CD3zeta) SEQ ID NO: 163 | MLLLVTSLLLCELPHPAFLLIPEVQLVESGGGLVQPGGSLRLSC VASGFTFSSYGMHWVRQAPGKGLEWIGYSYYSGSTYYNPSLK SLVTISRDNSKNTLYLQMNSLRAEDTATYYCARDGSSWYSFPY YYGMDVWGQGTTVTVSSAAATTTPAPRPPTPAPTIASQPLSLRP EACRPAAGGAVHTRGLDFACDIYIWAPLAGTCGVLLLSLVITLY CKRGRKKLLYIFKQPFMRPVQTTQEEDGCSCRFPEEEEGGCELR VKFSRSADAPAYKQGQNQLYNELNLGRREEYDVLDKRRGRDP EMGGKPRRKNPQEGLYNELQKDKMAEAYSEIGMKGERRRGK GHDGLYQGLSTATKDTYDALHMQALPPR |
| RJ145 CAR (D92/CD8TM/ 4-1BB/CD3zeta) SEQ ID NO: 164 | ATGCTTCTGCTCGTGACAAGCCTGCTGCTGTGCGAGCTGCCC CACCCTGCCTTTCTGCTGATCCCTGAGGTGCAGCTGGTTGAA TCTGGCGGAGGACTGGTTCAGCCTGGCGGATCTCTGAGACTG AGCTGTGTGGCCAGCGGCTTCACCTTTAGCAGCTACGGCATG CACTGGGTCCGACAGGCACCTGGCAAAGGCCTGGAATGGAT CGGCTACAGCTACTACAGCGGCAGCACCTACTACAACCCCA GCCTGAAGTCCCTGGTCACCATCAGCAGAGACAACAGCAAG AACACCCTGTACCTGCAGATGAACAGCCTGAGAGCCGAGGA CACCGCCACCTACTATTGTGCCAGAGATGGCAGCAGCTGGT ACAGCTTCCCCTACTACTATGGCATGGACGTGTGGGGCCAG GGCACCACAGTGACAGTTTCTTCTGCGGCCGCAACCACTACT CCGGCACCTAGGCCCCCCACTCCGGCACCGACCATTGCATCA CAACCACTGAGTCTTAGACCTGAAGCCTGTCGACCCGCAGCT GGGGGGGCAGTCCACACACGGGGATTGGATTTCGCCTGCGA TATATACATTTGGGCGCCACTGGCAGGCACCTGCGGGGTCCT GCTCTTGTCCCTTGTCATCACCCTGTACTGTAAGAGAGGAAG AAAGAAGTTGTTGTATATTTTCAAACAGCCATTCATGAGGCC GGTCCAGACCACTCAGGAGGAGGATGGATGCAGTTGCCGCT TTCCGGAAGAGGAAGAGGGTGGGTGTGAACTCCGAGTTAAA TTTTCTCGCAGTGCTGATGCCCCAGCGTATAAACAGGGTCAG AACCAACTGTATAATGAACTCAATTTGGGGAGGCGAGAGGA GTATGATGTATTGGACAAGCGGCGGGGGCGGGATCCTGAAA TGGGCGGTAAGCCAAGGCGCAAGAATCCACAGGAGGGTTTG TATAATGAGTTGCAGAAGGATAAAATGGCGGAAGCGTATTC AGAAATCGGAATGAAGGGAGAGCGCCGCAGAGGGAAAGGG CATGATGGCCTCTACCAAGGTTTGTCAACAGCGACCAAGGA TACCTATGACGCACTTCATATGCAAGCACTGCCCCCCAGG |
| D8 binder SEQ ID NO: 165 | GAGGTGCAGCTGGTTGAATCTGGCGGAGGACTGGTTCAGCC TGGCGGATCTCTGAGACTGTCTTGTGCCGCCAGCGGCTTCAC CTTCAGCAACTACGGCATGAGCTGGGTCCGACAGGCCCCTG GAAAAGCCCTGGAATGGATCGGCGAGATCAACCACAGCGGC AGCACCAACTACAACCCCAGCCTGAAGTCCAGAGTGACCAT CAGCCGGGACAACAGCAAGAACACCCTGTACCTGCAGATGA ACAGCCTGAGAGCCGAGGACACCGCCATCTACTACTGTAGA GGCGGCTGGGTCGGATATTGGGGCCAGGGAACACTGGTCAC CGTGTCTAGT |
| RJ146 CAR (D8/CD8 TM/ 4-1BB/CD3zeta) SEQ ID NO: 166 | MLLLVTSLLLCELPHPAFLLIPEVQLVESGGGLVQPGGSLRLSC AASGFTFSNYGMSWVRQAPGKALEWIGEINHSGSTNYNPSLKS RVTISRDNSKNTLYLQMNSLRAEDTAIYYCRGGWVGYWGQGT LVTVSSAAATTTPAPRPPTPAPTIASQPLSLRPEACRPAAGGAVH TRGLDFACDIYIWAPLAGTCGVLLLSLVITLYCKRGRKKLLYIF KQPFMRPVQTTQEEDGCSCRFPEEEEGGCELRVKFSRSADAPA YKQGQNQLYNELNLGRREEYDVLDKRRGRDPEMGGKPRRKN PQEGLYNELQKDKMAEAYSEIGMKGERRRGKGHDGLYQGLST ATKDTYDALHMQALPPR |
| RJ146 CAR (D8/CD8 TM/ 4-1BB/CD3zeta) SEQ ID NO: 167 | ATGCTTCTGCTCGTGACAAGCCTGCTGCTGTGCGAGCTGCCC CACCCTGCCTTTCTGCTGATCCCTGAGGTGCAGCTGGTTGAA TCTGGCGGAGGACTGGTTCAGCCTGGCGGATCTCTGAGACTG TCTTGTGCCGCCAGCGGCTTCACCTTCAGCAACTACGGCATG AGCTGGGTCCGACAGGCCCCTGGAAAAGCCCTGGAATGGAT CGGCGAGATCAACCACAGCGGCAGCACCAACTACAACCCCA GCCTGAAGTCCAGAGTGACCATCAGCCGGGACAACAGCAAG AACACCCTGTACCTGCAGATGAACAGCCTGAGAGCCGAGGA CACCGCCATCTACTACTGTAGAGGCGGCTGGGTCGGATATTG GGGCCAGGGAACACTGGTCACCGTGTCTAGTGCGGCCGCAA CCACTACTCCGGCACCTAGGCCCCCCACTCCGGCACCGACCA TTGCATCACAACCACTGAGTCTTAGACCTGAAGCCTGTCGAC CCGCAGCTGGGGGGGCAGTCCACACACGGGGATTGGATTTC GCCTGCGATATATACATTTGGGCGCCACTGGCAGGCACCTGC GGGGTCCTGCTCTTGTCCCTTGTCATCACCCTGTACTGTAAG AGAGGAAGAAAGAAGTTGTTGTATATTTTCAAACAGCCATT CATGAGGCCGGTCCAGACCACTCAGGAGGAGGATGGATGCA GTTGCCGCTTTCCGGAAGAGGAAGAGGGTGGGTGTGAACTC |

TABLE 6-continued

| Feature SEQ ID NO | Sequence |
|---|---|
| | CGAGTTAAATTTTCTCGCAGTGCTGATGCCCCAGCGTATAAA CAGGGTCAGAACCAACTGTATAATGAACTCAATTTGGGGAG GCGAGAGGAGTATGATGTATTGGACAAGCGGCGGGGGCGGG ATCCTGAAATGGGCGGTAAGCCAAGGCGCAAGAATCCACAG GAGGGTTTGTATAATGAGTTGCAGAAGGATAAAATGGCGGA AGCGTATTCAGAAATCGGAATGAAGGGAGAGCGCCGCAGAG GGAAAGGGCATGATGGCCTCTACCAAGGTTTGTCAACAGCG ACCAAGGATACCTATGACGCACTTCATATGCAAGCACTGCC CCCCAGG |
| F11 binder SEQ ID NO: 168 | GAGGTGCAGCTGGTTGAATCTGGCGGAGGACTGGTTCAGCC TGGCGGATCTCTGAGACTGTCTTGTGCCGCCAGCGGCTTCAC CTTCAGCAACTACGGCATGAGCTGGGTCCGACAGGCTCCTG GACAAGGCTTGGAGTGGGTGTCCTACATCAGCAATGGCGGC GGAACCATGTACTACGCCGACAGCGTGAAGGGCAGATTCAC CATCAGCCGGGACAACAGCAAGAACACCCTGTACCTGCAGA TGAACAGCCTGAGAGCCGAGGACACCGCCACCTACTACTGT ACAAGAGCCCCTTACTGCTCTGGCGGCGACTGCTACCCTATG AGCACACACGAGCTGGATTCTTGGGGCCAGGGCACACTGGT CACAGTGTCATCT |
| RJ147 CAR (F11/CD8TM/ 4-1BB/CD3zeta) SEQ ID NO: 169 | MLLLVTSLLLCELPHPAFLLIPEVQLVESGGGLVQPGGSLRLSC AASGFTFSNYGMSWVRQAPGQGLEWYSYISNGGGTMYYADS VKGRFTISRDNSKNTLYLQMNSLRAEDTATYYCTRAPYCSGGD CYPMSTHELDSWGQGTLVTVSSAAATTTPAPRPPTPAPTIASQP LSLRPEACRPAAGGAVHTRGLDFACDIYIWAPLAGTCGVLLLS LVITLYCKRGRKKLLYIFKQPFMRPVQTTQEEDGCSCRFPEEEE GGCELRVKFSRSADAPAYKQGQNQLYNELNLGRREEYDVLDK RRGRDPEMGGKPRRKNPQEGLYNELQKDKMAEAYSEIGMKGE RRRGKGHDGLYQGLSTATKDTYDALHMQALPPR |
| RJ147 CAR (F11/CD8TM/ 4-1BB/CD3zeta) SEQ ID NO: 170 | ATGCTTCTGCTCGTGACAAGCCTGCTGCTGTGCGAGCTGCCC CACCCTGCCTTTCTGCTGATCCCTGAGGTGCAGCTGGTTGAA TCTGGCGGAGGACTGGTTCAGCCTGGCGGATCTCTGAGACTG TCTTGTGCCGCCAGCGGCTTCACCTTCAGCAACTACGGCATG AGCTGGGTCCGACAGGCTCCTGGACAAGGCTTGGAGTGGGT GTCCTACATCAGCAATGGCGGCGGAACCATGTACTACGCCG ACAGCGTGAAGGGCAGATTCACCATCAGCCGGGACAACAGC AAGAACACCCTGTACCTGCAGATGAACAGCCTGAGAGCCGA GGACACCGCCACCTACTACTGTACAAGAGCCCCTTACTGCTC TGGCGGCGACTGCTACCCTATGAGCACACACGAGCTGGATT CTTGGGGCCAGGGCACACTGGTCACAGTGTCATCTGCGGCC GCAACCACTACTCCGGCACCTAGGCCCCCCACTCCGGCACC GACCATTGCATCACAACCACTGAGTCTTAGACCTGAAGCCTG TCGACCCGCAGCTGGGGGGGCAGTCCACACACGGGGATTGG ATTTCGCCTGCGATATATACATTTGGGCGCCACTGGCAGGCA CCTGCGGGGTCCTGCTCTTGTCCCTTGTCATCACCCTGTACTG TAAGAGAGGAAGAAAGAAGTTGTTGTATATTTTCAAACAGC CATTCATGAGGCCGGTCCAGACCACTCAGGAGGAGGATGGA TGCAGTTGCCGCTTTCCGGAAGAGGAAGAGGGTGGGTGTGA ACTCCGAGTTAAATTTTCTCGCAGTGCTGATGCCCCAGCGTA TAAACAGGGTCAGAACCAACTGTATAATGAACTCAATTTGG GGAGGCGAGAGGAGTATGATGTATTGGACAAGCGGGGGG GCGGGATCCTGAAATGGGCGGTAAGCCAAGGCGCAAGAATC CACAGGAGGGTTTGTATAATGAGTTGCAGAAGGATAAAATG GCGGAAGCGTATTCAGAAATCGGAATGAAGGGAGAGCGCCG CAGAGGGAAAGGGCATGATGGCCTCTACCAAGGTTTGTCAA CAGCGACCAAGGATACCTATGACGCACTTCATATGCAAGCA CTGCCCCCCAGG |
| C52 binder SEQ ID NO: 171 | GAGGTGCAGCTGGTTGAATCTGGCGGAGGACTGGTTCAGCC TGGCGGATCTCTGAGACTGTCTTGTGCCGCCAGCGGCTTTAC CCTGAGCAGCTACTGGATGAGCTGGGTCCGACAGGCCCCTG GCAAAGGACTGGAATGGATCGGCGTGATCTACTACAGCGGC GCCACCTACTACAACCCCAGCCTGAAGTCTCTGGTCACCATC AGCCGGGACAACAGCAAGAACACCCTGTACCTGCAGATGAA CAGCCTGAGAGCCGAGGACACCGCCGTGTACTATTGTGCTA GAGGCGCCCTGGACTACTTCGACCTTTGGGGACAAGGCGCC CTCGTGACAGTCTCTTCT |
| RJ148 CAR (C52/CD8TM/ 4-1BB/CD3zeta) SEQ ID NO: 172 | MLLLVTSLLLCELPHPAFLLIPEVQLVESGGGLVQPGGSLRLSC AASGFTLSSYWMSWVRQAPGKGLEWIGVIYYSGATYYNPSLK SLVTISRDNSKNTLYLQMNSLRAEDTAVYYCARGALDYFDLW GQGALVTVSSAAATTTPAPRPPTPAPTIASQPLSLRPEACRPAAG GAVHTRGLDFACDIYIWAPLAGTCGVLLLSLVITLYCKRGRKK LLYIFKQPFMRPVQTTQEEDGCSCRFPEEEEGGCELRVKFSRSA DAPAYKQGQNQLYNELNLGRREEYDVLDKRRGRDPEMGGKP |

TABLE 6-continued

| Feature SEQ ID NO | Sequence |
|---|---|
| | RRKNPQEGLYNELQKDKMAEAYSEIGMKGERRRGKGHDGLY QGLSTATKDTYDALHMQALPPR |
| RJ148 CAR (C52/CD8TM/ 4-1BB/CD3zeta) SEQ ID NO: 173 | ATGCTTCTGCTCGTGACAAGCCTGCTGCTGTGCGAGCTGCCC CACCCTGCCTTTCTGCTGATCCCTGAGGTGCAGCTGGTTGAA TCTGGCGGAGGACTGGTTCAGCCTGGCGGATCTCTGAGACTG TCTTGTGCCGCCAGCGGCTTTACCCTGAGCAGCTACTGGATG AGCTGGGTCCGACAGGCCCCTGGCAAAGGACTGGAATGGAT CGGCGTGATCTACTACAGCGGCGCCACCTACTACAACCCCA GCCTGAAGTCTCTGGTCACCATCAGCCGGGACAACAGCAAG AACACCCTGTACCTGCAGATGAACAGCCTGAGAGCCGAGGA CACCGCCGTGTACTATTGTGCTAGAGGCGCCCTGGACTACTT CGACCTTTGGGGACAAGGCGCCCTCGTGACAGTCTCTTCTGC GGCCGCAACCACTACTQCGGCACCTAGGCCCCCCACTCCGG CACCGACCATTGCATCACAACCACTGAGTCTTAGACCTGAA GCCTGTCGACCCGCAGCTGGGGGGGCAGTCCACACACGGGG ATTGGATTTCGCCTGCGATATATACATTTGGGCGCCACTGGC AGGCACCTGCGGGGTCCTGCTCTTGTCCCTTGTCATCACCCT GTACTGTAAGAGAGGAAGAAAGAAGTTGTTGTATATTTTCA AACAGCCATTCATGAGGCCGGTCCAGACCACTCAGGAGGAG GATGGATGCAGTTGCCGCTTTCCGGAAGAGGAAGAGGGTGG GTGTGAACTCCGAGTTAAATTTTCTCGCAGTGCTGATGCCCC AGCGTATAAACAGGGTCAGAACCAACTGTATAATGAACTCA ATTTGGGGAGGCGAGAGGAGTATGATGTATTGGACAAGCGG CGGGGGCGGGATCCTGAAATGGGCGGTAAGCCAAGGCGCA AGAATCCACAGGAGGGTTTGTATAATGAGTTGCAGAAGGAT AAAATGGCGGAAGCGTATTCAGAAATCGGAATGAAGGGAG AGCGCCGCAGAGGGAAAGGGCATGATGGCCTCTACCAAGGT TTGTCAACAGCGACCAAGGATACCTATGACGCACTTCATATG CAAGCACTGCCCCCCAGG |
| H4 L chain SEQ ID NO: 174 | DIQMTQSPSSLSASVGDRVTITCRASQSISSYLNWYQQKPGKAP KLLIYAASSLQSGVPSRFSGSGSGTDFTLTISSLQPEDVGVYYCL QITHWPHTFGQGTKLEIKR |
| H4 L chain SEQ ID NO: 175 | GACATCCAGATGACACAGAGCCCTAGCAGCCTGTCTGCCAG CGTGGGAGACAGAGTGACCATCACCTGTAGAGCCAGCCAGA GCATCAGCAGCTACCTGAACTGGTATCAGCAGAAGCCCGGC AAGGCCCCTAAACTGCTGATCTATGCCGCCAGCTCTCTGCAG TCTGGCGTGCCATCTAGATTTTCCGGCAGCGGCTCTGGCACC GACTTCACCCTGACCATATCTAGCCTGCAGCCTGAGGACGTG GGCGTGTACTACTGCCTGCAGATCACACACTGGCCCCACAC ATTTGGCCAGGGCACCAAGCTGGAAATCAAGAGA |
| H4 H chain SEQ ID NO: 176 | QVQLVESGGGLVKPGGSLRLSCAASGFTFSDYYMSWIRQAPGK GLEWVSYISSSGSTIYYADSVKGRFTISRDNAKNSLYLQMNSLR AEDTAMYYCARDAPDLLAVPTVIFSGYHYGADVWGQGATVT VSS |
| H4 H chain SEQ ID NO: 177 | CAAGTTCAGCTGGTTGAATCTGGCGGCGGACTGGTTAAGCCT GGCGGTTCTCTGAGACTGAGCTGTGCCGCCTCCGGCTTCACC TTCAGCGACTACTACATGAGCTGGATCAGACAGGCCCCTGG CAAAGGCCTGGAATGGGTGTCCTACATCAGCTCCAGCGGCA GCACCATCTACTACGCCGATAGCGTGAAGGGCAGATTCACC ATCAGCCGGGACAACGCCAAGAACAGCCTGTACCTGCAGAT GAACTCCCTGAGAGCCGAGGACACCGCCATGTACTATTGCG CCAGAGATGCCCCTGACCTGCTGGCTGTGCCTACCGTGATCT TTAGCGGCTACCACTACGGCGCTGACGTTTGGGGACAAGGC GCCACAGTGACAGTGTCTAGT |
| H4LH binder SEQ ID NO: 178 | GACATCCAGATGACACAGAGCCCTAGCAGCCTGTCTGCCAG CGTGGGAGACAGAGTGACCATCACCTGTAGAGCCAGCCAGA GCATCAGCAGCTACCTGAACTGGTATCAGCAGAAGCCCGGC AAGGCCCCTAAACTGCTGATCTATGCCGCCAGCTCTCTGCAG TCTGGCGTGCCATCTAGATTTTCCGGCAGCGGCTCTGGCACC GACTTCACCCTGACCATATCTAGCCTGCAGCCTGAGGACGTG GGCGTGTACTACTGCCTGCAGATCACACACTGGCCCCACAC ATTTGGCCAGGGCACCAAGCTGGAAATCAAGAGAGGTGGCG GAGGATCTGGCGGAGGTGGAAGCGGCGGAGGCGGATCTCAA GTTCAGCTGGTTGAATCTGGCGGCGGACTGGTTAAGCCTGGC GGTTCTCTGAGACTGAGCTGTGCCGCCTCCGGCTTCACCTTC AGCGACTACTACATGAGCTGGATCAGACAGGCCCCTGGCAA AGGCCTGGAATGGGTGTCCTACATCAGCTCCAGCGGCAGCA CCATCTACTACGCCGATAGCGTGAAGGGCAGATTCACCATC AGCCGGGACAACGCCAAGAACAGCCTGTACCTGCAGATGAA CTCCCTGAGAGCCGAGGACACCGCCATGTACTATTGCGCCA GAGATGCCCCTGACCTGCTGGCTGTGCCTACCGTGATCTTTA |

TABLE 6-continued

| Feature SEQ ID NO | Sequence |
|---|---|
| | GCGGCTACCACTACGGCGCTGACGTTTGGGGACAAGGCGCC ACAGTGACAGTGTCTAGT |
| H4HL binder SEQ ID NO: 179 | CAAGTTCAGCTGGTTGAATCTGGCGGCGGACTGGTTAAGCCT GGCGGTTCTCTGAGACTGAGCTGTGCCGCCTCCGGCTTCACC TTCAGCGACTACTACATGAGCTGGATCAGACAGGCCCCTGG CAAAGGCCTGGAATGGGTGTCCTACATCAGCTCCAGCGGCA GCACCATCTACTACGCCGATAGCGTGAAGGGCAGATTCACC ATCAGCCGGGACAACGCCAAGAACAGCCTGTACCTGCAGAT GAACTCCCTGAGAGCCGAGGACACCGCCATGTACTATTGCG CCAGAGATGCCCCTGACCTGCTGGCTGTGCCTACCGTGATCT TTAGCGGCTACCACTACGGCGCTGACGTTTGGGGACAAGGC GCCACAGTGACAGTGTCTAGTGGTGGCGGAGGATCTGGCGG AGGTGGAAGCGGCGGAGGCGGATCTGACATCCAGATGACAC AGAGCCCTAGCAGCCTGTCTGCCAGCGTGGGAGACAGAGTG ACCATCACCTGTAGAGCCAGCCAGAGCATCAGCAGCTACCT GAACTGGTATCAGCAGAAGCCCGGCAAGGCCCCTAAACTGC TGATCTATGCCGCCAGCTCTCTGCAGTCTGGCGTGCCATCTA GATTTTCCGGCAGCGGCTCTGGCACCGACTTCACCCTGACCA TATCTAGCCTGCAGCCTGAGGACGTGGGCGTGTACTACTGCC TGCAGATCACACACTGGCCCCACACATTTGGCCAGGGCACC AAGCTGGAAATCAAGAGA |
| RJ149LH CAR (H4LH/CD8TM/ 4-1BB/CD3zeta) SEQ ID NO: 180 | MLLLVTSLLLCELPHPAFLLIPDIQMTQSPSSLSASVGDRVTITC RASQSISSYLNWYQQKPGKAPKLLIYAASSLQSGVPSRFSGSGS GTDFTLTISSLQPEDVGVYYCLQITHWPHTFGQGTKLEIKRGGG GSGGGGSGGGGSQVQLVESGGGLVKPGGSLRLSCAASGFTFSD YYMSWIRQAPGKGLEWVSYISSSGSTIYYADSVKGRFTISRDNA KNSLYLQMNSLRAEDTAMYYCARDAPDLLAVPTVIFSGYHYG ADVWGQGATVTVSSAAATTTPAPRPPTPAPTIASQPLSLRPEAC RPAAGGAVHTRGLDFACDIYIWAPLAGTCGVLLLSLVITLYCK RGRKKLLYIFKQPFMRPVQTTQEEDGCSCRFPEEEEGGCELRVK FSRSADAPAYKQGQNQLYNELNLGRREEYDVLDKRRGRDPEM GGKPRRKNPQEGLYNELQKDKMAEAYSEIGMKGERRRGKGH DGLYQGLSTATKDTYDALHMQALPPR |
| RJ149LH CAR (H4LH/CD8TM/ 4-1BB/CD3zeta) SEQ ID NO: 181 | ATGCTTCTGCTCGTGACAAGCCTGCTGCTGTGCGAGCTGCCC CACCCTGCCTTTCTGCTGATCCCTGACATCCAGATGACACAG AGCCCTAGCAGCCTGTCTGCCAGCGTGGGAGACAGAGTGAC CATCACCTGTAGAGCCAGCCAGAGCATCAGCAGCTACCTGA ACTGGTATCAGCAGAAGCCCGGCAAGGCCCCTAAACTGCTG ATCTATGCCGCCAGCTCTCTGCAGTCTGGCGTGCCATCTAGA TTTTCCGGCAGCGGCTCTGGCACCGACTTCACCCTGACCATA TCTAGCCTGCAGCCTGAGGACGTGGGCGTGTACTACTGCCTG CAGATCACACACTGGCCCCACACATTTGGCCAGGGCACCAA GCTGGAAATCAAGAGAGGTGGCGGAGGATCTGGCGGAGGTG GAAGCGGCGGAGGCGGATCTCAAGTTCAGCTGGTTGAATCT GGCGGCGGACTGGTTAAGCCTGGCGGTTCTCTGAGACTGAG CTGTGCCGCCTCCGGCTTCACCTTCAGCGACTACTACATGAG CTGGATCAGACAGGCCCCTGGCAAAGGCCTGGAATGGGTGT CCTACATCAGCTCCAGCGGCAGCACCATCTACTACGCCGATA GCGTGAAGGGCAGATTCACCATCAGCCGGGACAACGCCAAG AACAGCCTGTACCTGCAGATGAACTCCCTGAGAGCCGAGGA CACCGCCATGTACTATTGCGCCAGAGATGCCCCTGACCTGCT GGCTGTGCCTACCGTGATCTTTAGCGGCTACCACTACGGCGC TGACGTTTGGGGACAAGGCGCCACAGTGACAGTGTCTAGTG CGGCCGCAACCACTACTCCGGCACCTAGGCCCCCCACTCCG GCACCGACCATTGCATCACAACCACTGAGTCTTAGACCTGA AGCCTGTCGACCCGCAGCTGGGGGGGCAGTCCACACACGGG GATTGGATTTCGCCTGCGATATATACATTTGGGCGCCACTGG CAGGCACCTGCGGGGTCCTGCTCTTGTCCCTTGTCATCACCC TGTACTGTAAGAGAGGAAGAAAGAAGTTGTTGTATATTTTCA AACAGCCATTCATGAGGCCGGTCCAGACCACTCAGGAGGAG GATGGATGCAGTTGCCGCTTTCCGGAAGAGGAAGAGGGTGG GTGTGAACTCCGAGTTAAATTTTCTCGCAGTGCTGATGCCCC AGCGTATAAACAGGGTCAGAACCAACTGTATAATGAACTCA ATTTGGGGAGGCGAGAGGAGTATGATGTATTGGACAAGCGG CGGGGGGGGATCCTGAAATGGGCGGTAAGCCAAGGCGCA AGAATCCACAGGAGGGTTTGTATAATGAGTTGCAGAAGGAT AAAATGGCGGAAGCGTATTCAGAAATCGGAATGAAGGGAG AGCGCCGCAGAGGGAAAGGGCATGATGGCCTCTACCAAGGT TTGTCAACAGCGACCAAGGATACCTATGACGCACTTCATATG CAAGCACTGCCCCCCAGG |

TABLE 6-continued

| Feature SEQ ID NO | Sequence |
|---|---|
| RJ149HL CAR (H4HL/CD8TM/ 4-1BB/CD3zeta) SEQ ID NO: 182 | MLLLVTSLLLCELPHPAFLLIPQVQLVESGGGLVKPGGSLRLSC AASGFTFSDYYMSWIRQAPGKGLEWVSYISSSGSTIYYADSVK GRFTISRDNAKNSLYLQMNSLRAEDTAMYYCARDAPDLLAVP TVIFSGYHYGADVWGQGATVTVSSGGGGSGGGGSGGGGSDIQ MTQSPSSLSASVGDRVTITCRASQSISSYLNWYQQKPGKAPKLL IYAASSLQSGVPSRFSGSGSGTDFTLTISSLQPEDVGVYYCLQIT HWPHTFGQGTKLEIKRAAATTTPAPRPPTPAPTIASQPLSLRPEA CRPAAGGAVHTRGLDFACDIYIWAPLAGTCGVLLLSLVITLYC KRGRKKLLYIFKQPFMRPVQTTQEEDGCSCRFPEEEEGGCELRV KFSRSADAPAYKQGQNQLYNELNLGRREEYDVLDKRRGRDPE MGGKPRRKNPQEGLYNELQKDKMAEAYSEIGMKGERRRGKG HDGLYQGLSTATKDTYDALHMQALPPR |
| RJ149HL CAR (H4HL/CD8TM/ 4-1BB/CD3zeta) SEQ ID NO: 183 | ATGCTTCTGCTCGTGACAAGCCTGCTGCTGTGCGAGCTGCCC CACCCTGCCTTTCTGCTGATCCCTCAAGTTCAGCTGGTTGAA TCTGGCGGCGGACTGGTTAAGCCTGGCGGTTCTCTGAGACTG AGCTGTGCCGCCTCCGGCTTCACCTTCAGCGACTACTACATG AGCTGGATCAGACAGGCCCCTGGCAAAGGCCTGGAATGGGT GTCCTACATCAGCTCCAGCGGCAGCACCATCTACTACGCCGA TAGCGTGAAGGGCAGATTCACCATCAGCCGGGACAACGCCA AGAACAGCCTGTACCTGCAGATGAACTCCCTGAGAGCCGAG GACACCGCCATGTACTATTGCGCCAGAGATGCCCCTGACCTG CTGGCTGTGCCTACCGTGATCTTTAGCGGCTACCACTACGGC GCTGACGTTTGGGGACAAGGCGCCACAGTGACAGTGTCTAG TGGTGGCGGAGGATCTGGCGGAGGTGGAAGCGGCGGAGGC GGATCTGACATCCAGATGACACAGAGCCCTAGCAGCCTGTC TGCCAGCGTGGGAGACAGAGTGACCATCACCTGTAGAGCCA GCCAGAGCATCAGCAGCTACCTGAACTGGTATCAGCAGAAG CCCGGCAAGGCCCCTAAACTGCTGATCTATGCCGCCAGCTCT CTGCAGTCTGGCGTGCCATCTAGATTTTCCGGCAGCGGCTCT GGCACCGACTTCACCCTGACCATATCTAGCCTGCAGCCTGAG GACGTGGGCGTGTACTACTGCCTGCAGATCACACACTGGCC CCACACATTTGGCCAGGGCACCAAGCTGGAAATCAAGAGAG CGGCCGCAACCACTACTCCGGCACCTAGGCCCCCCACTCCG GCACCGACCATTGCATCACAACCACTGAGTCTTAGACCTGA AGCCTGTCGACCCGCAGCTGGGGGGGCAGTCCACACACGGG GATTGGATTTCGCCTGCGATATATACATTTGGGCGCCACTGG CAGGCACCTGCGGGGTCCTGCTCTTGTCCCTTGTCATCACCC TGTACTGTAAGAGAGGAAGAAAGAAGTTGTTGTATATTTTCA AACAGCCATTCATGAGGCCGGTCCAGACCACTCAGGAGGAG GATGGATGCAGTTGCCGCTTTCCGGAAGAGGAAGAGGGTGG GTGTGAACTCCGAGTTAAATTTTCTCGCAGTGCTGATGCCCC AGCGTATAAACAGGGTCAGAACCAACTGTATAATGAACTCA ATTTGGGGAGGCGAGAGGAGTATGATGTATTGGACAAGCGG CGGGGGCGGGATCCTGAAATGGGCGGTAAGCCAAGGCGCA AGAATCCACAGGAGGGTTTGTATAATGAGTTGCAGAAGGAT AAAATGGCGGAAGCGTATTCAGAAATCGGAATGAAGGGAG AGCGCCGCAGAGGGAAAGGGCATGATGGCCTCTACCAAGGT TTGTCAACAGCGACCAAGGATACCTATGACGCACTTCATATG CAAGCACTGCCCCCCAGG |
| G6 L chain SEQ ID NO: 184 | DIQMTQSPSSLSASVGDRVTITCRASQSISSYLNWYQQKPGKAP KLLIYAASSLQSGVPSRFSGSGSGTDFTLTISSLQPEDAATYYCQ HYGTFGQGTKLEIKR |
| G6 L chain SEQ ID NO: 185 | GACATCCAGATGACACAGAGCCCTAGCAGCCTGTCTGCCAG CGTGGGAGACAGAGTGACCATCACCTGTAGAGCCAGCCAGA GCATCAGCAGCTACCTGAACTGGTATCAGCAGAAGCCCGGC AAGGCCCCTAAACTGCTGATCTATGCCGCCAGCTCTCTGCAG TCTGGCGTGCCATCTAGATTTTCCGGCAGCGGCTCTGGCACC GACTTCACCCTGACCATATCTAGCCTGCAGCCTGAGGATGCC GCCACCTACTACTGTCAGCACTACGGCACATTTGGCCAGGGC ACCAAGCTGGAAATCAAGAGA |
| G6 H chain SEQ ID NO: 186 | QVQLVESGGGLVKPGGSLRLSCAASGFTFSDYYMSWIRQAPGK GLEWVSYISSSGSTIYYADSVKGRFTISRDNAKNSLYLQMNSLR AEDTAVYYCARHKTSLNDYDFWSGYLLDYWGQGTLVTVSS |
| G6 H chain SEQ ID NO: 187 | CAAGTTCAGCTGGTTGAATCTGGCGGCGGACTGGTTAAGCCT GGCGGTTCTCTGAGACTGAGCTGTGCCGCCTCCGGCTTCACC TTCAGCGACTACTACATGAGCTGGATCAGACAGGCCCCTGG CAAAGGCCTGGAATGGGTGTCCTACATCAGCTCCAGCGGCA GCACCATCTACTACGCCGATAGCGTGAAGGGCAGATTCACC ATCAGCCGGGACAACGCCAAGAACAGCCTGTACCTGCAGAT GAACTCCCTGAGAGCCGAGGACACCGCCGTGTACTATTGCG CCAGACACAAGACCAGCCTGAACGACTACGACTTTTGGAGC |

TABLE 6-continued

| Feature SEQ ID NO | Sequence |
|---|---|
| | GGCTACCTGCTGGACTATTGGGGCCAGGGAACACTGGTCAC CGTGTCTAGT |
| G6LH binder SEQ ID NO: 188 | GACATCCAGATGACACAGAGCCCTAGCAGCCTGTCTGCCAG CGTGGGAGACAGAGTGACCATCACCTGTAGAGCCAGCCAGA GCATCAGCAGCTACCTGAACTGGTATCAGCAGAAGCCCGGC AAGGCCCCTAAACTGCTGATCTATGCCGCCAGCTCTCTGCAG TCTGGCGTGCCATCTAGATTTTCCGGCAGCGGCTCTGGCACC GACTTCACCCTGACCATATCTAGCCTGCAGCCTGAGGATGCC GCCACCTACTACTGTCAGCACTACGGCACATTTGGCCAGGGC ACCAAGCTGGAAATCAAGAGAGGTGGCGGAGGATCTGGCGG AGGTGGAAGCGGCGGAGGCGGATCTCAAGTTCAGCTGGTTG AATCTGGCGGCGGACTGGTTAAGCCTGGCGGTTCTCTGAGAC TGAGCTGTGCCGCCTCCGGCTTCACCTTCAGCGACTACTACA TGAGCTGGATCAGACAGGCCCCTGGCAAAGGCCTGGAATGG GTGTCCTACATCAGCTCCAGCGGCAGCACCATCTACTACGCC GATAGCGTGAAGGGCAGATTCACCATCAGCCGGGACAACGC CAAGAACAGCCTGTACCTGCAGATGAACTCCCTGAGAGCCG AGGACACCGCCGTGTACTATTGCGCCAGACACAAGACCAGC CTGAACGACTACGACTTTTGGAGCGGCTACCTGCTGGACTAT TGGGGCCAGGGAACACTGGTCACCGTGTCTAGT |
| G6HL binder SEQ ID NO: 189 | CAAGTTCAGCTGGTTGAATCTGGCGGCGGACTGGTTAAGCCT GGCGGTTCTCTGAGACTGAGCTGTGCCGCCTCCGGCTTCACC TTCAGCGACTACTACATGAGCTGGATCAGACAGGCCCCTGG CAAAGGCCTGGAATGGGTGTCCTACATCAGCTCCAGCGGCA GCACCATCTACTACGCCGATAGCGTGAAGGGCAGATTCACC ATCAGCCGGGACAACGCCAAGAACAGCCTGTACCTGCAGAT GAACTCCCTGAGAGCCGAGGACACCGCCGTGTACTATTGCG CCAGACACAAGACCAGCCTGAACGACTACGACTTTTGGAGC GGCTACCTGCTGGACTATTGGGGCCAGGGAACACTGGTCAC CGTGTCTAGTGGTGGCGGAGGATCTGGCGGAGGTGGAAGCG GCGGAGGCGGATCTGACATCCAGATGACACAGAGCCCTAGC AGCCTGTCTGCCAGCGTGGGAGACAGAGTGACCATCACCTG TAGAGCCAGCCAGAGCATCAGCAGCTACCTGAACTGGTATC AGCAGAAGCCCGGCAAGGCCCCTAAACTGCTGATCTATGCC GCCAGCTCTCTGCAGTCTGGCGTGCCATCTAGATTTTCCGGC AGCGGCTCTGGCACCGACTTCACCCTGACCATATCTAGCCTG CAGCCTGAGGATGCCGCCACCTACTACTGTCAGCACTACGG CACATTTGGCCAGGGCACCAAGCTGGAAATCAAGAGA |
| RJ150LH CAR (G6LH/CD8TM/ 4-1BB/CD3zeta) SEQ ID NO: 190 | MLLLVTSLLLCELPHPAFLLIPDIQMTQSPSSLSASVGDRVTITC RASQSISSYLNWYQQKPGKAPKLLIYAASSLQSGVPSRFSGSGS GTDFTLTISSLQPEDAATYYCQHYGTFGQGTKLEIKRGGGGSGG GGSGGGGSQVQLVESGGGLVKPGGSLRLSCAASGFTFSDYYMS WIRQAPGKGLEWVSYISSSGSTIYYADSVKGRFTISRDNAKNSL YLQMNSLRAEDTAVYYCARHKTSLNDYDFWSGYLLDYWGQG TLVTVSSAAATTTPAPRPPTPAPTIASQPLSLRPEACRPAAGGAV HTRGLDFACDIYIWAPLAGTCGVLLLSLVITLYCKRGRKKLLYI FKQPFMRPVQTTQEEDGCSCRFPEEEEGGCELRVKFSRSADAPA YKQGQNQLYNELNLGRREEYDVLDKRRGRDPEMGGKPRRKN PQEGLYNELQKDKMAEAYSEIGMKGERRRGKGHDGLYQGLST ATKDTYDALHMQALPPR |
| RJ150LH CAR (G6LH/CD8TM/ 4-1BB/CD3zeta) SEQ ID NO: 191 | ATGCTTCTGCTCGTGACAAGCCTGCTGCTGTGCGAGCTGCCC CACCCTGCCTTTCTGCTGATCCCTGACATCCAGATGACACAG AGCCCTAGCAGCCTGTCTGCCAGCGTGGGAGACAGAGTGAC CATCACCTGTAGAGCCAGCCAGAGCATCAGCAGCTACCTGA ACTGGTATCAGCAGAAGCCCGGCAAGGCCCCTAAACTGCTG ATCTATGCCGCCAGCTCTCTGCAGTCTGGCGTGCCATCTAGA TTTTCCGGCAGCGGCTCTGGCACCGACTTCACCCTGACCATA TCTAGCCTGCAGCCTGAGGATGCCGCCACCTACTACTGTCAG CACTACGGCACATTTGGCCAGGGCACCAAGCTGGAAATCAA GAGAGGTGGCGGAGGATCTGGCGGAGGTGGAAGCGGCGGA GGCGGATCTCAAGTTCAGCTGGTTGAATCTGGCGGCGGACT GGTTAAGCCTGGCGGTTCTCTGAGACTGAGCTGTGCCGCCTC CGGCTTCACCTTCAGCGACTACTACATGAGCTGGATCAGACA GGCCCCTGGCAAAGGCCTGGAATGGGTGTCCTACATCAGCT CCAGCGGCAGCACCATCTACTACGCCGATAGCGTGAAGGGC AGATTCACCATCAGCCGGGACAACGCCAAGAACAGCCTGTA CCTGCAGATGAACTCCCTGAGAGCCGAGGACACCGCCGTGT ACTATTGCGCCAGACACAAGACCAGCCTGAACGACTACGAC TTTTGGAGCGGCTACCTGCTGGACTATTGGGGCCAGGGAAC ACTGGTCACCGTGTCTAGTGCGGCCGCAACCACTACTCCGGC ACCTAGGCCCCCCACTCCGGCACCGACCATTGCATCACAACC ACTGAGTCTTAGACCTGAAGCCTGTCGACCCGCAGCTGGGG GGGCAGTCCACACACGGGGATTGGATTTCGCCTGCGATATAT |

TABLE 6-continued

| Feature SEQ ID NO | Sequence |
|---|---|
| | ACATTTGGGCGCCACTGGCAGGCACCTGCGGGGTCCTGCTCT TGTCCCTTGTCATCACCCTGTACTGTAAGAGAGGAAGAAAG AAGTTGTTGTATATTTTCAAACAGCCATTCATGAGGCCGGTC CAGACCACTCAGGAGGAGGATGGATGCAGTTGCCGCTTTCC GGAAGAGGAAGAGGGTGGGTGTGAACTCCGAGTTAAATTTT CTCGCAGTGCTGATGCCCCAGCGTATAAACAGGGTCAGAAC CAACTGTATAATGAACTCAATTTGGGGAGGCGAGAGGAGTA TGATGTATTGGACAAGCGGCGGGGGCGGGATCCTGAAATGG GCGGTAAGCCAAGGCGCAAGAATCCACAGGAGGGTTTGTAT AATGAGTTGCAGAAGGATAAAATGGCGGAAGCGTATTCAGA AATCGGAATGAAGGGAGAGCGCCGCAGAGGGAAAGGGCAT GATGGCCTCTACCAAGGTTTGTCAACAGCGACCAAGGATAC CTATGACGCACTTCATATGCAAGCACTGCCCCCCAGG |
| RJ150HL CAR (G6HL/CD8TM/ 4-1BB/CD3zeta) SEQ ID NO: 192 | MLLLVTSLLLCELPHPAFLLIPQVQLVESGGGLVKPGGSLRLSC AASGFTFSDYYMSWIRQAPGKGLEWVSYISSSGSTIYYADSVK GRFTISRDNAKNSLYLQMNSLRAEDTAVYYCARHKTSLNDYD FWSGYLLDYWGQGTLVTVSSGGGGSGGGGSGGGGSDIQMTQS PSSLSASVGDRVTITCRASQSISSYLNWYQQKPGKAPKLLIYAA SSLQSGVPSRFSGSGSGTDFTLTISSLQPEDAATYYCQHYGTFG QGTKLEIKRAAATTTPAPRPPTPAPTIASQPLSLRPEACRPAAGG AVHTRGLDFACDIYIWAPLAGTCGVLLLSLVITLYCKRGRKKLL YIFKQPFMRPVQTTQEEDGCSCRFPEEEEGGCELRVKFSRSADA PAYKQGQNQLYNELNLGRREEYDVLDKRRGRDPEMGGKPRR KNPQEGLYNELQKDKMAEAYSEIGMKGERRRGKGHDGLYQG LSTATKDTYDALHMQALPPR |
| RJ150HL CAR (G6HL/CD8TM/ 4-1BB/CD3zeta) SEQ ID NO: 193 | ATGCTTCTGCTCGTGACAAGCCTGCTGCTGTGCGAGCTGCCC CACCCTGCCTTTCTGCTGATCCCTCAAGTTCAGCTGGTTGAA TCTGGCGGCGGACTGGTTAAGCCTGGCGGTTCTCTGAGACTG AGCTGTGCCGCCTCCGGCTTCACCTTCAGCGACTACTACATG AGCTGGATCAGACAGGCCCCTGGCAAAGGCCTGGAATGGGT GTCCTACATCAGCTCCAGCGGCAGCACCATCTACTACGCCGA TAGCGTGAAGGGCAGATTCACCATCAGCCGGGACAACGCCA AGAACAGCCTGTACCTGCAGATGAACTCCCTGAGAGCCGAG GACACCGCCGTGTACTATTGCGCCAGACACAAGACCAGCCT GAACGACTACGACTTTTGGAGCGGCTACCTGCTGGACTATTG GGGCCAGGGAACACTGGTCACCGTGTCTAGTGGTGGCGGAG GATCTGGCGGAGGTGGAAGCGGCGGAGGCGGATCTGACATC CAGATGACACAGAGCCCTAGCAGCCTGTCTGCCAGCGTGGG AGACAGAGTGACCATCACCTGTAGAGCCAGCCAGAGCATCA GCAGCTACCTGAACTGGTATCAGCAGAAGCCCGGCAAGGCC CCTAAACTGCTGATCTATGCCGCCAGCTCTCTGCAGTCTGGC GTGCCATCTAGATTTTCCGGCAGCGGCTCTGGCACCGACTTC ACCCTGACCATATCTAGCCTGCAGCCTGAGGATGCCGCCACC TACTACTGTCAGCACTACGGCACATTTGGCCAGGGCACCAA GCTGGAAATCAAGAGAGCGGCCGCAACCACTACTCCGGCAC CTAGGCCCCCCACTCCGGCACCGACCATTGCATCACAACCAC TGAGTCTTAGACCTGAAGCCTGTCGACCCGCAGCTGGGGGG GCAGTCCACACACGGGGATTGGATTTCGCCTGCGATATATAC ATTTGGGCGCCACTGGCAGGCACCTGCGGGGTCCTGCTCTTG TCCCTTGTCATCACCCTGTACTGTAAGAGAGGAAGAAAGAA GTTGTTGTATATTTTCAAACAGCCATTCATGAGGCCGGTCCA GACCACTCAGGAGGAGGATGGATGCAGTTGCCGCTTTCCGG AAGAGGAAGAGGGTGGGTGTGAACTCCGAGTTAAATTTTCT CGCAGTGCTGATGCCCCAGCGTATAAACAGGGTCAGAACCA ACTGTATAATGAACTCAATTTGGGGAGGCGAGAGGAGTATG ATGTATTGGACAAGCGGCGGGGGCGGGATCCTGAAATGGGC GGTAAGCCAAGGCGCAAGAATCCACAGGAGGGTTTGTATAA TGAGTTGCAGAAGGATAAAATGGCGGAAGCGTATTCAGAAA TCGGAATGAAGGGAGAGCGCCGCAGAGGGAAAGGGCATGA TGGCCTCTACCAAGGTTTGTCAACAGCGACCAAGGATACCT ATGACGCACTTCATATGCAAGCACTGCCCCCCAGG |
| C9 L chain SEQ ID NO: 194 | DIQMTQSPSSLSASVGDRVTITCRASQSISSYLNWYQQKPGKAP KLLIYAASSLQSGVPSRFSGSGSGTDFTLTISSLQPEDFAVYYCQ QRSNWPPTFGQGTKLEIKR |
| C9 L chain SEQ ID NO: 195 | GACATCCAGATGACACAGAGCCCTAGCAGCCTGTCTGCCAG CGTGGGAGACAGAGTGACCATCACCTGTAGAGCCAGCCAGA GCATCAGCAGCTACCTGAACTGGTATCAGCAGAAGCCCGGC AAGGCCCCTAAACTGCTGATCTATGCCGCCAGCTCTCTGCAG TCTGGCGTGCCATCTAGATTTTCCGGCAGCGGCTCTGGCACC GACTTCACCCTGACCATATCTAGCCTGCAGCCTGAGGACTTC GCCGTGTACTACTGCCAGCAGAGAAGCAACTGGCCTCCTAC CTTTGGCCAGGGCACCAAGCTGGAAATCAAGAGA |

TABLE 6-continued

| Feature SEQ ID NO | Sequence |
|---|---|
| C9 H chain SEQ ID NO: 196 | QVQLVESGGGLVKPGGSLRLSCAASGFTFSDYYMSWIRQAPGK GLEWVSYISSSGSTIYYADSVKGRFTISRDNAKNSLYLQMNSLR AEDTAKYYCATAVFSLGPEGYYYYMDVWGKGTTVTVSS |
| C9 H chain SEQ ID NO: 197 | CAAGTTCAGCTGGTTGAATCTGGCGGCGGACTGGTTAAGCCT GGCGGTTCTCTGAGACTGAGCTGTGCCGCCTCCGGCTTCACC TTCAGCGACTACTACATGAGCTGGATCAGACAGGCCCCTGG CAAAGGCCTGGAATGGGTGTCCTACATCAGCTCCAGCGGCA GCACCATCTACTACGCCGATAGCGTGAAGGGCAGATTCACC ATCAGCCGGGACAACGCCAAGAACAGCCTGTACCTGCAGAT GAACTCCCTGAGAGCCGAGGATACCGCCAAGTACTACTGTG CCACCGCCGTGTTTTCTCTGGGCCCTGAGGGCTACTACTACT ATATGGACGTGTGGGGCAAGGGCACCACCGTGACAGTTTCT TCT |
| C9LH binder SEQ ID NO: 198 | GACATCCAGATGACACAGAGCCCTAGCAGCCTGTCTGCCAG CGTGGGAGACAGAGTGACCATCACCTGTAGAGCCAGCCAGA GCATCAGCAGCTACCTGAACTGGTATCAGCAGAAGCCCGGC AAGGCCCCTAAACTGCTGATCTATGCCGCCAGCTCTCTGCAG TCTGGCGTGCCATCTAGATTTTCCGGCAGCGGCTCTGGCACC GACTTCACCCTGACCATATCTAGCCTGCAGCCTGAGGACTTC GCCGTGTACTACTGCCAGCAGAGAAGCAACTGGCCTCCTAC CTTTGGCCAGGGCACCAAGCTGGAAATCAAGAGAGGTGGCG GAGGATCTGGCGGAGGTGGAAGCGGCGGAGGCGGATCTCAA GTTCAGCTGGTTGAATCTGGCGGCGGACTGGTTAAGCCTGGC GGTTCTCTGAGACTGAGCTGTGCCGCCTCCGGCTTCACCTTC AGCGACTACTACATGAGCTGGATCAGACAGGCCCCTGGCAA AGGCCTGGAATGGGTGTCCTACATCAGCTCCAGCGGCAGCA CCATCTACTACGCCGATAGCGTGAAGGGCAGATTCACCATC AGCCGGGACAACGCCAAGAACAGCCTGTACCTGCAGATGAA CTCCCTGAGAGCCGAGGATACCGCCAAGTACTACTGTGCCA CCGCCGTGTTTTCTCTGGGCCCTGAGGGCTACTACTACTATA TGGACGTGTGGGGCAAGGGCACCACCGTGACAGTTTCTTCT |
| C9HL binder SEQ ID NO: 199 | CAAGTTCAGCTGGTTGAATCTGGCGGCGGACTGGTTAAGCCT GGCGGTTCTCTGAGACTGAGCTGTGCCGCCTCCGGCTTCACC TTCAGCGACTACTACATGAGCTGGATCAGACAGGCCCCTGG CAAAGGCCTGGAATGGGTGTCCTACATCAGCTCCAGCGGCA GCACCATCTACTACGCCGATAGCGTGAAGGGCAGATTCACC ATCAGCCGGGACAACGCCAAGAACAGCCTGTACCTGCAGAT GAACTCCCTGAGAGCCGAGGATACCGCCAAGTACTACTGTG CCACCGCCGTGTTTTCTCTGGGCCCTGAGGGCTACTACTACT ATATGGACGTGTGGGGCAAGGGCACCACCGTGACAGTTTCT TCTGGTGGCGGAGGATCTGGCGGAGGTGGAAGCGGCGGAGG CGGATCTGACATCCAGATGACACAGAGCCCTAGCAGCCTGT CTGCCAGCGTGGGAGACAGAGTGACCATCACCTGTAGAGCC AGCCAGAGCATCAGCAGCTACCTGAACTGGTATCAGCAGAA GCCCGGCAAGGCCCCTAAACTGCTGATCTATGCCGCCAGCTC TCTGCAGTCTGGCGTGCCATCTAGATTTTCCGGCAGCGGCTC TGGCACCGACTTCACCCTGACCATATCTAGCCTGCAGCCTGA GGACTTCGCCGTGTACTACTGCCAGCAGAGAAGCAACTGGC CTCCTACCTTTGGCCAGGGCACCAAGCTGGAAATCAAGAGA |
| RJ151LH CAR (C9LH/CD8TM/ 4-1BB/CD3zeta) SEQ ID NO: 200 | MLLLVTSLLLCELPHPAFLLIPDIQMTQSPSSLSASVGDRVTITC RASQSISSYLNWYQQKPGKAPKLLIYAASSLQSGVPSRFSGSGS GTDFTLTISSLQPEDFAVYYCQQRSNWPPTFGQGTKLEIKRGGG GSGGGGSGGGGSQVQLVESGGGLVKPGGSLRLSCAASGFTFSD YYMSWIRQAPGKGLEWVSYISSSGSTIYYADSVKGRFTISRDNA KNSLYLQMNSLRAEDTAKYYCATAVFSLGPEGYYYYMDVWG KGTTVTVSSAAATTTPAPRPPTPAPTIASQPLSLRPEACRPAAGG AVHTRGLDFACDIYIWAPLAGTCGVLLLSLVITLYCKRGRKKLL YIFKQPFMRPVQTTQEEDGCSCRFPEEEEGGCELRVKFSRSADA PAYKQGQNQLYNELNLGRREEYDVLDKRRGRDPEMGGKPRR KNPQEGLYNELQKDKMAEAYSEIGMKGERRRGKGHDGLYQG LSTATKDTYDALHMQALPPR |
| RJ151LH CAR (C9LH/CD8TM/ 4-1BB/CD3zeta) SEQ ID NO: 201 | ATGCTTCTGCTCGTGACAAGCCTGCTGCTGTGCGAGCTGCCC CACCCTGCCTTTCTGCTGATCCCTGACATCCAGATGACACAG AGCCCTAGCAGCCTGTCTGCCAGCGTGGGAGACAGAGTGAC CATCACCTGTAGAGCCAGCCAGAGCATCAGCAGCTACCTGA ACTGGTATCAGCAGAAGCCCGGCAAGGCCCCTAAACTGCTG ATCTATGCCGCCAGCTCTCTGCAGTCTGGCGTGCCATCTAGA TTTTCCGGCAGCGGCTCTGGCACCGACTTCACCCTGACCATA TCTAGCCTGCAGCCTGAGGACTTCGCCGTGTACTACTGCCAG CAGAGAAGCAACTGGCCTCCTACCTTTGGCCAGGGCACCAA GCTGGAAATCAAGAGAGGTGGCGGAGGATCTGGCGGAGGTG GAAGCGGCGGAGGCGGATCTCAAGTTCAGCTGGTTGAATCT |

TABLE 6-continued

| Feature SEQ ID NO | Sequence |
|---|---|
| | GGCGGCGGACTGGTTAAGCCTGGCGGTTCTCTGAGACTGAG<br>CTGTGCCGCCTCCGGCTTCACCTTCAGCGACTACTACATGAG<br>CTGGATCAGACAGGCCCCTGGCAAAGGCCTGGAATGGGTGT<br>CCTACATCAGCTCCAGCGGCAGCACCATCTACTACGCCGATA<br>GCGTGAAGGGCAGATTCACCATCAGCCGGGACAACGCCAAG<br>AACAGCCTGTACCTGCAGATGAACTCCCTGAGAGCCGAGGA<br>TACCGCCAAGTACTACTGTGCCACCGCCGTGTTTTCTCTGGG<br>CCCTGAGGGCTACTACTACTATATGGACGTGTGGGGCAAGG<br>GCACCACCGTGACAGTTTCTTCTGCGGCCGCAACCACTACTC<br>CGGCACCTAGGCCCCCCACTCCGGCACCGACCATTGCATCAC<br>AACCACTGAGTCTTAGACCTGAAGCCTGTCGACCCGCAGCT<br>GGGGGGGCAGTCCACACACGGGGATTGGATTTCGCCTGCGA<br>TATATACATTTGGGCGCCACTGGCAGGCACCTGCGGGGTCCT<br>GCTCTTGTCCCTTGTCATCACCCTGTACTGTAAGAGAGGAAG<br>AAAGAAGTTGTTGTATATTTTCAAACAGCCATTCATGAGGCC<br>GGTCCAGACCACTCAGGAGGAGGATGGATGCAGTTGCCGCT<br>TTCCGGAAGAGGAAGAGGGTGGGTGTGAACTCCGAGTTAAA<br>TTTTCTCGCAGTGCTGATGCCCCAGCGTATAAACAGGGTCAG<br>AACCAACTGTATAATGAACTCAATTTGGGGAGGCGAGAGGA<br>GTATGATGTATTGGACAAGCGGCGGGGGGGGGATCCTGAAA<br>TGGGCGGTAAGCCAAGGCGCAAGAATCCACAGGAGGGTTTG<br>TATAATGAGTTGCAGAAGGATAAAATGGCGGAAGCGTATTC<br>AGAAATCGGAATGAAGGGAGAGCGCCGCAGAGGGAAAGGG<br>CATGATGGCCTCTACCAAGGTTTGTCAACAGCGACCAAGGA<br>TACCTATGACGCACTTCATATGCAAGCACTGCCCCCCAGGT |
| RJ151HL CAR (C9HL/CD8TM/ 4-1BB/CD3zeta) SEQ ID NO: 202 | MLLLVTSLLLCELPHPAFLLIPQVQLVESGGGLVKPGGSLRLSC<br>AASGFTFSDYYMSWIRQAPGKGLEWVSYISSSGSTIYYADSVK<br>GRFTISRDNAKNSLYLQMNSLRAEDTAKYYCATAVFSLGPEGY<br>YYYMDVWGKGTTVTVSSGGGGSGGGGSGGGGSDIQMTQSPSS<br>LSASVGDRVTITCRASQSISSYLNWYQQKPGKAPKLLIYAASSL<br>QSGVPSRFSGSGSGTDFTLTISSLQPEDFAVYYCQQRSNWPPTF<br>GQGTKLEIKRAAATTTPAPRPPTPAPTIASQPLSLRPEACRPAAG<br>GAVHTRGLDFACDIYIWAPLAGTCGVLLLSLVITLYCKRGRKK<br>LLYIFKQPFMRPVQTTQEEDGCSCRFPEEEEGGCELRVKFSRSA<br>DAPAYKQGQNQLYNELNLGRREEYDVLDKRRGRDPEMGGKP<br>RRKNPQEGLYNELQKDKMAEAYSEIGMKGERRRGKGHDGLY<br>QGLSTATKDTYDALHMQALPPR |
| RJ151HL CAR (C9HL/CD8TM/ 4-1BB/CD3zeta) SEQ ID NO: 203 | ATGCTTCTGCTCGTGACAAGCCTGCTGCTGTGCGAGCTGCCC<br>CACCCTGCCTTTCTGCTGATCCCTCAAGTTCAGCTGGTTGAA<br>TCTGGCGGCGGACTGGTTAAGCCTGGCGGTTCTCTGAGACTG<br>AGCTGTGCCGCCTCCGGCTTCACCTTCAGCGACTACTACATG<br>AGCTGGATCAGACAGGCCCCTGGCAAAGGCCTGGAATGGGT<br>GTCCTACATCAGCTCCAGCGGCAGCACCATCTACTACGCCGA<br>TAGCGTGAAGGGCAGATTCACCATCAGCCGGGACAACGCCA<br>AGAACAGCCTGTACCTGCAGATGAACTCCCTGAGAGCCGAG<br>GATACCGCCAAGTACTACTGTGCCACCGCCGTGTTTTCTCTG<br>GGCCCTGAGGGCTACTACTACTATATGGACGTGTGGGGCAA<br>GGGCACCACCGTGACAGTTTCTTCTGGTGGCGGAGGATCTGG<br>CGGAGGTGGAAGCGGCGGAGGCGGATCTGACATCCAGATGA<br>CACAGAGCCCTAGCAGCCTGTCTGCCAGCGTGGGAGACAGA<br>GTGACCATCACCTGTAGAGCCAGCCAGAGCATCAGCAGCTA<br>CCTGAACTGGTATCAGCAGAAGCCCGGCAAGGCCCCTAAAC<br>TGCTGATCTATGCCGCCAGCTCTCTGCAGTCTGGCGTGCCAT<br>CTAGATTTTCCGGCAGCGGCTCTGGCACCGACTTCACCCTGA<br>CCATATCTAGCCTGCAGCCTGAGGACTTCGCCGTGTACTACT<br>GCCAGCAGAGAAGCAACTGGCCTCCTACCTTTGGCCAGGGC<br>ACCAAGCTGGAAATCAAGAGAGCGGCCGCAACCACTACTCC<br>GGCACCTAGGCCCCCCACTCCGGCACCGACCATTGCATCAC<br>AACCACTGAGTCTTAGACCTGAAGCCTGTCGACCCGCAGCT<br>GGGGGGGCAGTCCACACACGGGGATTGGATTTCGCCTGCGA<br>TATATACATTTGGGCGCCACTGGCAGGCACCTGCGGGGTCCT<br>GCTCTTGTCCCTTGTCATCACCCTGTACTGTAAGAGAGGAAG<br>AAAGAAGTTGTTGTATATTTTCAAACAGCCATTCATGAGGCC<br>GGTCCAGACCACTCAGGAGGAGGATGGATGCAGTTGCCGCT<br>TTCCGGAAGAGGAAGAGGGTGGGTGTGAACTCCGAGTTAAA<br>TTTTCTCGCAGTGCTGATGCCCCAGCGTATAAACAGGGTCAG<br>AACCAACTGTATAATGAACTCAATTTGGGGAGGCGAGAGGA<br>GTATGATGTATTGGACAAGCGGCGGGGGCGGGATCCTGAAA<br>TGGGCGGTAAGCCAAGGCGCAAGAATCCACAGGAGGGTTTG<br>TATAATGAGTTGCAGAAGGATAAAATGGCGGAAGCGTATTC<br>AGAAATCGGAATGAAGGGAGAGCGCCGCAGAGGGAAAGGG<br>CATGATGGCCTCTACCAAGGTTTGTCAACAGCGACCAAGGA<br>TACCTATGACGCACTTCATATGCAAGCACTGCCCCCCAGG |

TABLE 6-continued

| Feature SEQ ID NO | Sequence |
|---|---|
| D7 L chain SEQ ID NO: 204 | DIQMTQSPSSLSASVGDRVTITCRASQSISSYLNWYQQKPGKAP KLLIYAASSLQSGVPSRFSGSGSGTDFTLTISSLQPEDIAAYYCQ HYGTFGQGTKLEIKR |
| D7 L chain SEQ ID NO: 205 | GACATCCAGATGACACAGAGCCCTAGCAGCCTGTCTGCCAG CGTGGGAGACAGAGTGACCATCACCTGTAGAGCCAGCCAGA GCATCAGCAGCTACCTGAACTGGTATCAGCAGAAGCCCGGC AAGGCCCCTAAACTGCTGATCTATGCCGCCAGCTCTCTGCAG TCTGGCGTGCCATCTAGATTTTCCGGCAGCGGCTCTGGCACC GACTTCACCCTGACCATATCTAGCCTGCAGCCTGAGGATATC GCCGCCTACTACTGTCAGCACTACGGCACATTTGGCCAGGGC ACCAAGCTGGAAATCAAGAGA |
| D7 H chain SEQ ID NO: 206 | QVQLVESGGGLVKPGGSLRLSCAASGFTFSDYYMSWIRQAPGK GLEWVSYISSSGSTIYYADSVKGRFTISRDNAKNSLYLQMNSLR AEDTAVYYCARDGYPLGGGYDFWSGYYPDYWGQGTLVTVSS |
| D7 H chain SEQ ID NO: 207 | CAAGTTCAGCTGGTTGAATCTGGCGGCGGACTGGTTAAGCCT GGCGGTTCTCTGAGACTGAGCTGTGCCGCCTCCGGCTTCACC TTCAGCGACTACTACATGAGCTGGATCAGACAGGCCCCTGG CAAAGGCCTGGAATGGGTGTCCTACATCAGCTCCAGCGGCA GCACCATCTACTACGCCGATAGCGTGAAGGGCAGATTCACC ATCAGCCGGGACAACGCCAAGAACAGCCTGTACCTGCAGAT GAACTCCCTGAGAGCCGAGGACACCGCCGTGTACTACTGTG CCAGAGATGGCTATCCTCTTGGCGGAGGCTACGACTTTTGGA GCGGCTACTACCCCGATTACTGGGGCCAGGGAACACTGGTC ACAGTGTCTAGT |
| D7LH binder SEQ ID NO: 208 | GACATCCAGATGACACAGAGCCCTAGCAGCCTGTCTGCCAG CGTGGGAGACAGAGTGACCATCACCTGTAGAGCCAGCCAGA GCATCAGCAGCTACCTGAACTGGTATCAGCAGAAGCCCGGC AAGGCCCCTAAACTGCTGATCTATGCCGCCAGCTCTCTGCAG TCTGGCGTGCCATCTAGATTTTCCGGCAGCGGCTCTGGCACC GACTTCACCCTGACCATATCTAGCCTGCAGCCTGAGGATATC GCCGCCTACTACTGTCAGCACTACGGCACATTTGGCCAGGGC ACCAAGCTGGAAATCAAGAGAGGTGGCGGAGGATCTGGCGG AGGTGGAAGCGGCGGAGGCGGATCTCAAGTTCAGCTGGTTG AATCTGGCGGCGGACTGGTTAAGCCTGGCGGTTCTCTGAGAC TGAGCTGTGCCGCCTCCGGCTTCACCTTCAGCGACTACTACA TGAGCTGGATCAGACAGGCCCCTGGCAAAGGCCTGGAATGG GTGTCCTACATCAGCTCCAGCGGCAGCACCATCTACTACGCC GATAGCGTGAAGGGCAGATTCACCATCAGCCGGGACAACGC CAAGAACAGCCTGTACCTGCAGATGAACTCCCTGAGAGCCG AGGACACCGCCGTGTACTACTGTGCCAGAGATGGCTATCCTC TTGGCGGAGGCTACGACTTTTGGAGCGGCTACTACCCCGATT ACTGGGGCCAGGGAACACTGGTCACAGTGTCTAGT |
| D7HL binder SEQ ID NO: 209 | CAAGTTCAGCTGGTTGAATCTGGCGGCGGACTGGTTAAGCCT GGCGGTTCTCTGAGACTGAGCTGTGCCGCCTCCGGCTTCACC TTCAGCGACTACTACATGAGCTGGATCAGACAGGCCCCTGG CAAAGGCCTGGAATGGGTGTCCTACATCAGCTCCAGCGGCA GCACCATCTACTACGCCGATAGCGTGAAGGGCAGATTCACC ATCAGCCGGGACAACGCCAAGAACAGCCTGTACCTGCAGAT GAACTCCCTGAGAGCCGAGGACACCGCCGTGTACTACTGTG CCAGAGATGGCTATCCTCTTGGCGGAGGCTACGACTTTTGGA GCGGCTACTACCCCGATTACTGGGGCCAGGGAACACTGGTC ACAGTGTCTAGTGGTGGCGGAGGATCTGGCGGAGGTGGAAG CGGCGGAGGCGGATCTGACATCCAGATGACACAGAGCCCTA GCAGCCTGTCTGCCAGCGTGGGAGACAGAGTGACCATCACC TGTAGAGCCAGCCAGAGCATCAGCAGCTACCTGAACTGGTA TCAGCAGAAGCCCGGCAAGGCCCCTAAACTGCTGATCTATG CCGCCAGCTCTCTGCAGTCTGGCGTGCCATCTAGATTTTCCG GCAGCGGCTCTGGCACCGACTTCACCCTGACCATATCTAGCC TGCAGCCTGAGGATATCGCCGCCTACTACTGTCAGCACTACG GCACATTTGGCCAGGGCACCAAGCTGGAAATCAAGAGA |
| RJ152LH CAR (D7LH/CD8TM/ 4-1BB/CD3zeta) SEQ ID NO: 210 | MLLLVTSLLLCELPHPAFLLIPDIQMTQSPSSLSASVGDRVTITC RASQSISSYLNWYQQKPGKAPKLLIYAASSLQSGVPSRFSGSGS GTDFTLTISSLQPEDIAAYYCQHYGTFGQGTKLEIKRGGGGSGG GGSGGGGSQVQLVESGGGLVKPGGSLRLSCAASGFTFSDYYMS WIRQAPGKGLEWVSYISSSGSTIYYADSVKGRFTISRDNAKNSL YLQMNSLRAEDTAVYYCARDGYPLGGGYDFWSGYYPDYWG QGTLVTVSSAAATTTPAPRPPTPAPTIASQPLSLRPEACRPAAGG AVHTRGLDFACDIYIWAPLAGTCGVLLLSLVITLYCKRGRKKLL YIFKQPFMRPVQTTQEEDGCSCRFPEEEEGGCELRVKFSRSADA PAYKQGQNQLYNELNLGRREEYDVLDKRRGRDPEMGGKPRR |

TABLE 6-continued

| Feature<br>SEQ ID NO | Sequence |
|---|---|
| | KNPQEGLYNELQKDKMAEAYSEIGMKGERRRGKGHDGLYQG<br>LSTATKDTYDALHMQALPPR |
| RJ152LH CAR<br>(D7LH/CD8TM/<br>4-1BB/CD3zeta)<br>SEQ ID NO: 211 | ATGCTTCTGCTCGTGACAAGCCTGCTGCTGTGCGAGCTGCCC<br>CACCCTGCCTTTCTGCTGATCCCTGACATCCAGATGACACAG<br>AGCCCTAGCAGCCTGTCTGCCAGCGTGGGAGACAGAGTGAC<br>CATCACCTGTAGAGCCAGCCAGAGCATCAGCAGCTACCTGA<br>ACTGGTATCAGCAGAAGCCCGGCAAGGCCCCTAAACTGCTG<br>ATCTATGCCGCCAGCTCTCTGCAGTCTGGCGTGCCATCTAGA<br>TTTTCCGGCAGCGGCTCTGGCACCGACTTCACCCTGACCATA<br>TCTAGCCTGCAGCCTGAGGATATCGCCGCCTACTACTGTCAG<br>CACTACGGCACATTTGGCCAGGGCACCAAGCTGGAAATCAA<br>GAGAGGTGGCGGAGGATCTGGCGGAGGTGGAAGCGGCGGA<br>GGCGGATCTCAAGTTCAGCTGGTTGAATCTGGCGGCGGACT<br>GGTTAAGCCTGGCGGTTCTCTGAGACTGAGCTGTGCCGCCTC<br>CGGCTTCACCTTCAGCGACTACTACATGAGCTGGATCAGACA<br>GGCCCCTGGCAAAGGCCTGGAATGGGTGTCCTACATCAGCT<br>CCAGCGGCAGCACCATCTACTACGCCGATAGCGTGAAGGGC<br>AGATTCACCATCAGCCGGGACAACGCCAAGAACAGCCTGTA<br>CCTGCAGATGAACTCCCTGAGAGCCGAGGACACCGCCGTGT<br>ACTACTGTGCCAGAGATGGCTATCCTCTTGGCGGAGGCTACG<br>ACTTTTGGAGCGGCTACTACCCCGATTACTGGGGCCAGGGA<br>ACACTGGTCACAGTGTCTAGTGCGGCCGCAACCACTACTCCG<br>GCACCTAGGCCCCCCACTCCGGCACCGACCATTGCATCACA<br>ACCACTGAGTCTTAGACCTGAAGCCTGTCGACCCGCAGCTG<br>GGGGGGCAGTCCACACACGGGGATTGGATTTCGCCTGCGAT<br>ATATACATTTGGGCGCCACTGGCAGGCACCTGCGGGGTCCT<br>GCTCTTGTCCCTTGTCATCACCCTGTACTGTAAGAGAGGAAG<br>AAAGAAGTTGTTGTATATTTTCAAACAGCCATTCATGAGGCC<br>GGTCCAGACCACTCAGGAGGAGGATGGATGCAGTTGCCGCT<br>TTCCGGAAGAGGAAGAGGGTGGGTGTGAACTCCGAGTTAAA<br>TTTTCTCGCAGTGCTGATGCCCCAGCGTATAAACAGGGTCAG<br>AACCAACTGTATAATGAACTCAATTTGGGGAGGCGAGAGGA<br>GTATGATGTATTGGACAAGCGGCGGGGGCGGGATCCTGAAA<br>TGGGCGGTAAGCCAAGGCGCAAGAATCCACAGGAGGGTTTG<br>TATAATGAGTTGCAGAAGGATAAAATGGCGGAAGCGTATTC<br>AGAAATCGGAATGAAGGGAGAGCGCCGCAGAGGGAAAGGG<br>CATGATGGCCTCTACCAAGGTTTGTCAACAGCGACCAAGGA<br>TACCTATGACGCACTTCATATGCAAGCACTGCCCCCCAGG |
| RJ152HL<br>(D7HL/CD8TM/<br>4-1BB/CD3zeta)<br>SEQ ID NO: 212 | MLLLVTSLLLCELPHPAFLLIPQVQLVESGGGLVKPGGSLRLSC<br>AASGFTFSDYYMSWIRQAPGKGLEWVSYISSSGSTIYYADSVK<br>GRFTISRDNAKNSLYLQMNSLRAEDTAVYYCARDGYPLGGGY<br>DFWSGYYPDYWGQGTLVTVSSGGGGSGGGGSGGGGSDIQMT<br>QSPSSLSASVGDRVTITCRASQSISSYLNWYQQKPGKAPKLLIY<br>AASSLQSGVPSRFSGSGSGTDFTLTISSLQPEDIAAYYCQHYGTF<br>GQGTKLEIKRAAATTTPAPRPPTPAPTIASQPLSLRPEACRPAAG<br>GAVHTRGLDFACDIYIWAPLAGTCGVLLLSLVITLYCKRGRKK<br>LLYIFKQPFMRPVQTTQEEDGCSCRFPEEEEGGCELRVKFSRSA<br>DAPAYKQGQNQLYNELNLGRREEYDVLDKRRGRDPEMGGKP<br>RRKNPQEGLYNELQKDKMAEAYSEIGMKGERRRGKGHDGLY<br>QGLSTATKDTYDALHMQALPPR |
| RJ152HL<br>(D7HL/CD8TM/<br>4-1BB/CD3zeta)<br>SEQ ID NO: 213 | ATGCTTCTGCTCGTGACAAGCCTGCTGCTGTGCGAGCTGCCC<br>CACCCTGCCTTTCTGCTGATCCCTCAAGTTCAGCTGGTTGAA<br>TCTGGCGGCGGACTGGTTAAGCCTGGCGGTTCTCTGAGACTG<br>AGCTGTGCCGCCTCCGGCTTCACCTTCAGCGACTACTACATG<br>AGCTGGATCAGACAGGCCCCTGGCAAAGGCCTGGAATGGGT<br>GTCCTACATCAGCTCCAGCGGCAGCACCATCTACTACGCCGA<br>TAGCGTGAAGGGCAGATTCACCATCAGCCGGGACAACGCCA<br>AGAACAGCCTGTACCTGCAGATGAACTCCCTGAGAGCCGAG<br>GACACCGCCGTGTACTACTGTGCCAGAGATGGCTATCCTCTT<br>GGCGGAGGCTACGACTTTTGGAGCGGCTACTACCCCGATTA<br>CTGGGGCCAGGGAACACTGGTCACAGTGTCTAGTGGTGGCG<br>GAGGATCTGGCGGAGGTGGAAGCGGCGGAGGCGGATCTGAC<br>ATCCAGATGACACAGAGCCCTAGCAGCCTGTCTGCCAGCGT<br>GGGAGACAGAGTGACCATCACCTGTAGAGCCAGCCAGAGCA<br>TCAGCAGCTACCTGAACTGGTATCAGCAGAAGCCCGGCAAG<br>GCCCCTAAACTGCTGATCTATGCCGCCAGCTCTCTGCAGTCT<br>GGCGTGCCATCTAGATTTTCCGGCAGCGGCTCTGGCACCGAC<br>TTCACCCTGACCATATCTAGCCTGCAGCCTGAGGATATCGCC<br>GCCTACTACTGTCAGCACTACGGCACATTTGGCCAGGGCACC<br>AAGCTGGAAATCAAGAGAGCGGCCGCAACCACTACTCCGGC<br>ACCTAGGCCCCCCACTCCGGCACCGACCATTGCATCACAACC<br>ACTGAGTCTTAGACCTGAAGCCTGTCGACCCGCAGCTGGGG<br>GGCAGTCCACACACGGGGATTGGATTTCGCCTGCGATATAT<br>ACATTTGGGCGCCACTGGCAGGCACCTGCGGGGTCCTGCTCT |

TABLE 6-continued

| Feature SEQ ID NO | Sequence |
| --- | --- |
| | TGTCCCTTGTCATCACCCTGTACTGTAAGAGAGGAAGAAAG AAGTTGTTGTATATTTTCAAACAGCCATTCATGAGGCCGGTC CAGACCACTCAGGAGGAGGATGGATGCAGTTGCCGCTTTCC GGAAGAGGAAGAGGGTGGGTGTGAACTCCGAGTTAAATTTT CTCGCAGTGCTGATGCCCCAGCGTATAAACAGGGTCAGAAC CAACTGTATAATGAACTCAATTTGGGGAGGCGAGAGGAGTA TGATGTATTGGACAAGCGGCGGGGGGGGGATCCTGAAATGG GCGGTAAGCCAAGGCGCAAGAATCCACAGGAGGGTTTGTAT AATGAGTTGCAGAAGGATAAAATGGCGGAAGCGTATTCAGA AATCGGAATGAAGGGAGAGCGCCGCAGAGGGAAAGGGCAT GATGGCCTCTACCAAGGTTTGTCAACAGCGACCAAGGATAC CTATGACGCACTTCATATGCAAGCACTGCCCCCCAGG |
| B7 L chain SEQ ID NO: 214 | DIQMTQSPSSLSASVGDRVTITCRASQSISSYLNWYQQKPGKAP KLLIYAASSLQSGVPSRFSGSGSGTDFTLTISSLQPEDFAVYYCQ HYGTFGQGTKVEIKR |
| B7 L chain SEQ ID NO: 215 | GACATCCAGATGACACAGAGCCCTAGCAGCCTGTCTGCCAG CGTGGGAGACAGAGTGACCATCACCTGTAGAGCCAGCCAGA GCATCAGCAGCTACCTGAACTGGTATCAGCAGAAGCCCGGC AAGGCCCCTAAACTGCTGATCTATGCCGCCAGCTCTCTGCAG TCTGGCGTGCCATCTAGATTTTCCGGCAGCGGCTCTGGCACC GACTTCACCCTGACCATATCTAGCCTGCAGCCTGAGGACTTC GCCGTGTACTACTGTCAGCACTACGGCACCTTTGGCCAGGGC ACCAAGGTGGAAATCAAGAGA |
| B7 H chain SEQ ID NO: 216 | QVQLVESGGGLVKPGGSLRLSCAASGFTFSDYYMSWIRQAPGK GLEWVSYISSSGSTIYYADSVKGRFTISRDNAKNSLYLQMNSLR AEDTAMYYCARHKTSLNDYDFWSGYLLDYWGQGTLVTVSS |
| B7 H chain SEQ ID NO: 217 | CAAGTTCAGCTGGTTGAATCTGGCGGCGGACTGGTTAAGCCT GGCGGTTCTCTGAGACTGAGCTGTGCCGCCTCCGGCTTCACC TTCAGCGACTACTACATGAGCTGGATCAGACAGGCCCCTGG CAAAGGCCTGGAATGGGTGTCCTACATCAGCTCCAGCGGCA GCACCATCTACTACGCCGATAGCGTGAAGGGCAGATTCACC ATCAGCCGGGACAACGCCAAGAACAGCCTGTACCTGCAGAT GAACTCCCTGAGAGCCGAGGACACAGCCATGTACTATTGCG CCAGACACAAGACCAGCCTGAACGACTACGACTTTTGGAGC GGCTACCTGCTGGACTATTGGGGCCAGGGAACACTGGTCAC CGTGTCTAGT |
| B7LH binder SEQ ID NO: 218 | GACATCCAGATGACACAGAGCCCTAGCAGCCTGTCTGCCAG CGTGGGAGACAGAGTGACCATCACCTGTAGAGCCAGCCAGA GCATCAGCAGCTACCTGAACTGGTATCAGCAGAAGCCCGGC AAGGCCCCTAAACTGCTGATCTATGCCGCCAGCTCTCTGCAG TCTGGCGTGCCATCTAGATTTTCCGGCAGCGGCTCTGGCACC GACTTCACCCTGACCATATCTAGCCTGCAGCCTGAGGACTTC GCCGTGTACTACTGTCAGCACTACGGCACCTTTGGCCAGGGC ACCAAGGTGGAAATCAAGAGAGGTGGCGGAGGATCTGGCG GAGGTGGAAGCGGCGGAGGCGGATCTCAAGTTCAGCTGGTT GAATCTGGCGGCGGACTGGTTAAGCCTGGCGGTTCTCTGAG ACTGAGCTGTGCCGCCTCCGGCTTCACCTTCAGCGACTACTA CATGAGCTGGATCAGACAGGCCCCTGGCAAAGGCCTGGAAT GGGTGTCCTACATCAGCTCCAGCGGCAGCACCATCTACTACG CCGATAGCGTGAAGGGCAGATTCACCATCAGCCGGGACAAC GCCAAGAACAGCCTGTACCTGCAGATGAACTCCCTGAGAGC CGAGGACACAGCCATGTACTATTGCGCCAGACACAAGACCA GCCTGAACGACTACGACTTTTGGAGCGGCTACCTGCTGGACT ATTGGGGCCAGGGAACACTGGTCACCGTGTCTAGT |
| B7HL binder SEQ ID NO: 219 | CAAGTTCAGCTGGTTGAATCTGGCGGCGGACTGGTTAAGCCT GGCGGTTCTCTGAGACTGAGCTGTGCCGCCTCCGGCTTCACC TTCAGCGACTACTACATGAGCTGGATCAGACAGGCCCCTGG CAAAGGCCTGGAATGGGTGTCCTACATCAGCTCCAGCGGCA GCACCATCTACTACGCCGATAGCGTGAAGGGCAGATTCACC ATCAGCCGGGACAACGCCAAGAACAGCCTGTACCTGCAGAT GAACTCCCTGAGAGCCGAGGACACAGCCATGTACTATTGCG CCAGACACAAGACCAGCCTGAACGACTACGACTTTTGGAGC GGCTACCTGCTGGACTATTGGGGCCAGGGAACACTGGTCAC CGTGTCTAGTGGTGGCGGAGGATCTGGCGGAGGTGGAAGCG GCGGAGGCGGATCTGACATCCAGATGACACAGAGCCCTAGC AGCCTGTCTGCCAGCGTGGGAGACAGAGTGACCATCACCTG TAGAGCCAGCCAGAGCATCAGCAGCTACCTGAACTGGTATC AGCAGAAGCCCGGCAAGGCCCCTAAACTGCTGATCTATGCC GCCAGCTCTCTGCAGTCTGGCGTGCCATCTAGATTTTCCGGC AGCGGCTCTGGCACCGACTTCACCCTGACCATATCTAGCCTG |

TABLE 6-continued

| Feature SEQ ID NO | Sequence |
|---|---|
| | CAGCCTGAGGACTTCGCCGTGTACTACTGTCAGCACTACGGC ACCTTTGGCCAGGGCACCAAGGTGGAAATCAAGAGA |
| RJ153LH CAR (B7LH/CD8TM/ 4-1BB/CD3zeta) SEQ ID NO: 220 | MLLLVTSLLLCELPHPAFLLIPDIQMTQSPSSLSASVGDRVTITC RASQSISSYLNWYQQKPGKAPKLLIYAASSLQSGVPSRFSGSGS GTDFTLTISSLQPEDFAVYYCQHYGTFGQGTKVEIKRGGGGSG GGGSGGGGSQVQLVESGGGLVKPGGSLRLSCAASGFTFSDYY MSWIRQAPGKGLEWVSYISSSGSTIYYADSVKGRFTISRDNAKN SLYLQMNSLRAEDTAMYYCARHKTSLNDYDFWSGYLLDYWG QGTLVTVSSAAATTTPAPRPPTPAPTIASQPLSLRPEACRPAAGG AVHTRGLDFACDIYIWAPLAGTCGVLLLSLVITLYCKRGRKKLL YIFKQPFMRPVQTTQEEDGCSCRFPEEEEGGCELRVKFSRSADA PAYKQGQNQLYNELNLGRREEYDVLDKRRGRDPEMGGKPRR KNPQEGLYNELQKDKMAEAYSEIGMKGERRRGKGHDGLYQG LSTATKDTYDALHMQALPPR |
| RJ153LH CAR (B7LH/CD8TM/ 4-1BB/CD3zeta) SEQ ID NO: 221 | ATGCTTCTGCTCGTGACAAGCCTGCTGCTGTGCGAGCTGCCC CACCCTGCCTTTCTGCTGATCCCTGACATCCAGATGACACAG AGCCCTAGCAGCCTGTCTGCCAGCGTGGGAGACAGAGTGAC CATCACCTGTAGAGCCAGCCAGAGCATCAGCAGCTACCTGA ACTGGTATCAGCAGAAGCCCGGCAAGGCCCCTAAACTGCTG ATCTATGCCGCCAGCTCTCTGCAGTCTGGCGTGCCATCTAGA TTTTCCGGCAGCGGCTCTGGCACCGACTTCACCCTGACCATA TCTAGCCTGCAGCCTGAGGACTTCGCCGTGTACTACTGTCAG CACTACGGCACCTTTGGCCAGGGCACCAAGGTGGAAATCAA GAGAGGTGGCGGAGGATCTGGCGGAGGTGGAAGCGGCGGA GGCGGATCTCAAGTTCAGCTGGTTGAATCTGGCGGCGGACT GGTTAAGCCTGGCGGTTCTCTGAGACTGAGCTGTGCCGCCTC CGGCTTCACCTTCAGCGACTACTACATGAGCTGGATCAGACA GGCCCCTGGCAAAGGCCTGGAATGGGTGTCCTACATCAGCT CCAGCGGCAGCACCATCTACTACGCCGATAGCGTGAAGGGC AGATTCACCATCAGCCGGGACAACGCCAAGAACAGCCTGTA CCTGCAGATGAACTCCCTGAGAGCCGAGGACACAGCCATGT ACTATTGCGCCAGACACAAGACCAGCCTGAACGACTACGAC TTTTGGAGCGGCTACCTGCTGGACTATTGGGGCCAGGGAAC ACTGGTCACCGTGTCTAGTGCGGCCGCAACCACTACTCCGGC ACCTAGGCCCCCCACTCCGGCACCGACCATTGCATCACAACC ACTGAGTCTTAGACCTGAAGCCTGTCGACCCGCAGCTGGGG GGGCAGTCCACACACGGGGATTGGATTTCGCCTGCGATATAT ACATTTGGGCGCCACTGGCAGGCACCTGCGGGGTCCTGCTCT TGTCCCTTGTCATCACCCTGTACTGTAAGAGAGGAAGAAAG AAGTTGTTGTATATTTTCAAACAGCCATTCATGAGGCCGGTC CAGACCACTCAGGAGGAGGATGGATGCAGTTGCCGCTTTCC GGAAGAGGAAGAGGGTGGGTGTGAACTCCGAGTTAAATTTT CTCGCAGTGCTGATGCCCCAGCGTATAAACAGGGTCAGAAC CAACTGTATAATGAACTCAATTTGGGGAGGCGAGAGGAGTA TGATGTATTGGACAAGCGGCGGGGGCGGGATCCTGAAATGG GCGGTAAGCCAAGGCGCAAGAATCCACAGGAGGGTTTGTAT AATGAGTTGCAGAAGGATAAAATGGCGGAAGCGTATTCAGA AATCGGAATGAAGGGAGAGCGCCGCAGAGGGAAAGGGCAT GATGGCCTCTACCAAGGTTTGTCAACAGCGACCAAGGATAC CTATGACGCACTTCATATGCAAGCACTGCCCCCCAGG |
| RJ153HL CAR (B7HL/CD8TM/ 4-1BB/CD3zeta) SEQ ID NO: 222 | MLLLVTSLLLCELPHPAFLLIPQVQLVESGGGLVKPGGSLRLSC AASGFTFSDYYMSWIRQAPGKGLEWVSYISSSGSTIYYADSVK GRFTISRDNAKNSLYLQMNSLRAEDTAMYYCARHKTSLNDYD FWSGYLLDYWGQGTLVTVSSGGGGSGGGGSGGGGSDIQMTQS PSSLSASVGDRVTITCRASQSISSYLNWYQQKPGKAPKLLIYAA SSLQSGVPSRFSGSGSGTDFTLTISSLQPEDFAVYYCQHYGTFGQ GTKVEIKRAAATTTPAPRPPTPAPTIASQPLSLRPEACRPAAGGA VHTRGLDFACDIYIWAPLAGTCGVLLLSLVITLYCKRGRKKLLY IFKQPFMRPVQTTQEEDGCSCRFPEEEEGGCELRVKFSRSADAP AYKQGQNQLYNELNLGRREEYDVLDKRRGRDPEMGGKPRRK NPQEGLYNELQKDKMAEAYSEIGMKGERRRGKGHDGLYQGLS TATKDTYDALHMQALPPR |
| RJ153HL CAR (B7HL/CD8TM/ 4-1BB/CD3zeta) SEQ ID NO: 223 | ATGCTTCTGCTCGTGACAAGCCTGCTGCTGTGCGAGCTGCCC CACCCTGCCTTTCTGCTGATCCCTCAAGTTCAGCTGGTTGAA TCTGGCGGCGGACTGGTTAAGCCTGGCGGTTCTCTGAGACTG AGCTGTGCCGCCTCCGGCTTCACCTTCAGCGACTACTACATG AGCTGGATCAGACAGGCCCCTGGCAAAGGCCTGGAATGGGT GTCCTACATCAGCTCCAGCGGCAGCACCATCTACTACGCCGA TAGCGTGAAGGGCAGATTCACCATCAGCCGGGACAACGCCA AGAACAGCCTGTACCTGCAGATGAACTCCCTGAGAGCCGAG GACACAGCCATGTACTATTGCGCCAGACACAAGACCAGCCT GAACGACTACGACTTTTGGAGCGGCTACCTGCTGGACTATTG GGGCCAGGGAACACTGGTCACCGTGTCTAGTGGTGGCGGAG |

TABLE 6-continued

| Feature SEQ ID NO | Sequence |
|---|---|
| | GATCTGGCGGAGGTGGAAGCGGCGGAGGCGGATCTGACATC CAGATGACACAGAGCCCTAGCAGCCTGTCTGCCAGCGTGGG AGACAGAGTGACCATCACCTGTAGAGCCAGCCAGAGCATCA GCAGCTACCTGAACTGGTATCAGCAGAAGCCCGGCAAGGCC CCTAAACTGCTGATCTATGCCGCCAGCTCTCTGCAGTCTGGC GTGCCATCTAGATTTTCCGGCAGCGGCTCTGGCACCGACTTC ACCCTGACCATATCTAGCCTGCAGCCTGAGGACTTCGCCGTG TACTACTGTCAGCACTACGGCACCTTTGGCCAGGGCACCAA GGTGGAAATCAAGAGAGCGGCCGCAACCACTACTCCGGCAC CTAGGCCCCCCACTCCGGCACCGACCATTGCATCACAACCAC TGAGTCTTAGACCTGAAGCCTGTCGACCCGCAGCTGGGGGG GCAGTCCACACACGGGGATTGGATTTCGCCTGCGATATATAC ATTTGGGCGCCACTGGCAGGCACCTGCGGGGTCCTGCTCTTG TCCCTTGTCATCACCCTGTACTGTAAGAGAGGAAGAAAGAA GTTGTTGTATATTTTCAAACAGCCATTCATGAGGCCGGTCCA GACCACTCAGGAGGAGGATGGATGCAGTTGCCGCTTTCCGG AAGAGGAAGAGGGTGGGTGTGAACTCCGAGTTAAATTTTCT CGCAGTGCTGATGCCCCAGCGTATAAACAGGGTCAGAACCA ACTGTATAATGAACTCAATTTGGGGAGGCGAGAGGAGTATG ATGTATTGGACAAGCGGCGGGGGGGGGATCCTGAAATGGGC GGTAAGCCAAGGCGCAAGAATCCACAGGAGGGTTTGTATAA TGAGTTGCAGAAGGATAAAATGGCGGAAGCGTATTCAGAAA TCGGAATGAAGGGAGAGCGCCGCAGAGGGAAAGGGCATGA TGGCCTCTACCAAGGTTTGTCAACAGCGACCAAGGATACCT ATGACGCACTTCATATGCAAGCACTGCCCCCCAGG |
| A6 L chain SEQ ID NO: 224 | DIQMTQSPSSLSASVGDRVTITCRASQSISSYLNWYQQKPGKAP KLLIYAASSLQSGVPSRFSGSGSGTDFTLTISSLQPEDAATYYCQ RYGTFGQGTKVDIKR |
| A6 L chain SEQ ID NO: 225 | GACATCCAGATGACACAGAGCCCTAGCAGCCTGTCTGCCAG CGTGGGAGACAGAGTGACCATCACCTGTAGAGCCAGCCAGA GCATCAGCAGCTACCTGAACTGGTATCAGCAGAAGCCCGGC AAGGCCCCTAAACTGCTGATCTATGCCGCCAGCTCTCTGCAG TCTGGCGTGCCATCTAGATTTTCCGGCAGCGGCTCTGGCACC GACTTCACCCTGACCATATCTAGCCTGCAGCCTGAGGATGCC GCCACCTACTACTGTCAGAGATACGGCACATTCGGCCAGGG CACCAAGGTGGACATTAAGAGA |
| A6 H chain SEQ ID NO: 226 | QVQLVESGGGLVKPGGSLRLSCAASGFTFSDYYMSWIRQAPGK GLEWVSYISSSGSTIYYADSVKGRFTISRDNAKNSLYLQMNSLR AEDTAVYYCARHKTSLNDYDFWSGYLLDYWGQGTLVTVSS |
| A6 H chain SEQ ID NO: 227 | CAAGTTCAGCTGGTTGAATCTGGCGGCGGACTGGTTAAGCCT GGCGGTTCTCTGAGACTGAGCTGTGCCGCCTCCGGCTTCACC TTCAGCGACTACTACATGAGCTGGATCAGACAGGCCCCTGG CAAAGGCCTGGAATGGGTGTCCTACATCAGCTCCAGCGGCA GCACCATCTACTACGCCGATAGCGTGAAGGGCAGATTCACC ATCAGCCGGGACAACGCCAAGAACAGCCTGTACCTGCAGAT GAACTCCCTGAGAGCCGAGGACACCGCCGTGTACTATTGCG CCAGACACAAGACCAGCCTGAACGACTACGACTTTTGGAGC GGCTACCTGCTGGACTATTGGGGCCAGGGAACACTGGTCAC CGTGTCTAGT |
| A6LH binder SEQ ID NO: 228 | GACATCCAGATGACACAGAGCCCTAGCAGCCTGTCTGCCAG CGTGGGAGACAGAGTGACCATCACCTGTAGAGCCAGCCAGA GCATCAGCAGCTACCTGAACTGGTATCAGCAGAAGCCCGGC AAGGCCCCTAAACTGCTGATCTATGCCGCCAGCTCTCTGCAG TCTGGCGTGCCATCTAGATTTTCCGGCAGCGGCTCTGGCACC GACTTCACCCTGACCATATCTAGCCTGCAGCCTGAGGATGCC GCCACCTACTACTGTCAGAGATACGGCACATTCGGCCAGGG CACCAAGGTGGACATTAAGAGAGGTGGCGGAGGATCTGGCG GAGGTGGAAGCGGCGGAGGCGGATCTCAAGTTCAGCTGGTT GAATCTGGCGGCGGACTGGTTAAGCCTGGCGGTTCTCTGAG ACTGAGCTGTGCCGCCTCCGGCTTCACCTTCAGCGACTACTA CATGAGCTGGATCAGACAGGCCCCTGGCAAAGGCCTGGAAT GGGTGTCCTACATCAGCTCCAGCGGCAGCACCATCTACTACG CCGATAGCGTGAAGGGCAGATTCACCATCAGCCGGGACAAC GCCAAGAACAGCCTGTACCTGCAGATGAACTCCCTGAGAGC CGAGGACACCGCCGTGTACTATTGCGCCAGACACAAGACCA GCCTGAACGACTACGACTTTTGGAGCGGCTACCTGCTGGACT ATTGGGGCCAGGGAACACTGGTCACCGTGTCTAGT |
| A6HL binder SEQ ID NO: 229 | CAAGTTCAGCTGGTTGAATCTGGCGGCGGACTGGTTAAGCCT GGCGGTTCTCTGAGACTGAGCTGTGCCGCCTCCGGCTTCACC TTCAGCGACTACTACATGAGCTGGATCAGACAGGCCCCTGG CAAAGGCCTGGAATGGGTGTCCTACATCAGCTCCAGCGGCA |

TABLE 6-continued

| Feature SEQ ID NO | Sequence |
|---|---|
| | GCACCATCTACTACGCCGATAGCGTGAAGGGCAGATTCACC ATCAGCCGGGACAACGCCAAGAACAGCCTGTACCTGCAGAT GAACTCCCTGAGAGCCGAGGACACCGCCGTGTACTATTGCG CCAGACACAAGACCAGCCTGAACGACTACGACTTTTGGAGC GGCTACCTGCTGGACTATTGGGGCCAGGGAACACTGGTCAC CGTGTCTAGTGGTGGCGGAGGATCTGGCGGAGGTGGAAGCG GCGGAGGCGGATCTGACATCCAGATGACACAGAGCCCTAGC AGCCTGTCTGCCAGCGTGGGAGACAGAGTGACCATCACCTG TAGAGCCAGCCAGAGCATCAGCAGCTACCTGAACTGGTATC AGCAGAAGCCCGGCAAGGCCCCTAAACTGCTGATCTATGCC GCCAGCTCTCTGCAGTCTGGCGTGCCATCTAGATTTTCCGGC AGCGGCTCTGGCACCGACTTCACCCTGACCATATCTAGCCTG CAGCCTGAGGATGCCGCCACCTACTACTGTCAGAGATACGG CACATTCGGCCAGGGCACCAAGGTGGACATTAAGAGA |
| RJ154LH CAR (A6LH/CD8TM/ 4-1BB/CD3zeta) SEQ ID NO: 230 | MLLLVTSLLLCELPHPAFLLIPDIQMTQSPSSLSASVGDRVTITC RASQSISSYLNWYQQKPGKAPKLLIYAASSLQSGVPSRFSGSGS GTDFTLTISSLQPEDAATYYCQRYGTFGQGTKVDIKRGGGGSG GGGSGGGGSQVQLVESGGGLVKPGGSLRLSCAASGFTFSDYY MSWIRQAPGKGLEWVSYISSSGSTIYYADSVKGRFTISRDNAKN SLYLQMNSLRAEDTAVYYCARHKTSLNDYDFWSGYLLDYWG QGTLVTVSSAAATTTPAPRPPTPAPTIASQPLSLRPEACRPAAGG AVHTRGLDFACDIYIWAPLAGTCGVLLLSLVITLYCKRGRKKLL YIFKQPFMRPVQTTQEEDGCSCRFPEEEEGGCELRVKFSRSADA PAYKQGQNQLYNELNLGRREEYDVLDKRRGRDPEMGGKPRR KNPQEGLYNELQKDKMAEAYSEIGMKGERRRGKGHDGLYQG LSTATKDTYDALHMQALPPR |
| RJ154LH CAR (A6LH/CD8TM/ 4-1BB/CD3zeta) SEQ ID NO: 231 | ATGCTTCTGCTCGTGACAAGCCTGCTGCTGTGCGAGCTGCCC CACCCTGCCTTTCTGCTGATCCCTGACATCCAGATGACACAG AGCCCTAGCAGCCTGTCTGCCAGCGTGGGAGACAGAGTGAC CATCACCTGTAGAGCCAGCCAGAGCATCAGCAGCTACCTGA ACTGGTATCAGCAGAAGCCCGGCAAGGCCCCTAAACTGCTG ATCTATGCCGCCAGCTCTCTGCAGTCTGGCGTGCCATCTAGA TTTTCCGGCAGCGGCTCTGGCACCGACTTCACCCTGACCATA TCTAGCCTGCAGCCTGAGGATGCCGCCACCTACTACTGTCAG AGATACGGCACATTCGGCCAGGGCACCAAGGTGGACATTAA GAGAGGTGGCGGAGGATCTGGCGGAGGTGGAAGCGGCGGA GGCGGATCTCAAGTTCAGCTGGTTGAATCTGGCGGCGGACT GGTTAAGCCTGGCGGTTCTCTGAGACTGAGCTGTGCCGCCTC CGGCTTCACCTTCAGCGACTACTACATGAGCTGGATCAGACA GGCCCCTGGCAAAGGCCTGGAATGGGTGTCCTACATCAGCT CCAGCGGCAGCACCATCTACTACGCCGATAGCGTGAAGGGC AGATTCACCATCAGCCGGGACAACGCCAAGAACAGCCTGTA CCTGCAGATGAACTCCCTGAGAGCCGAGGACACCGCCGTGT ACTATTGCGCCAGACACAAGACCAGCCTGAACGACTACGAC TTTTGGAGCGGCTACCTGCTGGACTATTGGGGCCAGGGAAC ACTGGTCACCGTGTCTAGTGCGGCCGCAACCACTACTCCGGC ACCTAGGCCCCCCACTCCGGCACCGACCATTGCATCACAACC ACTGAGTCTTAGACCTGAAGCCTGTCGACCCGCAGCTGGGG GGGCAGTCCACACACGGGGATTGGATTTCGCCTGCGATATAT ACATTTGGGCGCCACTGGCAGGCACCTGCGGGGTCCTGCTCT TGTCCCTTGTCATCACCCTGTACTGTAAGAGAGGAAGAAAG AAGTTGTTGTATATTTTCAAACAGCCATTCATGAGGCCGGTC CAGACCACTCAGGAGGAGGATGGATGCAGTTGCCGCTTTCC GGAAGAGGAAGAGGGTGGGTGTGAACTCCGAGTTAAATTTT CTCGCAGTGCTGATGCCCCAGCGTATAAACAGGGTCAGAAC CAACTGTATAATGAACTCAATTTGGGGAGGCGAGAGGAGTA TGATGTATTGGACAAGCGGCGGGGGGGGGATCCTGAAATGG GCGGTAAGCCAAGGCGCAAGAATCCACAGGAGGGTTTGTAT AATGAGTTGCAGAAGGATAAAATGGCGGAAGCGTATTCAGA AATCGGAATGAAGGGAGAGCGCCGCAGAGGGAAAGGGCAT GATGGCCTCTACCAAGGTTTGTCAACAGCGACCAAGGATAC CTATGACGCACTTCATATGCAAGCACTGCCCCCCAGG |
| RJ154HL CAR (A6HL/CD8TM/ 4-1BB/CD3zeta) SEQ ID NO: 232 | MLLLVTSLLLCELPHPAFLLIPQVQLVESGGGLVKPGGSLRLSC AASGFTFSDYYMSWIRQAPGKGLEWVSYISSSGSTIYYADSVK GRFTISRDNAKNSLYLQMNSLRAEDTAVYYCARHKTSLNDYD FWSGYLLDYWGQGTLVTVSSGGGGSGGGGSGGGGSDIQMTQS PSSLSASVGDRVTITCRASQSISSYLNWYQQKPGKAPKLLIYAA SSLQSGVPSRFSGSGSGTDFTLTISSLQPEDAATYYCQRYGTFGQ GTKVDIKRAAATTTPAPRPPTPAPTIASQPLSLRPEACRPAAGGA VHTRGLDFACDIYIWAPLAGTCGVLLLSLVITLYCKRGRKKLLY IFKQPFMRPVQTTQEEDGCSCRFPEEEEGGCELRVKFSRSADAP AYKQGQNQLYNELNLGRREEYDVLDKRRGRDPEMGGKPRRK NPQEGLYNELQKDKMAEAYSEIGMKGERRRGKGHDGLYQGLS TATKDTYDALHMQALPPR |

TABLE 6-continued

| Feature SEQ ID NO | Sequence |
|---|---|
| RJ154HL CAR (A6HL/CD8TM/ 4-1BB/CD3zeta) SEQ ID NO: 233 | ATGCTTCTGCTCGTGACAAGCCTGCTGCTGTGCGAGCTGCCC CACCCTGCCTTTCTGCTGATCCCTCAAGTTCAGCTGGTTGAA TCTGGCGGCGGACTGGTTAAGCCTGGCGGTTCTCTGAGACTG AGCTGTGCCGCCTCCGGCTTCACCTTCAGCGACTACTACATG AGCTGGATCAGACAGGCCCCTGGCAAAGGQCTGGAATGGGT GTCCTACATCAGCTCCAGCGGCAGCACCATCTACTACGCCGA TAGCGTGAAGGGCAGATTCACCATCAGCCGGGACAACGCCA AGAACAGCCTGTACCTGCAGATGAACTCCCTGAGAGCCGAG GACACCGCCGTGTACTATTGCGCCAGACACAAGACCAGCCT GAACGACTACGACTTTTGGAGCGGCTACCTGCTGGACTATTG GGGCCAGGGAACACTGGTCACCGTGTCTAGTGGTGGCGGAG GATCTGGCGGAGGTGGAAGCGGCGGAGGCGGATCTGACATC CAGATGACACAGAGCCCTAGCAGCCTGTCTGCCAGCGTGGG AGACAGAGTGACCATCACCTGTAGAGCCAGCCAGAGCATCA GCAGCTACCTGAACTGGTATCAGCAGAAGCCCGGCAAGGCC CCTAAACTGCTGATCTATGCCGCCAGCTCTCTGCAGTCTGGC GTGCCATCTAGATTTTCCGGCAGCGGCTCTGGCACCGACTTC ACCCTGACCATATCTAGCCTGCAGCCTGAGGATGCCGCCACC TACTACTGTCAGAGATACGGCACATTCGGCCAGGGCACCAA GGTGGACATTAAGAGAGCGGCCGCAACCACTACTCCGGCAC CTAGGCCCCCCACTCCGGCACCGACCATTGCATCACAACCAC TGAGTCTTAGACCTGAAGCCTGTCGACCCGCAGCTGGGGGG GCAGTCCACACACGGGGATTGGATTTCGCCTGCGATATATAC ATTTGGGCGCCACTGGCAGGCACCTGCGGGGTCCTGCTCTTG TCCCTTGTCATCACCCTGTACTGTAAGAGAGGAAGAAAGAA GTTGTTGTATATTTTCAAACAGCCATTCATGAGGCCGGTCCA GACCACTCAGGAGGAGGATGGATGCAGTTGCCGCTTTCCGG AAGAGGAAGAGGGTGGGTGTGAACTCCGAGTTAAATTTTCT CGCAGTGCTGATGCCCCAGCGTATAAACAGGGTCAGAACCA ACTGTATAATGAACTCAATTTGGGGAGGCGAGAGGAGTATG ATGTATTGGACAAGCGGCGGGGGCGGGATCCTGAAATGGGC GGTAAGCCAAGGCGCAAGAATCCACAGGAGGGTTTGTATAA TGAGTTGCAGAAGGATAAAATGGCGGAAGCGTATTCAGAAA TCGGAATGAAGGGAGAGCGCCGCAGAGGGAAAGGGCATGA TGGCCTCTACCAAGGTTTGTCAACAGCGACCAAGGATACCT ATGACGCACTTCATATGCAAGCACTGCCCCCCAGG |
| C1 L chain SEQ ID NO: 234 | DIQMTQSPSSLSASVGDRVTITCRASQSISSYLNWYQQKPGKAP KLLIYAASSLQSGVPSRFSGSGSGTDFTLTISSLQPEDAATYYCQ HYGTFGQGTKVEIKR |
| C1 L chain SEQ ID NO: 235 | GACATCCAGATGACACAGAGCCCTAGCAGCCTGTCTGCCAG CGTGGGAGACAGAGTGACCATCACCTGTAGAGCCAGCCAGA GCATCAGCAGCTACCTGAACTGGTATCAGCAGAAGCCCGGC AAGGCCCCTAAACTGCTGATCTATGCCGCCAGCTCTCTGCAG TCTGGCGTGCCATCTAGATTTTCCGGCAGCGGCTCTGGCACC GACTTCACCCTGACCATATCTAGCCTGCAGCCTGAGGATGCC GCCACCTACTACTGTCAGCACTACGGCACATTTGGCCAGGGC ACCAAGGTGGAAATCAAGAGA |
| C1 H chain SEQ ID NO: 236 | QVQLVESGGGLVKPGGSLRLSCAASGFTFSDYYMSWIRQAPGK GLEWVSYISSSGSTIYYADSVKGRFTISRDNAKNSLYLQMNSLR AEDTAVYYCARHAPHKHYDFWSGYYPDYWGQGTLVTVSS |
| C1 H chain SEQ ID NO: 237 | CAAGTTCAGCTGGTTGAATCTGGCGGCGGACTGGTTAAGCCT GGCGGTTCTCTGAGACTGAGCTGTGCCGCCTCCGGCTTCACC TTCAGCGACTACTACATGAGCTGGATCAGACAGGCCCCTGG CAAAGGCCTGGAATGGGTGTCCTACATCAGCTCCAGCGGCA GCACCATCTACTACGCCGATAGCGTGAAGGGCAGATTCACC ATCAGCCGGGACAACGCCAAGAACAGCCTGTACCTGCAGAT GAACTCCCTGAGAGCCGAGGACACCGCCGTGTACTATTGTG CCAGACACGCCCCTCACAAGCACTACGACTTTTGGAGCGGC TACTACCCCGACTATTGGGGCCAGGGAACACTGGTCACAGT GTCCTCT |
| C1LH binder SEQ ID NO: 238 | GACATCCAGATGACACAGAGCCCTAGCAGCCTGTCTGCCAG CGTGGGAGACAGAGTGACCATCACCTGTAGAGCCAGCCAGA GCATCAGCAGCTACCTGAACTGGTATCAGCAGAAGCCCGGC AAGGCCCCTAAACTGCTGATCTATGCCGCCAGCTCTCTGCAG TCTGGCGTGCCATCTAGATTTTCCGGCAGCGGCTCTGGCACC GACTTCACCCTGACCATATCTAGCCTGCAGCCTGAGGATGCC GCCACCTACTACTGTCAGCACTACGGCACATTTGGCCAGGGC ACCAAGGTGGAAATCAAGAGAGGTGGCGGAGGATCTGGCG GAGGTGGAAGCGGCGGAGGCGGATCTCAAGTTCAGCTGGTT GAATCTGGCGGCGGACTGGTTAAGCCTGGCGGTTCTCTGAG ACTGAGCTGTGCCGCCTCCGGCTTCACCTTCAGCGACTACTA |

TABLE 6-continued

| Feature SEQ ID NO | Sequence |
|---|---|
| | CATGAGCTGGATCAGACAGGCCCCTGGCAAAGGCCTGGAAT GGGTGTCCTACATCAGCTCCAGCGGCAGCACCATCTACTACG CCGATAGCGTGAAGGGCAGATTCACCATCAGCCGGGACAAC GCCAAGAACAGCCTGTACCTGCAGATGAACTCCCTGAGAGC CGAGGACACCGCCGTGTACTATTGTGCCAGACACGCCCCTC ACAAGCACTACGACTTTTGGAGCGGCTACTACCCCGACTATT GGGGCCAGGGAACACTGGTCACAGTGTCCTCT |
| C1HL binder SEQ ID NO: 239 | CAAGTTCAGCTGGTTGAATCTGGCGGCGGACTGGTTAAGCCT GGCGGTTCTCTGAGACTGAGCTGTGCCGCCTCCGGCTTCACC TTCAGCGACTACTACATGAGCTGGATCAGACAGGCCCCTGG CAAAGGCCTGGAATGGGTGTCCTACATCAGCTCCAGCGGCA GCACCATCTACTACGCCGATAGCGTGAAGGGCAGATTCACC ATCAGCCGGGACAACGCCAAGAACAGCCTGTACCTGCAGAT GAACTCCCTGAGAGCCGAGGACACCGCCGTGTACTATTGTG CCAGACACGCCCCTCACAAGCACTACGACTTTTGGAGCGGC TACTACCCCGACTATTGGGGCCAGGGAACACTGGTCACAGT GTCCTCTGGTGGCGGAGGATCTGGCGGAGGTGGAAGCGGCG GAGGCGGATCTGACATCCAGATGACACAGAGCCCTAGCAGC CTGTCTGCCAGCGTGGGAGACAGAGTGACCATCACCTGTAG AGCCAGCCAGAGCATCAGCAGCTACCTGAACTGGTATCAGC AGAAGCCCGGCAAGGCCCCTAAACTGCTGATCTATGCCGCC AGCTCTCTGCAGTCTGGCGTGCCATCTAGATTTTCCGGCAGC GGCTCTGGCACCGACTTCACCCTGACCATATCTAGCCTGCAG CCTGAGGATGCCGCCACCTACTACTGTCAGCACTACGGCAC ATTTGGCCAGGGCACCAAGGTGGAAATCAAGAGA |
| RJ155LH CAR (C1LH/CD8TM/ 4-1BB/CD3zeta) SEQ ID NO: 240 | MLLLVTSLLLCELPHPAFLLIPDIQMTQSPSSLSASVGDRVTITC RASQSISSYLNWYQQKPGKAPKLLIYAASSLQSGVPSRFSGSGS GTDFTLTISSLQPEDAATYYCQHYGTFGQGTKVEIKRGGGGSG GGGSGGGGSQVQLVESGGGLVKPGGSLRLSCAASGFTFSDYY MSWIRQAPGKGLEWVSYISSSGSTIYYADSVKGRFTISRDNAKN SLYLQMNSLRAEDTAVYYCARHAPHKHYDFWSGYYPDYWGQ GTLVTVSSAAATTTPAPRPPTPAPTIASQPLSLRPEACRPAAGGA VHTRGLDFACDIYIWAPLAGTCGVLLLSLVITLYCKRGRKKLLY IFKQPFMRPVQTTQEEDGCSCRFPEEEEGGCELRVKFSRSADAP AYKQGQNQLYNELNLGRREEYDVLDKRRGRDPEMGGKPRRK NPQEGLYNELQKDKMAEAYSEIGMKGERRRGKGHDGLYQGLS TATKDTYDALHMQALPPR |
| RJ155LH CAR (C1LH/CD8TM/ 4-1BB/CD3zeta) SEQ ID NO: 241 | ATGCTTCTGCTCGTGACAAGCCTGCTGCTGTGCGAGCTGCCC CACCCTGCCTTTCTGCTGATCCCTGACATCCAGATGACACAG AGCCCTAGCAGCCTGTCTGCCAGCGTGGGAGACAGAGTGAC CATCACCTGTAGAGCCAGCCAGAGCATCAGCAGCTACCTGA ACTGGTATCAGCAGAAGCCCGGCAAGGCCCCTAAACTGCTG ATCTATGCCGCCAGCTCTCTGCAGTCTGGCGTGCCATCTAGA TTTTCCGGCAGCGGCTCTGGCACCGACTTCACCCTGACCATA TCTAGCCTGCAGCCTGAGGATGCCGCCACCTACTACTGTCAG CACTACGGCACATTTGGCCAGGGCACCAAGGTGGAAATCAA GAGAGGTGGCGGAGGATCTGGCGGAGGTGGAAGCGGCGGA GGCGGATCTCAAGTTCAGCTGGTTGAATCTGGCGGCGGACT GGTTAAGCCTGGCGGTTCTCTGAGACTGAGCTGTGCCGCCTC CGGCTTCACCTTCAGCGACTACTACATGAGCTGGATCAGACA GGCCCCTGGCAAAGGCCTGGAATGGGTGTCCTACATCAGCT CCAGCGGCAGCACCATCTACTACGCCGATAGCGTGAAGGGC AGATTCACCATCAGCCGGGACAACGCCAAGAACAGCCTGTA CCTGCAGATGAACTCCCTGAGAGCCGAGGACACCGCCGTGT ACTATTGTGCCAGACACGCCCCTCACAAGCACTACGACTTTT GGAGCGGCTACTACCCCGACTATTGGGGCCAGGGAACACTG GTCACAGTGTCCTCTGCGGCCGCAACCACTACTCCGGCACCT AGGCCCCCCACTCCGGCACCGACCATTGCATCACAACCACT GAGTCTTAGACCTGAAGCCTGTCGACCCGCAGCTGGGGGGG CAGTCCACACACGGGGATTGGATTTCGCCTGCGATATATACA TTTGGGCGCCACTGGCAGGCACCTGCGGGGTCCTGCTCTTGT CCCTTGTCATCACCCTGTACTGTAAGAGAGGAAGAAAGAAG TTGTTGTATATTTTCAAACAGCCATTCATGAGGCCGGTCCAG ACCACTCAGGAGGAGGATGGATGCAGTTGCCGCTTTCCGGA AGAGGAAGAGGGTGGGTGTGAACTCCGAGTTAAATTTTCTC GCAGTGCTGATGCCCCAGCGTATAAACAGGGTCAGAACCAA CTGTATAATGAACTCAATTTGGGGAGGCGAGAGGAGTATGA TGTATTGGACAAGCGGCGGGGGCGGGATCCTGAAATGGGCG GTAAGCCAAGGCGCAAGAATCCACAGGAGGGTTTGTATAAT GAGTTGCAGAAGGATAAAATGGCGGAAGCGTATTCAGAAAT CGGAATGAAGGGAGAGCGCCGCAGAGGGAAAGGGCATGAT GGCCTCTACCAAGGTTTGTCAACAGCGACCAAGGATACCTA TGACGCACTTCATATGCAAGCACTGCCCCCCAGG |

TABLE 6-continued

| Feature SEQ ID NO | Sequence |
|---|---|
| RJ15SHL CAR (C1HL/CD8TM/ 4-1BB/CD3zeta) SEQ ID NO: 242 | MLLLVTSLLLCELPHPAFLLIPQVQLVESGGGLVKPGGSLRLSC AASGFTFSDYYMSWIRQAPGKGLEWVSYISSSGSTIYYADSVK GRFTISRDNAKNSLYLQMNSLRAEDTAVYYCARHAPHKHYDF WSGYYPDYWGQGTLVTVSSGGGGSGGGGSGGGGSDIQMTQSP SSLSASVGDRVTITCRASQSISSYLNWYQQKPGKAPKLLIYAAS SLQSGVPSRFSGSGSGTDFTLTISSLQPEDAATYYCQHYGTFGQ GTKVEIKRAAATTTPAPRPPTPAPTIASQPLSLRPEACRPAAGGA VHTRGLDFACDIYIWAPLAGTCGVLLLSLVITLYCKRGRKKLLY IFKQPFMRPVQTTQEEDGCSCRFPEEEEGGCELRVKFSRSADAP AYKQGQNQLYNELNLGRREEYDVLDKRRGRDPEMGGKPRRK NPQEGLYNELQKDKMAEAYSEIGMKGERRRGKGHDGLYQGLS TATKDTYDALHMQALPPR |
| RJ155HL CAR (C1HL/CD8TM/ 4-1BB/CD3zeta) SEQ ID NO: 243 | ATGCTTCTGCTCGTGACAAGCCTGCTGCTGTGCGAGCTGCCC CACCCTGCCTTTCTGCTGATCCCTCAAGTTCAGCTGGTTGAA TCTGGCGGCGGACTGGTTAAGCCTGGCGGTTCTCTGAGACTG AGCTGTGCCGCCTCCGGCTTCACCTTCAGCGACTACTACATG AGCTGGATCAGACAGGCCCCTGGCAAAGGCCTGGAATGGGT GTCCTACATCAGCTCCAGCGGCAGCACCATCTACTACGCCGA TAGCGTGAAGGGCAGATTCACCATCAGCCGGGACAACGCCA AGAACAGCCTGTACCTGCAGATGAACTCCCTGAGAGCCGAG GACACCGCCGTGTACTATTGTGCCAGACACGCCCCTCACAA GCACTACGACTTTTGGAGCGGCTACTACCCCGACTATTGGGG CCAGGGAACACTGGTCACAGTGTCCTCTGGTGGCGGAGGAT CTGGCGGAGGTGGAAGCGGCGGAGGCGGATCTGACATCCAG ATGACACAGAGCCCTAGCAGCCTGTCTGCCAGCGTGGGAGA CAGAGTGACCATCACCTGTAGAGCCAGCCAGAGCATCAGCA GCTACCTGAACTGGTATCAGCAGAAGCCCGGCAAGGCCCCT AAACTGCTGATCTATGCCGCCAGCTCTCTGCAGTCTGGCGTG CCATCTAGATTTTCCGGCAGCGGCTCTGGCACCGACTTCACC CTGACCATATCTAGCCTGCAGCCTGAGGATGCCGCCACCTAC TACTGTCAGCACTACGGCACATTTGGCCAGGGCACCAAGGT GGAAATCAAGAGAGCGGCCGCAACCACTACTCCGGCACCTA GGCCCCCCACTCCGGCACCGACCATTGCATCACAACCACTG AGTCTTAGACCTGAAGCCTGTCGACCCGCAGCTGGGGGGGC AGTCCACACACGGGGATTGGATTTCGCCTGCGATATATACAT TTGGGCGCCACTGGCAGGCACCTGCGGGGTCCTGCTCTTGTC CCTTGTCATCACCCTGTACTGTAAGAGAGGAAGAAAGAAGT TGTTGTATATTTTCAAACAGCCATTCATGAGGCCGGTCCAGA CCACTCAGGAGGAGGATGGATGCAGTTGCCGCTTTCCGGAA GAGGAAGAGGGTGGGTGTGAACTCCGAGTTAAATTTTCTCG CAGTGCTGATGCCCCAGCGTATAAACAGGGTCAGAACCAAC TGTATAATGAACTCAATTTGGGGAGGCGAGAGGAGTATGAT GTATTGGACAAGCGGCGGGGGGGGGATCCTGAAATGGGCGG TAAGCCAAGGCGCAAGAATCCACAGGAGGGTTTGTATAATG AGTTGCAGAAGGATAAAATGGCGGAAGCGTATTCAGAAATC GGAATGAAGGGAGAGCGCCGCAGAGGGAAAGGGCATGATG GCCTCTACCAAGGTTTGTCAACAGCGACCAAGGATACCTAT GACGCACTTCATATGCAAGCACTGCCCCCCAGG |

EXAMPLES

Example 1-Preliminary Studies on Anti-FGFR4 CARs

Anti-FGFR4 CARs were developed. A recombinant extracellular domain for FGFR4 was used to screen a human scFv phage display library. The following svFv binders for FGFR4 were isolated, screened as scFv-Fc proteins, then cloned into a second-generation CAR lentiviral expression vector, featuring a human CD8 linker and transmembrane region, 4-1BB (CD137) and CD3-zeta chain (BBz) signaling domains: M408, M409, M412, M414, M415, M418, M418, M422, M424. Anti-FGR4 CARs were tested for anti-tumor lytic activity (FIG. 1). Briefly, CAR-T expressing anti-FGFR4 binders were tested against the CD19+/FGFR4$^+$ cell line RH30_19, the CD19(−)/FGFR4$^+$ line RMS559. Raji, a positive control for CD19-CAR, was not lysed by FGFR4-specific CARs. A control included a murine MAb-derived binder BT53-CAR; an FMC63-based CD19-specific CAR and untransduced activated T cells (UTD) served as positive and negative controls.

In some vectors the CAR sequence was followed by a T2A ribosomal skip sequence and a truncated human EGFR, to facilitate detection of T cell transductants (Wang X et al., 2011, Blood, 118:1255-63). When expressed as scFv-Fc fusion proteins, they bound FGFR4 on the surface of the following RMS tumor cell lines by flow cytometry: RMS559, R14, RH30, as well as lines including: HEK-293T expressing FGFR4, and RH30 transduced to express CD19 (RH30_19). Calculated Kd from SPR analysis (Biacore) using immobilized FGFR4 for M408, M409, M410, M414, M417 scFv-Fc and mouse BT53 (scFv from a mouse anti-FGFR4 antibody that should be effective as a CAR were 9.3 nM, 56.7 nM, 1.6 nM, 23.7 nM, 42.5 nM, and 4.2 nM, respectively. The strong activity of the CD19-CAR against the RH30_19 cell line may have been due to the higher density of the target antigen on the cell line. Using Quanti-Brite bead-based estimation of target molecule numbers per cell, the endogenously encoded FGFR4 has 19,974 targets per cell while the transgene encoded CD19 has 57,238.

A differentiator between the initial scFv candidates for CAR-T activity included in vivo activity. NSG mice were inoculated i.v. with Rh30_19 expressing FFLuc, and 3 days later following imaging, post i.p injection of luciferin, on an IVIS system were inoculated i.v. with CAR-T (Tumor+CAR), untransduced T cells (Tumor+UTD), or no T cells (Tumor Only). Weekly images were captured, with scaling changed on day 32 due to signal brightness. By day 59 all mice that did not receive FGFR4-specific CARs were sacrificed per protocol, while mice that did were alive on day 66.

Figure 2:
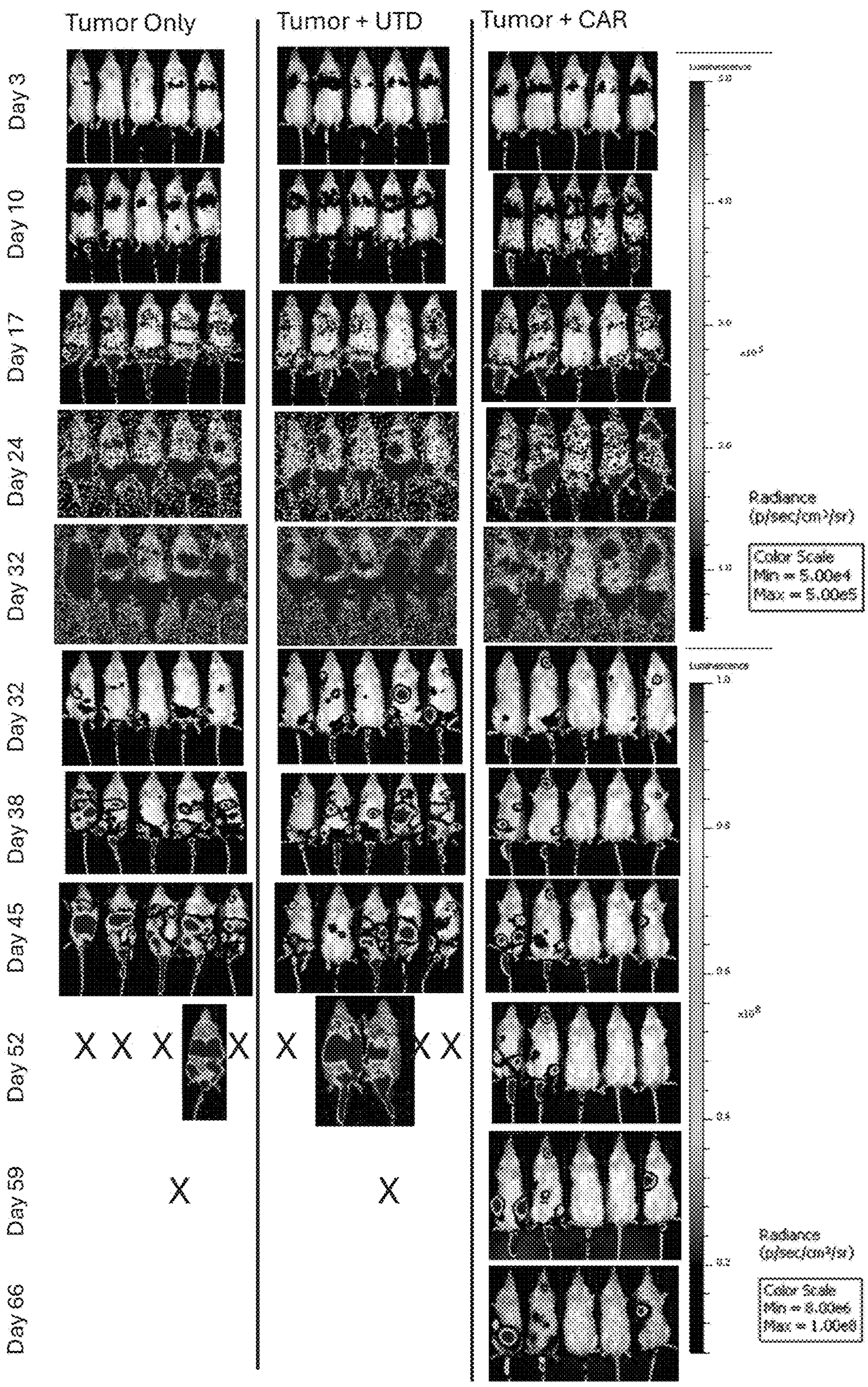
FIG. 2 depicts an analysis for in vivo activity of anti-FGFR4 CAR T cells in a xenograft model. NSG mice were inoculated i.v. with Rh30_19 (expressing FFLuc) and 3 days later (following imaging, post i.p injection of luciferin, on an I^VIS system) inoculated i.v. with CAR T-cells (Tumor+CAR), untransduced T cells (Tumor+UTD), or no T cells (Tumor Only). Weekly images were captured, with scaling changed on day 32. By day 59 all mice that did not receive FGFR4-specific CARs were sacrificed per protocol, while mice that did were alive on day 66.

When Rh30_19 cells were given i.v., followed 3 days later by CAR-T, only mice that received FGFR4-CAR were alive at day 66. (FIG. 2). This result indicated that the M410-based CAR was active in vivo. However, when a more challenging treatment model was used, where the RH30_19 RMS cell line was injected intramuscularly (i.m.), followed by CAR-T on day 3, neither FGFR4-CAR-T nor a CD19-CAR-T had an impact on tumor progression. The incomplete protection seen with FGFR4 CAR could have been due to T cell exhaustion or elimination. When peripheral blood was taken at day 11 and day 42, human T cells expressing the anti-FGFR4 CAR were readily detected by flow cytometry. On day 42, CAR+ cells accounted for 61.5% and 71.6% of the CD45+ CD8+ cells and 66.5% and 34.9% of the CD45+ CD4+ cells detected in the peripheral blood when either 3 million or 1 million CAR-T were injected i.v., respectively. Untransduced T cells accounted for 0.3 and 0.2% of the gating strategy, demonstrating antigen-dependent specificity for persistence.

As persistence per se, was not the reason for the lack of therapeutic effect, the tumor microenvironment was examined to determine if the tumor lesion contained infiltrating T cells. Tumors can be classified according to their inflammatory pathology. "Cold tumors" are non-inflamed and contain few if any T cells. "Hot" or immune-predominant tumors are abundant in lymphocytic infiltrates and are associated with better outcome and responsiveness to immune checkpoint inhibitors (Santoiemma P P, et al., 2015, Cancer Biol Ther, 16:807-20, Pages F, el al., 2018, Lancet, 391:2128-2139).

A third category of tumor-immune architecture is called "immune-excluded," where lymphocytes are present, but appear restricted to certain regions or to the periphery of the tumor and appear to interact with stromal elements. In the i.v. Rh30_19 model, M410-based CAR, had a partially therapeutic effect (FIG. 2). Tumor progression was associated with liver metastases, while animals at takedown that did not show a luciferase signal had few or no liver metastases. Histopathology of liver metastases established two important parameters. First, tumor alone had very little stromal element in NSG mice. Second, in treated animals, a clear stroma-rich immune-excluded architecture expressing a diffuse PD-L1 staining pattern was seen.

Figure 3:
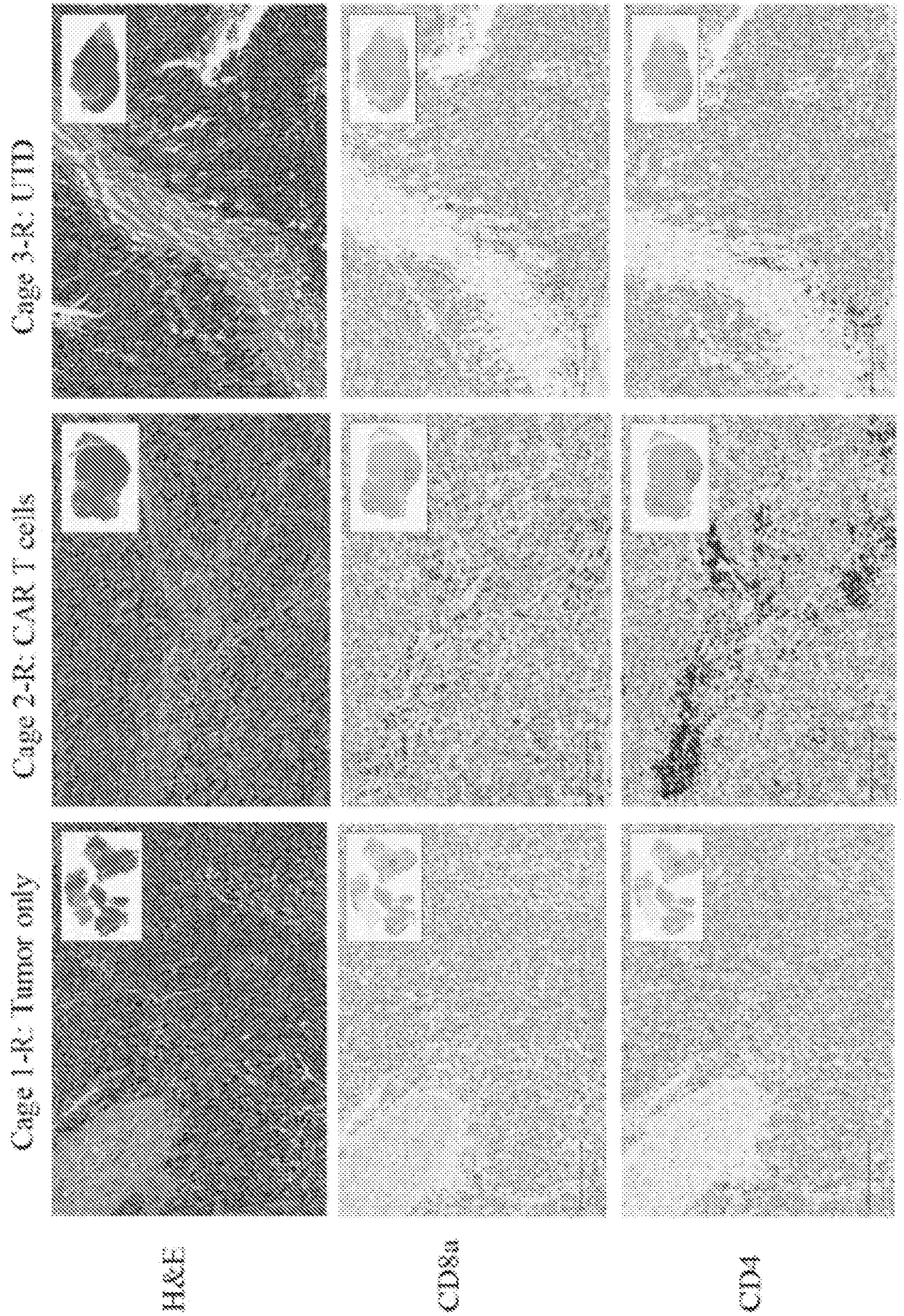
FIG. 3 depicts an analysis of Rh30_19-bearing mice treated with M410-CAR-T. NSG mice were injected i.m. with tumor in the hind limb and subsequently untreated (left column, Tumor only), treated with M410-CAR-T (center column, CAR T cells), or infused with untransduced T cells (right column, UTD). Tumors were excised, fixed, sectioned and stained for human CD8a, CD4, or with H&E, rows 2, 3, and 1, respectively.

When i.m. RH30_19 tumors were analyzed by histopathology, a similar morphology was noted in that lymphocytes were excluded or only weakly able to infiltrate the tumor (FIG. 3). Briefly, Rh30_19-bearing mice treated with M410-CAR-T were analyzed. NSG mice were injected i.m. with tumor in the hind limb and subsequently untreated, treated with M410-CAR-T, or infused with untransduced T cells. Tumors were excised, fixed, sectioned and stained for human CD8a, CD4, or with H&E. Mice that received tumor only showed no lymphocytic infiltrates. Mice that received anti-FGFR4 CAR showed an immune excluded phenotype. H&E staining revealed that tumor in CAR-treated animals had a rich stroma with broad bands of collagen, while untreated animals did not. Thus, both model systems can be used to study immune control and disease progression.

Example 2-Screening for FGFR4-Binding Polypeptides

Figure 4:
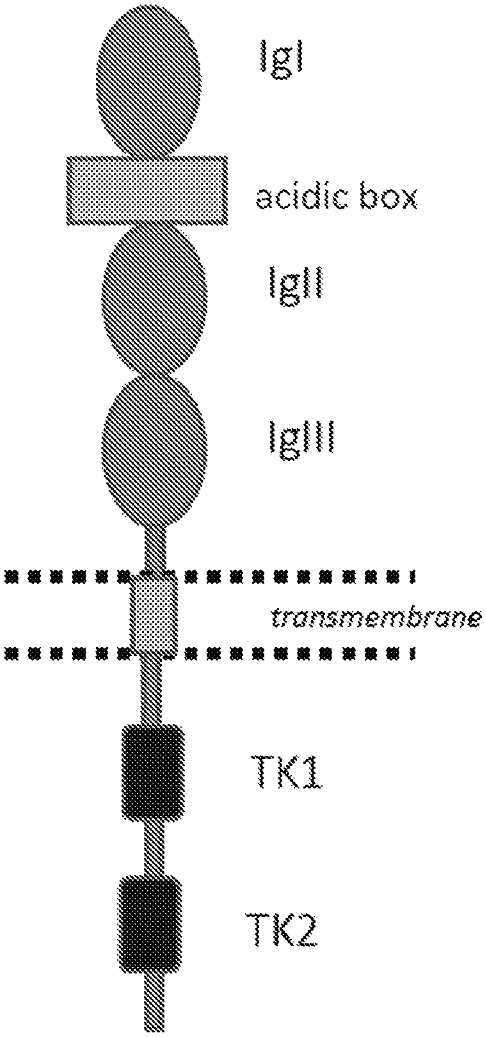
FIG. 4 is a schematic of a FGFR4 protein with extracellular domains including: an IgI domain, an acidic box, an IgII domain, and a membrane-proximal IgIII domain; a transmembrane domain; and intracellular domains including: a TK1 domain, and a TK2 domain.

Epitope mapping studies on FGFR4 protein demonstrated that the M410 scFv binding site was located at a site distal to the membrane, in the vicinity of the acidic box depicted in FIG. 4. It was hypothesized that creating a binder to a more membrane-proximal region would improve anti-FGFR4 CAR activity. To generate optimal anti-FGFR4 CARs, a membrane proximal domain (IgGIII) of FGFR4 was expressed as a recombinant protein and used as bait in expression library screens. Phage-display libraries were used to identify two kinds of binders. In a first set of screenings, an expression library composed of VH-only single chain binders was utilized (VH only). In a second set of screenings, a F(ab)-based library was used.

For the first set of screenings, a domain antibody (dAB) phage display library was created. The library used a single VH domain as a scaffold, and was screened for FGFR4 binders (Chen W, et al., 2008, J Mol Biol 382:779-789; Chen W, et al., 2010, Mol Immunol, 47:912-21; Chen W, et al., 2008, PNAS 105:17121-6). The phage library was cycled through at least 3 rounds of panning using plate bound recombinant extracellular domain (ECD) FGFR4 or biotin-labeled soluble antigen, and specific binders identified using soluble expression-based monoclonal ELISA (semELISA). Binders were expressed as recombinant antibodies with an HA-tag, and binding against ECD-FGFR4 quantified by ELISA was performed. For the F(ab) screening, VL-VH domain binders were identified. A set of VH-VL domain binders was derived from the VL-VH domain binders in which the VH domain preceded the VL domain in the polypeptide. Both the VL-VH domain binders and the VH-VL domain binders included a triple repeat of the amino acid sequence "GGGGS", which linked the VH and VL chains. TABLE 3 lists certain FGFR4-binding polypeptides including: VH domain only binders identified in a screening; VL-VH domain binders identified in a screening; and VH-VL domain derived from the identified VL-VH domain binders.

Example 3-Generation of Anti-FGFR4 CARs

Figure 5:
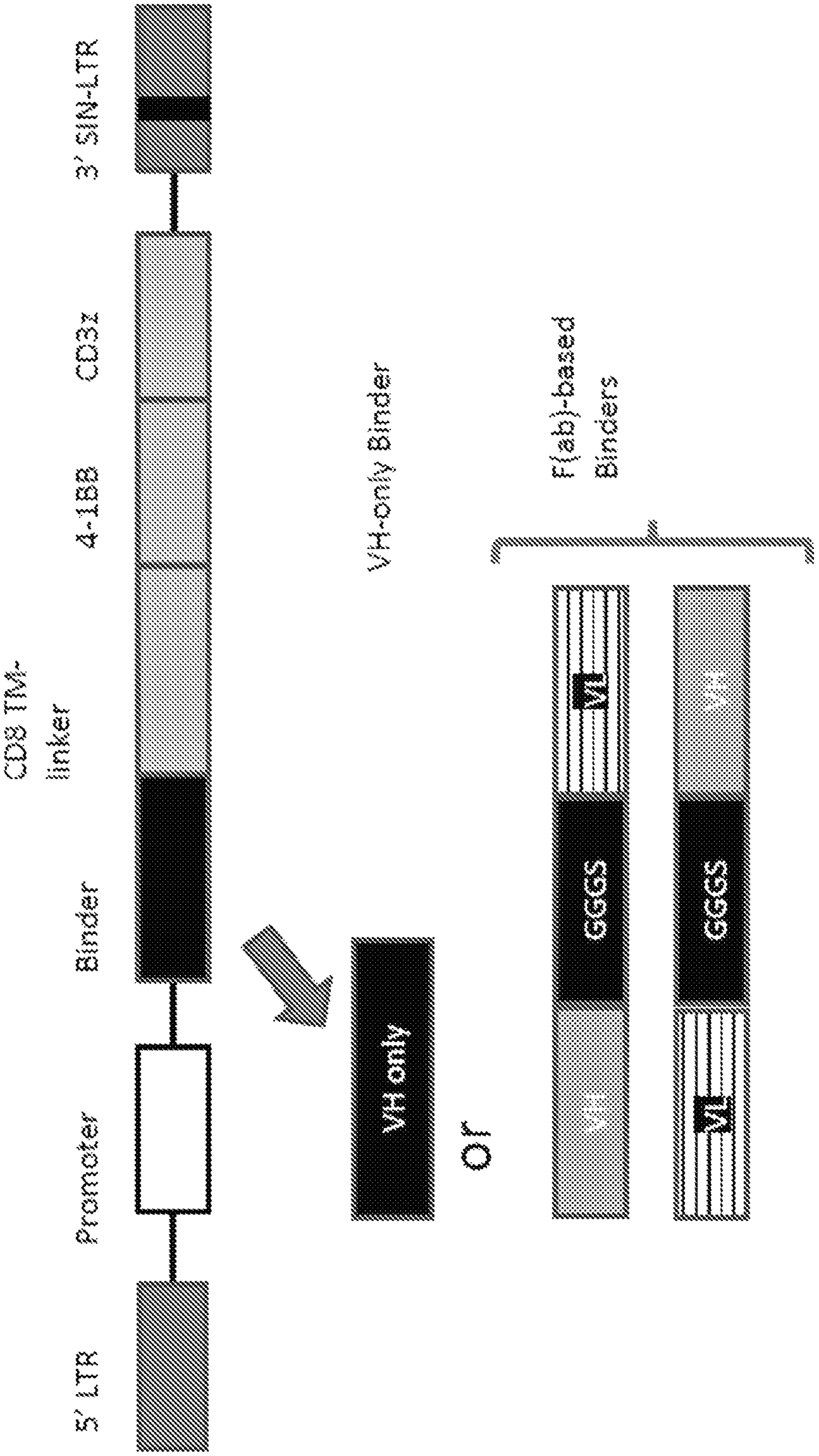
FIG. 5 is a schematic of polynucleotides encoding anti-FGFR4 CARs and depicts certain regions encoding: a ligand binding domain (binder), such as an FGFR4-binding polypeptide; a CD8 transmembrane domain and linker domain; a 4-1BB domain; and a CD3 zeta domain. Some polynucleotides also included a promoter, and lentiviral vector sequences such as 5' LTR, and 3' SIN-LTR A ligand binding domain (binder) can be derived from a VH domain polypeptide, a polypeptide containing a VH domain linked to a VL domain via a linker, or a polypeptide containing a VL domain linked to a VH domain via a linker.

Polynucleotides were constructed comprising expression vectors encoding anti-FGFR4 CARs. FIG. 5 is a schematic drawing and depicts certain polynucleotides encoding: a ligand binding domain (binder), such as an FGFR4-binding polypeptide listed in TABLE 3; a CD8 transmembrane domain and linker domain; a 4-1BB domain; and a CD3 zeta domain. Some polynucleotides also included a promoter, and lentiviral vector sequences such as 5' LTR, and 3' SIN-LTR (SIN: self-inactivating). Some polynucleotides also included nucleic acids encoding: a leader sequence for extracellular expression; and a short 'AAA' linker. TABLE 7 lists anti-FGFR4 CARs containing FGFR4-binding polypeptides. Some embodiments include CARs encoded by nucleotide sequences, or comprising amino acid sequences listed in TABLE 3, TABLE 4, TABLE 5 and TABLE 6.

TABLE 7

| Anti FGFR4-CAR | FGFR4 binding polypeptide (binder) |
|---|---|
| RJ141 | E9 |
| RJ142 | A4 |

TABLE 7-continued

| Anti FGFR4-CAR | FGFR4 binding polypeptide (binder) |
|---|---|
| RJ143 | E61 |
| RJ144 | A7 |
| RJ145 | D92 |
| RJ146 | D8 |
| RJ147 | F11 |
| RJ148 | C52 |
| RJ149LH | H4-VLVH |
| RJ149HL | H4-VHVL |
| RJ150LV | G6-VLVH |
| RJ150HL | G6-VHVL |
| RJ151LH | C9-VLVH |
| RJ151HL | C9-VHVLH |
| RJ152LH | D7-VLVH |
| RJ152HL | D7-VHVL |
| RJ153LH | B7-VLVH |
| RJ153HL | B7-VHVL |
| RJ154LH | A6-VLVH |
| RJ154HL | A6-VHVL |
| RJ155LH | C1-VLVH |
| RJ155HL | C1-VHVL |

Example 4-Cell Surface Expression of Anti-FGFR4 CARs

Polynucleotides comprising expression vectors encoding anti-FGFR4 CARs were transduced into activated T-cells.

To detect cell surface expression of the CARs, CAR T-cells were incubated with biotinylated FGFR4 protein, washed by standard centrifugation methods, incubated with streptavidin (SA)-linked-PE (phycoerythrin), washed again, and analyzed by flow cytometry. Controls included: activated T cells analyzed with no staining (unstained), or with exposure to both biotinylated FGFR4 and SA-PE (UTD, untransduced); and CARs including m410 and m412 binders.

Figure 6:
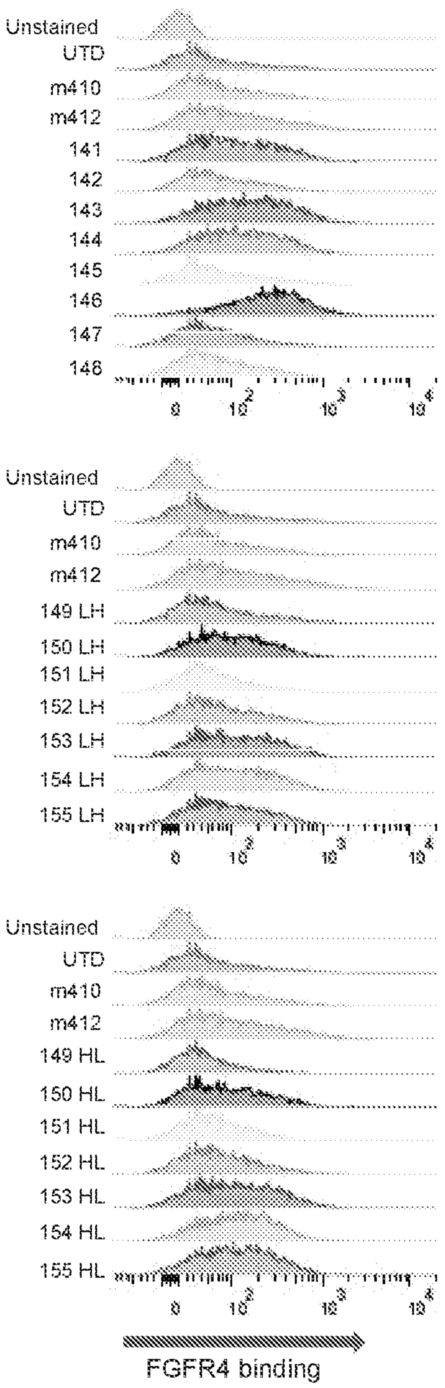
FIG. 6 depicts graphs of relative levels of expression of CARs in transduced T-cells. Upper panel depicts relative levels of expression of CARs containing various VH domain only FGFR4-binding polypeptides; middle panel depicts relative levels of expression of CARs containing various VL-VH domain FGFR4-binding polypeptides; and lower panel depicts relative levels of expression of CARs containing various VH-VL domain FGFR4-binding polypeptides.

Cells expressing the RJ146 CAR containing the VH-only binder 'D8' consistently showed the highest levels of binding between all CARs (FIG. 6). Cells expressing the RJ154HL CAR containing the 'A6-VHVL' binder showed the highest levels of binding between CARs containing the F(ab)-derived binders (FIG. 6, middle and lower panels). FIG. 6 also illustrates that not all the CARs containing binders has a specific anti-FGFR4 binding activity greater than control levels. For example, the RJ145 CAR containing the VH-only 'D92' binder, and the RJ148 CAR containing the VH-only 'C52' binder did not bind FGFR4 at levels substantially greater than control levels. In addition, a number of CARs containing the F(ab)-format binders also show essentially no FGFR4 binding, such as the RJ152LH CAR, and the RJI49HL CAR.

Example 5-In Vitro Cytotoxic Activity of Anti-FGFR4 CARs

Human T cells were activated in the presence of the cytokine IL-2, and then transduced with lentiviral (LV) vectors encoding CARs containing FGFR4 binders. To test cytotoxic activity of the anti-FGFR4 CAR T-cells, the CAR T-cells (effector cells, 'E') were incubated at various ratios with Rh30 cells (target cells, 'T') which express FGFR and also express a luciferase reporter protein. A Raji cell line, which did not express FGFR4, was used as a negative control. CAR T-cells that were activated but not transduced with LV (UTD) were used as CAR T-cell control.

Figure 7:
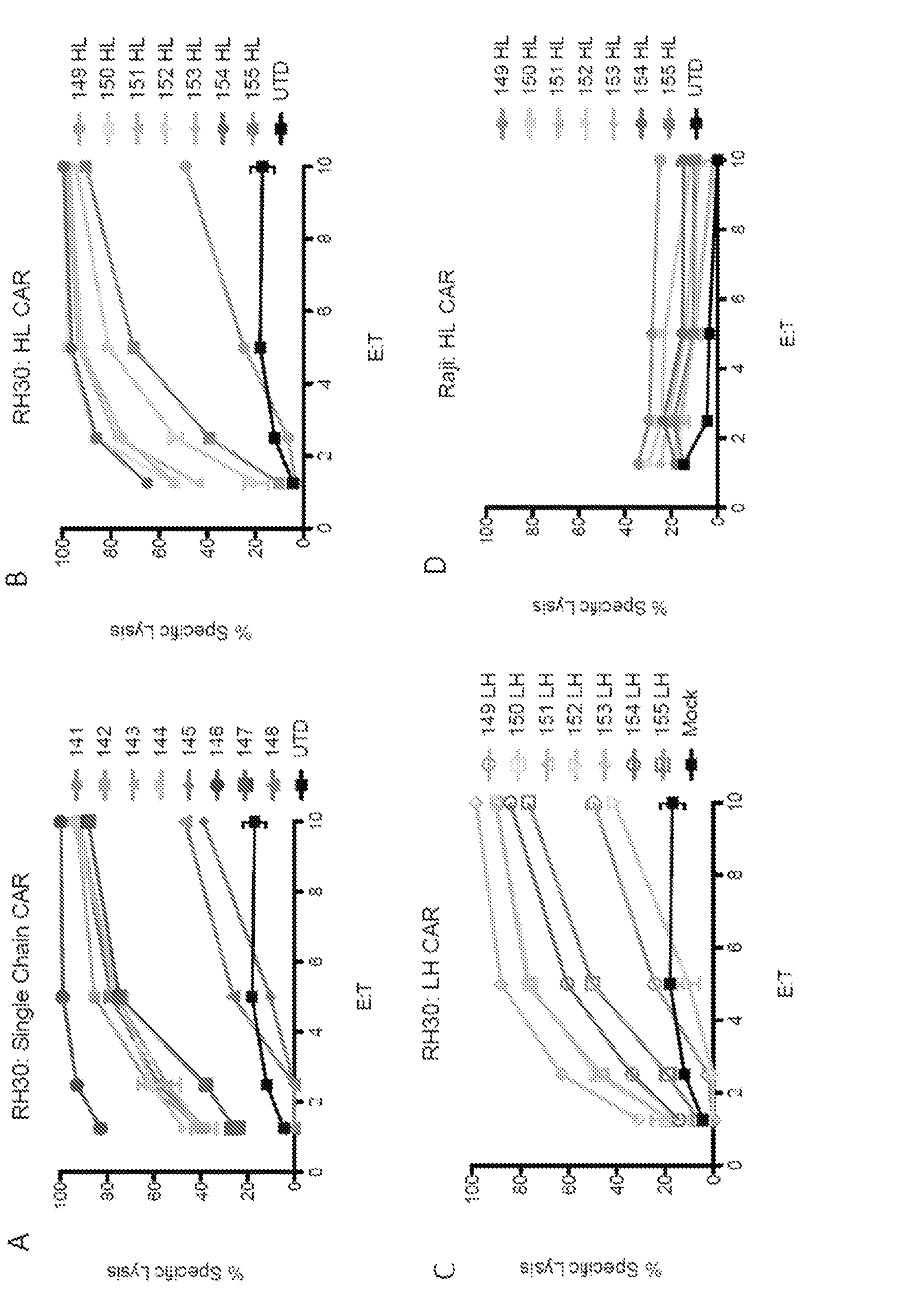
FIG. 7 depicts graphs of percentage specific lysis of target cells for various ratios of effector:target cells. Effector cells included anti-FGFR4 CAR T-cells containing different CARs. Target cells included RH30 cells, and Raji cells.

As shown in FIG. 7, at lower E:T ratios, most of the effector CAR T-cells readily lysed the target Rh30 cells, and most of cells containing each CAR showed distinct killing activity. Cells containing the RJ145 CAR and the RJ148 CAR, which each contain a single chain binder had levels of killing similar to UTD controls. Cells containing the RJ149HL CAR, RJ149LH CAR, or RJ152LH CAR which each contain F(ab) derived binder also had levels of killing similar to UTD controls.

Example 6-In Vitro Cytokine Production of Anti-FGFR4 CARs

Figure 8:
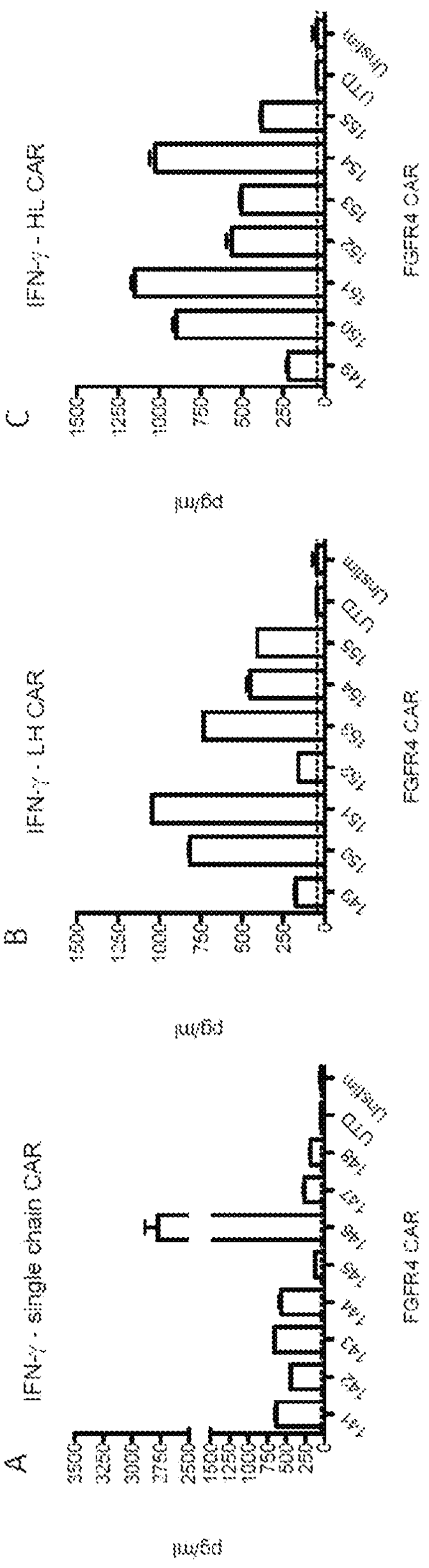
FIG. 8 depicts graphs of interferon gamma production from anti-FGFR4 CAR T-cells containing different CARs incubated with Rh30 cells, which is a rhabdomyosarcoma cell line.

To evaluate the activity of anti-FGFR4 CAR T-cells to express interferon gamma (IFNG), the anti-FGFR4 CAR T-cells were incubated with Rh30 cells which is a rhabdomyosarcoma cell line. Cells were cultured overnight, supernatant collected, and tested for the presence of IFNG by ELISA. Unstimulated and untransduced (UTD) T cells were included as negative controls. Levels of TNF-A were also tested. As shown in FIG. 8, anti-FGFR4 CAR T-cells containing the RJ146 CAR had significant and substantially greater levels of IFNG than any other tested CAR TABLE 8 summarizes results from the foregoing Examples. The activities of the anti-FGFR4 CAR 'RJ146' which contained the VH domain only 'D8' binder were superior to all other tested CARs.

TABLE 8

| CAR | FGFR4 binding polypeptide (binder) | Screen | CAR expression level | Cytotoxic activity | IFN-G expression level | TNF-A expression level |
|---|---|---|---|---|---|---|
| RJ141 | E9 | VH domain only | | high | high | medium |
| RJ142 | A4 | VH domain only | | high | | medium |
| RJ143 | E61 | VH domain only | medium | high | high | medium |
| RJ144 | A7 | VH domain only | medium | high | high | medium |
| RJ145 | D92 | VH domain only | none | | | |

TABLE 8-continued

| CAR | FGFR4 binding polypeptide (binder) | Screen | CAR expression level | Cytotoxic activity | IFN-G expression level | TNF-A expression level |
|---|---|---|---|---|---|---|
| RJ146 | D8 | VH domain only | highest | highest | high | high |
| RJ147 | F11 | VH domain only | | high | | medium |
| RJ148 | C52 | VH domain only | none | | | |
| RJ149LH | H4-VLVH | F(ab) screen | none | | | |
| RJ149HL | H4-VHVL | — | none | | | |
| RJ150LV | G6-VLVH | F(ab) screen | high | high | high | |
| RJ150HL | G6-VHVL | — | medium | high | high | high |
| RJ151LH | C9-VLVH | F(ab) screen | low | high | high | high |
| RJ151HL | C9-VHVL H | — | low | high | high | high |
| RJ152LH | D7-VLVH | F(ab) screen | | | | |
| RJ152HL | D7-VHVL | — | | medium | | |
| RJ153LH | B7-VLVH | F(ab) screen | | high | | |
| RJ153HL | B7-VHVL | — | medium | high | medium | high |
| RJ154LH | A6-VLVH | F(ab) screen | | medium | | |
| RJ154HL | A6-VHVL | — | high | high | high | high |
| RJ155LH | C1-VLVH | F(ab) screen | | medium | high | |
| RJ55SHL | C1-VHVL | — | | medium | medium | |

The term "comprising" as used herein is synonymous with "including," "containing," or "characterized by," and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A chimeric antigen receptor (CAR) comprising:

(a) an antigen binding region which specifically binds an IgIII membrane-proximal domain of a human fibroblast growth factor receptor 4 (FGFR4) protein, comprising:

(i) a complementarity determining region 1 of a heavy chain variable region (H-CDR1) comprising the amino acid sequence set forth in SEQ ID NO:132, (ii) an H-CDR2 comprising the amino acid sequence set forth in SEQ ID NO: 133, (iii) an H-CDR3 comprising the amino acid sequence set forth in any one of SEQ ID NOs: 74, 98, 110, 134 and 146, (iv) a complementarity determining region 1 of a light chain variable region (L-CDR1) comprising the amino acid sequence set forth in SEQ ID NO:135, (v) an L-CDR2 comprising the amino acid sequence set forth in SEQ ID NO: 136, (vi) an L-CDR3 comprising the amino acid sequence set forth in any one of SEQ ID NOs: 77, 101 and 137;

(b) a transmembrane domain; and (c) an intracellular signaling domain.

2. The CAR of claim 1, wherein the L-CDR3 comprises the amino acid sequence of SEQ ID NO: 137.

3. The CAR of claim 2, wherein the H-CD3 comprises the amino acid sequence of SEQ ID NO:134.

4. The CAR of claim 1, wherein:

(i) the light chain variable region comprises an amino acid sequence having at least 90% sequence identity to the amino acid sequence set forth in any one of SEQ ID NOs: 174, 194 and 224; and (ii) the heavy chain variable region comprises an amino acid sequence having at least 90% sequence identity to the amino acid sequence set forth in any one of SEQ ID NOs: 176, 196, 206, 226 and 236.

5. The CAR of claim 4, wherein the light chain variable region comprises an amino acid sequence having at least 90% sequence identity to the amino acid sequence set forth in SEQ ID NO:224.

6. The CAR of claim 5, wherein the heavy chain variable region comprises an amino acid sequence having at least 90% sequence identity to the amino acid sequence set forth in SEQ ID NO:226.

7. The CAR of claim 4, wherein the antigen binding region comprises an amino acid sequence having at least 90% sequence identity to the amino acid sequence set forth in any one of SEQ ID NOs: 09-22.

8. The CAR of claim 7, wherein the antigen binding region comprises an amino acid sequence having at least 90% sequence identity to the amino acid sequence set forth in SEQ ID NO:19 or SEQ ID: 20.

9. The CAR of claim 1, further comprising a polypeptide spacer located between the antigen binding domain and the transmembrane domain.

10. The CAR of claim 9, wherein the polypeptide spacer comprises a hinge domain.

11. The CAR of claim 10, wherein the polypeptide spacer comprises a CD28 hinge domain.

12. The CAR of claim 1, wherein the transmembrane domain comprises a CD8 transmembrane domain or a CD28 transmembrane domain.

13. The CAR of claim 12, wherein the transmembrane domain comprises the CD28 transmembrane domain.

14. The CAR of claim 1, wherein the intracellular signaling domain comprises a costimulatory domain selected from the group consisting of CD27, CD28, 4-1BB, OX-40, CD30, CD40, PD-1, ICOS, LFA-1, CD2, CD7, NKG2C, B7-H3, and CD3-zeta.

15. The CAR of claim 14, wherein the intracellular signaling domain comprises the 4-1BB domain and the CD3-zeta domain.

16. A nucleic acid encoding the CAR of claim 1.

17. A cell comprising the CAR of claim 1.

18. The cell of claim 17, wherein the cell is a T cell, a stem cell, a precursor T-cell, or a hematopoietic stem cell or an NK cell.

19. A pharmaceutical composition comprising the cell of claim 17 and a pharmaceutically acceptable excipient.

20. A method of treating, inhibiting or ameliorating a cancer in a subject, comprising: administering the cell of claim 17 to the subject, wherein the cancer comprises an FGFR4-expressing cell.

* * * * *